United States Patent
Foote et al.

(10) Patent No.: US 11,623,061 B2
(45) Date of Patent: Apr. 11, 2023

(54) OUTLET CONNECTION ASSEMBLY

(71) Applicant: ResMed Pty Ltd, Bella Vista (AU)

(72) Inventors: Roger Mervyn Lloyd Foote, Sydney (AU); Ronald James Huby, Sydney (AU); Saad Nasr, Sydney (AU); Luke Andrew Stanislas, Sydney (AU); Zhuo Ran Tang, Sydney (AU); Ernie Wei-Chih Tsai, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/747,052

(22) Filed: May 18, 2022

(65) Prior Publication Data

US 2022/0273901 A1 Sep. 1, 2022

Related U.S. Application Data

(60) Division of application No. 17/518,996, filed on Nov. 4, 2021, now Pat. No. 11,471,640, which is a
(Continued)

(51) Int. Cl.
*A61M 16/00* (2006.01)
*A61M 16/08* (2006.01)
(Continued)

(52) U.S. Cl.
CPC .... *A61M 16/0816* (2013.01); *A61M 16/0066* (2013.01); *A61M 16/0875* (2013.01);
(Continued)

(58) Field of Classification Search
CPC .......... A61M 16/0816; A61M 16/1095; A61M 16/06; A61M 39/10
See application file for complete search history.

(56) References Cited

U.S. PATENT DOCUMENTS

| 3,936,026 A | 2/1976 | Hampel et al. |
| 4,782,832 A | 11/1988 | Trimble et al. |

(Continued)

FOREIGN PATENT DOCUMENTS

| CN | 1204266 A | 1/1996 |
| CN | 1691437 | 11/2005 |

(Continued)

OTHER PUBLICATIONS

Office Action dated Oct. 15, 2019 issued in Japanese Application No. 2018-188219 with English translation (5 pages).
(Continued)

*Primary Examiner* — Margaret M Luarca
(74) *Attorney, Agent, or Firm* — Nixon & Vanderhye P.C.

(57) ABSTRACT

A connection assembly for a respiratory therapy system, comprising: an outlet assembly, said outlet assembly including an outlet housing and a swivelling disc located on said outlet housing, said outlet housing and said swivelling disc defining, at least in part, a recess; an outlet connector located at an end of a tube portion, said outlet connector including an electrical connector; and a cable having a first end to connect to the electrical connector and a second end to connect to at least one electrical component of the respiratory therapy system, said cable having a slack portion, wherein said outlet connector and said swivelling disc are rotatable in unison between a first position and a second position, and wherein the slack portion of the cable extends from the recess and wraps around the swivelling disc as the swivelling disc is rotated from the first position to the second position.

30 Claims, 91 Drawing Sheets

Related U.S. Application Data continuation of application No. 16/726,304, filed on Dec. 24, 2019, now Pat. No. 11,305,088, which is a continuation of application No. 14/392,306, filed as application No. PCT/AU2014/050089 on Jun. 24, 2014, now Pat. No. 10,549,060.

(60) Provisional application No. 61/987,245, filed on May 1, 2014, provisional application No. 61/838,971, filed on Jun. 25, 2013.

(51) Int. Cl.
  *A61M 16/10* (2006.01)
  *A61M 16/16* (2006.01)
  *A61M 16/06* (2006.01)

(52) U.S. Cl.
  CPC .... *A61M 16/1055* (2013.01); *A61M 16/1095* (2014.02); *A61M 16/16* (2013.01); *A61M 16/0694* (2014.02); *A61M 2205/505* (2013.01); *A61M 2205/581* (2013.01); *A61M 2205/582* (2013.01); *A61M 2205/583* (2013.01)

(56) References Cited

U.S. PATENT DOCUMENTS

| | | | |
|---|---|---|---|
| 4,944,310 A | 7/1990 | Sullivan | |
| 5,520,172 A * | 5/1996 | Obermayer | A61M 16/104 128/205.13 |
| 5,607,316 A | 3/1997 | Ishikawa | |
| 6,216,691 B1 | 4/2001 | Kenyon et al. | |
| 6,532,959 B1 | 3/2003 | Berthon-Jones | |
| 6,581,594 B1 | 6/2003 | Drew et al. | |
| 7,157,035 B2 | 1/2007 | Edirisuriya et al. | |
| 7,393,222 B2 | 7/2008 | Asakura | |
| 7,726,309 B2 | 6/2010 | Ho | |
| 7,866,944 B2 | 1/2011 | Kenyon et al. | |
| 7,942,824 B1 | 5/2011 | Kayyali et al. | |
| 8,636,479 B2 | 1/2014 | Kenyon et al. | |
| 8,638,014 B2 | 1/2014 | Sears et al. | |
| 9,512,856 B2 | 12/2016 | Nibu et al. | |
| 1,092,716 A1 | 10/2018 | Velzy et al. | |
| 10,124,135 B2 | 11/2018 | Kenyon et al. | |
| 10,549,060 B2 | 2/2020 | Foote et al. | |
| 11,305,088 B2 | 4/2022 | Foote et al. | |
| 11,471,640 B2 | 10/2022 | Foote et al. | |
| 2002/0014240 A1 | 2/2002 | Truschel | |
| 2003/0066526 A1 | 4/2003 | Thudor et al. | |
| 2003/0111249 A1 | 6/2003 | Edirisuriya et al. | |
| 2003/0236015 A1 | 12/2003 | Edirisuriya et al. | |
| 2004/0060559 A1 | 4/2004 | Virr et al. | |
| 2006/0055069 A1 | 3/2006 | Dimatteo et al. | |
| 2006/0144405 A1 | 7/2006 | Gunaratnam et al. | |
| 2006/0266365 A1 | 11/2006 | Stallard | |
| 2007/0132117 A1 | 6/2007 | Pujol et al. | |
| 2007/0169776 A1 | 7/2007 | Kepler et al. | |
| 2007/0193583 A1 | 8/2007 | Reed | |
| 2007/0277827 A1 | 12/2007 | Bordewick et al. | |
| 2008/0072900 A1 | 3/2008 | Kenyon et al. | |
| 2008/0105527 A1 | 5/2008 | Klasek | |
| 2008/0127976 A1 | 6/2008 | Acker et al. | |
| 2008/0276939 A1 | 11/2008 | Tiedje | |
| 2009/0007912 A1 | 1/2009 | Lindell et al. | |
| 2009/0044808 A1 | 2/2009 | Guney et al. | |
| 2009/0050156 A1 | 2/2009 | Ng et al. | |
| 2009/0110378 A1 | 4/2009 | Bradley et al. | |
| 2009/0120434 A1 * | 5/2009 | Smith | A61M 16/0075 128/202.13 |
| 2009/0156952 A1 | 6/2009 | Hunter et al. | |
| 2009/0194106 A1 | 8/2009 | Smith et al. | |
| 2009/0229606 A1 | 9/2009 | Tang et al. | |
| 2009/0301485 A1 | 12/2009 | Kenyon | |
| 2010/0000534 A1 | 1/2010 | Kooij et al. | |
| 2010/0154796 A1 | 6/2010 | Smith et al. | |
| 2011/0017212 A1 * | 1/2011 | Kenyon | F04D 17/16 128/203.26 |
| 2011/0023874 A1 | 2/2011 | Bath | |
| 2011/0155132 A1 | 6/2011 | Virr et al. | |
| 2011/0186139 A1 | 8/2011 | Walborn | |
| 2012/0012109 A1 | 1/2012 | Chalvignac | |
| 2012/0169044 A1 * | 7/2012 | Kendrick | A61M 16/0816 285/313 |
| 2012/0266880 A1 | 10/2012 | Young | |
| 2013/0226344 A1 | 8/2013 | Wong | |
| 2013/0310713 A1 | 11/2013 | Weber et al. | |
| 2014/0332003 A1 | 11/2014 | Crumblin et al. | |
| 2016/0022954 A1 | 1/2016 | Bath et al. | |
| 2016/0199612 A1 | 7/2016 | Foote et al. | |
| 2020/0129722 A1 | 4/2020 | Foote et al. | |
| 2022/0054788 A1 | 2/2022 | Foote et al. | |
| 2022/0323709 A1 | 10/2022 | Foote et al. | |

FOREIGN PATENT DOCUMENTS

| | | |
|---|---|---|
| CN | 201042552 Y | 4/2008 |
| CN | 101405058 A | 4/2009 |
| CN | 101541367 A | 9/2009 |
| CN | 102170932 A | 8/2011 |
| CN | 102686282 A | 9/2012 |
| CN | 103055400 A | 4/2013 |
| CN | 103124575 A | 5/2013 |
| EP | 1 127 583 A2 | 8/2001 |
| EP | 1 369 141 A1 | 12/2003 |
| EP | 1187648 | 10/2005 |
| EP | 1 898 337 A1 | 3/2008 |
| FR | 2579896 A1 | 10/1986 |
| GB | 1364127 A | 8/1974 |
| JP | H03213293 | 9/1991 |
| JP | 2006-109534 A | 4/2006 |
| JP | 2010-508875 | 3/2010 |
| JP | 2013-018017 A | 1/2013 |
| TW | 200711671 A | 4/2007 |
| WO | 97/18001 | 5/1997 |
| WO | WO 1998004310 | 2/1998 |
| WO | WO 1998034665 | 8/1998 |
| WO | WO 2000078381 | 12/2000 |
| WO | WO 02/078775 A2 | 10/2002 |
| WO | WO 2004073778 | 9/2004 |
| WO | WO 2005063328 | 7/2005 |
| WO | WO 2006074513 | 7/2006 |
| WO | WO 2006/138331 A1 | 12/2006 |
| WO | WO 2006130903 | 12/2006 |
| WO | WO 2007/051230 A1 | 5/2007 |
| WO | WO 2009052560 | 4/2009 |
| WO | WO 2010/031126 A1 | 3/2010 |
| WO | WO 2010135785 | 12/2010 |
| WO | WO 2011056080 | 5/2011 |
| WO | WO 2011/122964 A1 | 10/2011 |
| WO | WO 2011/149362 A1 | 12/2011 |
| WO | WO 2012/154064 A2 | 11/2012 |
| WO | WO 2012160477 | 11/2012 |
| WO | WO 2012171072 | 12/2012 |
| WO | WO 2013020167 | 2/2013 |
| WO | 2013/045575 A1 | 4/2013 |
| WO | 2014/025266 | 2/2014 |
| WO | WO 2014/053010 A1 | 4/2014 |
| WO | WO 2014/138804 A1 | 9/2014 |

OTHER PUBLICATIONS

First Examination Report issued in related New Zealand Application No. 749247 dated Jan. 18, 2019, (2 pages).
First Office Action issued in related Taiwanese Application No. 103121801 dated Jun. 20, 2018 with English translation (7 pages).
Extended European Search Report issued in related European Application No. 18 16 7630.5 dated Jun. 20, 2018, (10 pages).
First Office Action issued in related Japanese Application No. 2016-522136 dated May 14, 2018, with English translation, 8 pages.
European Search Report issued in related European Application No. 14871575.8-1664, dated Sep. 20, 2017, (16 pages).
Official Action (Restriction Requirement) issued in related Design U.S. Appl. No. 29/553,470 dated May 23, 2017, (16 pages).

(56) References Cited

OTHER PUBLICATIONS

Non-Final Office Action issued in related Design U.S. Appl. No. 29/570,182 dated May 5, 2017, (16 pages).
First Office Action issued in related Chinese Application No. 201480046956.3 with English translation, dated Mar. 28, 2017, 15 pages.
Extended Search Report issued in related European Application No. 14818607.5, dated Nov. 15, 2016, 8 pages.
International Preliminary Report on Patentability for PCT/AU2014/050426 dated Jun. 21, 2016, 8 pages.
Kin-Lu Wong, "Compact and Broadband Microstrip Antennas", 2002, John Wiley & Sons, Inc., 340 pages.
Written Opinion for PCT/AU2014/050426 dated Mar. 16, 2015, 7 pages.
International Search Report for PCT/AU2014/050426 dated Mar. 16, 2015, 8 pages.
First Examination Report issued in related New Zealand Application No. 631008, dated Feb. 18, 2016, 2 pages.
Patent Examination Report No. 1 issued in related Australian Application No. 2014301955, dated Feb. 16, 2016, 2 pages.
International Search Report for PCT/AU2014/050089, dated Oct. 1, 2014, 11 pages.
Written Opinion of the ISA for PCT/AU2014/050089, dated May 28, 2015, 6 pages.
Written Opinion of the ISA for PCT/AU2014/050089, dated Oct. 1, 2014, 7 pages.
International Preliminary Report on Patentability for PCT/AU2014/050089, dated Jun. 15, 2015, 50 pages.
West, "Respiratory Physiology", Lippincott Williams & Wilkins, 9th edition published 2011, 8 pages.
"BalContact Springs Current Carrying Contact Elements DM-7, BalContact Advantages", Bal Seal Canted Coil Spring Catalog, Report No. 621-9, 2003, Bal Seal Engineering Company, Inc., 27 pages.
Office Action dated Apr. 2, 2020 issued in Chinese Application No. 201810157519.9 with English Translation (25 pages).
Office Action dated Apr. 22, 2022 issued in U.S. Appl. No. 17/518,996 (16 pages).
Office Action dated Mar. 7, 2022 issued in Japanese Application No. 2021-074886 with English translation (5 pages).

\* cited by examiner

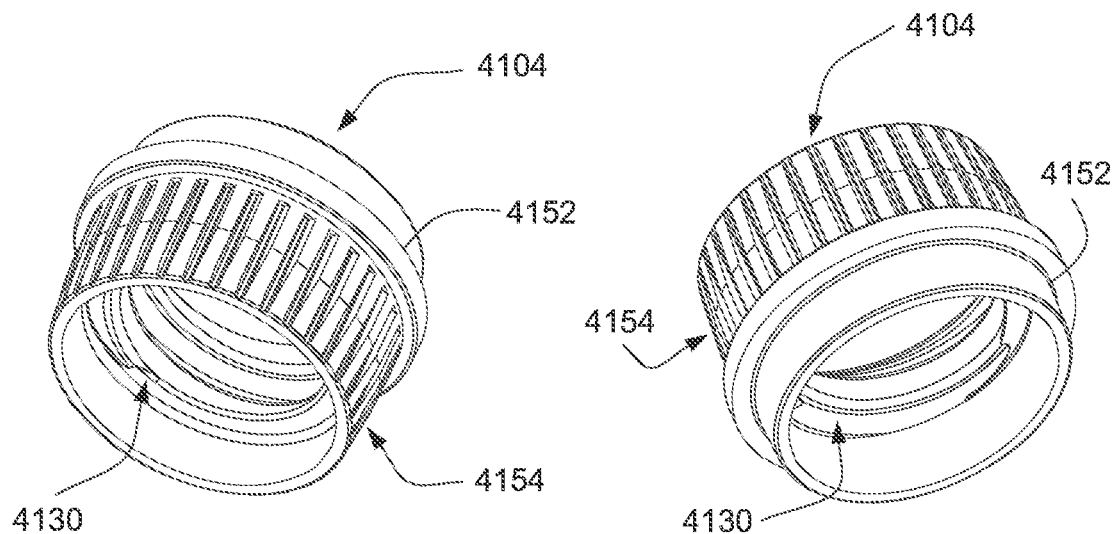
FIG. 7c    FIG. 7d
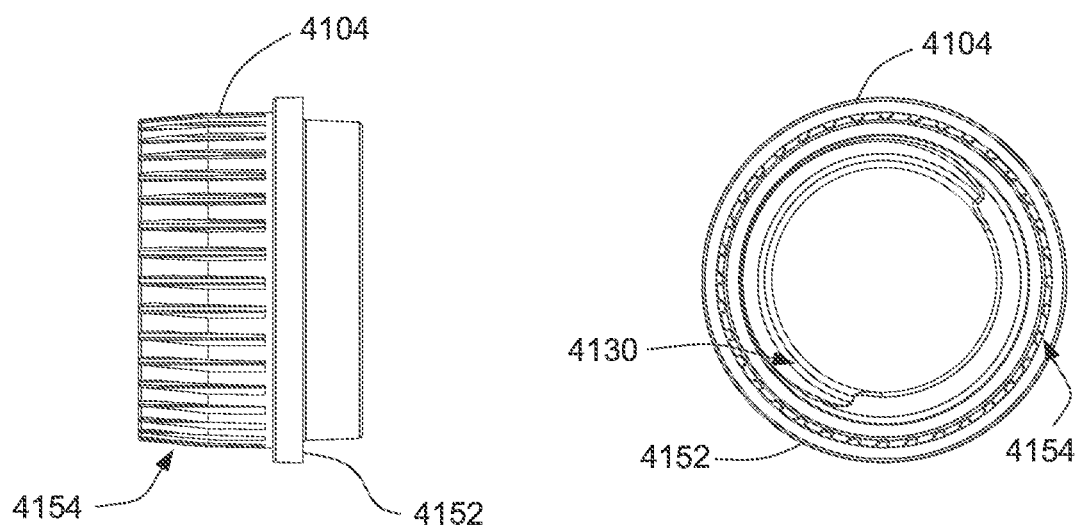
FIG. 7e    FIG. 7f

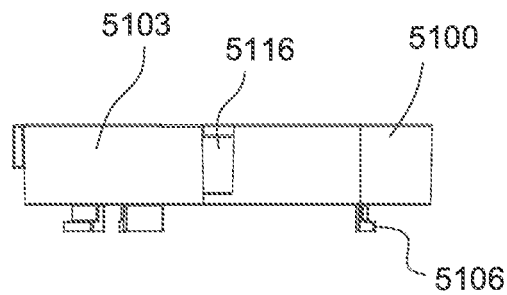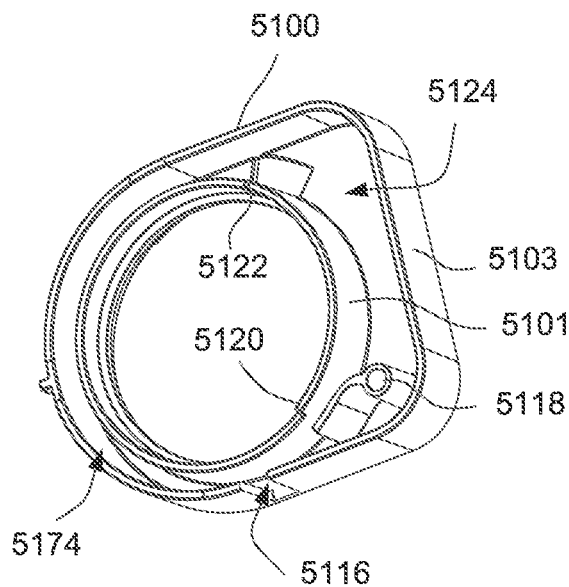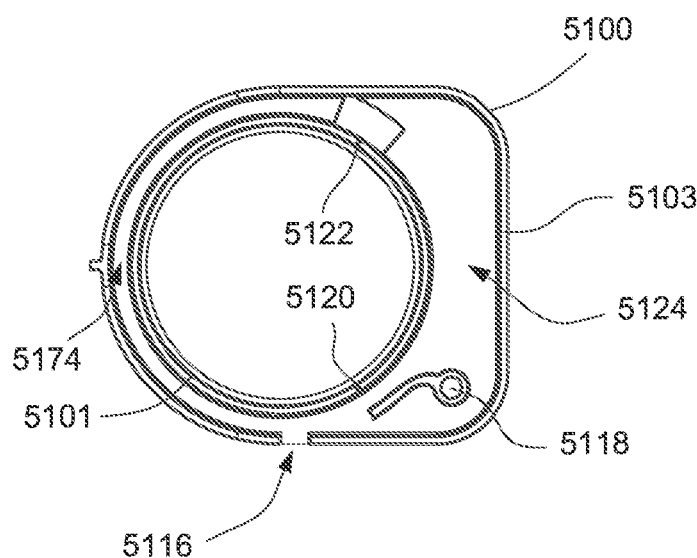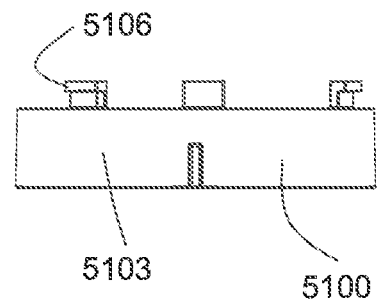
FIG. 11a
FIG. 11b
FIG. 11c
FIG. 11d

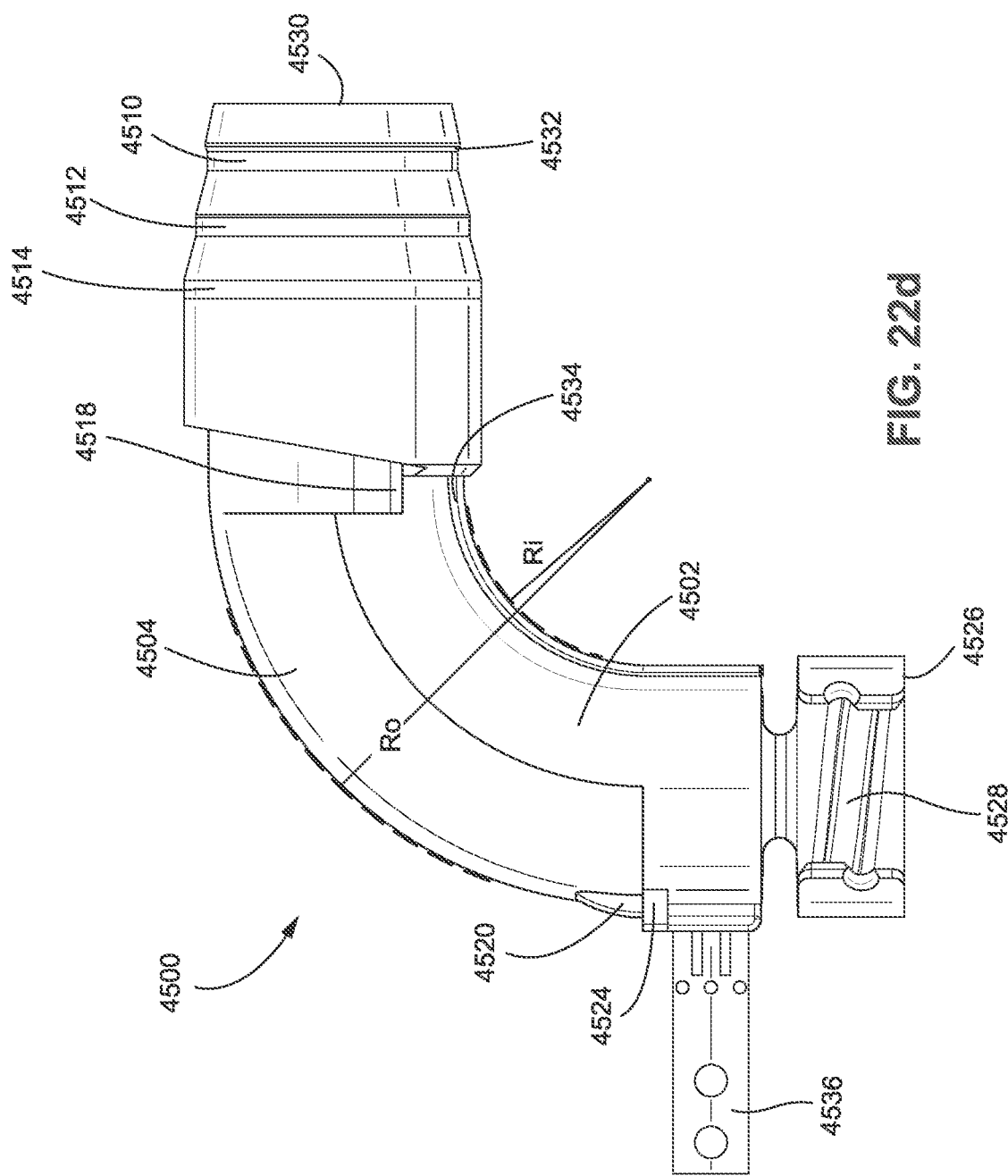

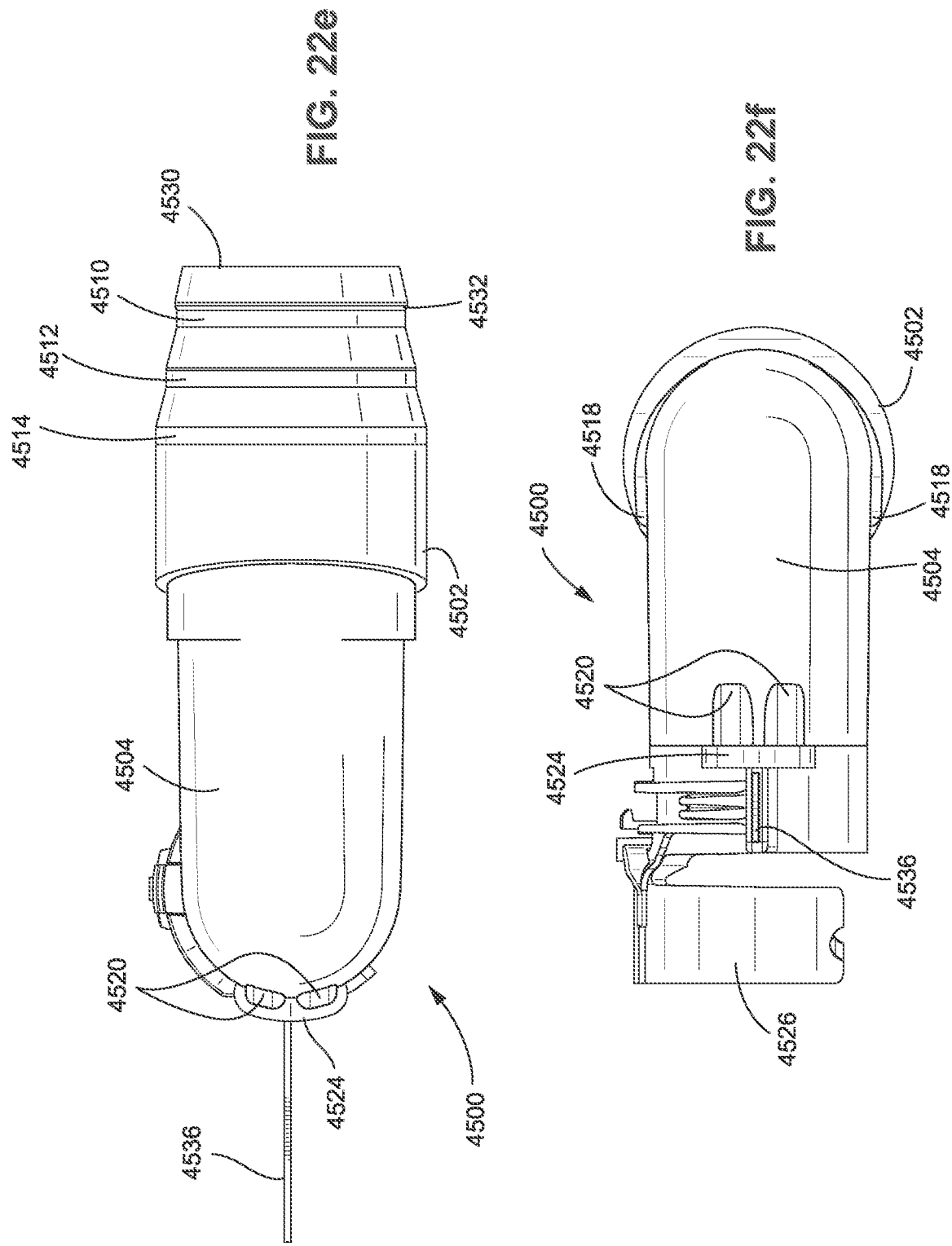

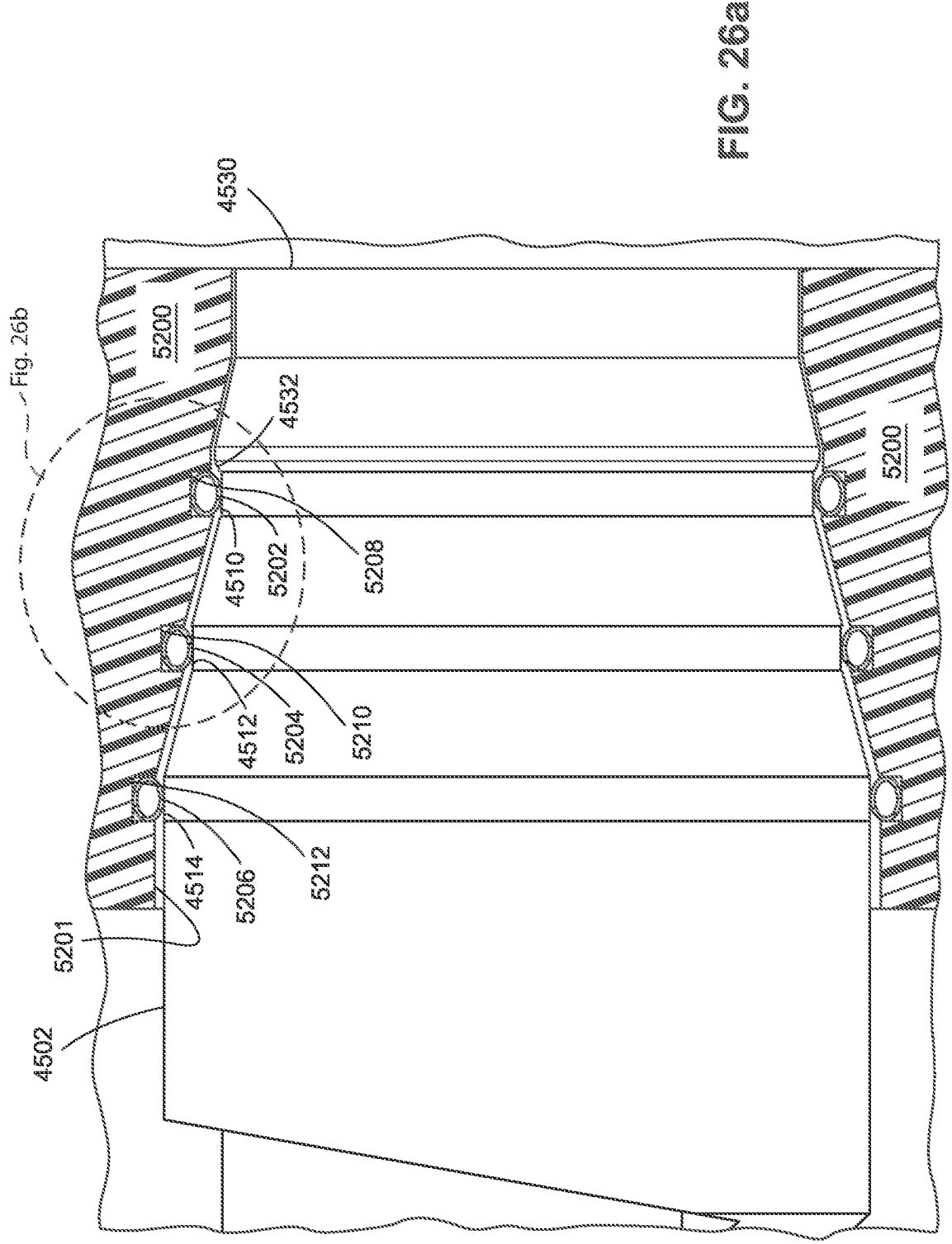

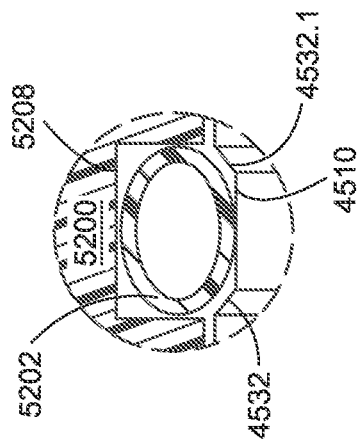
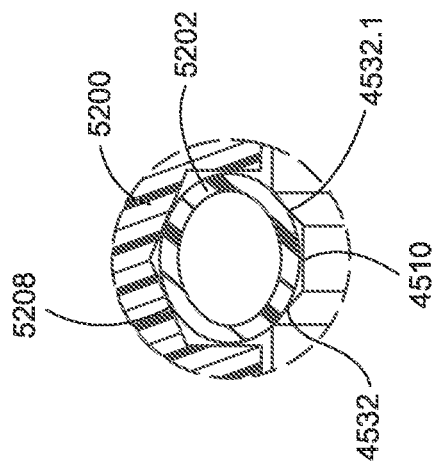
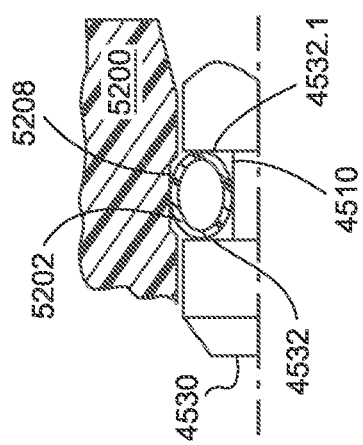
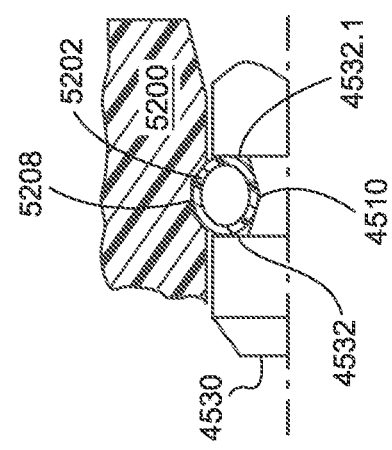
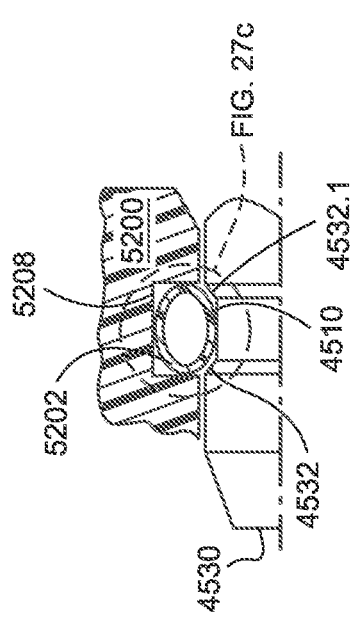
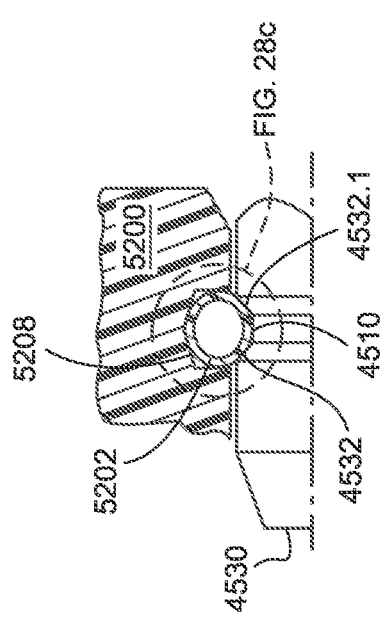

OUTLET CONNECTION ASSEMBLY

CROSS-REFERENCE TO RELATED APPLICATIONS

This application is a divisional of U.S. application Ser. No. 17/518,996, filed Nov. 4, 2021, now U.S. Pat. No. 11,471,640, which is a continuation of U.S. application Ser. No. 16/726,304, filed Dec. 24, 2019, now U.S. Pat. No. 11,305,088, which is a continuation of U.S. application Ser. No. 14/392,306, filed Dec. 24, 2015, now U.S. Pat. No. 10,549,060, which is the U.S. national phase of International Application No. PCT/AU2014/050089 filed 24 Jun. 2014, which designated the U.S. and claims the benefit of US Provisional Application Nos. 61/838,971, filed Jun. 25, 2013, and 61/987,245, filed May 1, 2014, each of which is incorporated herein by reference in its entirety.

BACKGROUND OF THE TECHNOLOGY

(1) Field of the Technology

The present technology relates to one or more of the diagnosis, treatment and amelioration of respiratory disorders, and to procedures to prevent respiratory disorders. In particular, the present technology relates to medical devices, and their use for treating respiratory disorders and for preventing respiratory disorders.

(2) Description of the Related Art

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnea (OSA), a form of Sleep Disordered Breathing (SDB), is characterized by occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchairbound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Otherwise healthy individuals may take advantage of systems and devices to prevent respiratory disorders from arising.

3.2.1 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) provides ventilatory support to a patient through the upper airways to assist the patient in taking a full breath and/or maintain adequate oxygen levels in the body by doing some or all of the work of breathing. The ventilatory support is provided via a patient interface. Non-invasive ventilation (NIV) has been used to treat OHS, COPD, MD and Chest Wall disorders.

Invasive ventilation (IV) provides ventilatory support to patients that are no longer able to effectively breathe themselves and may be provided using a tracheostomy tube.

Ventilators may control the timing and pressure of breaths pumped into the patient, and monitor the breaths taken by the patient. The methods of control and monitoring of patients typically include volume-cycled and pressure-cycled methods. The volume-cycled methods may include among others, Pressure-Regulated Volume Control (PRVC), Volume Ventilation (VV), and Volume Controlled Continuous Mandatory Ventilation (VC-CMV) techniques. The pressure-cycled methods may involve, among others, Assist Control (AC), Synchronized Intermittent Mandatory Ventilation (SIMV), Controlled Mechanical Ventilation (CMV), Pressure Support Ventilation (PSV), Continuous Positive Airway Pressure (CPAP), or Positive End Expiratory Pressure (PEEP) techniques.

3.2.2 Therapy Systems

A therapy system, or a respiratory therapy system, may comprise a Respiratory Pressure Therapy Device (RPT device), an air circuit, a humidifier, a patient interface, and data management.

3.2.2.1 Patient Interface

A patient interface may be used to interface respiratory equipment to its user, for example by providing a flow of air. The flow of air may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 cmH2O. For other forms of therapy, such as the delivery of oxygen, the patient interface may not include a seal sufficient to facilitate delivery to the airways of a supply of gas at a positive pressure of about 10 cmH2O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, mask designed as part of personal protection equipment (e.g. filter masks), SCUBA masks, or for the administration of anaesthetics may be tolerable for their original application, but nevertheless may be undesirably uncomfortable to be worn for extended periods of time, e.g. several hours. This discomfort may lead to a reduction in patient compliance with therapy. This is even more so if the mask is to be worn during sleep.

Nasal CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g. difficult to assemble or disassemble), patients may not clean their mask and this may impact negatively on patient compliance.

While a mask for other applications (e.g. aviators) may not be suitable for use in treating sleep disordered breathing, a mask designed for use in treating sleep disordered breathing may be suitable for other applications.

For these reasons, masks for delivery of nasal CPAP during sleep form a distinct field.

3.2.2.1.1 Seal-Forming Portion

Patient interfaces may include a seal-forming portion. Since it is in direct contact with the patient's face, the shape and configuration of the seal-forming portion can have a direct impact on the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to, for example, overlay an upper lip region and a nasal bridge region of a face. In one form of patient interface, a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be in appropriate in another region, e.g. because of the different shape, structure, variability and/or sensitivity regions of the patient's face. For example, a seal on swimming goggles that overlays a patient's forehead may not be appropriate to use on a patient's nose.

Certain seal-forming portions may be designed for mass manufacture such that one design is able to fit and be comfortable and effective for a wide range of different face shapes and sizes. To the extent to which there is a mismatch between the shape of the patient's face and the seal-forming portion of the mass-manufactured patient interface, one or both must adapt in order for a seal to form.

One type of seal-forming portion extends around the periphery of the patient interface, and is intended to seal against the user's face when force is applied to the patient interface with the seal-forming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may leak. Furthermore, if the shape of the seal-forming portion does not match that of the patient, it may crease or buckle in use, giving rise to leaks.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785. One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask, SWIFT II nasal pillows mask, SWIFT LT nasal pillows mask, SWIFT FX nasal pillows mask and LIBERTY full-face mask. The following patent applications, assigned to ResMed Limited, describe nasal pillows masks: International Patent Application WO2004/073,778 (describing amongst other things aspects of ResMed SWIFT nasal pillows), US Patent Application 2009/0044808 (describing amongst other things aspects of ResMed SWIFT LT nasal pillows); International Patent Applications WO 2005/063,328 and WO 2006/130,903 (describing amongst other things aspects of ResMed LIBERTY full-face mask); International Patent Application WO 2009/052,560 (describing amongst other things aspects of ResMed SWIFT FX nasal pillows).

3.2.2.1.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534.

Another technique is the use of one or more straps and stabilising harnesses. Many such harnesses suffer from being one or more of ill-fitting, bulky, uncomfortable and awkward to use.

3.2.2.1.3 Vent Technologies

Some forms of patient interface systems may include a vent to allow the washout of exhaled carbon dioxide. The vent may allow a flow of gas from an interior space of the patient interface, e.g. the plenum chamber, to an exterior of the patient interface, e.g. to ambient. The vent may comprise an orifice and gas may flow through the orifice in use of the mask. Many such vents are noisy. Others may block in use and provide insufficient washout. Some vents may be disruptive of the sleep of a bed-partner 1100 of the patient 1000, e.g. through noise or focused airflow.

ResMed Limited has developed a number of improved mask vent technologies. See WO 1998/034,665; WO 2000/078,381; U.S. Pat. No. 6,581,594; US Patent Application; US 2009/0050156; US Patent Application 2009/0044808.

Table of noise of prior masks (ISO 17510-2: 2007, 10 cmH$_2$O pressure at 1 m)

| Mask name | Mask type | A-weighted sound power level dbA (uncertainty) | A-weighted sound pressure dbA (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage (*) | nasal | 29.5 | 21.5 | 1998 |
| ResMed UltraMirage | nasal | 36 (3) | 28 (3) | 2000 |
| ResMed Mirage Activa | nasal | 32 (3) | 24 (3) | 2002 |
| ResMed Mirage Micro | nasal | 30 (3) | 22 (3) | 2008 |
| ResMed Mirage SoftGel | nasal | 29 (3) | 22 (3) | 2008 |
| ResMed Mirage FX | nasal | 26 (3) | 18 (3) | 2010 |
| ResMed Mirage Swift (*) | nasal pillows | 37 | 29 | 2004 |
| ResMed Mirage Swift II | nasal pillows | 28 (3) | 20 (3) | 2005 |
| ResMed Mirage Swift LT | nasal pillows | 25 (3) | 17 (3) | 2008 |

((*) one specimen only, measured using test method specified in ISO3744 in CPAP mode at 10 cmH$_2$O)

Sound pressure values of a variety of objects are listed below

| Object | A-weighted sound pressure dbA (uncertainty) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

3.2.2.2 Respiratory Pressure Therapy (RPT) Device

One known type of RPT device used for treating sleep disordered breathing is a positive airway pressure (PAP) device, such as the S9 Series, manufactured by ResMed. Other examples of RPT devices include a ventilator and a high flow therapy device. In some cases, RPT devices such as PAP devices have been known to be referred to as flow generators. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit.

RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface, such as those described above.

RPT devices typically also include an inlet filter, various transducers, and a microprocessor-based controller. A blower may include a servo-controlled motor, a volute, and an impeller. In some cases a brake for the motor may be implemented to more rapidly reduce the speed of the blower so as to overcome the inertia of the motor and impeller. The braking can permit the blower to more rapidly achieve a lower pressure condition in time for synchronization with expiration despite the inertia. In some cases the pressure generator may also include a valve capable of discharging generated air to atmosphere as a means for altering the pressure delivered to the patient as an alternative to motor speed control. The transducers may measure, amongst other things, motor speed, mass flow rate and outlet pressure, such as with a pressure transducer or the like. The controller may include data storage capacity with or without integrated data retrieval and display functions.

Table of noise output levels of prior RPT devices (one specimen only, measured using test method specified in ISO3744 in CPAP mode at 10 cmH2O).

| RPT Device name | A-weighted sound power level dB(A) | Year (approx.) |
| --- | --- | --- |
| C-Series Tango | 31.9 | 2007 |
| C-Series Tango with Humidifier | 33.1 | 2007 |
| S8 Escape II | 30.5 | 2005 |
| S8 Escape II with H4i Humidifier | 31.1 | 2005 |
| S9 AutoSet | 26.5 | 2010 |
| S9 AutoSet with H5i Humidifier | 28.6 | 2010 |

3.2.2.3 Humidifier

Delivery of a flow of air without humidification may cause drying of airways. Medical humidifiers are used to increase humidity and/or temperature of the flow of air in relation to ambient air when required, typically where the patient may be asleep or resting (e.g. at a hospital). As a result, a medical humidifier may be relatively small for bedside placement, and it may be configured to only humidify and/or heat the flow of air delivered to the patient without humidifying and/or heating the patient's surroundings. Room-based systems (e.g. a sauna, an air conditioner, an evaporative cooler), for example, may also humidify air that is breathed in by the patient, however they would also humidify and/or heat the entire room, which may cause discomfort to the occupants.

The use of a humidifier with a RPT device and the patient interface produces humidified gas that minimizes drying of the nasal mucosa and increases patient airway comfort. In addition in cooler climates, warm air applied generally to the face area in and about the patient interface is more comfortable than cold air.

Respiratory humidifiers are available in many forms and may be a standalone device that is coupled to a RPT device via an air circuit, is integrated with the RPT device or configured to be directly coupled to the relevant RPT device. While known passive humidifiers can provide some relief, generally a heated humidifier may be used to provide sufficient humidity and temperature to the air so that the patient will be comfortable. Humidifiers typically comprise a water reservoir or tub having a capacity of several hundred milliliters (ml), a heating element for heating the water in the reservoir, a control to enable the level of humidification to be varied, a gas inlet to receive air from the RPT device, and a gas outlet adapted to be connected to an air circuit that delivers the humidified air to the patient interface.

Heated passover humidification is one common form of humidification used with a RPT device. In such humidifiers the heating element may be incorporated in a heater plate which sits under, and is in thermal contact with, the water tub. Thus, heat is transferred from the heater plate to the water reservoir primarily by conduction. The air flow from the RPT device passes over the heated water in the water tub resulting in water vapour being taken up by the air flow. The ResMed H4i™ and H5i™ Humidifiers are examples of such heated passover humidifiers that are used in combination with ResMed S8 and S9 CPAP devices respectively.

Other humidifiers may also be used such as a bubble or diffuser humidifier, a jet humidifier or a wicking humidifier. In a bubble or diffuser humidifier the air is conducted below the surface of the water and allowed to bubble back to the top. A jet humidifier produces an aerosol of water and baffles or filters may be used so that the particles are either removed or evaporated before leaving the humidifier. A wicking humidifier uses a water absorbing material, such as sponge or paper, to absorb water by capillary action. The water absorbing material is placed within or adjacent at least a portion of the air flow path to allow evaporation of the water in the absorbing material to be taken up into the air flow.

An alternative form of humidification is provided by the ResMed HumiCare™ D900 humidifier that uses a Counter-Stream™ technology that directs the air flow over a large surface area in a first direction whilst supplying heated water to the large surface area in a second opposite direction. The ResMed HumiCare™ D900 humidifier may be used with a range of invasive and non-invasive ventilators.

BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

Another aspect of the present technology is directed to a connection assembly for a respiratory therapy system. The connection assembly may comprise: an outlet assembly, said outlet assembly including an outlet housing and a swivelling disc located on said outlet housing, said outlet housing comprising a void and an annular section; and a cable having a first end to connect to an electrical connector and a second end to connect to at least one electrical component of the respiratory therapy system, said cable having a slack portion, wherein said swivelling disc is rotatable relative to said outlet housing between a first position and a second position, and wherein the slack portion of the cable extends from the void and wraps around the annular section as the swivelling disc is rotated from the first position to the second position.

In examples, (a) said swivelling disc may include a first pair of stop surfaces and said outlet housing may include a second pair of stop surfaces to limit the rotation of the swivelling disc relative to the outlet housing, (b) each pair of stop surfaces may be arranged to limit the rotation of the swivelling disc relative to the outlet housing to less than 360°, (c) each pair of stop surfaces may be arranged to limit the rotation of the swivelling disc relative to the outlet housing to greater than 180°, (d) the first pair of stop surfaces may be located on either side of and adjacent to a receiver opening in the swivelling disc that receives the cable, (e) the outlet housing may include an inner wall, said second pair of stop surfaces may be located on the inner wall and said inner wall may be configured to rotatably receive said swivelling disc, (f) the void may be defined, at least in part, by the inner wall and an outer wall of the outlet housing, (g) a distance between the inner wall and the outer wall of the outlet housing and across the void may be in the range of about 2 mm to about 5 mm, (h) the cable may comprise a flexible circuit board or a ribbon cable, (i) the cable may have a substantially rectangular cross-section, and a major side of the substantially rectangular cross-section may be oriented in parallel to an axis of rotation of the swivelling disc, (j) the swivelling disc may include an electrical connector receiver to receive the electrical connector, and the electrical connector may be electrically connectable to the cable within the electrical connector receiver, (k) the electrical connector receiver may include an opening to receive the electrical connector when the outlet connector is connected to the outlet assembly, and the outlet connector may be shaped to cover the opening of the electrical connector receiver when the outlet connector is connected to the outlet assembly, (l) the outlet connector may include a recess proximal to the electrical connector shaped to correspond to a protruding portion of the electrical connector receiver, (m) the outlet housing may include a retainer, said retainer may be configured to retain the slack portion within the void of the outlet housing as the swivelling disc is rotated from the second position to the first position, (n) the outlet connector may include at least one retention feature to releasably connect the outlet connector to the swivelling disc via at least one corresponding notch located on the swivelling disc, (o) the outlet connector may include at least one tab, each said at least one retention feature may be located on a corresponding tab having a corresponding actuator, and each said actuator may be adapted to release each said retention feature from a corresponding notch of the swivelling disc, (p) the gas delivery tube may include a heating element disposed along at least a portion of the gas delivery tube, said heating element may be connected to the electrical connector, (q) the outlet connector may include a grommet to connect the gas delivery tube to a tube connection region of the outlet connector, (r) the grommet may include threads to receive corresponding coils of the gas delivery tube, (s) the grommet may be comprised of a thermoplastic elastomer, (t) the grommet may include at least one keyway for restraining the grommet during forming, (u) the grommet may include at least one radial flange to engage a mold tool during forming, (v) the grommet may include a grip section, (w) the grip section may include a plurality of ridges and recesses disposed radially about the grommet, (x) the outlet connector may comprise an elbow, (y) the elbow may be bent at about 90°, (z) when the outlet connector is connected to the outlet assembly a rotatable, electrical, and pneumatic connection may be formed, (aa) the outlet assembly may comprise an airflow tube having a tapered end to connect to the outlet connector and form a pneumatic seal therewith, (bb) the swivelling disc may include at least one tang to rotatably connect the swivelling disc to the outlet housing, (cc) the slack portion may comprise a fixed length that is less than a circumference of the swivelling disc, (dd) when the swivelling disc is in the first position the slack portion may gather in the void, (ee) a larger portion of the cable may be contained in the void when the swivelling disc is in the first position than when the swivelling disc is in the second position, (ff) an electrical connection formed by the connection assembly may comprise at least one wire to perform powering and/or signalling functions, (gg) the outlet connector may include at least one rib at an outlet connection region to support the outlet connector on the airflow tube when connected to the outlet assembly, (hh) the connection assembly may comprise an outlet connector located at an end of a gas delivery tube to connect the gas delivery tube to the outlet assembly, said outlet connector including an electrical connector, wherein said outlet connector and said swivelling disc are connectable such that said outlet connector and said swivelling disc are rotatable in unison, (ii) the annular section may be defined, at least in part, by the inner wall and an outer wall of the outlet housing, (jj) the void and annular section may be on opposing sides of the inner wall, (kk) the outlet housing may be comprised of thermoplastic elastomer, (ll) the elbow may be bent at an angle between about 0° and about 120°, (mm) the airflow tube may be removable, (nn) the outlet connector may include a receiver at a tube connection region, said receiver comprising receiver threads, a receiver flange, and at least one protrusion, (oo) the outlet connector may comprise a clip to secure the gas delivery tube within the receiver, the clip comprising clip threads, a clip flange, and at least one tab and each at least one tab may be structured to engage with a respective one of the at least one protrusion to secure the clip to the receiver, (pp) the clip threads and the receiver threads may be structured to receive corresponding coils of the gas delivery tube, and/or (qq) the clip flange and the receiver flange may be structured to engage a mold tool during forming.

Another aspect of the present technology is directed to a method of manufacturing an air circuit for use with a respiratory therapy device. The method may comprise: molding an outlet connector substructure including a tube connection region, wherein an interior of said tube connection region is formed around a mandrel such that an orifice is formed in the outlet connector substructure opposite the tube connection region; threading a grommet onto a first end of a gas delivery tube having a helical heating element disposed thereon such that a connection portion of the gas delivery tube extends through the grommet; connecting the connection portion of the gas delivery tube to the tube connection region of the outlet connector substructure; attaching an electrical connector to the helical heating element at the tube connection region of the outlet connector substructure; molding an outlet connector housing over the outlet connector substructure, at least in part by sealing the mold tool around the grommet; and attaching an end cap over the orifice.

Another aspect of the present technology is directed to a respiratory therapy system for the treatment of sleep disordered breathing in a patient. The respiratory therapy system may comprise: a pressure generator to provide a flow of air to the patient at positive pressure, the pressure generator comprising a housing; an outlet assembly located on the housing, said outlet assembly comprising: an outlet housing and a swivelling disc located on said outlet housing, said outlet housing comprising a void; and a cable having a first end to connect to an electrical connector and a second end to connect to at least one electrical component of the respiratory therapy system, said cable having a slack portion; and an air circuit configured to connect to the outlet assembly at a first end and to a patient interface at a second end, said air circuit comprising: an outlet connector located at the second end of a gas delivery tube to connect the gas delivery tube to the outlet assembly, said outlet connector including the electrical connector, wherein said outlet connector and said swivelling disc are connectable such that said outlet connector and said swivelling disc are rotatable in unison relative to said outlet housing between a first position and a second position, and wherein a larger portion of the cable is contained in the void when the swivelling disc is in the first position than when the swivelling disc is in the second position.

In examples, (a) said swivelling disc may include a first pair of stop surfaces and said outlet housing may include a second pair of stop surfaces to limit the rotation of the swivelling disc relative to the outlet housing, (b) each pair of stop surfaces may be arranged to limit the rotation of the swivelling disc relative to the outlet housing to less than 360°, (c) each pair of stop surfaces may be arranged to limit the rotation of the swivelling disc relative to the outlet housing to greater than 180°, (d) the first pair of stop surfaces may be located on either side of and adjacent to a receiver opening in the swivelling disc that receives the cable, (e) the outlet housing may include an inner wall, said second pair of stop surfaces may be located on the inner wall and said inner wall may be configured to rotatably receive said swivelling disc, (f) the void may be defined, at least in part, by the inner wall and an outer wall of the outlet housing, (g) a distance between the inner wall and the outer wall of the outlet housing and across the void may be in the range of about 2 mm to about 5 mm, (h) the cable may comprise a flexible circuit board or a ribbon cable, (i) the cable may have a substantially rectangular cross-section, and a major side of the substantially rectangular cross-section may be oriented in parallel to an axis of rotation of the swivelling disc, (j) the swivelling disc may include an electrical connector receiver to receive the electrical connector, and the electrical connector may be electrically connectable to the cable within the electrical connector receiver, (k) the electrical connector receiver may include an opening to receive the electrical connector when the outlet connector is connected to the outlet assembly, and the outlet connector may be shaped to cover the opening of the electrical connector receiver when the outlet connector is connected to the outlet assembly, (l) the outlet connector may include a recess proximal to the electrical connector shaped to correspond to a protruding portion of the electrical connector receiver, (m) the outlet housing may include a retainer, said retainer may be configured to retain the slack portion within the outlet housing as the swivelling disc is rotated from the second position to the first position, (n) the outlet connector may include at least one retention feature to releasably connect the outlet connector to the swivelling disc via at least one corresponding notch located on the swivelling disc, (o) the outlet connector may include at least one tab, each said at least one retention feature may be located on a corresponding tab having a corresponding actuator, and each said actuator may be adapted to release each said retention feature from a corresponding notch of the swivelling disc, (p) the gas delivery tube may include a heating element disposed along at least a portion of the gas delivery tube, said heating element may be connected to the electrical connector, (q) the outlet connector may include a grommet to connect the gas delivery tube to a tube connection region of the outlet connector, (r) the grommet may include threads to receive corresponding coils of the gas delivery tube, (s) the grommet may be comprised of a thermoplastic elastomer, (t) the grommet may include at least one keyway for restraining the grommet during forming, (u) the grommet may include at least one radial flange to engage a mold tool during forming, (v) the grommet may include a grip section, (w) the grip section may include a plurality of ridges and recesses disposed radially about the grommet, (x) the outlet connector may comprise an elbow, (y) the elbow may be bent at about 90°, (z) the outlet housing may be comprised of thermoplastic elastomer, (aa) when the outlet connector is connected to the outlet assembly a rotatable, electrical, and pneumatic connection may be formed, (bb) the outlet assembly may comprise a airflow tube having a tapered end to connect to the outlet connector and form a pneumatic seal therewith, (cc) the swivelling disc may include at least one tang to rotatably connect the swivelling disc to the outlet housing, (dd) the slack portion may comprise a fixed length that is less than a circumference of the swivelling disc, (ee) when the swivelling disc is in the first position the slack portion may gather in the void, (ff) the slack portion of the cable may extend from the void and wrap around the annular section as the swivelling disc is rotated from the first position to the second position, (gg) an electrical connection formed by the connection assembly may comprise at least one wire to perform powering and/or signalling functions, (hh) the outlet connector may include at least one rib at an outlet connection region to support the outlet connector on the airflow tube when connected to the outlet assembly, (ii) the respiratory therapy system may comprise a humidifier to humidify the flow of air, (jj) the outlet housing may comprise an annular section configured to receive the cable when the swivelling disc is in the second position, (kk) the elbow may be bent at an angle between about 0° and about 120°, (ll) the airflow tube may be removable, (mm) the outlet connector may include a receiver at a tube connection region, said receiver comprising receiver threads, a receiver flange, and at least one protrusion, (nn) the outlet connector may comprise a clip to secure the gas delivery tube within the receiver, the clip comprising clip threads, a clip flange, and at least one tab and each at least one tab may be structured to engage with a respective one of the at least one protrusion to secure the clip to the receiver, (oo) the clip threads and the receiver threads may be structured to receive corresponding coils of the gas delivery tube, and/or (pp) the clip flange and the receiver flange may be structured to engage a mold tool during forming.

Another aspect of the present technology is directed to a connection assembly for a respiratory therapy system. The connection assembly may comprise: a housing; an outlet assembly located on the housing and including an outlet tube; an outlet connector having a first end adapted to pneumatically connect to a gas delivery tube and a second end adapted to removably connect to the outlet assembly and form a pneumatic connection with the outlet tube; a plurality of first electrical connectors; and a second electrical connector adapted to electrically connect to one of the plurality of first electrical connectors, wherein the outlet assembly and the outlet connector are removably connectable in a plurality of predetermined and discrete positions to form both pneumatic and electrical connections.

In examples, (a) the quantity of the plurality of first electrical connectors may equal the quantity of the plurality of predetermined and discrete positions, (b) the outlet assembly may comprise the plurality of first electrical connectors and the outlet connector may comprise the second electrical connector, (c) the outlet assembly may include at least one cable to electrically connect the plurality of first electrical connectors to at least one electronic component of the respiratory therapy system, (d) the outlet assembly may comprise the second electrical connector and the outlet connector may comprise the plurality of first electrical connectors, (e) the connection assembly may comprise at least one dummy connector configured to cover at least one of the plurality of first electrical connectors that is not connected to the second electrical connector, (f) a quantity of the at least one dummy connectors may be one less than a quantity of the plurality of first electrical connectors, (g) the outlet connector may comprise an elbow, (h) the elbow may be bent at about 90°, (i) the outlet assembly may include a recess to receive the second end of the outlet connector, and the recess and the second end of the outlet connector may be shaped substantially correspondingly, (j) the elbow may be bent between about 0° and about 120°, and/or (k) an electrical connection formed by the connection assembly may comprise at least one wire to perform powering and/or signalling functions.

Another aspect of the present technology is directed to a method of manufacturing an air circuit for use with a respiratory therapy device. The method may comprise: molding an outlet connector substructure, the outlet connector substructure including a receiver and receiver threads at a tube connection region, wherein an interior of said outlet connector substructure is formed around a mandrel such that an orifice is formed in the outlet connector substructure opposite the tube connection region; threading a first end of a gas delivery tube having a helical heating element disposed thereon into the receiver threads such that a connection portion of the gas delivery tube extends through the receiver; connecting the connection portion of the gas delivery tube to the tube connection region of the outlet connector substructure by securing a clip around the connection portion of the gas delivery tube such that the connection portion of the gas delivery tube is substantially surrounded by the receiver and the clip; attaching an electrical connector to the helical heating element at the tube connection region of the outlet connector substructure; molding an outlet connector housing over the outlet connector substructure, at least in part by sealing the mold tool around the tube connection region; and attaching an end cap over the orifice.

In examples, (a) the clip may be a separate component from the receiver, the clip comprising a pair of tabs and the receiver comprising a pair of protrusions, and securing the clip may comprise snapping each of the pair of tabs onto respective ones of the pair of protrusions, and/or (b) the clip and the receiver may comprise one piece and the clip is joined to the receiver by a hinge, the clip comprising a tab and the receiver comprising a protrusion, and securing the clip may comprise snapping the tab onto the protrusion.

Another aspect of the present technology is directed to an outlet connector assembly for a device to deliver continuous positive airway pressure to a patient for treatment of sleep disordered breathing. The outlet connector assembly may comprise: a body having a tube connection region and an outlet connection region; a cap structured to attach to the body such that the cap and the body at least partially define an airflow path between the tube connection region and the outlet connection region; and an electrical contact assembly molded to the body and configured to form an electrical connection between the tube connection region and the outlet connection region.

In examples, (a) the airflow path defined at least partially by the cap and the body may have a curved shape and the airflow path may have a substantially uniform cross-section, (b) a radius of the curved shape of the airflow path may be 1 to 3 times the diameter of the airflow path, (c) an inner radius and an outer radius of the curved shape of the airflow may share a common arc center, (d) the tube connection region may comprise a shoulder and contact recesses, (e) the electrical contact assembly may comprise contacts positioned in the contact recesses, the contacts being extended completely around the outlet connection region, (f) the cap may comprise tabs and prongs and the body may comprise notches and detents, and the tabs may engage the notches and the prongs may engage the detents to attach the cap to the body, (g) the tube connection region may comprise a thread shaped to receive a helical coil of a gas delivery tube, and/or (h) the outlet connector assembly may comprise a housing overmolded to the body and the cap to pneumatically seal the airflow path.

Of course, portions of the examples/aspects may form sub-examples/sub-aspects of the present technology. Also, various ones of the sub-examples/sub-aspects and/or examples/aspects may be combined in various manners and also constitute additional examples/aspects or sub-examples/sub-aspects of the present technology.

Other features of the technology will be apparent from consideration of the information contained in the following detailed description, abstract, drawings and claims.

BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including.

5.1 Therapy Systems

5.2 Therapy 5.2.1 Respiratory System

Figure 2A:
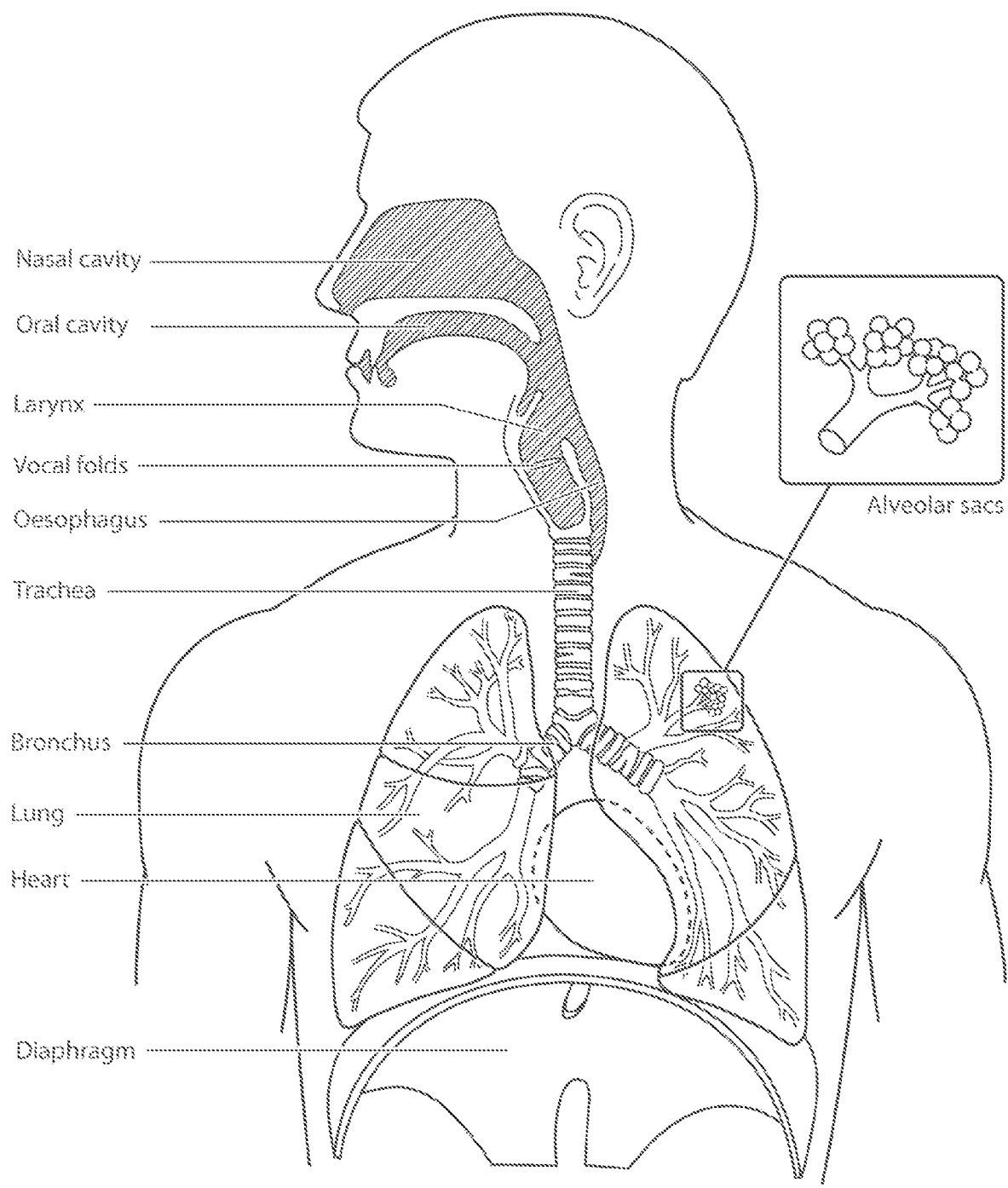

FIG. 2a shows an overview of a human respiratory system including the nasal and oral cavities, the larynx, vocal folds, oesophagus, trachea, bronchus, lung, alveolar sacs, heart and diaphragm.

Figure 2B:
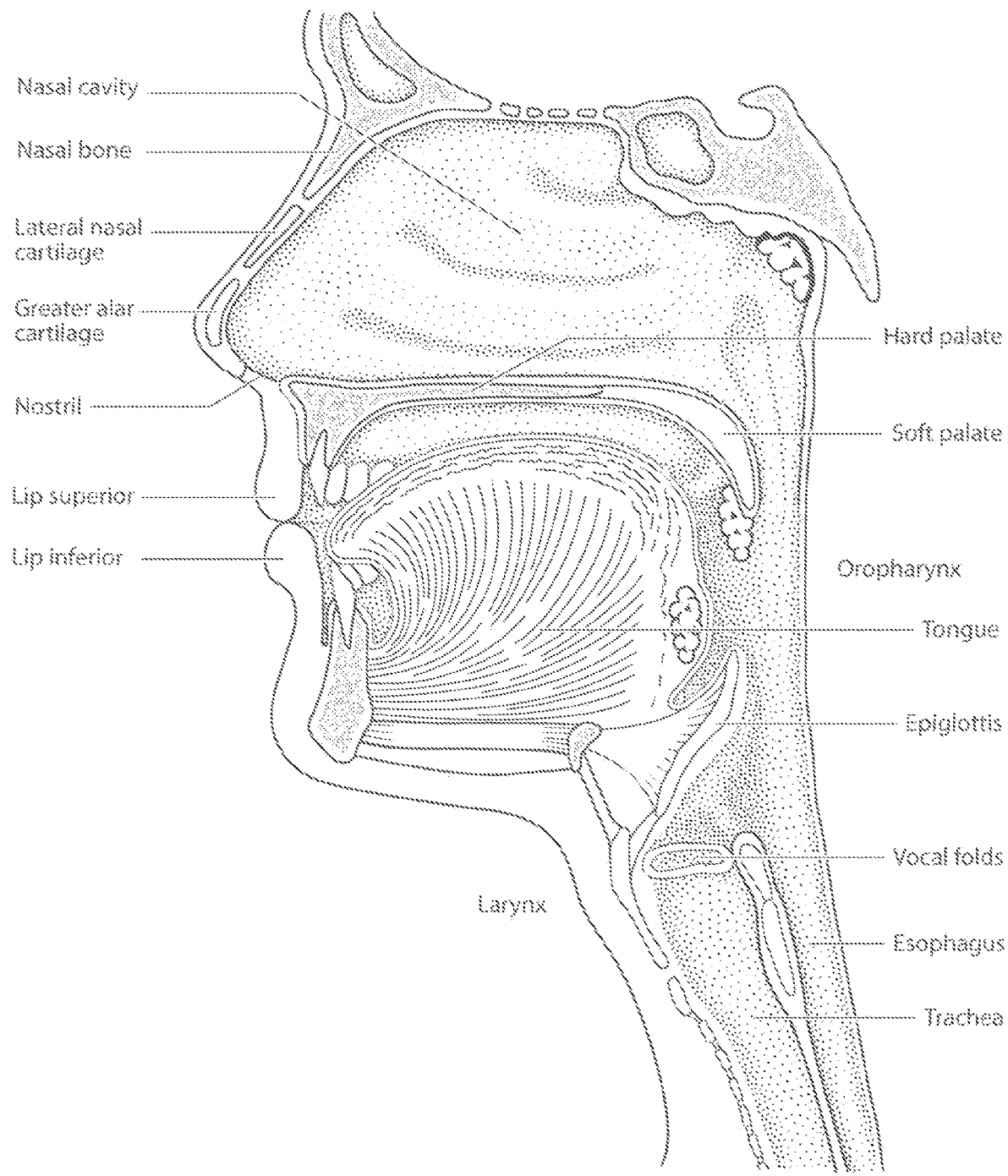

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

5.2.2 Patient Interface

Figure 2C:
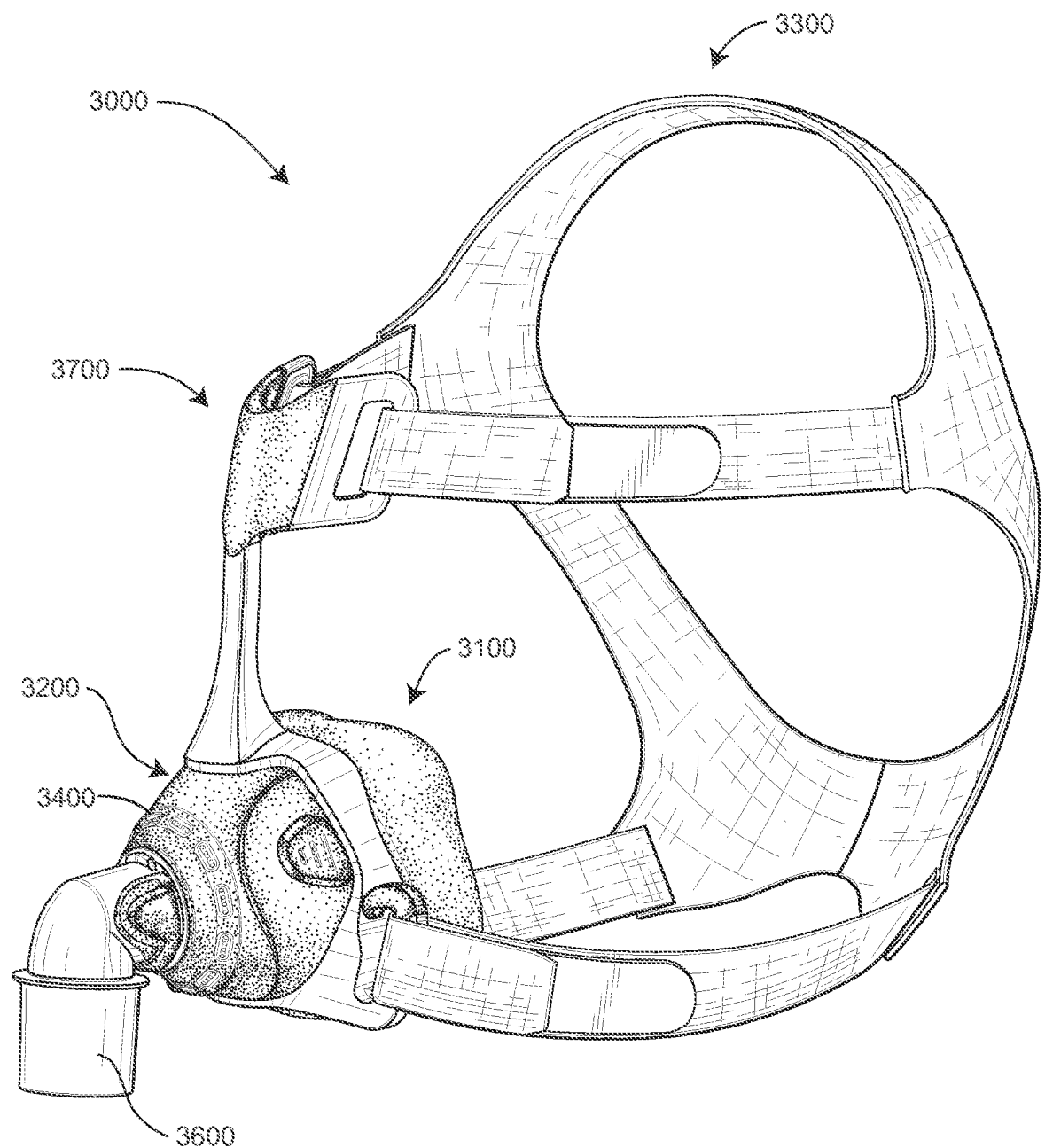

FIG. 2c shows a patient interface in the form of a nasal mask in accordance with one form of the present technology.

5.3 RPT Device and Humidifier

Figure 3A:
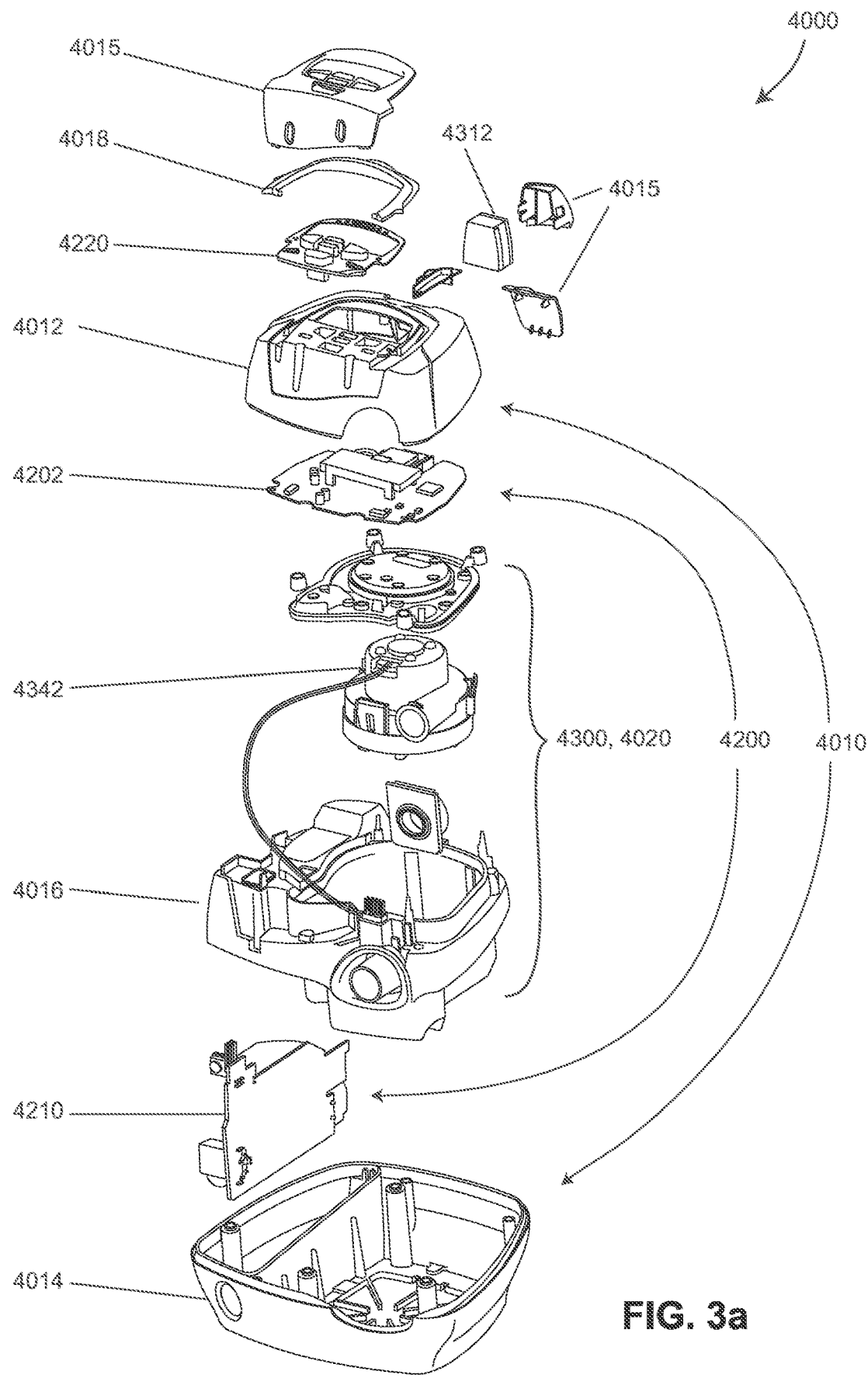

FIG. 3a shows a RPT device in an exploded view in accordance with one form of the present technology.

Figure 3B:
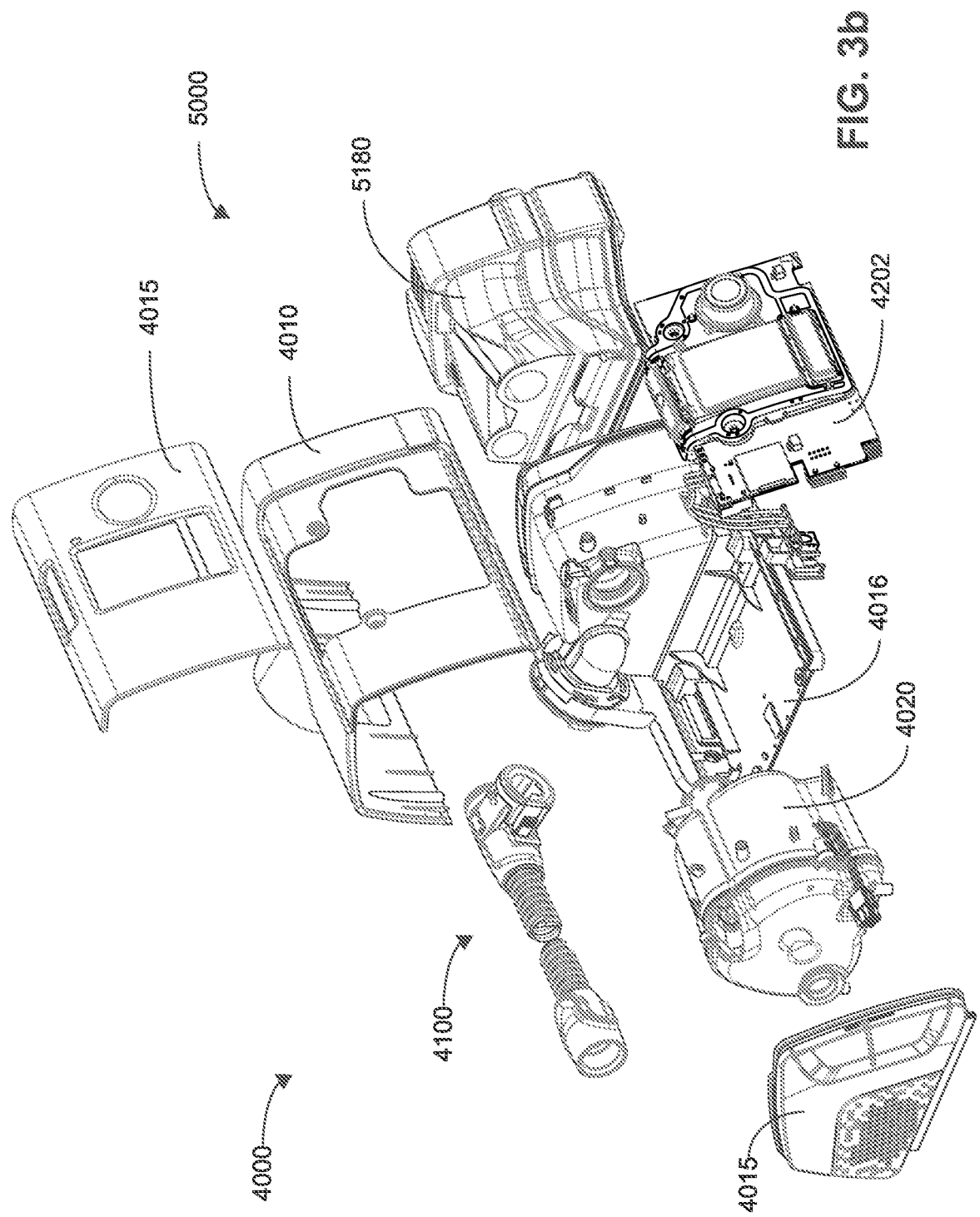

FIG. 3b shows another RPT device 4000 with an integrated humidifier 5000 in an exploded view in accordance with one aspect of the present technology.

Figure 3C:
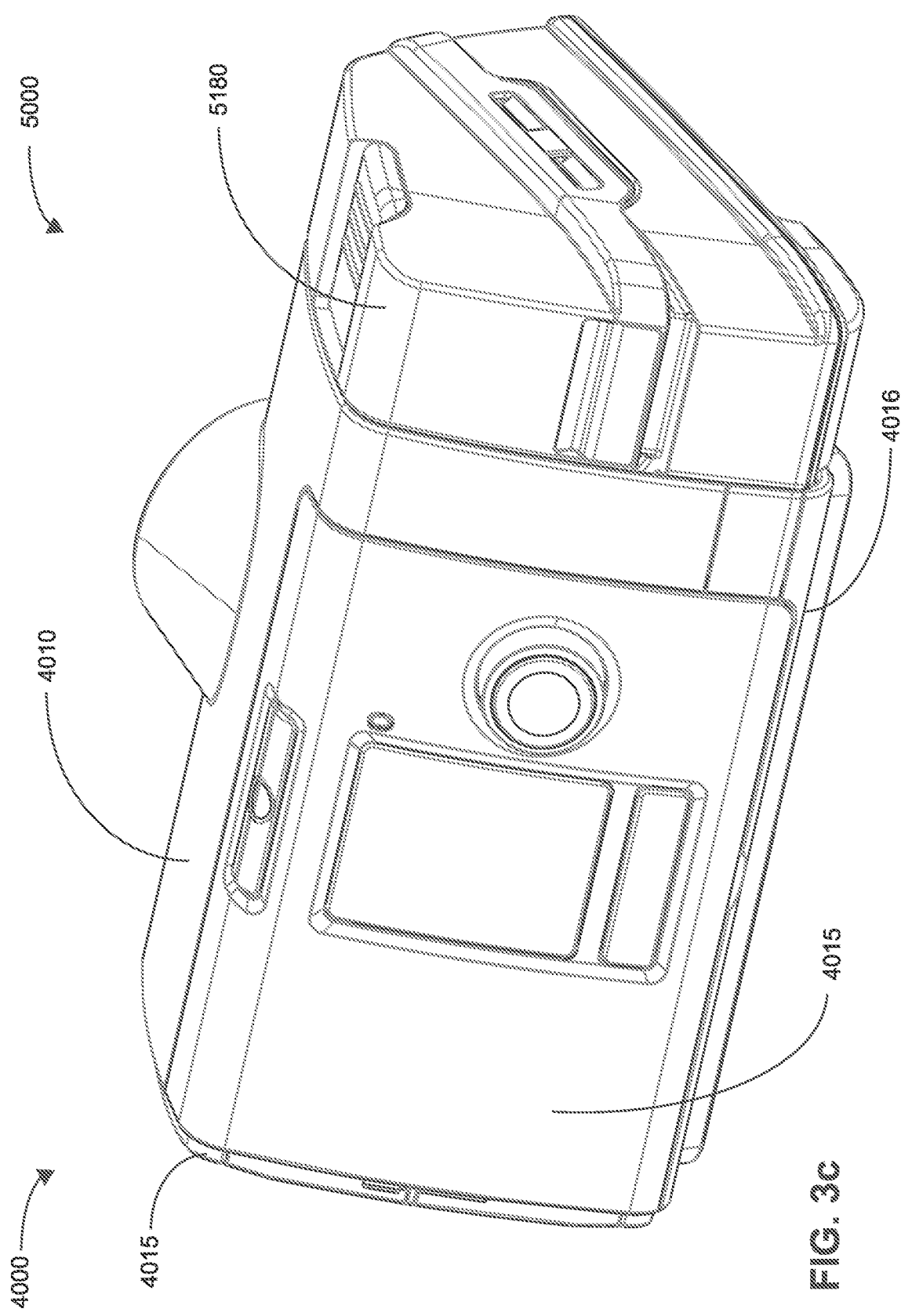

FIG. 3c shows a front perspective view of an RPT device 4000 with an integrated humidifier 5000 in accordance with one aspect of the present technology.

Figure 3D:
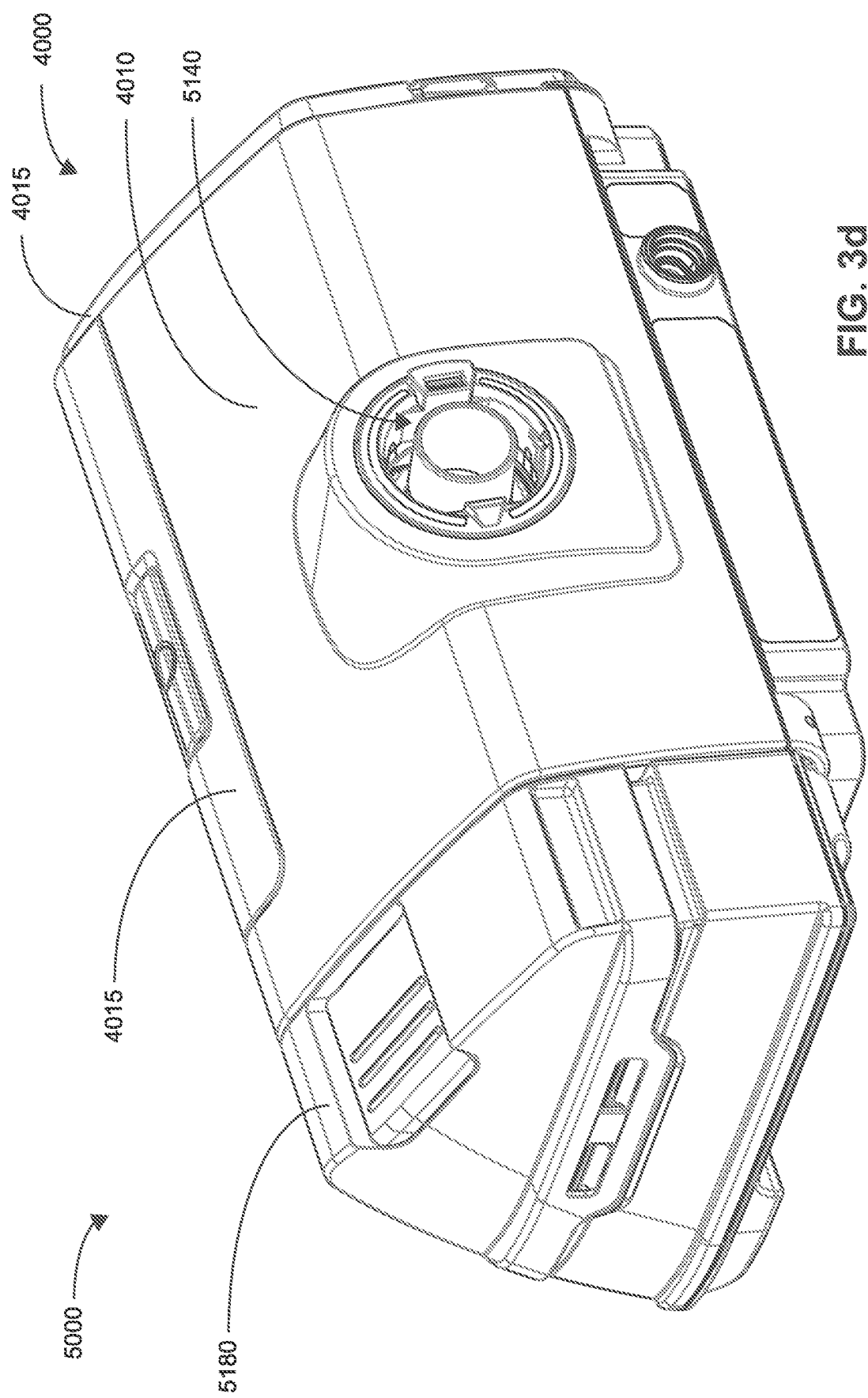

FIG. 3d shows a rear perspective view of an RPT device 4000 with an integrated humidifier 5000 in accordance with one aspect of the present technology.

Figure 3E:
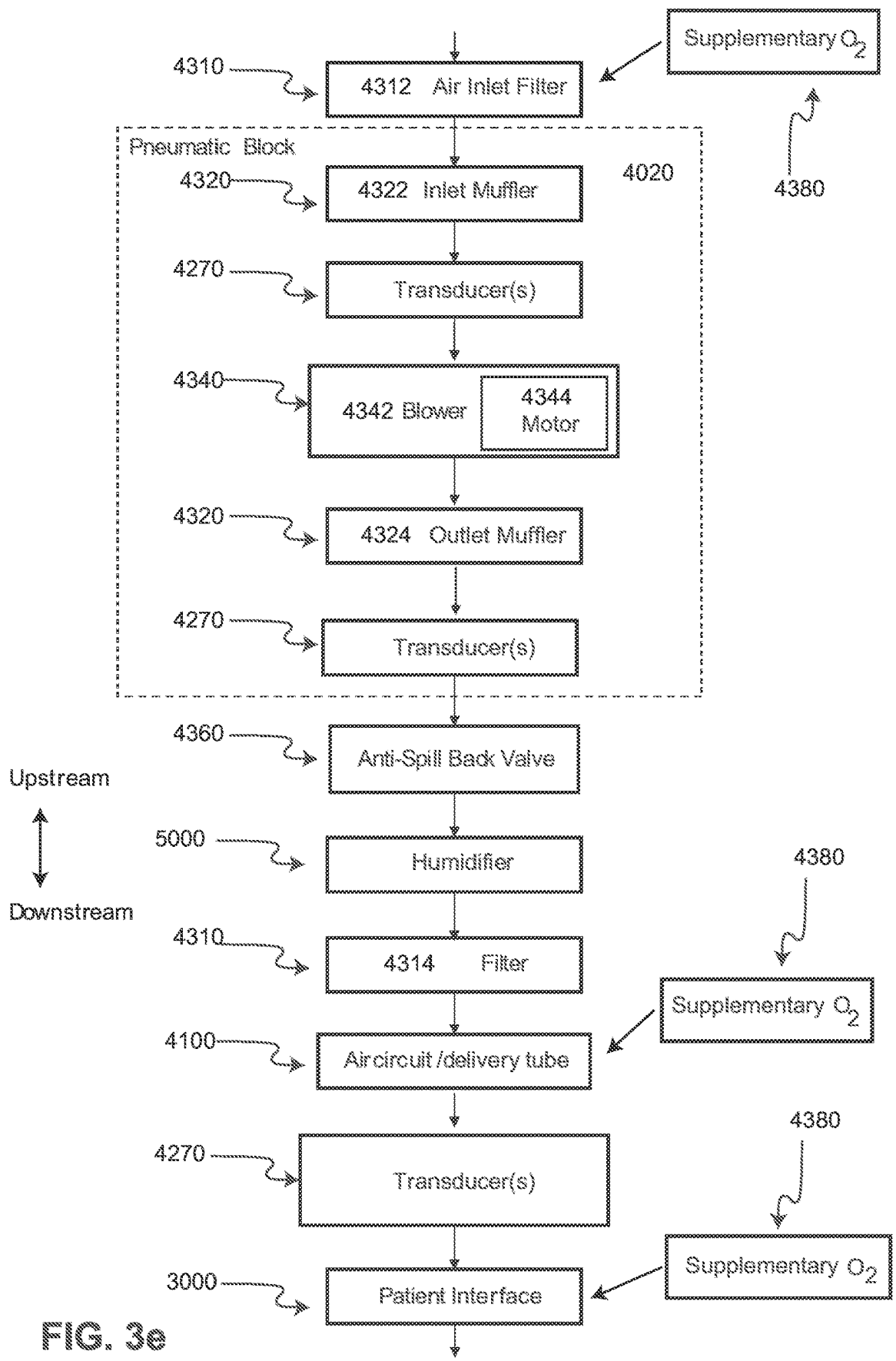

FIG. 3e shows a schematic diagram of the pneumatic circuit of a RPT device in accordance with one form of the present technology. The directions of upstream and downstream are indicated.

Figure 3F:
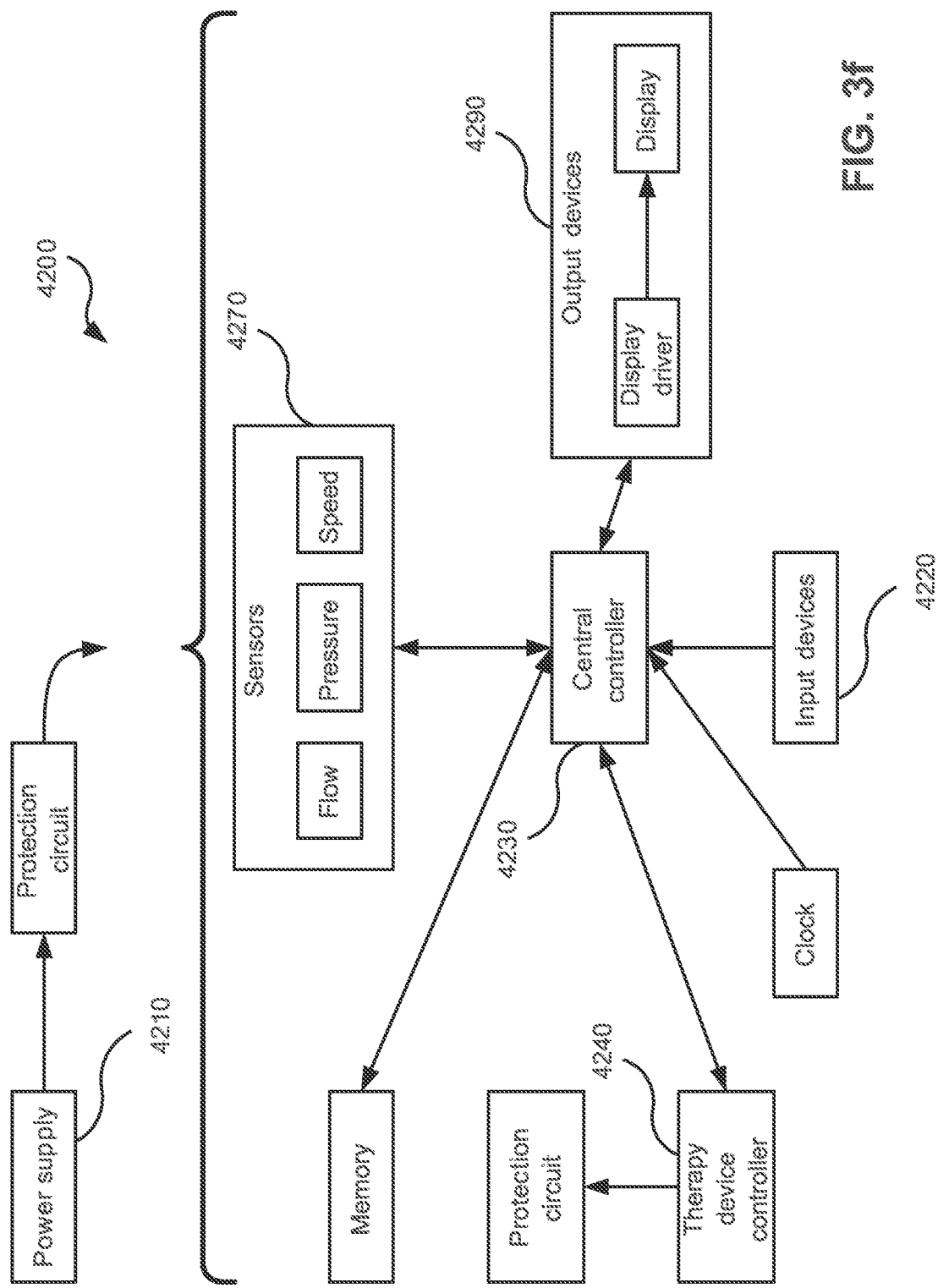

FIG. 3f shows a schematic diagram of electrical components of an RPT device in accordance with one form of the present technology.

Figure 3H:
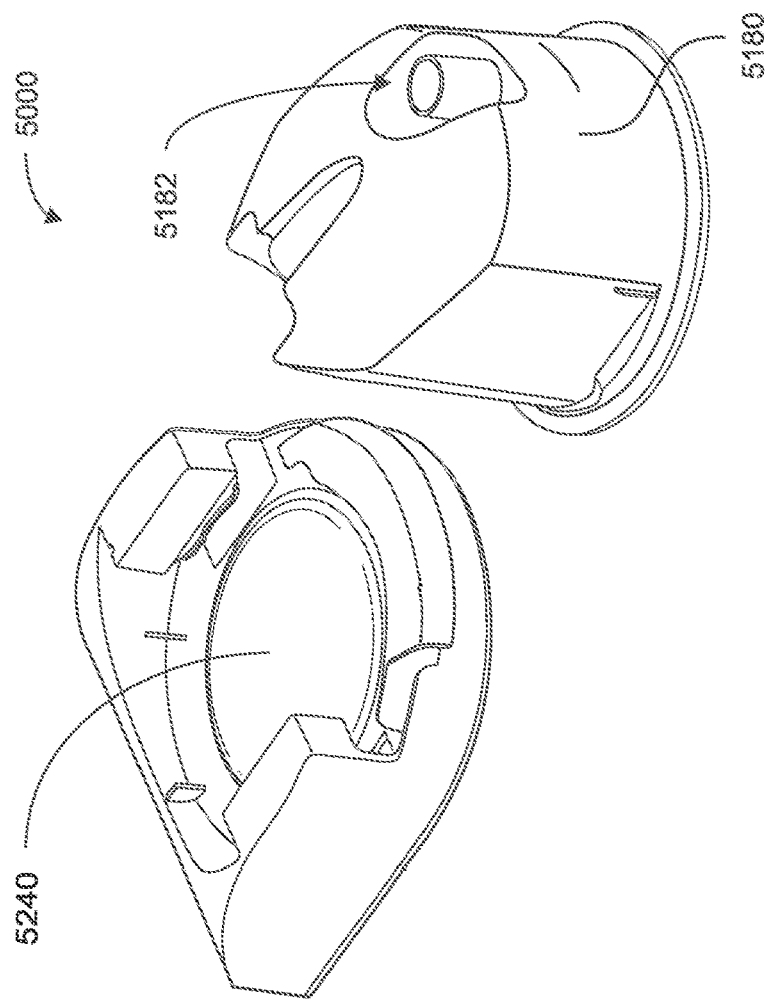
Figure 3G:
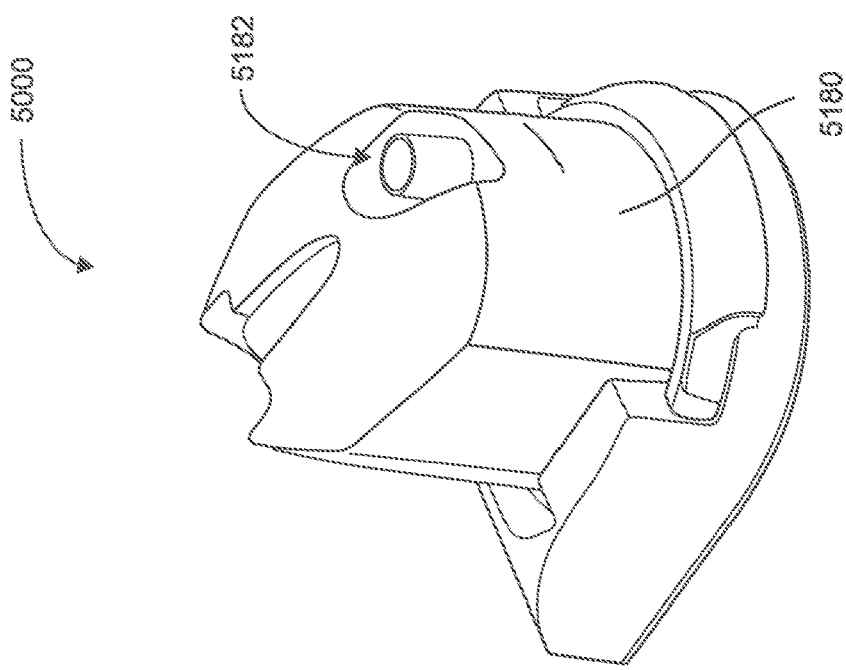

FIG. 3g shows a perspective view of a humidifier 5000 in accordance with one form of the present technology.

FIG. 3h shows a perspective view of a humidifier 5000 in accordance with one form of the present technology, showing the humidifier reservoir 5180 in an exploded state.

Figure 4A:
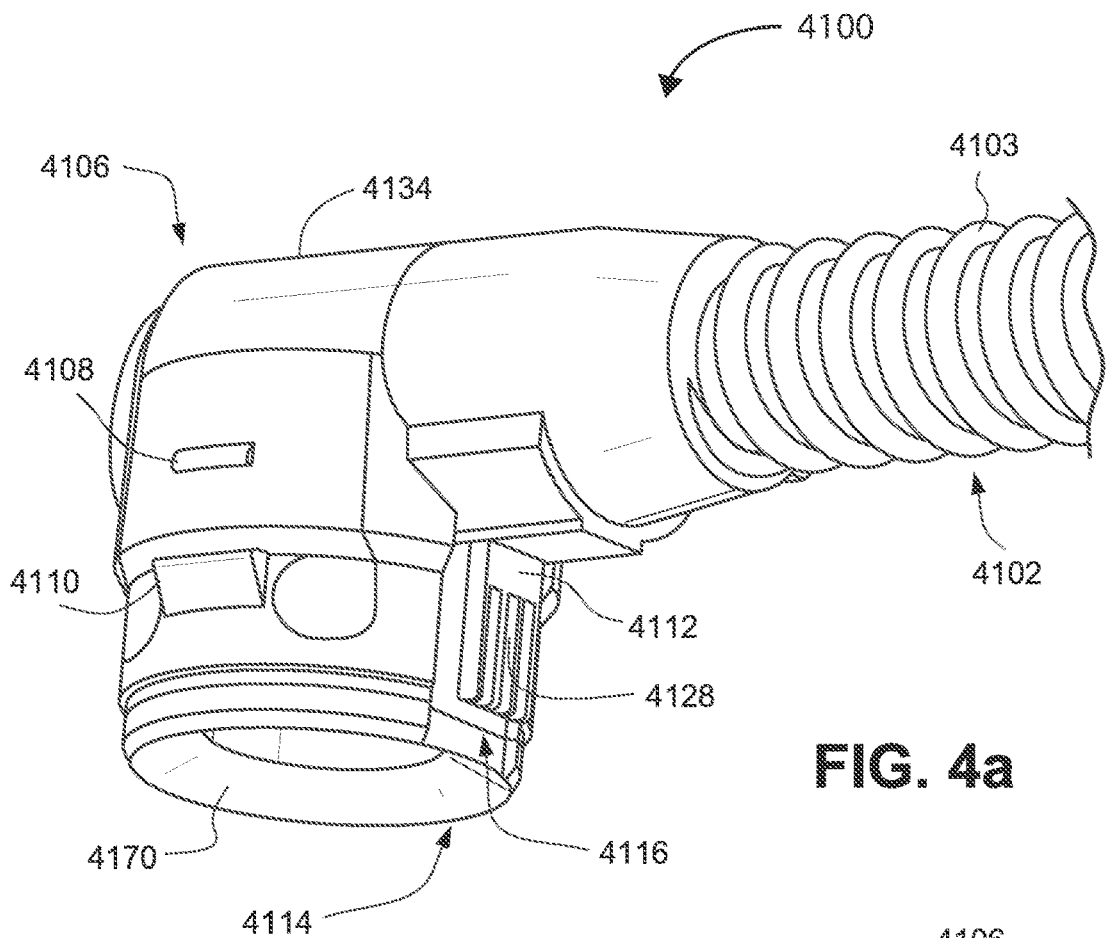

FIG. 4a shows a perspective view of an air circuit comprising an outlet connector according to an example of the present technology.

Figure 4B:
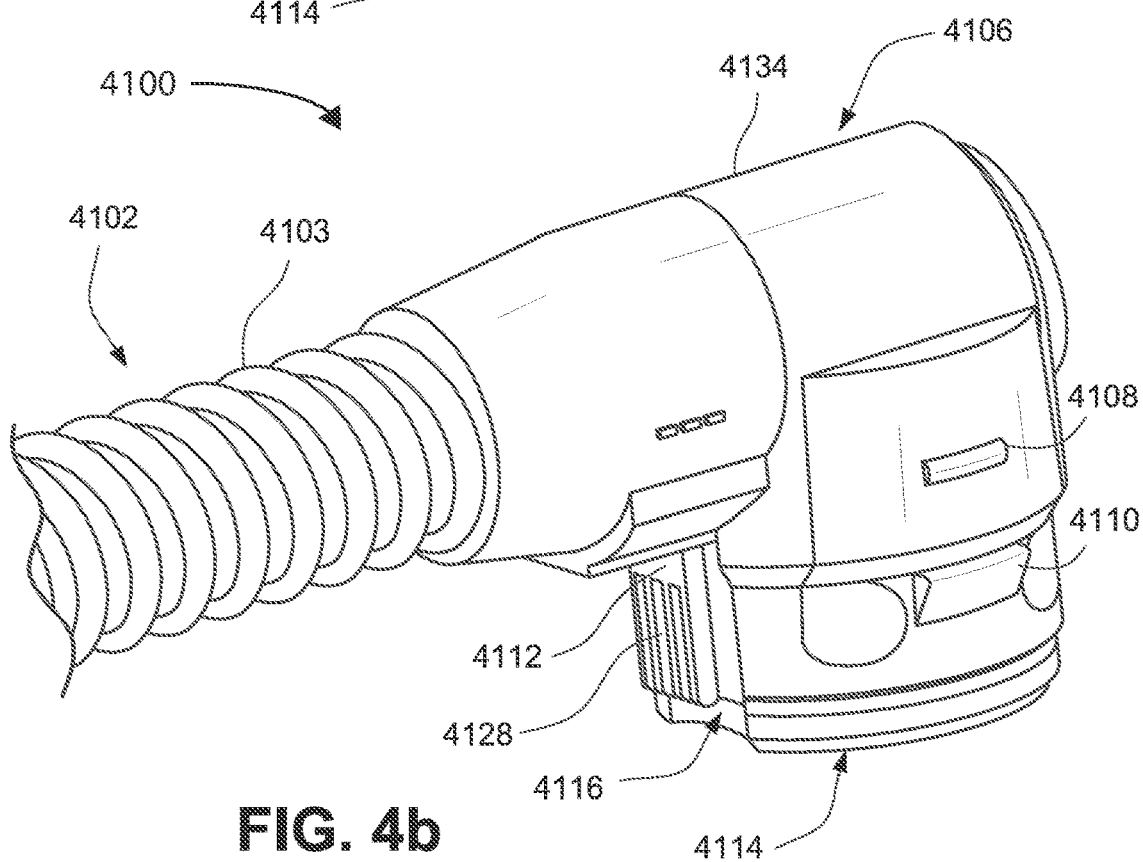

FIG. 4b shows another perspective view of an air circuit comprising an outlet connector according to an example of the present technology.

Figure 4C:
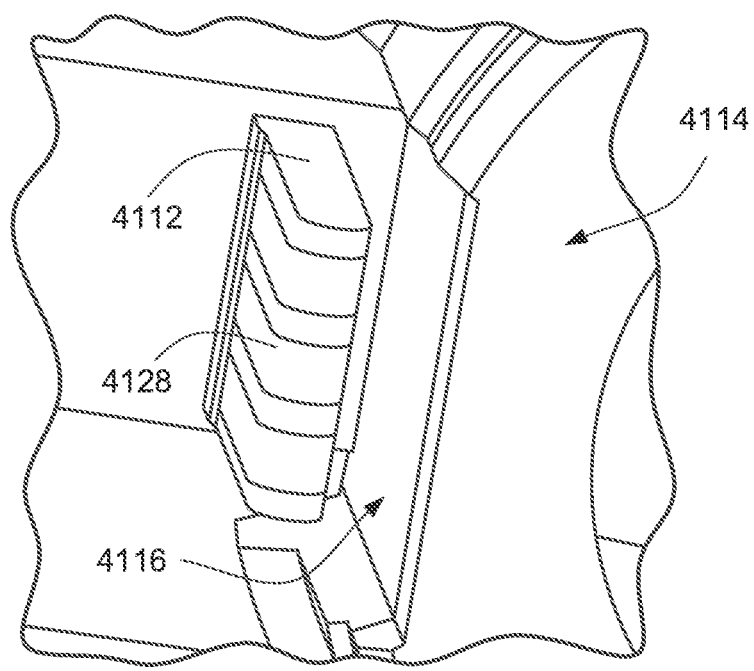

FIG. 4c shows a detailed view of an electrical connector of an outlet connector according to an example of the present technology.

Figure 4D:
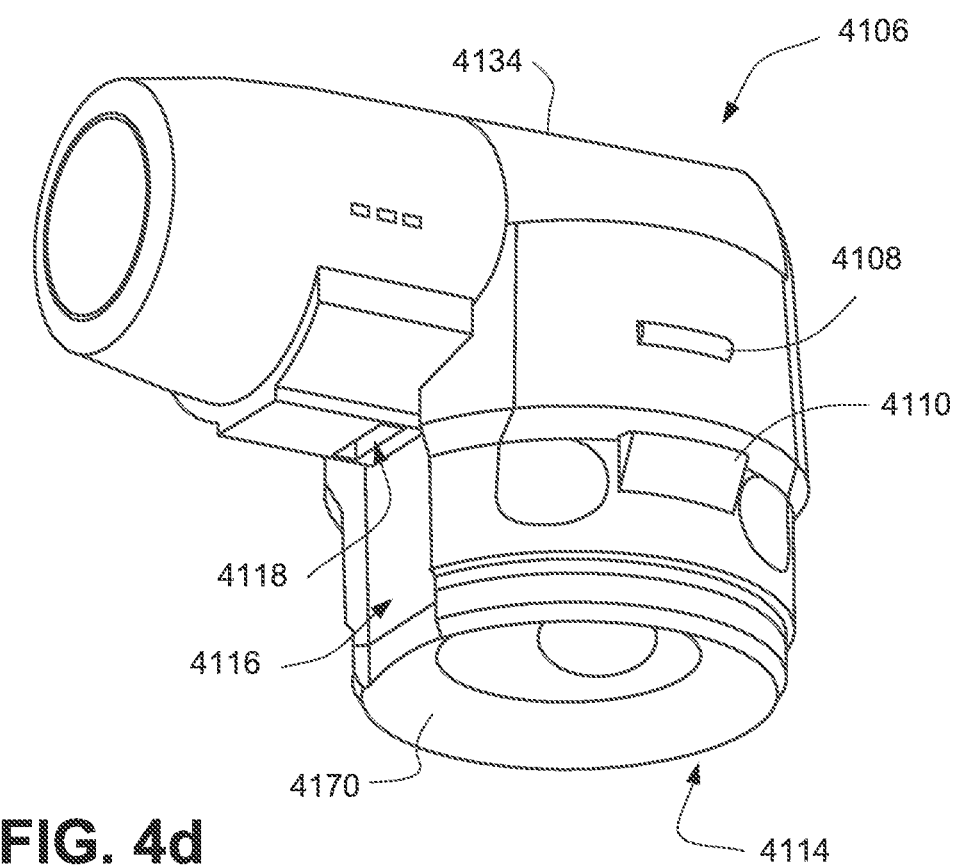

FIG. 4d shows another perspective view of a portion of an outlet connector according to an example of the present technology.

Figure 4E:
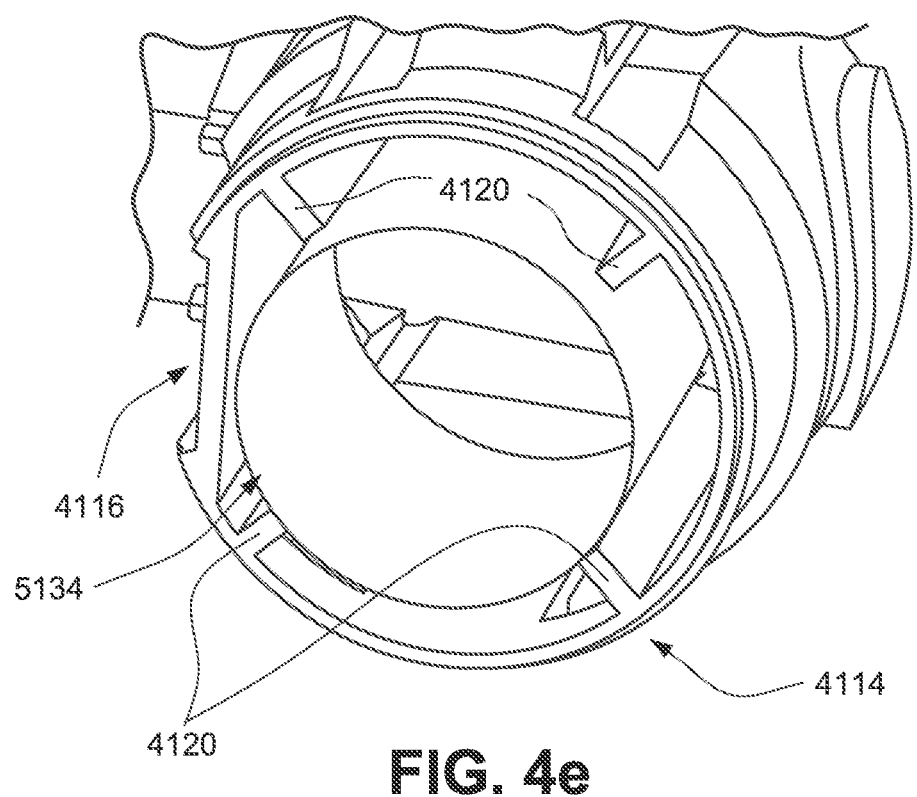

FIG. 4e shows a detailed bottom view of an outlet connector and a portion of an airflow tube according to an example of the present technology.

Figure 4F:
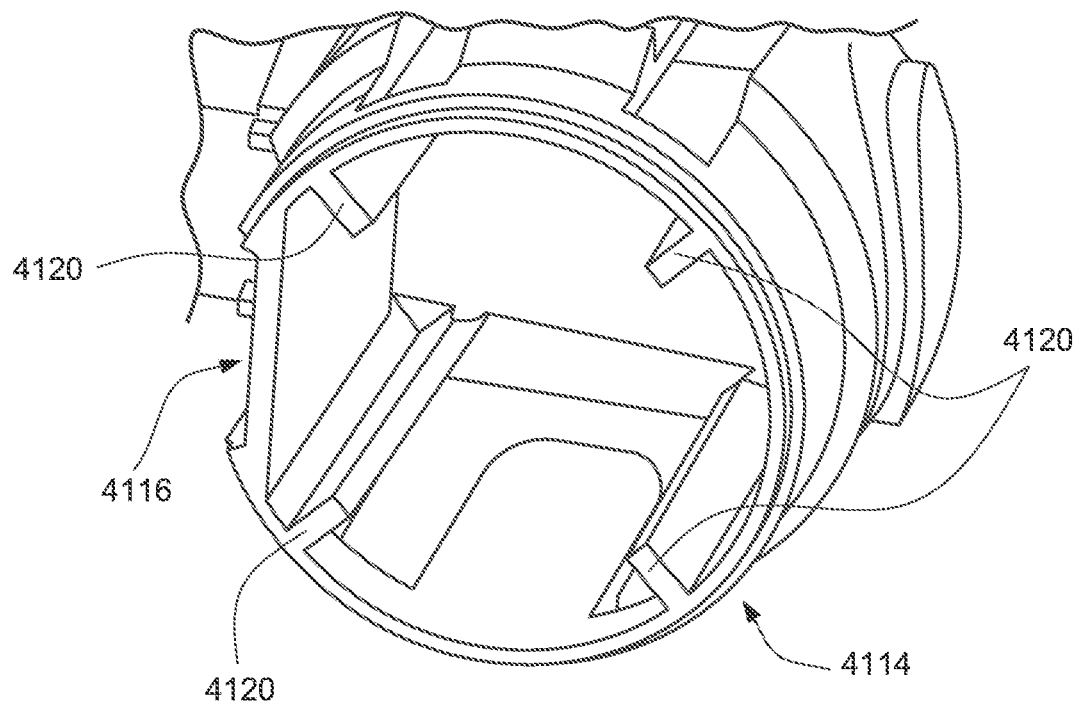

FIG. 4f shows another detailed bottom view of an outlet connector according to an example of the present technology.

Figure 4G:
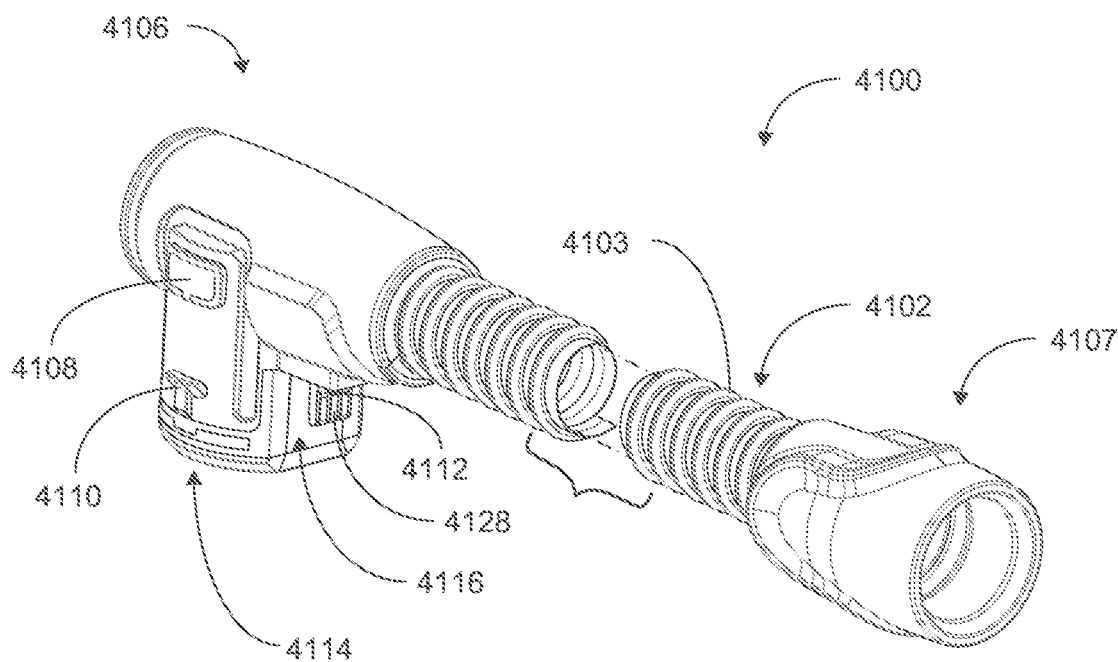

FIG. 4g shows another perspective view of an air circuit comprising an outlet connector according to an example of the present technology.

Figure 4H:
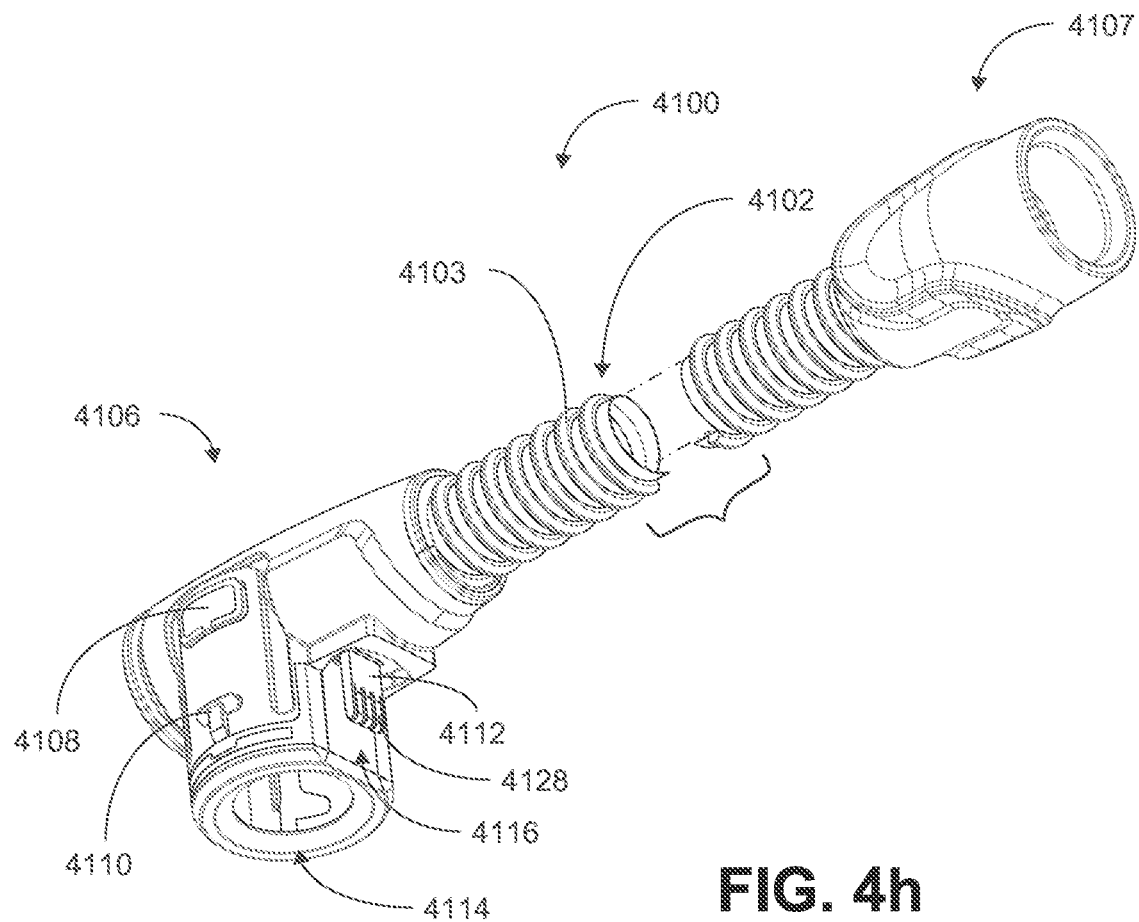

FIG. 4h shows another perspective view of an air circuit comprising an outlet connector according to an example of the present technology.

Figure 5A:
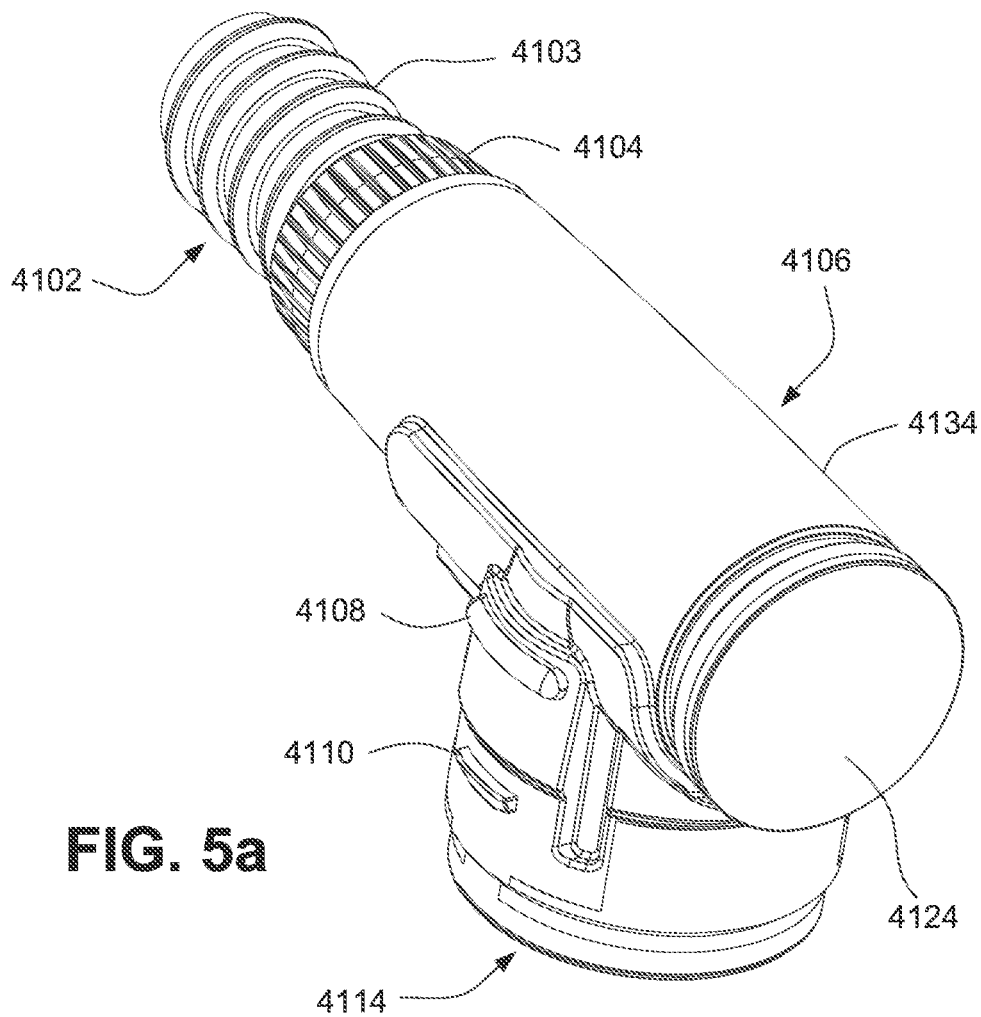

FIG. 5a shows a perspective view of an air circuit comprising an outlet connector and a tube according to an example of the present technology.

Figure 5B:
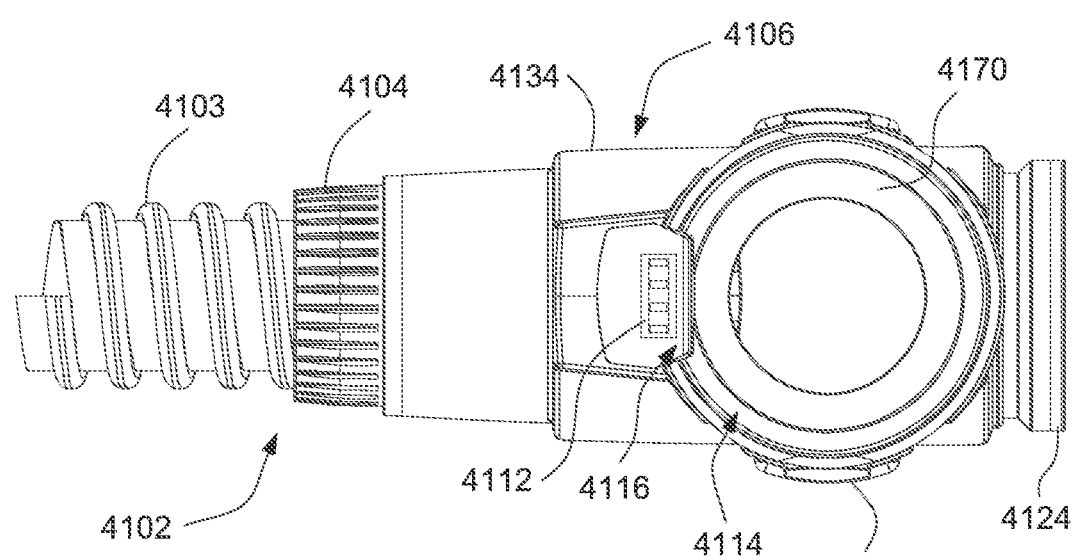

FIG. 5b shows a bottom view of an air circuit comprising an outlet connector and a tube according to an example of the present technology.

Figure 5C:
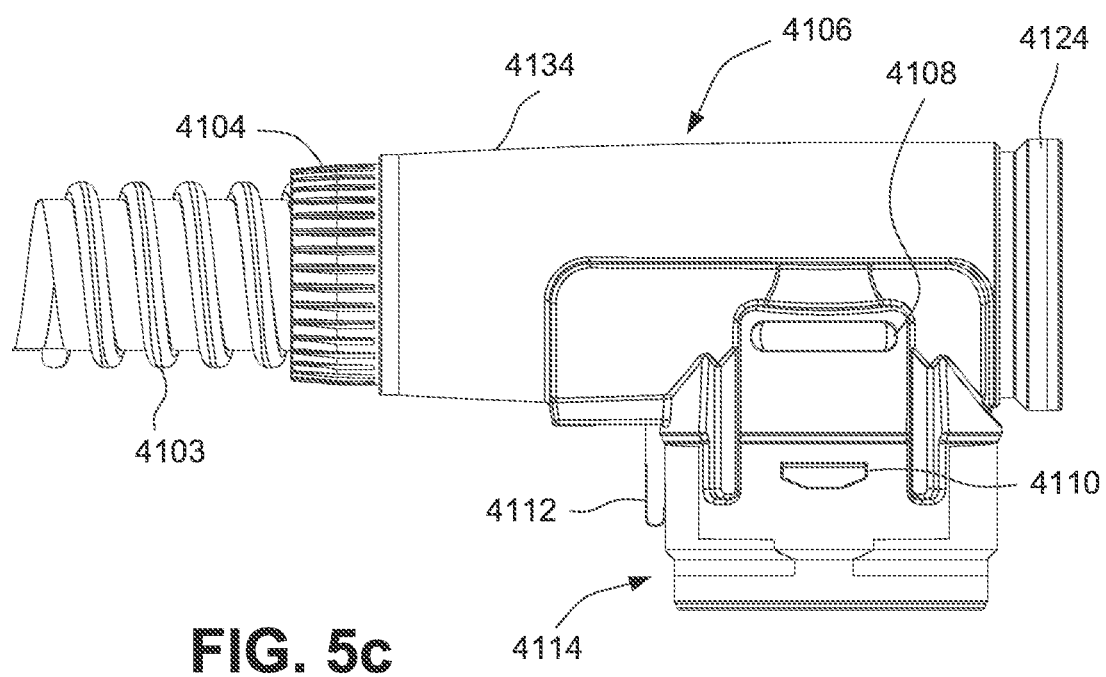

FIG. 5c shows a side view of an air circuit comprising an outlet connector and a tube according to an example of the present technology.

Figure 5D:
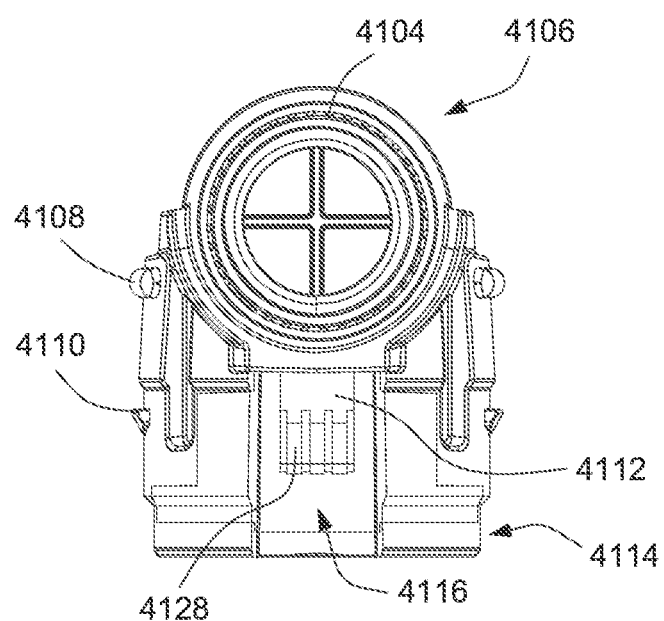

FIG. 5d shows an end view of an air circuit comprising an outlet connector and a tube according to an example of the present technology.

Figure 5E:
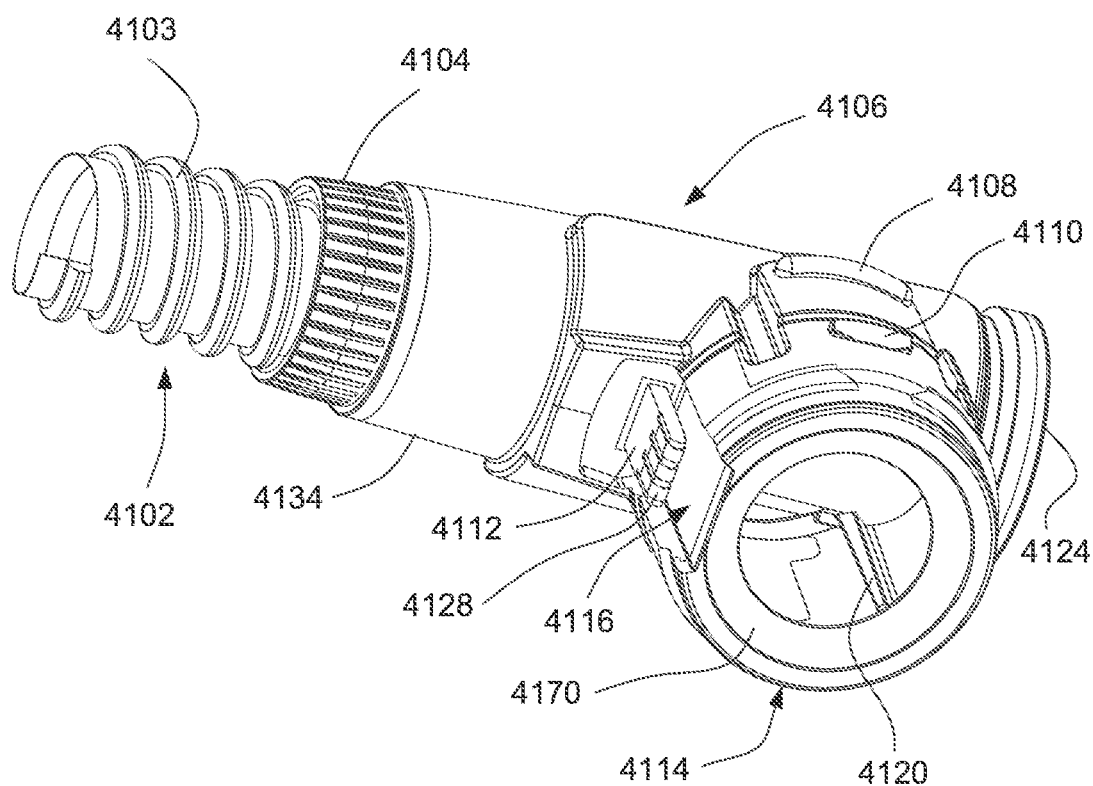

FIG. 5e shows a bottom perspective view of an air circuit comprising an outlet connector and a tube according to an example of the present technology.

Figure 5F:
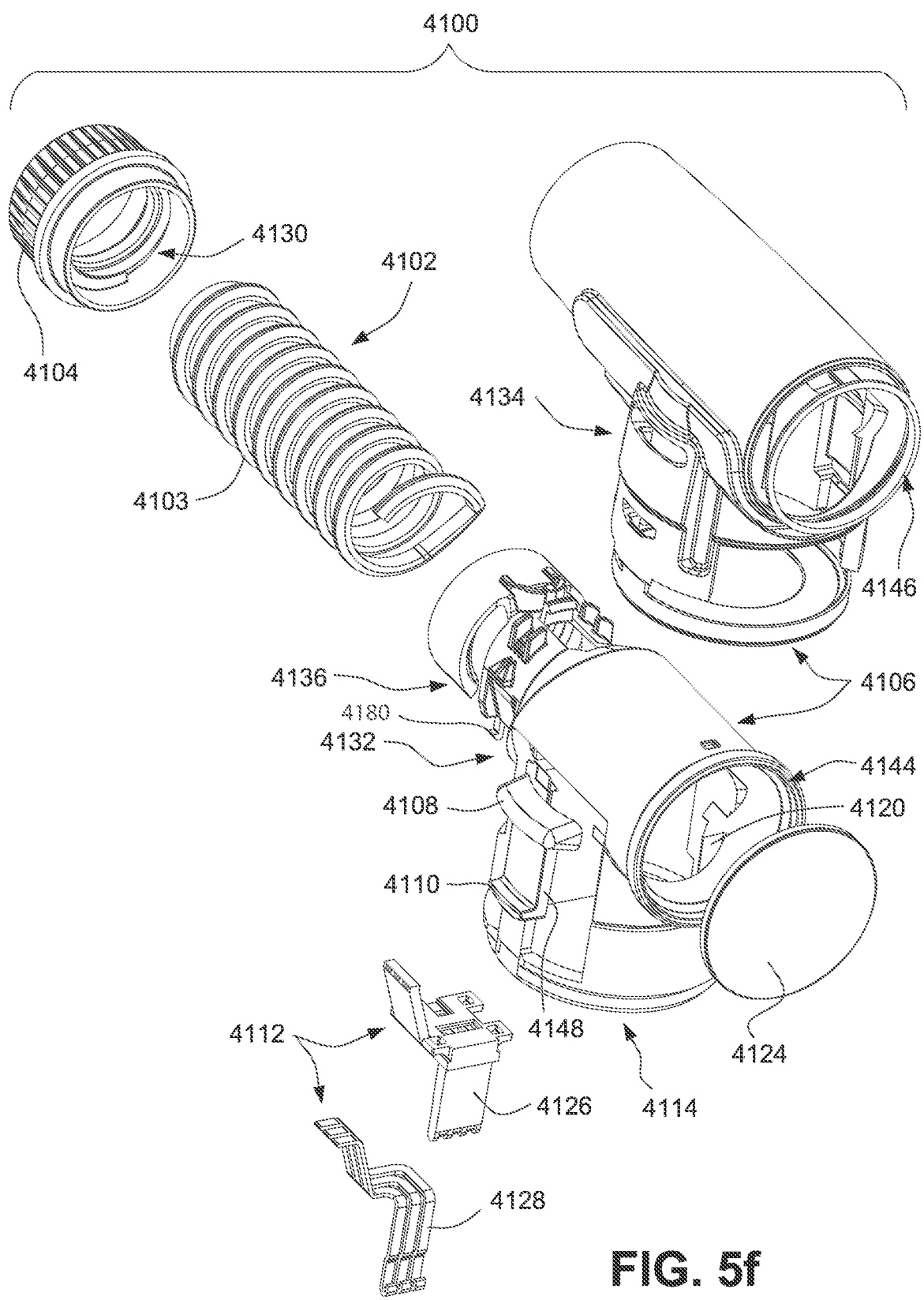

FIG. 5f shows an exploded perspective view of an air circuit comprising an outlet connector and a tube according to an example of the present technology.

Figure 5G:
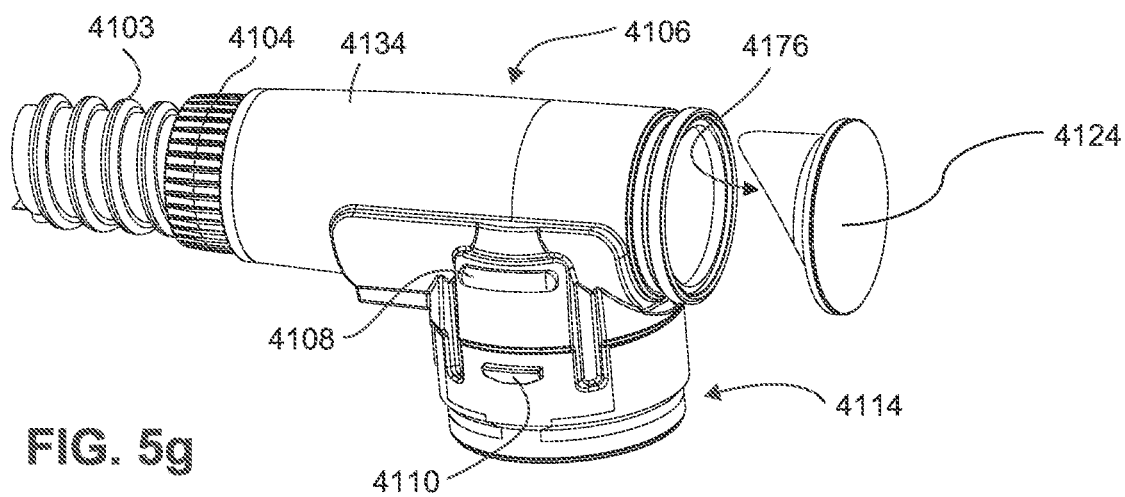

FIG. 5g shows a partially exploded perspective view of an air circuit comprising an outlet connector and a tube according to an example of the present technology.

Figure 5H:
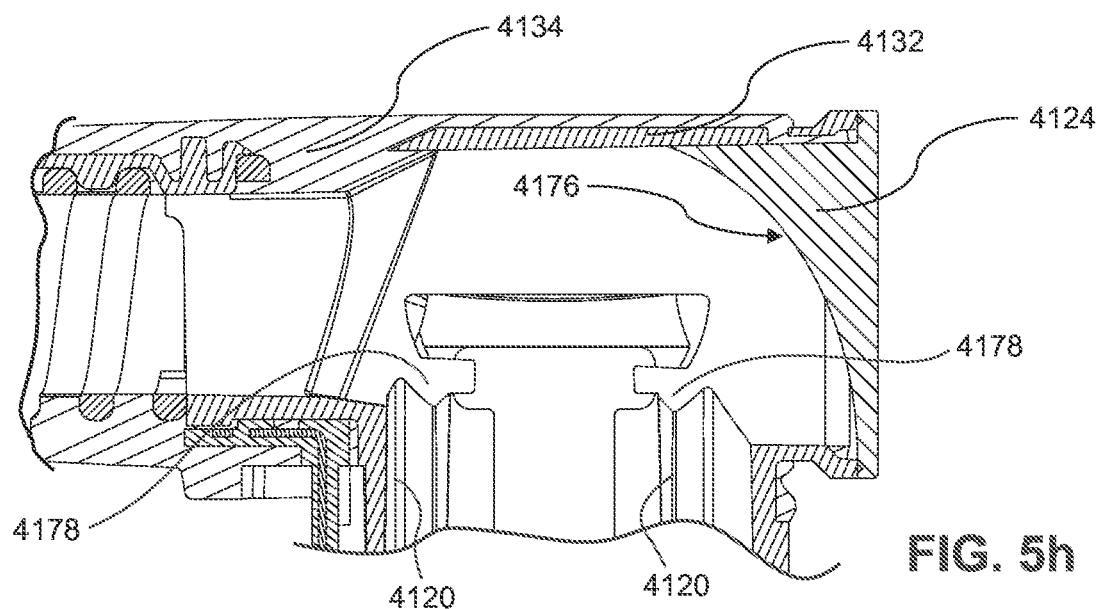

FIG. 5h shows a detailed side cross-section view of an air circuit comprising an outlet connector and a tube according to an example of the present technology.

Figure 5I:
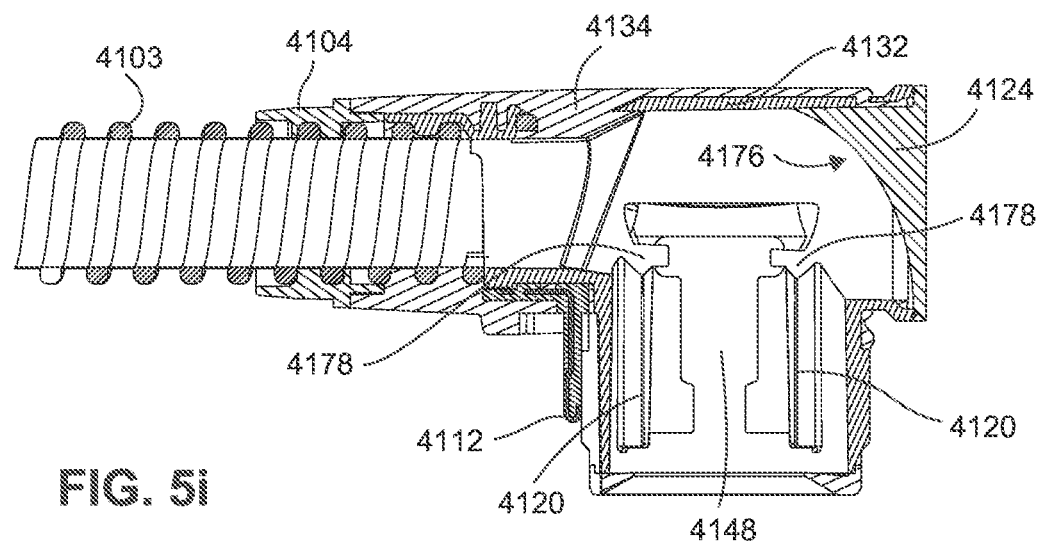

FIG. 5i shows a side cross-section view of an air circuit comprising an outlet connector and a tube according to an example of the present technology.

Figure 6A:
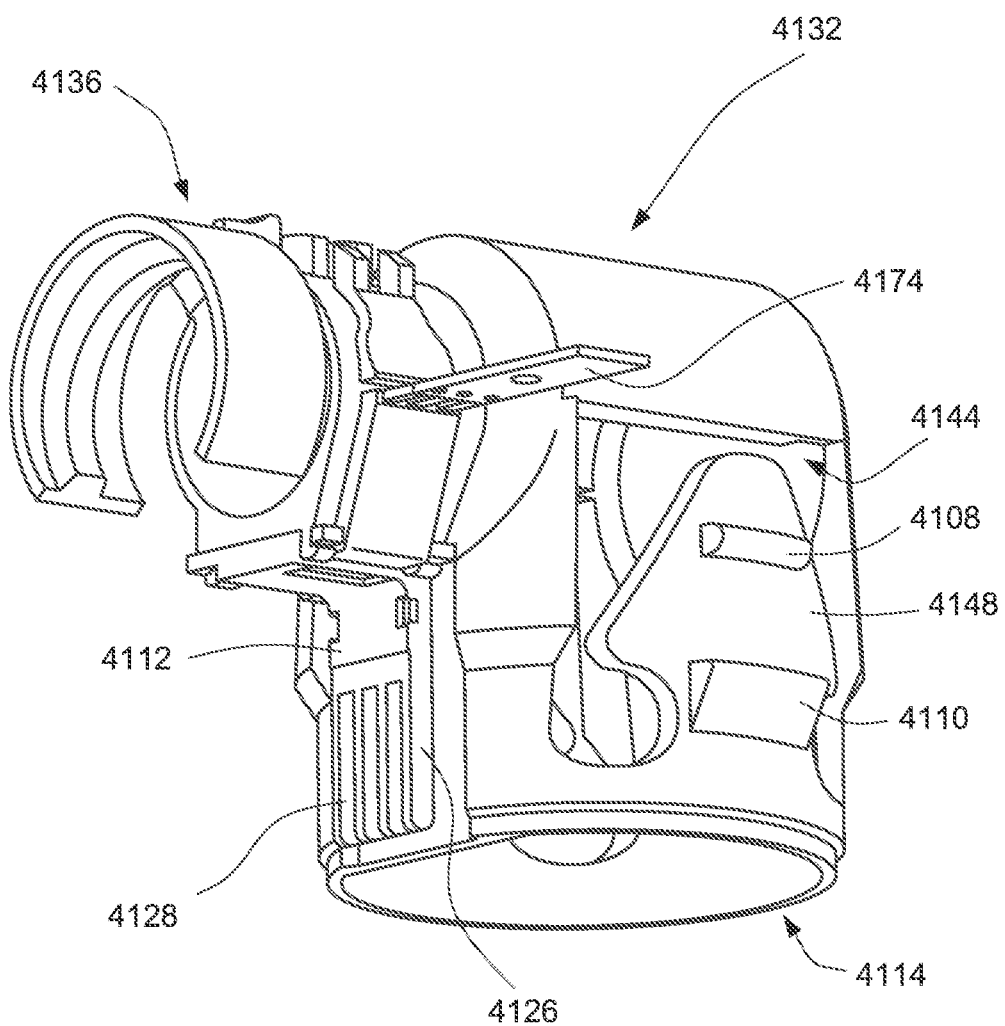

FIG. 6a shows a perspective view of a substructure of an outlet connector and an electrical connector according to an example of the present technology.

Figure 6B:
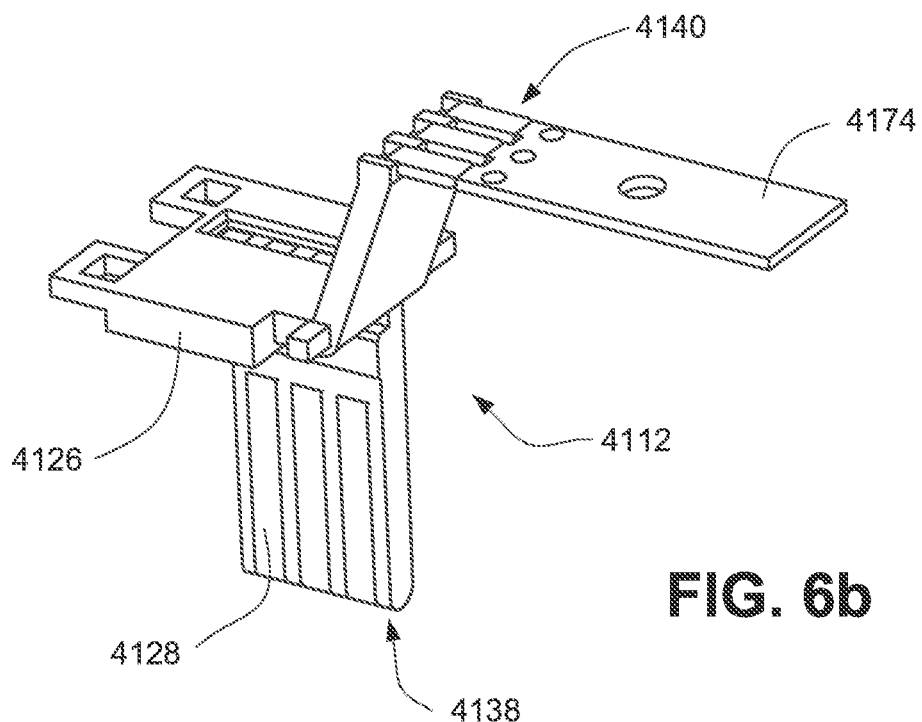

FIG. 6b shows a perspective view of an electrical connector of an outlet connector according to an example of the present technology.

Figure 6C:
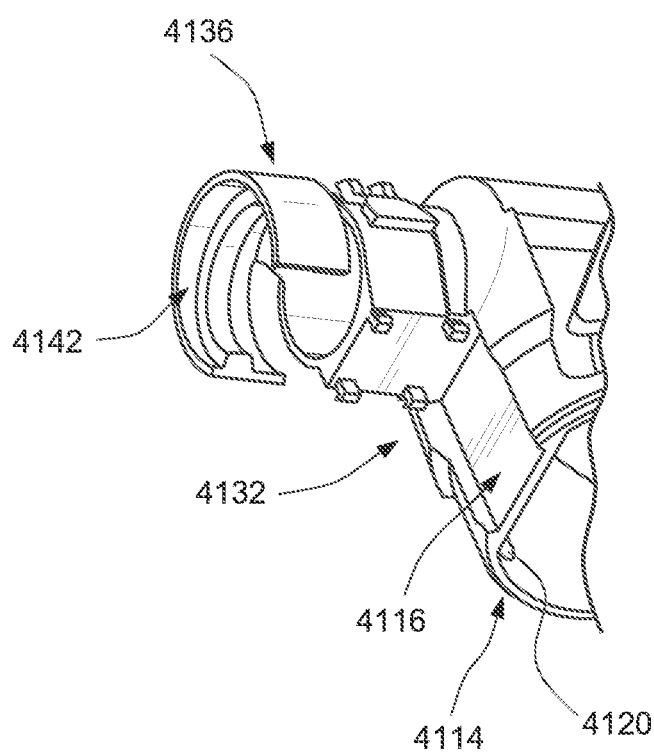

FIG. 6c shows a detailed perspective view of a substructure of an outlet connector according to an example of the present technology.

Figure 6D:
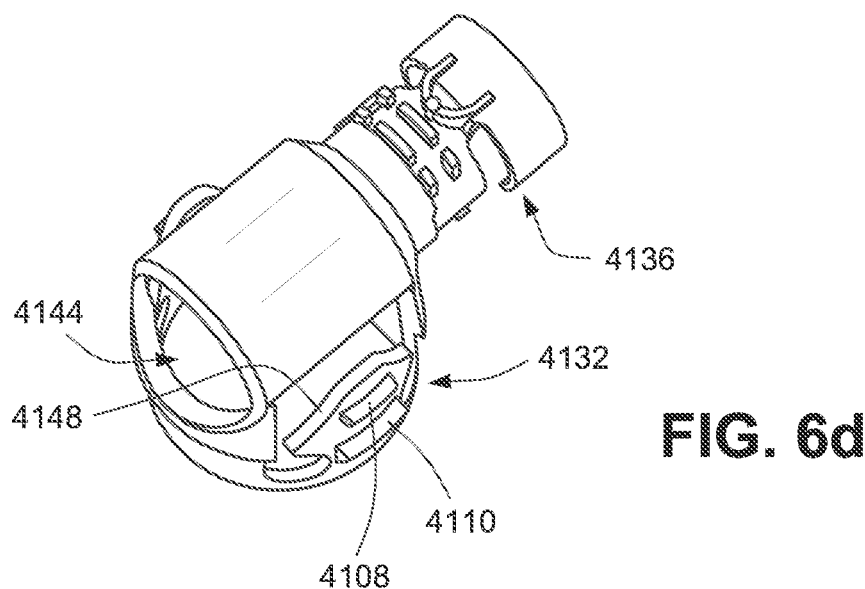

FIG. 6d shows a top perspective view of a substructure of an outlet connector according to an example of the present technology.

Figure 6E:
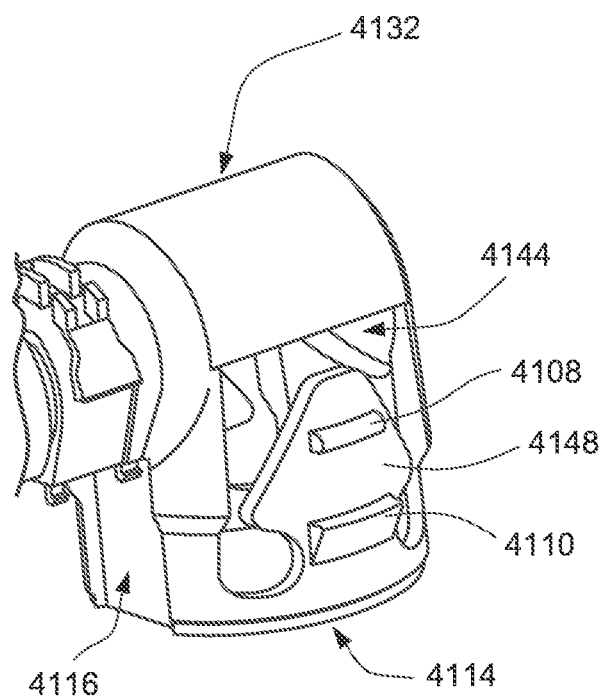

FIG. 6e shows another detailed perspective view of a substructure of an outlet connector according to an example of the present technology.

Figure 6F:
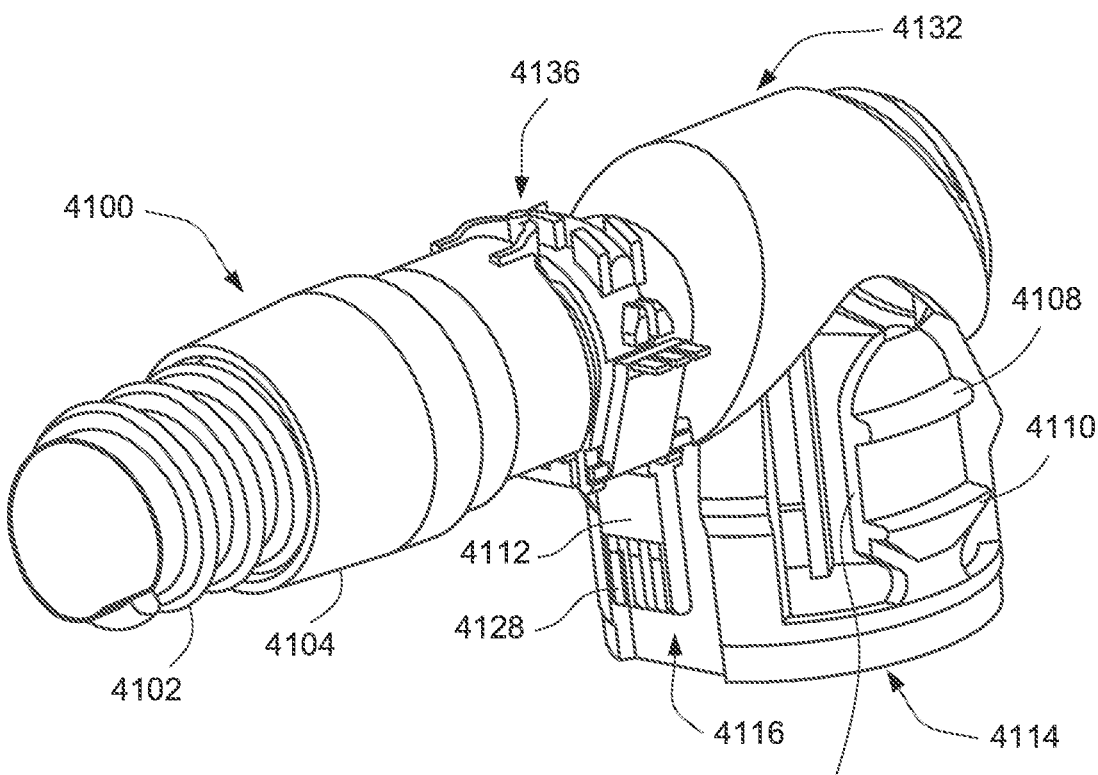

FIG. 6f shows a perspective view of a substructure of an outlet connector, a tube and an electrical connector according to an example of the present technology.

Figure 6G:
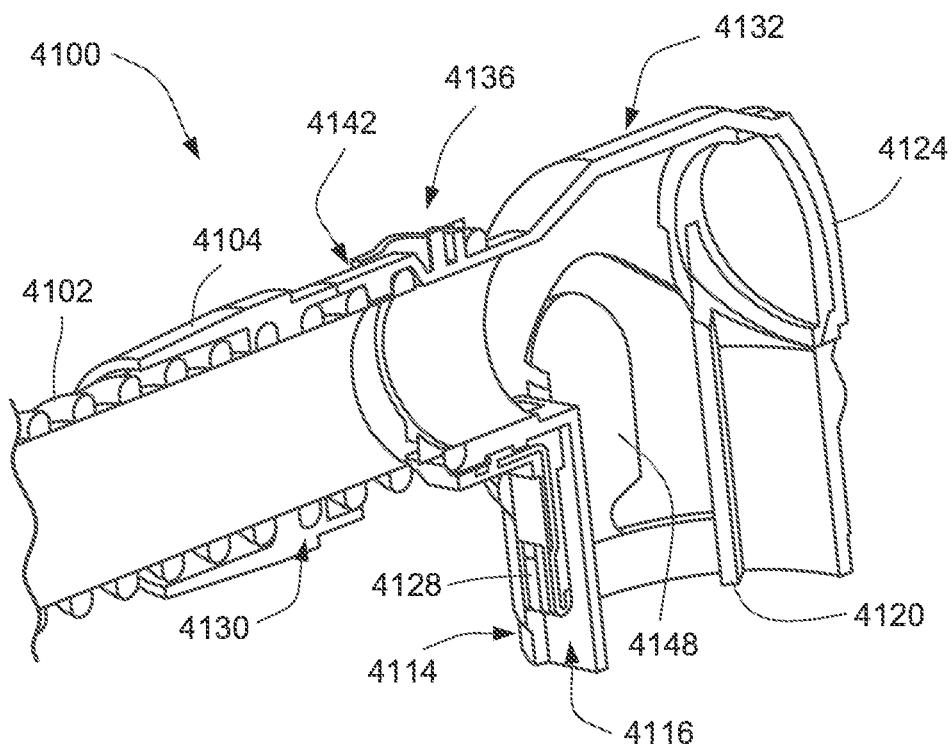

FIG. 6g shows a cross-sectional perspective view of a substructure of an outlet connector, a tube and an electrical connector according to an example of the present technology.

Figure 6H:
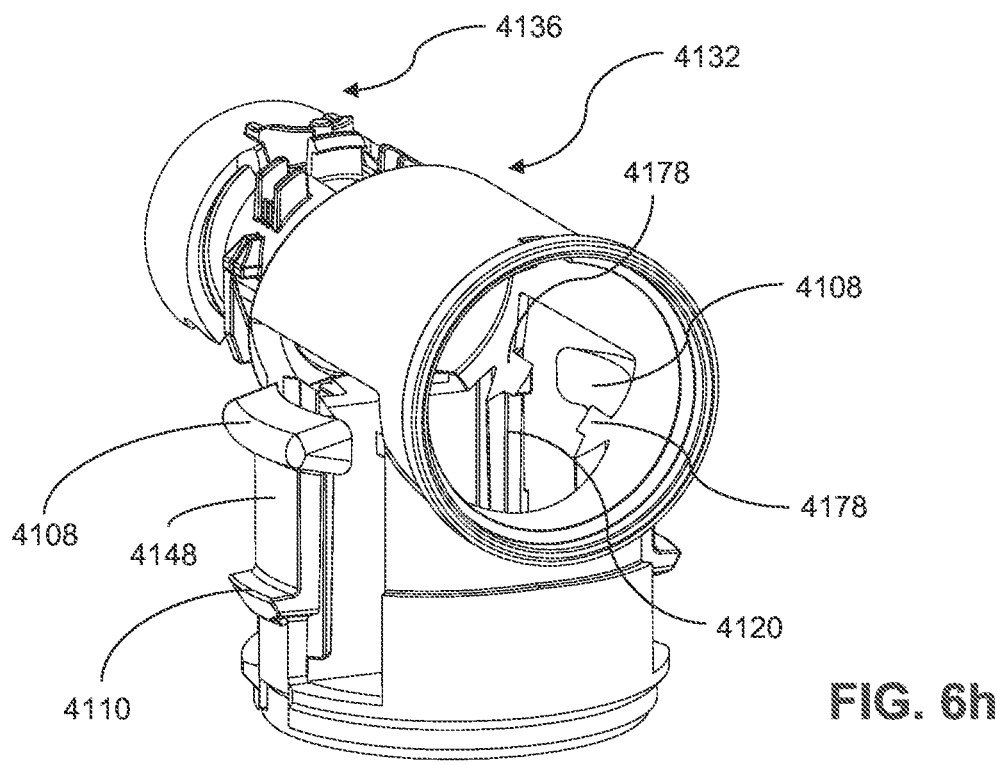

FIG. 6h shows a perspective view of a substructure of an outlet connector according to an example of the present technology.

Figure 6I:
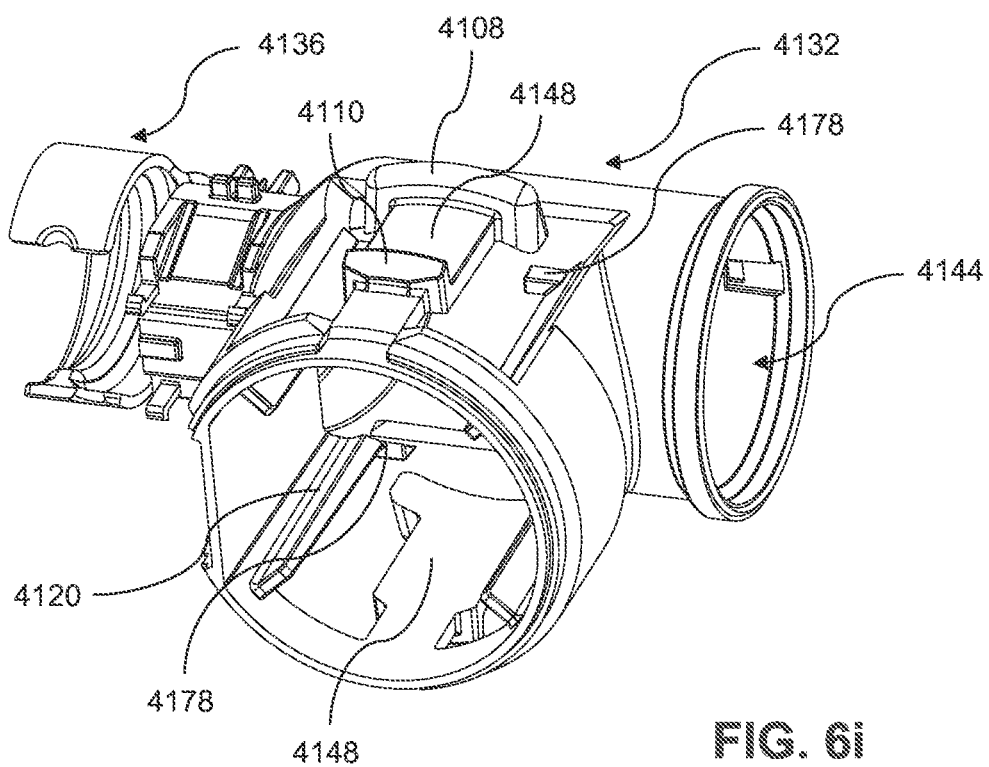

FIG. 6i shows a bottom perspective view of a substructure of an outlet connector according to an example of the present technology.

Figure 7A:
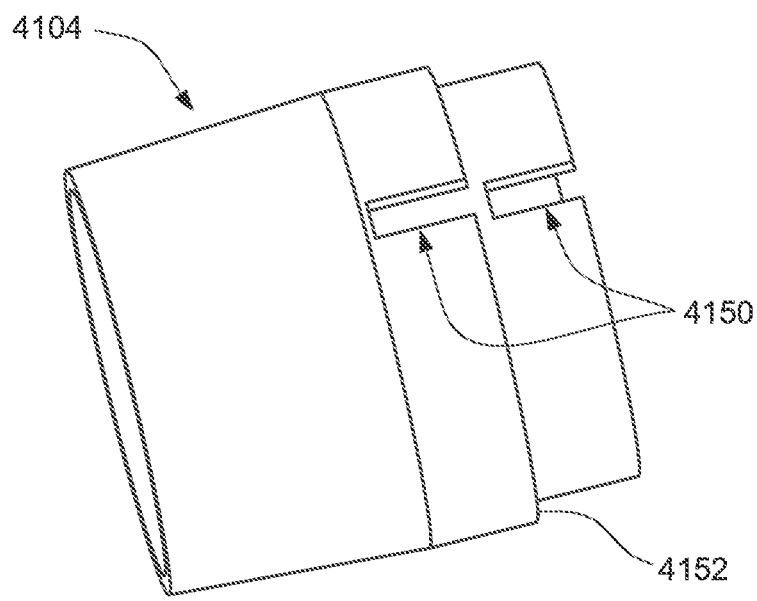

FIG. 7a shows a perspective view of a grommet according to an example of the present technology.

Figure 7B:
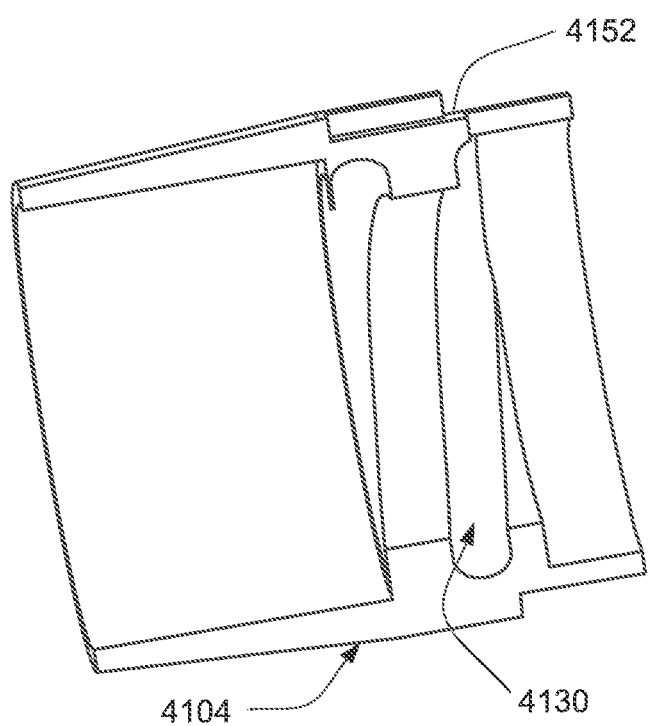

FIG. 7b shows a cross-sectional perspective view of a grommet according to an example of the present technology.

FIG. 7c shows a perspective view of a grommet according to an example of the present technology.

FIG. 7d shows another perspective view of a grommet according to an example of the present technology.

FIG. 7e shows a side view of a grommet according to an example of the present technology.

FIG. 7f shows an end view of a grommet according to an example of the present technology.

Figure 8A:
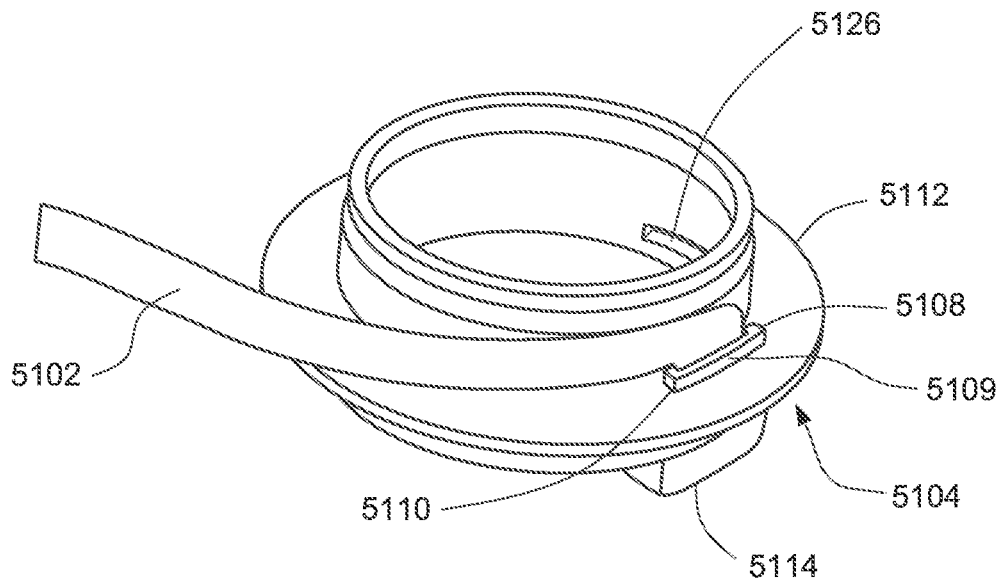

FIG. 8a shows a bottom perspective view of a swivelling disc and a cable according to an example of the present technology.

Figure 8B:
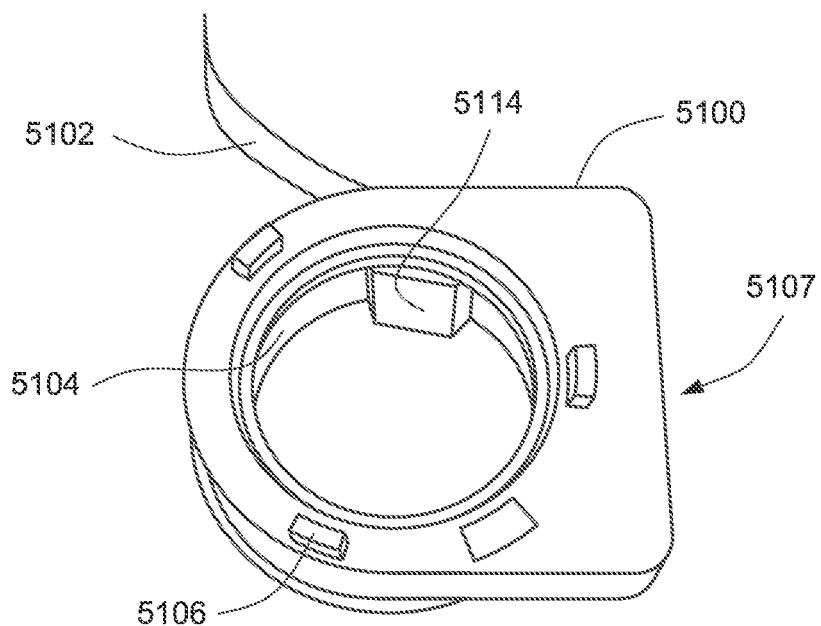

FIG. 8b shows a bottom perspective view of a cable housing, a swivelling disc, and a cable according to an example of the present technology.

Figure 8C:
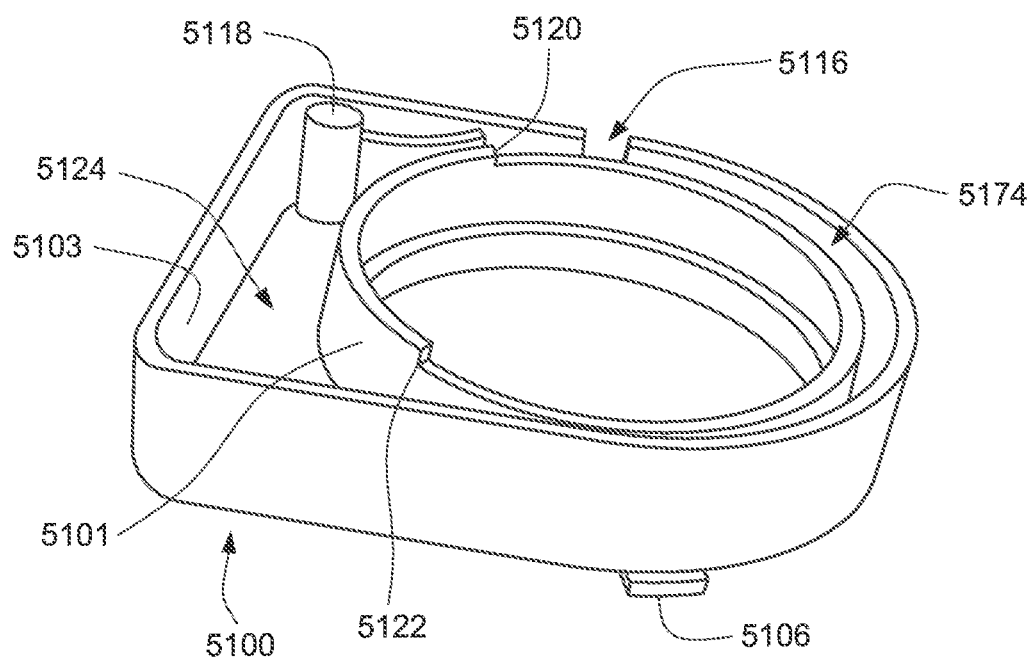

FIG. 8c shows a perspective view of a cable housing according to an example of the present technology.

Figure 8D:
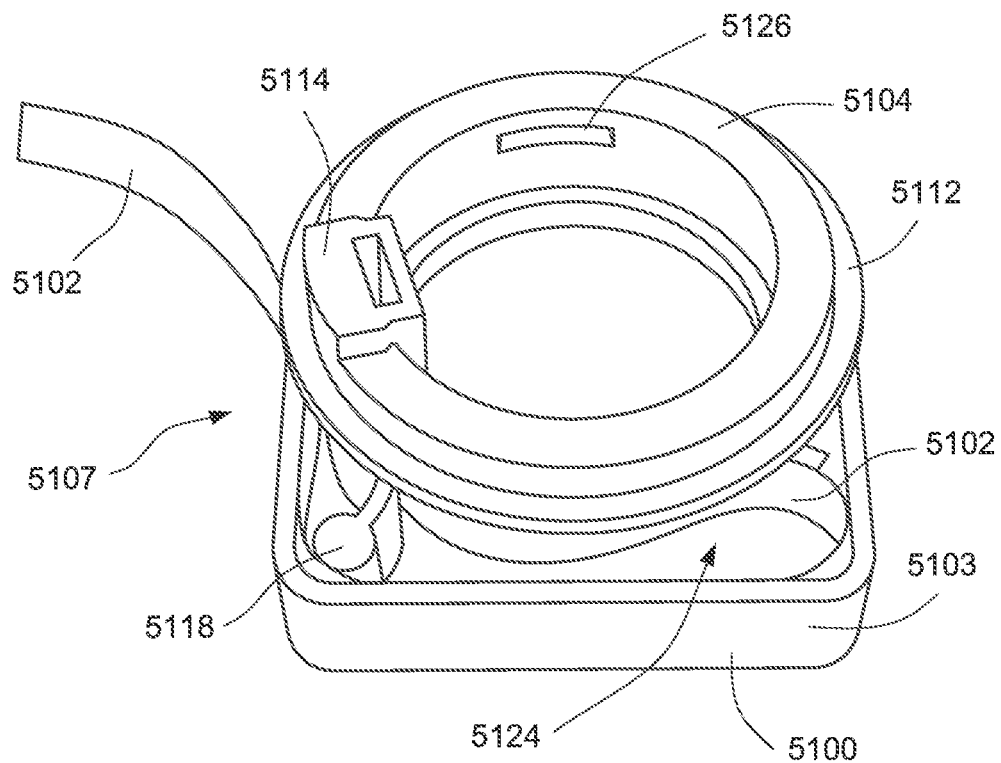

FIG. 8d shows a perspective view of a cable housing with a swivelling disc and a cable in a first position relative to the cable housing according to an example of the present technology.

Figure 8E:
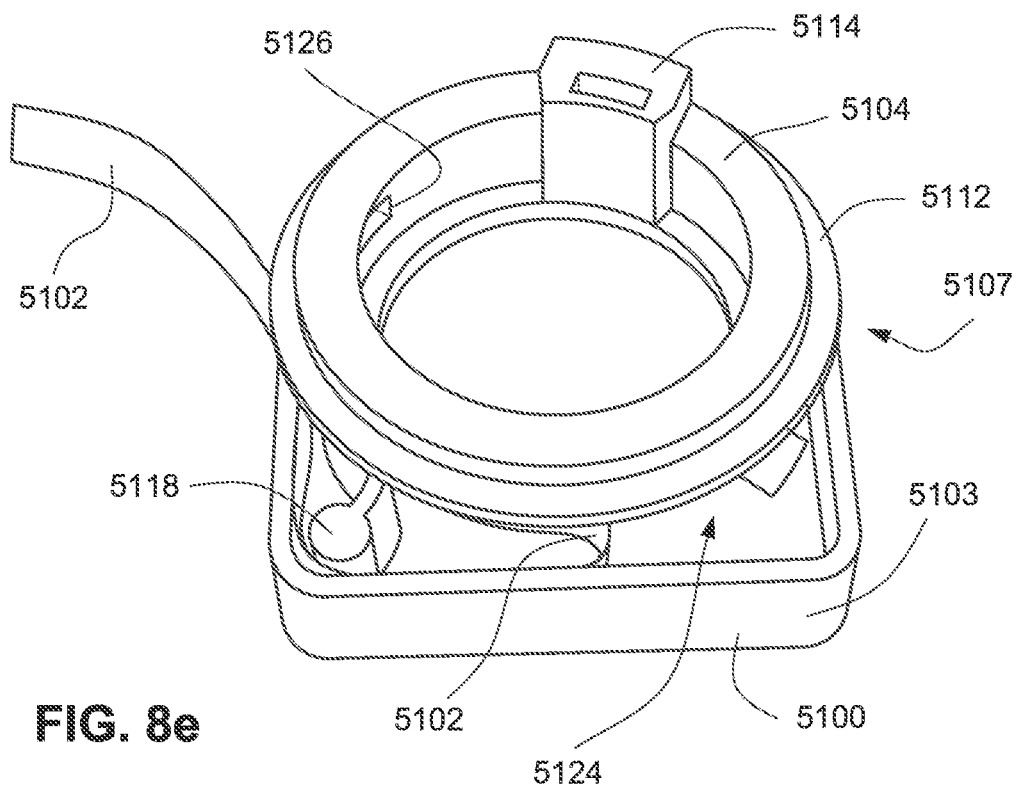

FIG. 8e shows a perspective view of a cable housing with a swivelling disc and a cable in a second position relative to the cable housing according to an example of the present technology.

Figure 8F:
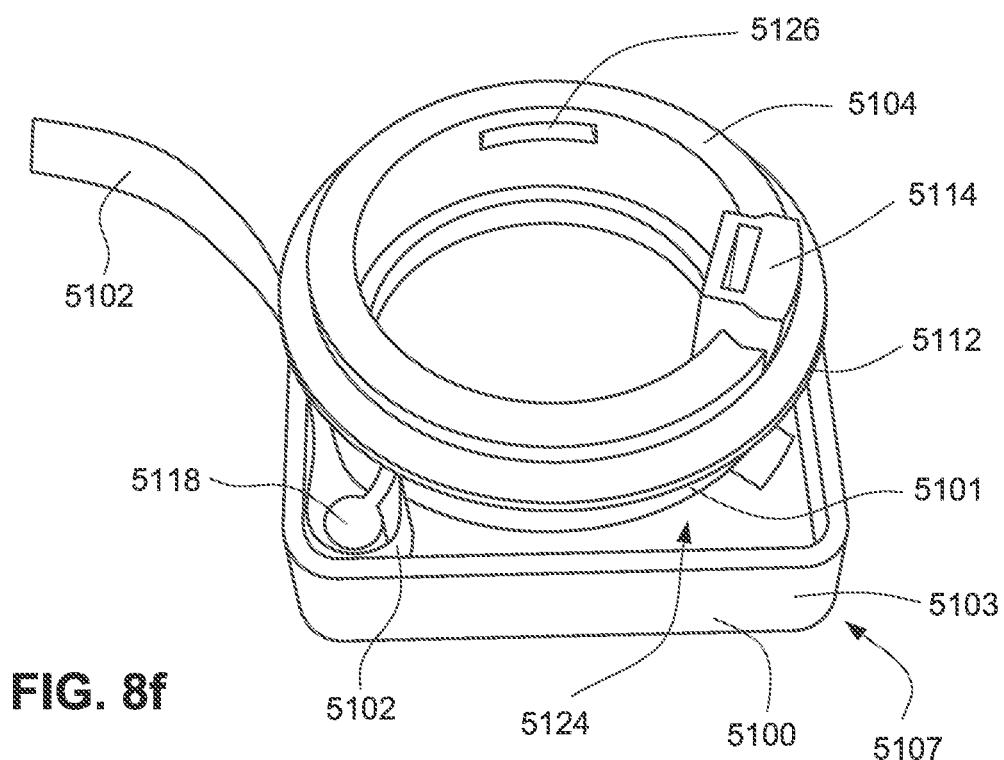

FIG. 8f shows a perspective view of a cable housing with a swivelling disc and a cable in a third position relative to the cable housing according to an example of the present technology.

Figure 8G:
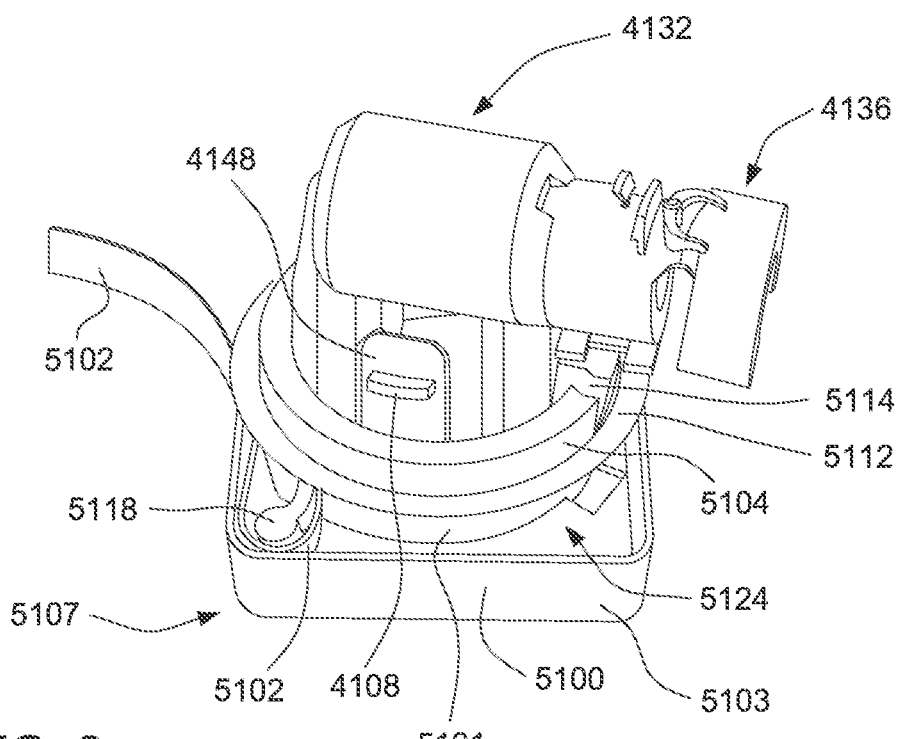

FIG. 8g shows a perspective view of a cable housing with a swivelling disc, a cable, and a substructure of an outlet connector in a first position relative to the cable housing according to an example of the present technology.

Figure 8H:
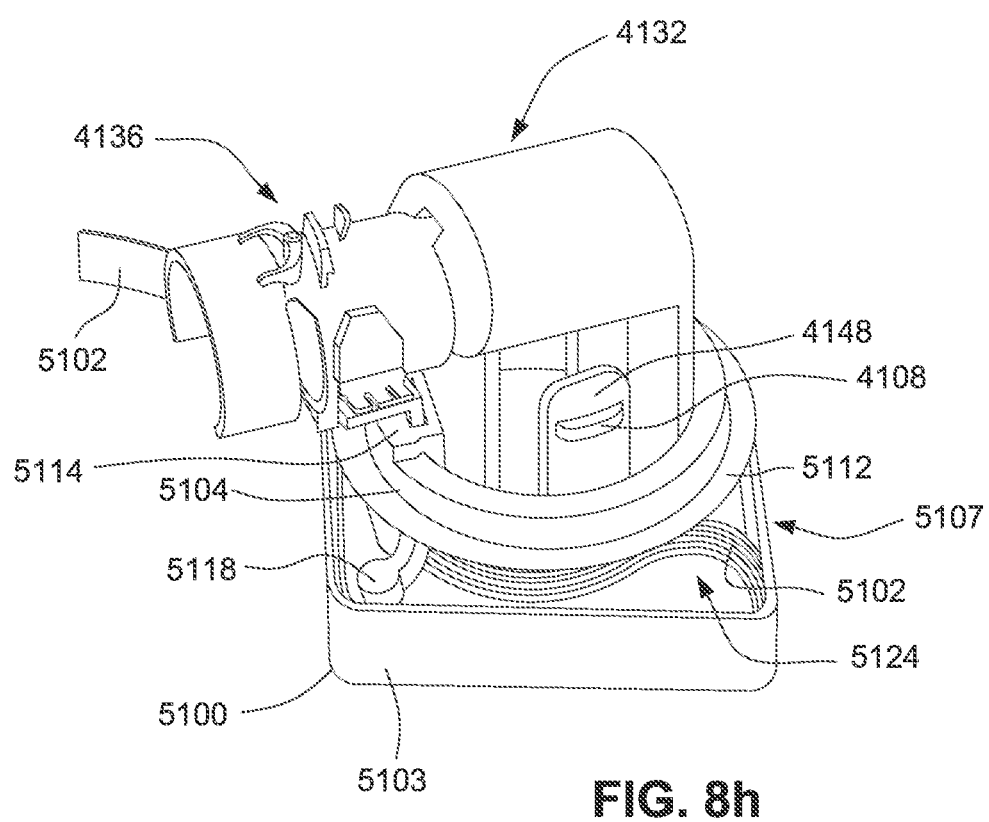

FIG. 8h shows a perspective view of a cable housing with a swivelling disc, a cable, and a substructure of an outlet connector in a second position relative to the cable housing according to an example of the present technology.

Figure 8I:
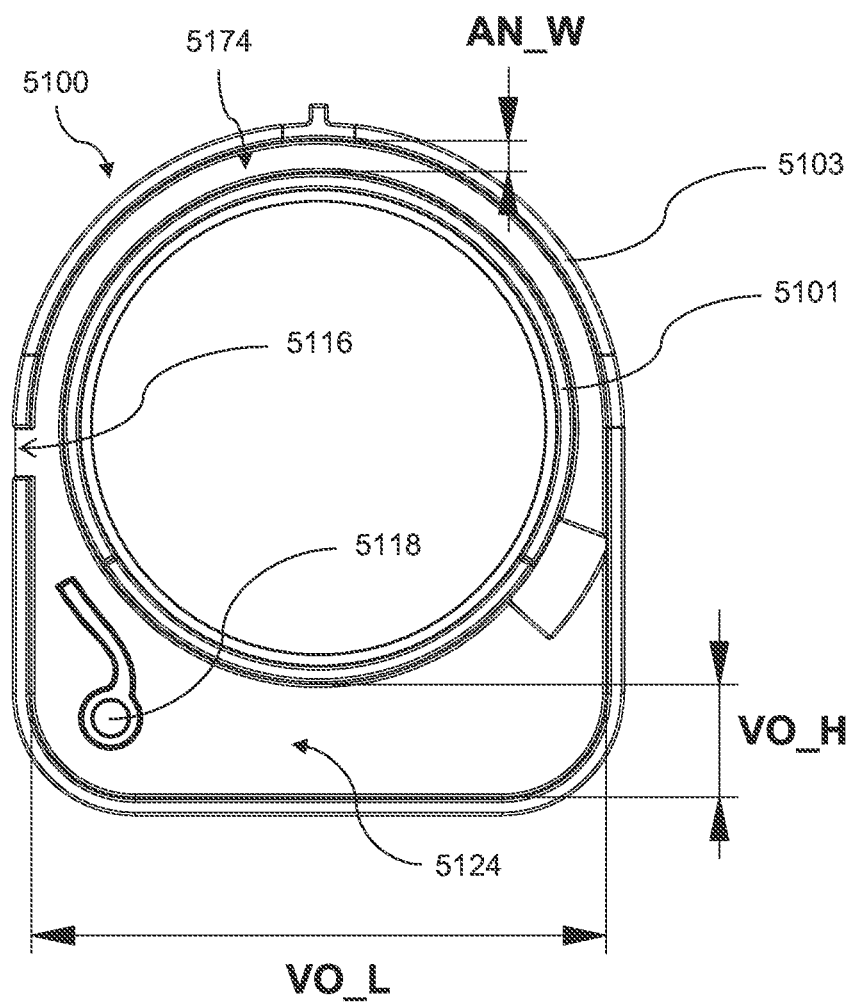

FIG. 8i shows a top view of a cable housing according to an example of the present technology.

Figure 9A:
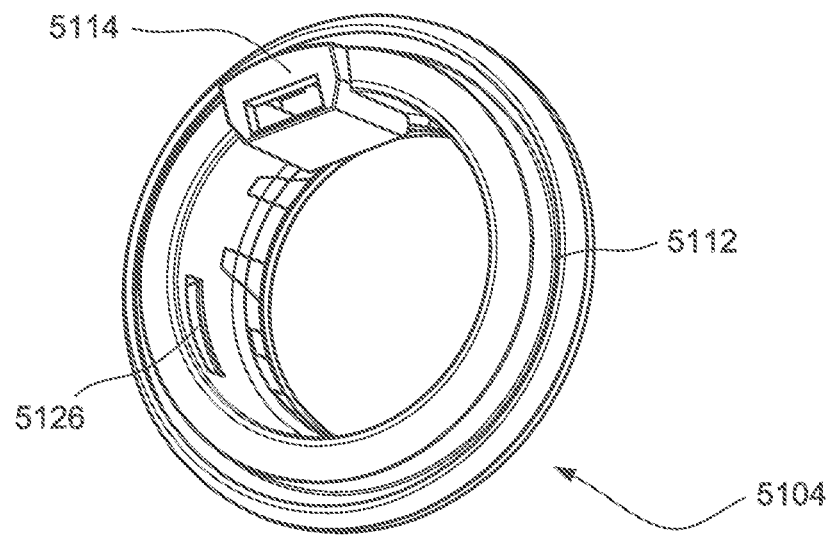

FIG. 9a shows a perspective view of a swivelling disc according to an example of the present technology.

Figures 9B, 9C:
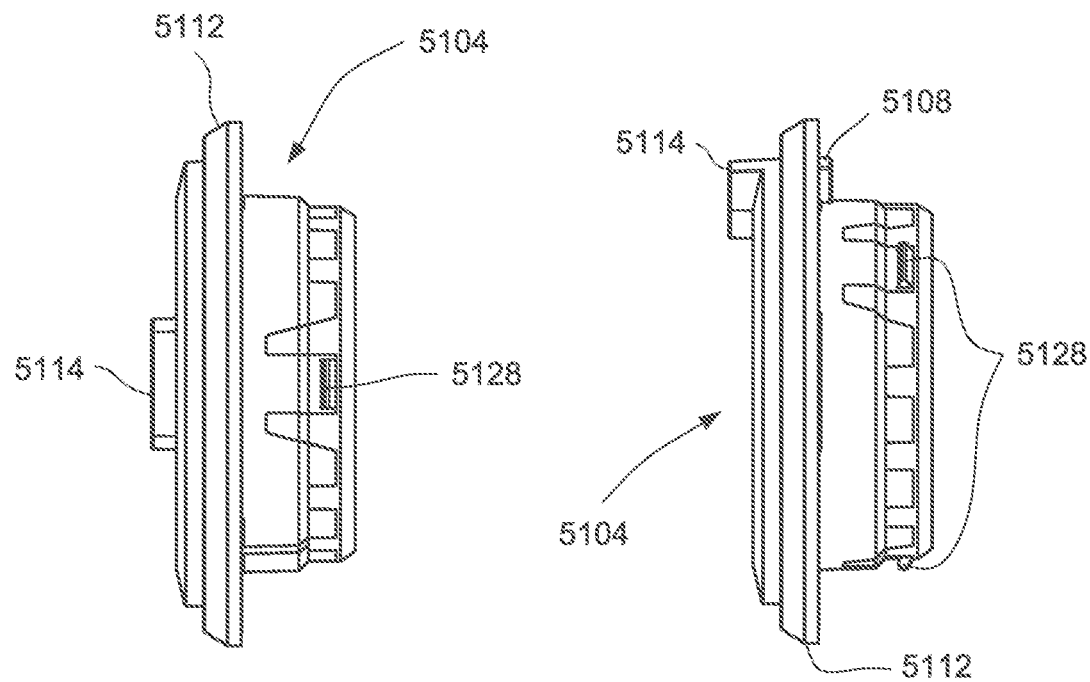

FIG. 9b shows a side view of a swivelling disc according to an example of the present technology.

FIG. 9c shows another side view of a swivelling disc according to an example of the present technology.

Figure 9D:
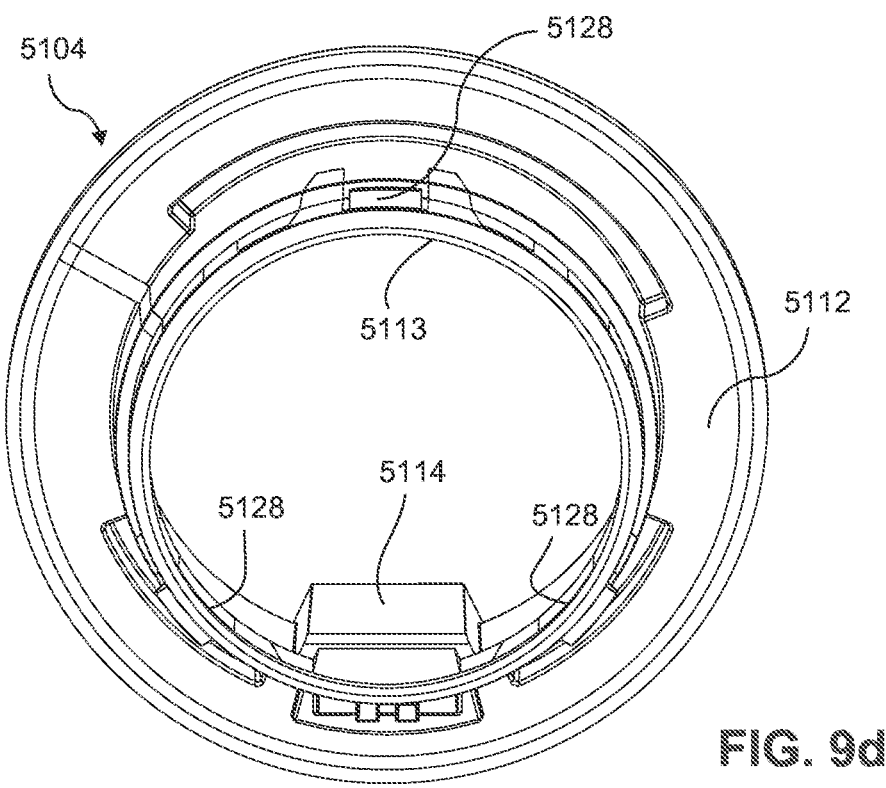

FIG. 9d shows a bottom perspective view of a swivelling disc according to an example of the present technology.

Figure 9E:
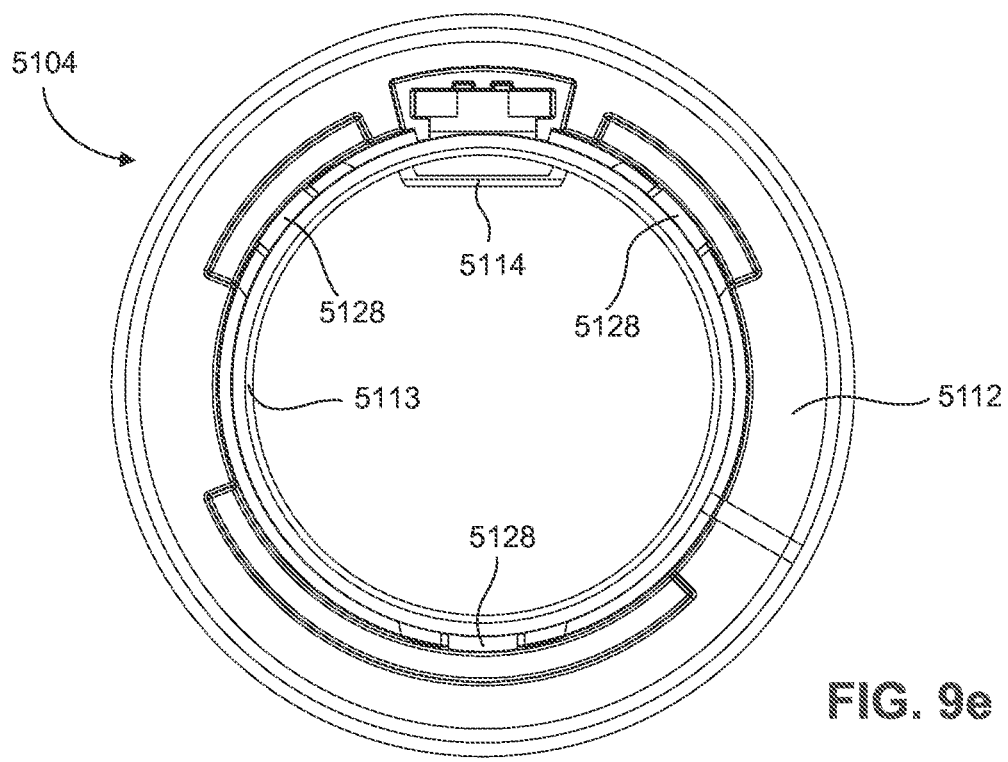

FIG. 9e shows a bottom view of a swivelling disc according to an example of the present technology.

Figure 10A:
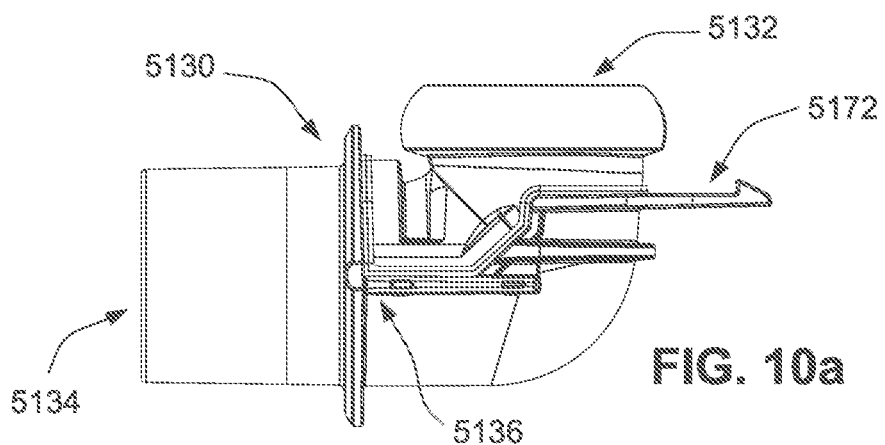

FIG. 10a shows a side view of an airflow tube according to an example of the present technology.

Figure 10B:
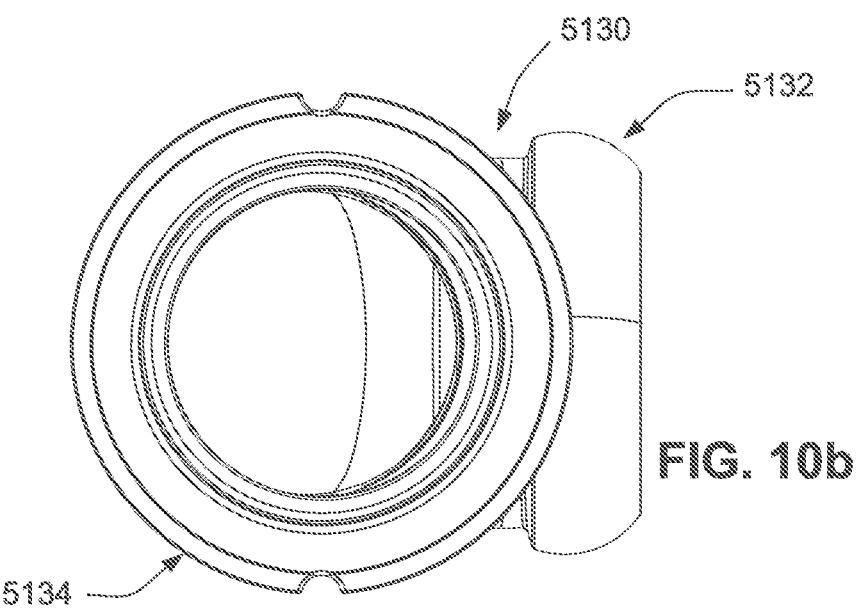

FIG. 10b shows another side view of an airflow tube according to an example of the present technology.

Figure 10C:
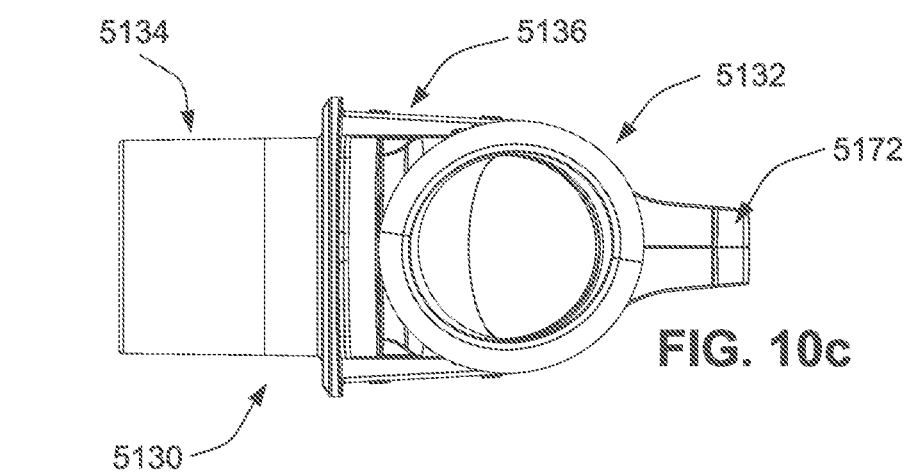

FIG. 10c shows another side view of an airflow tube according to an example of the present technology.

Figure 10D:
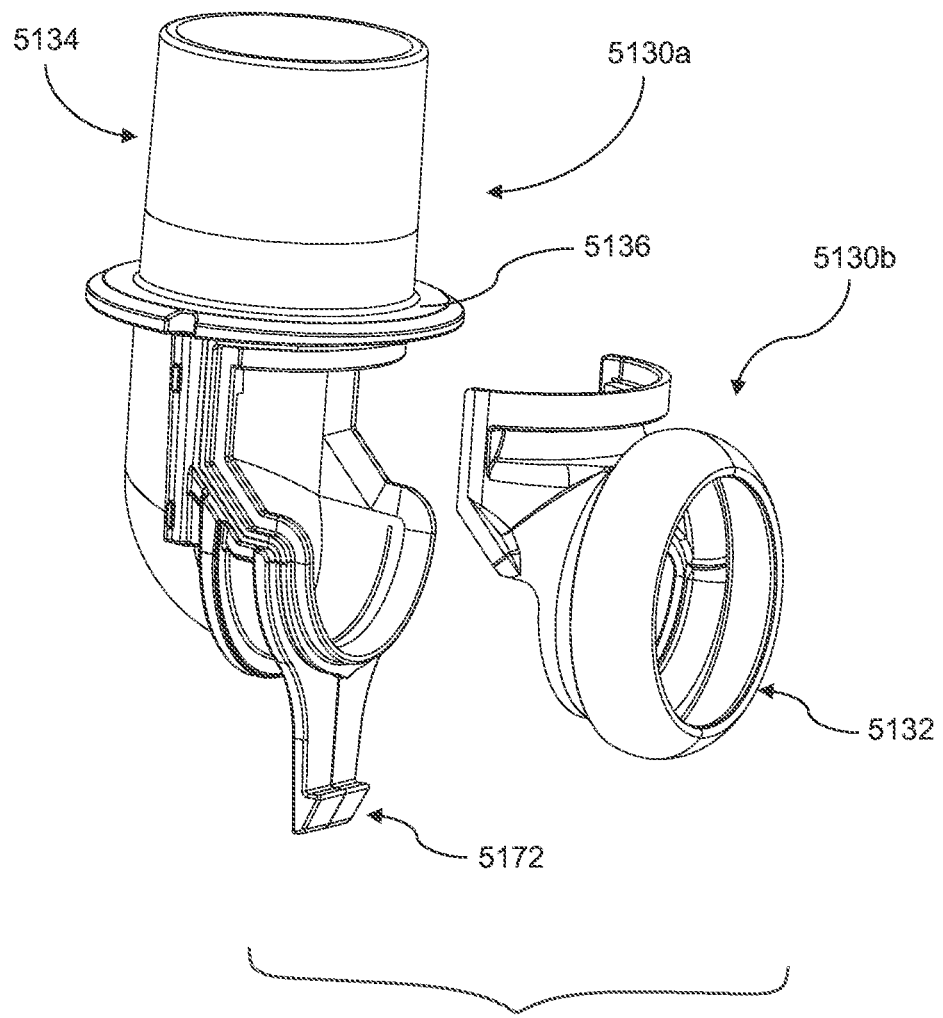

FIG. 10d shows an exploded perspective view of an airflow tube according to an example of the present technology.

FIG. 11a shows a side view of a cable housing according to an example of the present technology.

FIG. 11b shows a perspective view of a cable housing according to an example of the present technology.

FIG. 11c shows a top view of a cable housing according to an example of the present technology.

FIG. 11d shows another side view of a cable housing according to an example of the present technology.

Figure 12A:
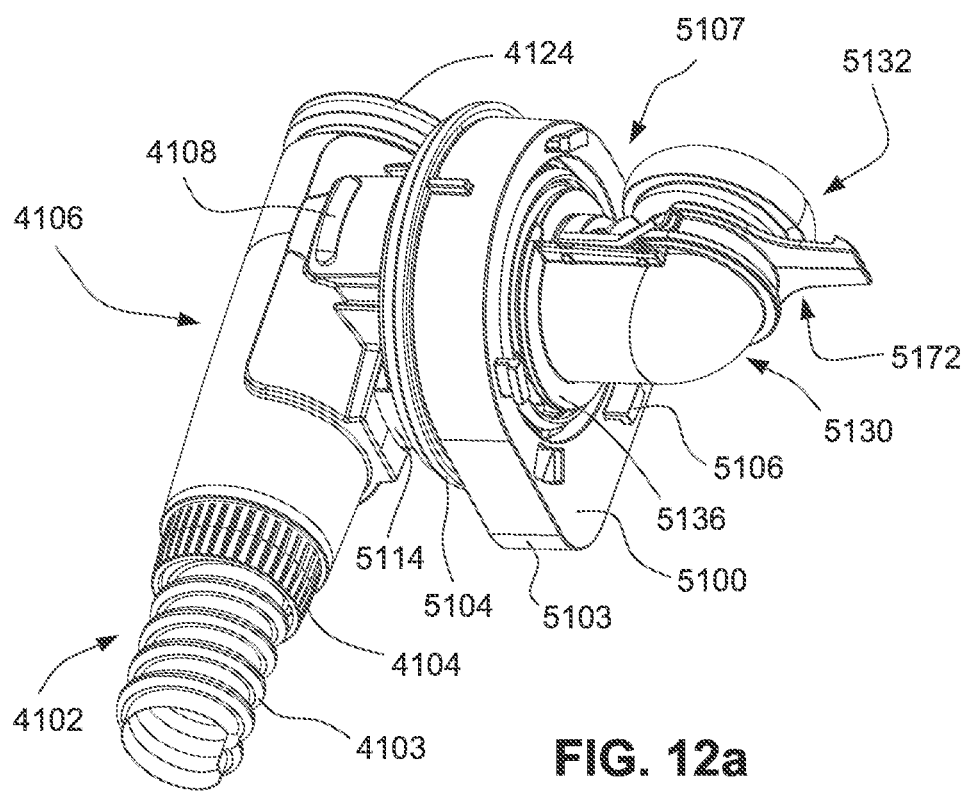

FIG. 12a shows a bottom perspective view of an air circuit comprising an outlet connector and a tube connected to a cable housing and an airflow tube according to an example of the present technology.

Figure 12B:
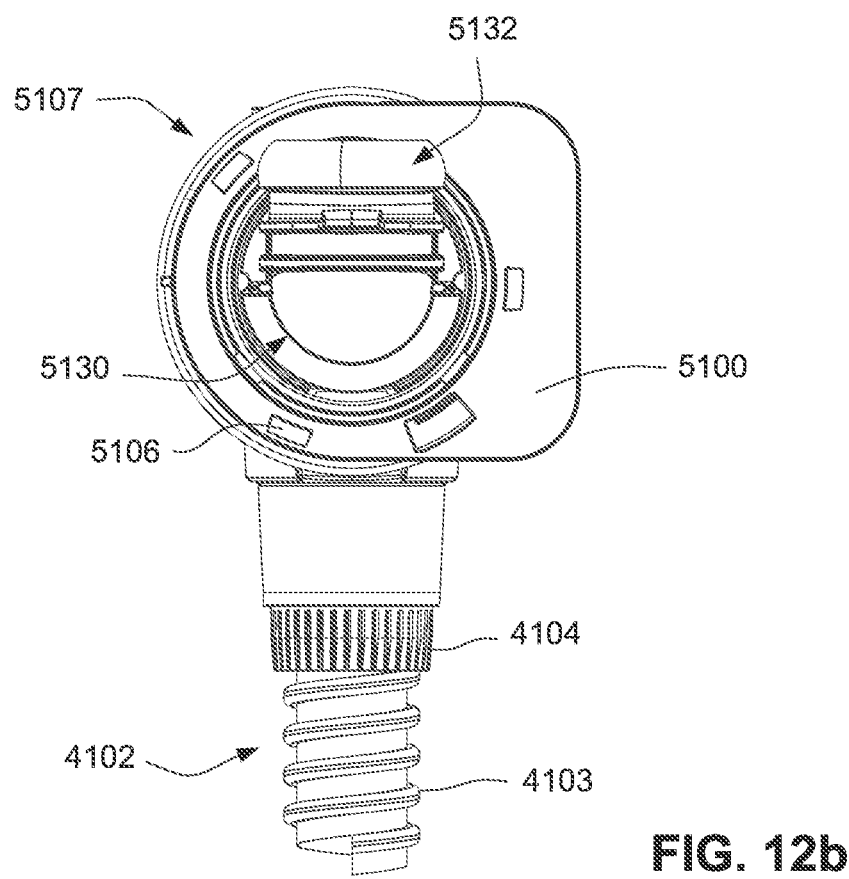

FIG. 12b shows a bottom view of an air circuit comprising an outlet connector and a tube connected to a cable housing and an airflow tube according to an example of the present technology.

Figure 12C:
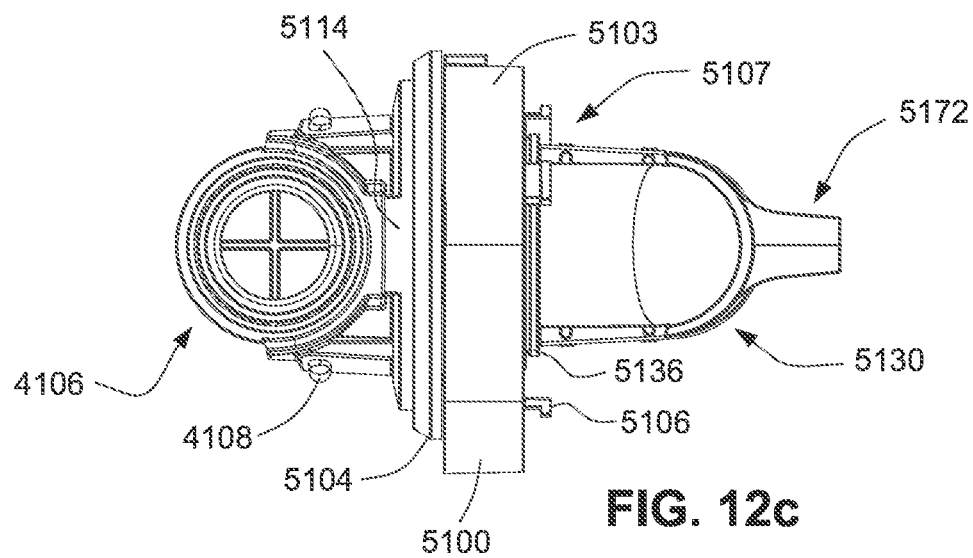

FIG. 12c shows an end view of an air circuit comprising an outlet connector and a tube connected to a cable housing and an airflow tube according to an example of the present technology.

Figure 12D:
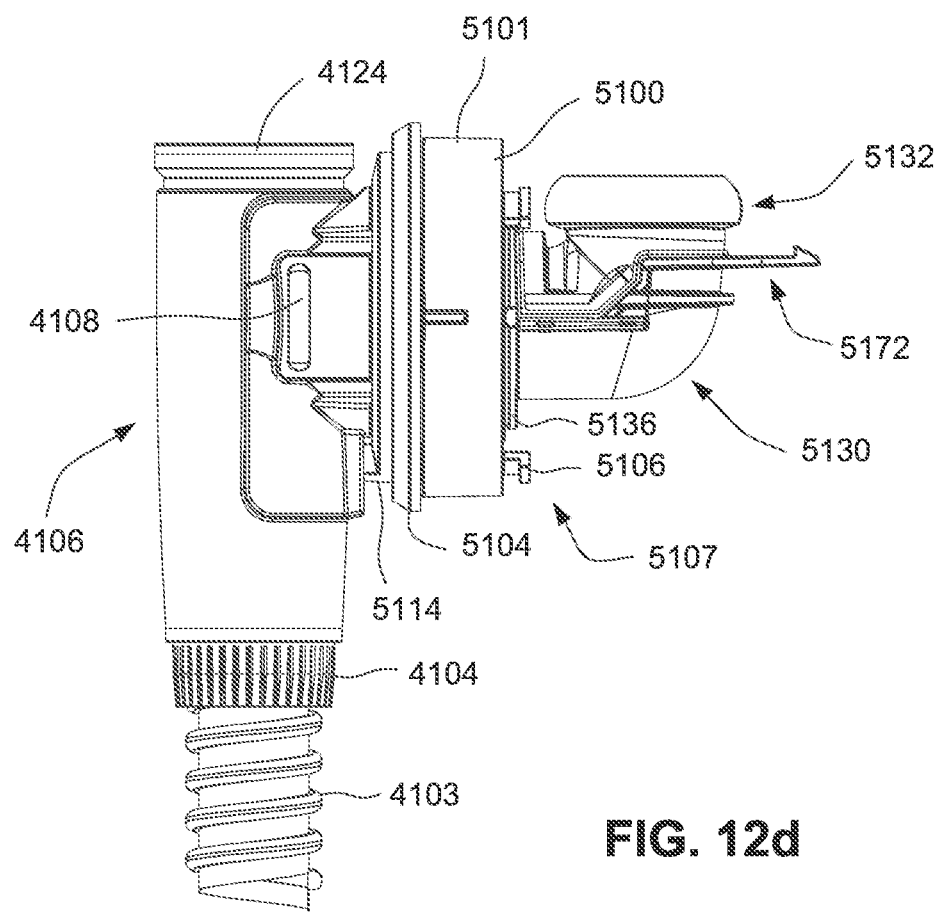

FIG. 12d shows a side view of an air circuit comprising an outlet connector and a tube connected to a cable housing and an airflow tube according to an example of the present technology.

Figure 12E:
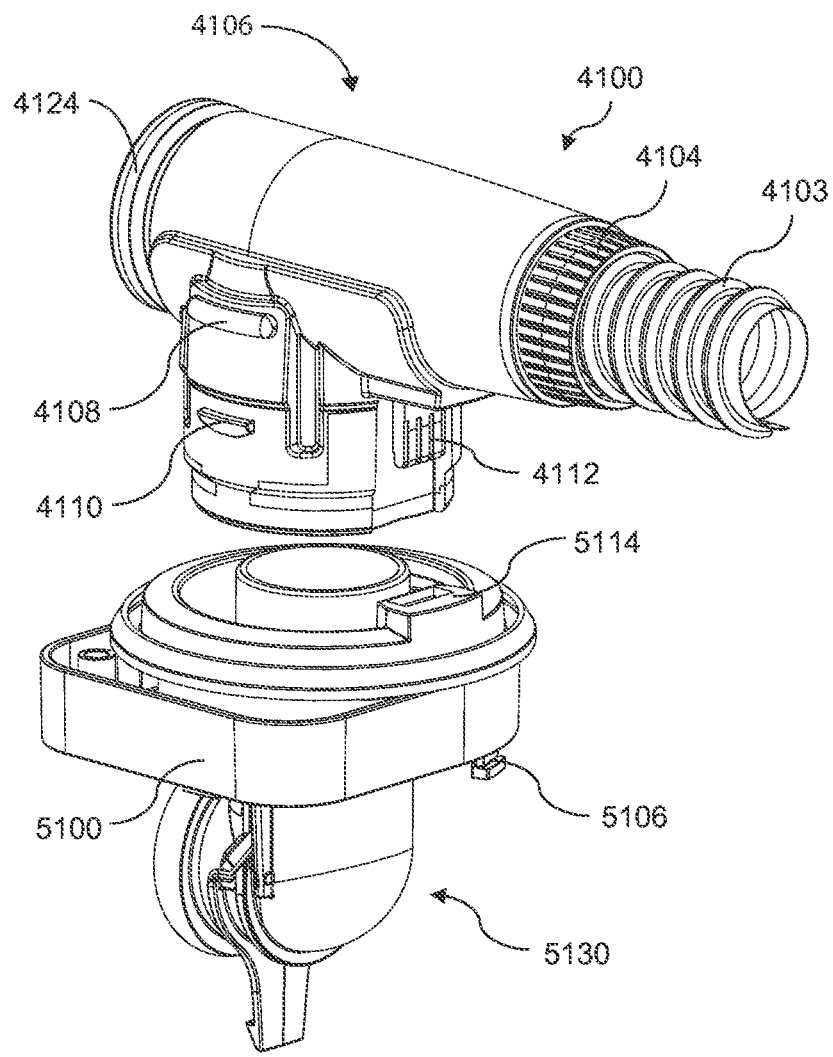

FIG. 12e shows a partially exploded perspective view of an air circuit comprising an outlet connector and a tube connected to a cable housing and an airflow tube according to an example of the present technology.

Figure 12F:
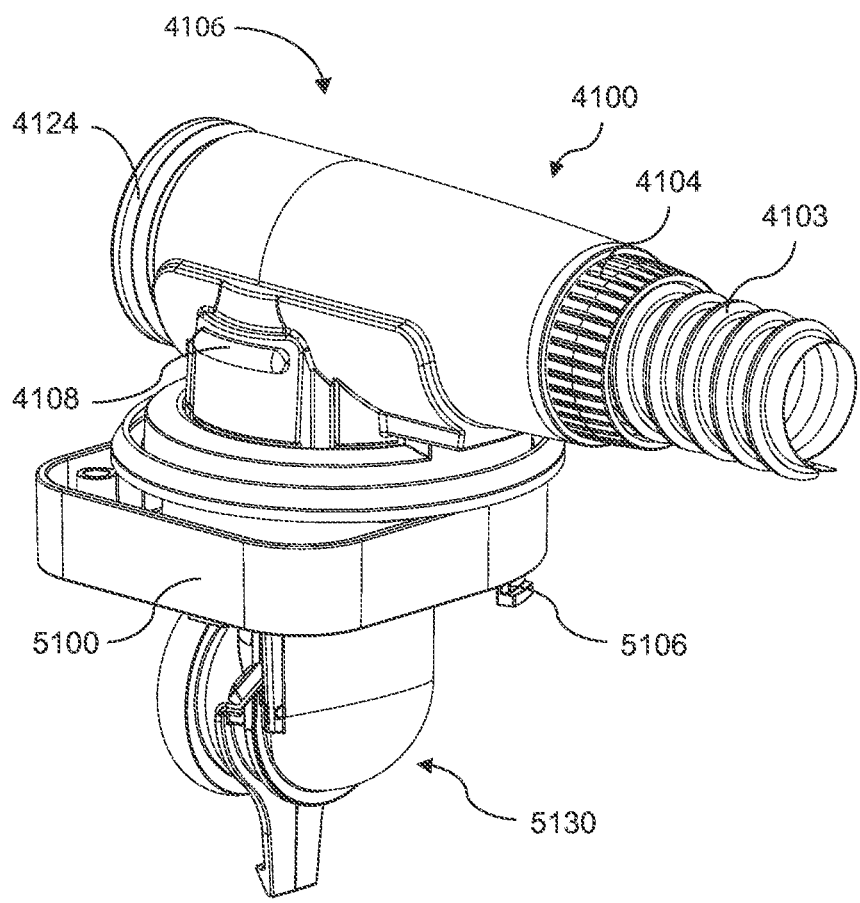

FIG. 12f shows a perspective view of an air circuit comprising an outlet connector and a tube connected to a cable housing and an airflow tube according to an example of the present technology.

Figure 13A:
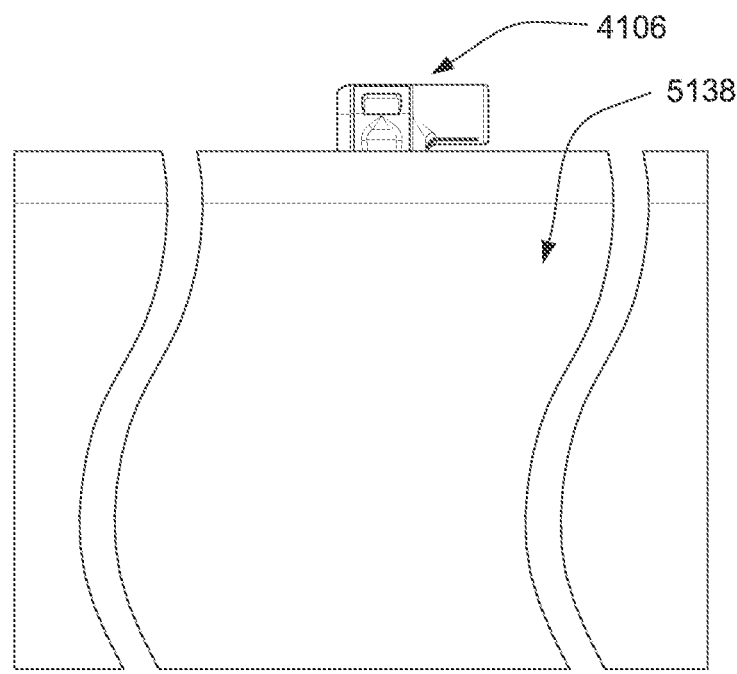

FIG. 13a shows a top view of an outlet connector connected to a humidifier housing according to an example of the present technology.

Figure 13B:
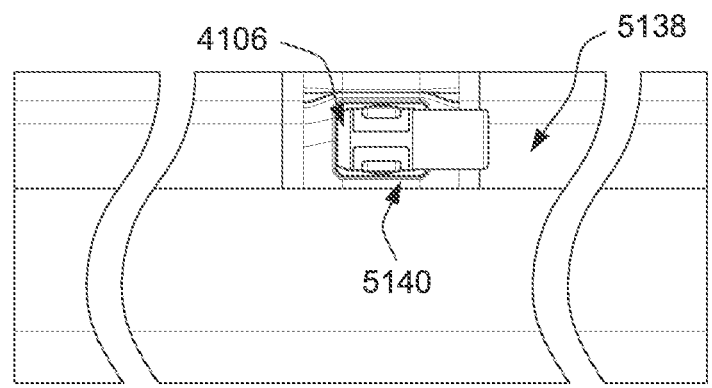

FIG. 13b shows a side view of an outlet connector connected to a humidifier housing according to an example of the present technology.

Figure 13C:
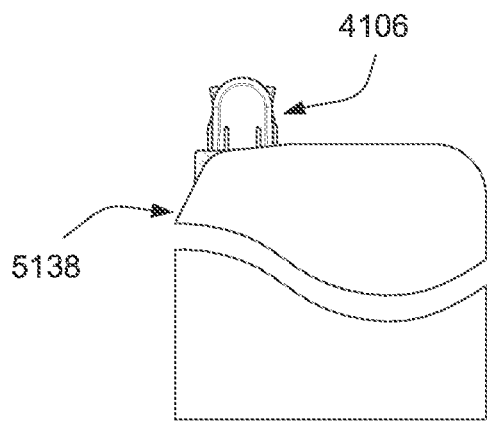

FIG. 13c shows another side view of an outlet connector connected to a humidifier housing according to an example of the present technology.

Figure 13D:
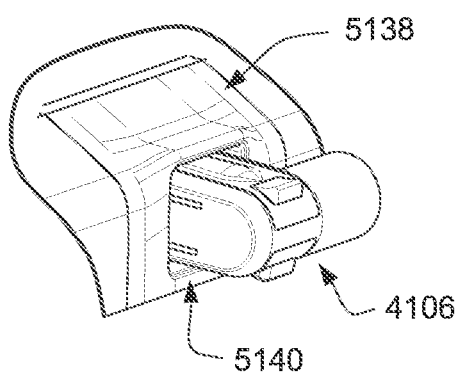

FIG. 13d shows a perspective view of an outlet connector connected to a humidifier housing according to an example of the present technology.

Figure 13E:
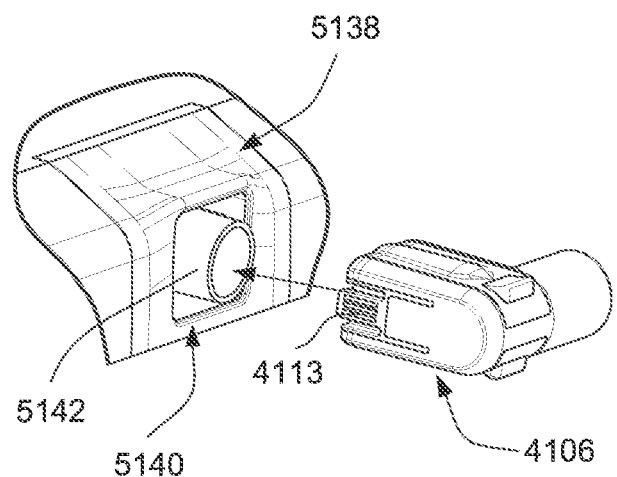

FIG. 13e shows a perspective view of an outlet connector detached from a humidifier housing according to an example of the present technology.

Figure 13F:
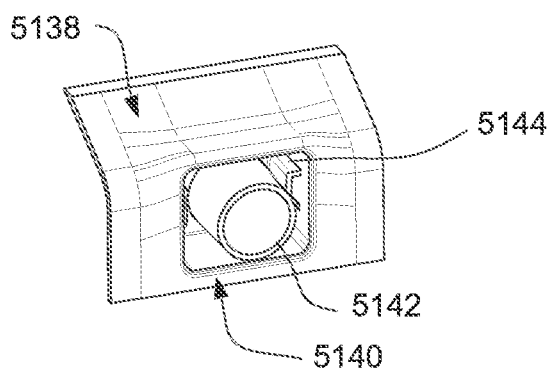

FIG. 13f shows a perspective view of an outlet of a humidifier housing according to an example of the present technology.

Figure 13G:
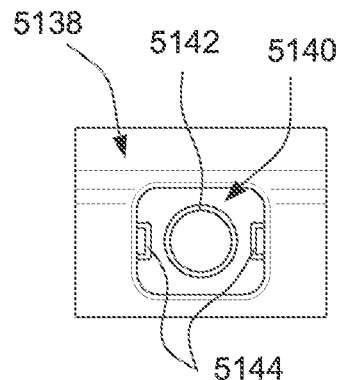

FIG. 13g shows a front view of an outlet of a humidifier housing according to an example of the present technology.

Figure 13H:
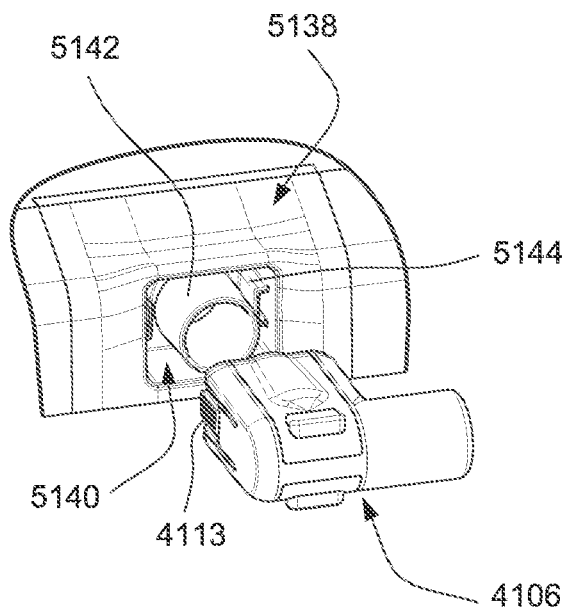

FIG. 13h shows another perspective view of an outlet connector detached from a humidifier housing according to an example of the present technology.

Figure 13J:
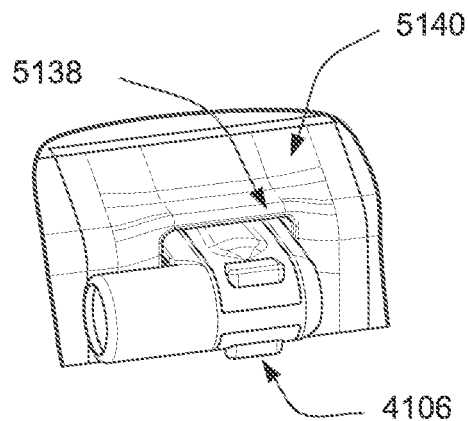

FIG. 13j shows a perspective view of an outlet connector connected to a humidifier housing according to an example of the present technology.

Figure 13K:
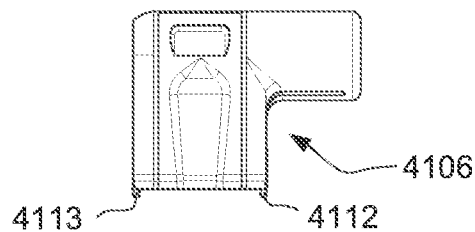

FIG. 13k shows a side view of an outlet connector according to an example of the present technology.

Figure 13L:
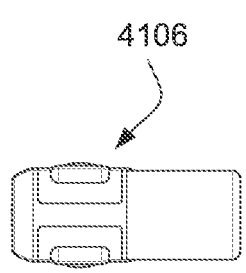

FIG. 13l shows a top view of an outlet connector according to an example of the present technology.

Figure 13M:
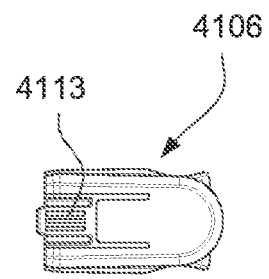

FIG. 13m shows another side view of an outlet connector according to an example of the present technology.

Figure 13N:
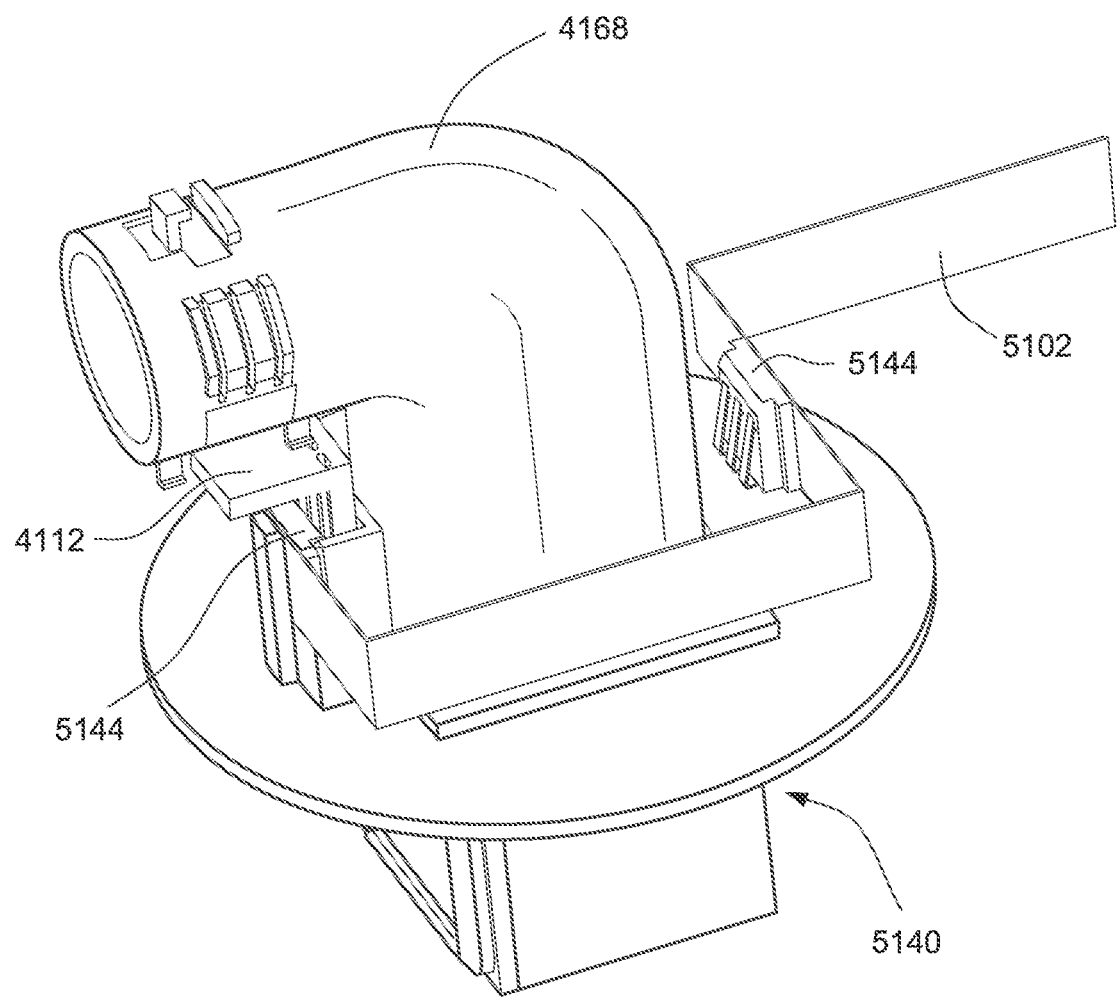

FIG. 13n shows a perspective view of an outlet assembly according to an example of the present technology.

Figure 14A:
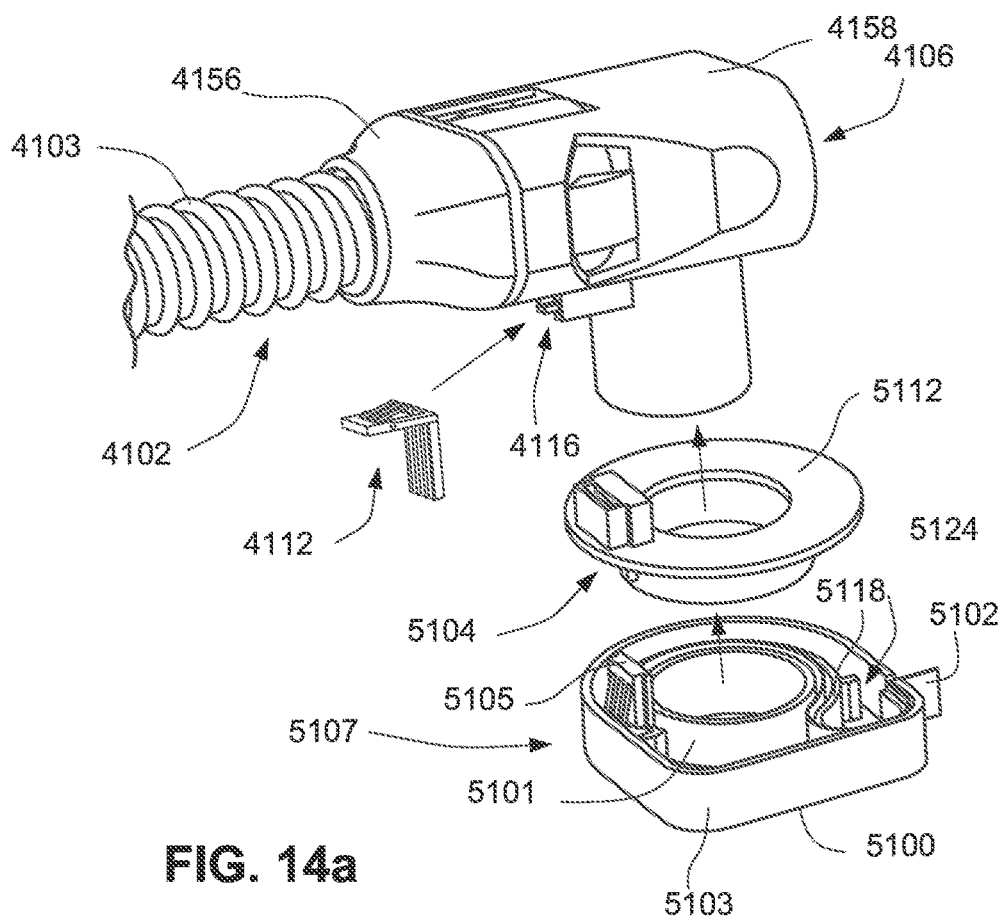

FIG. 14a shows a partially exploded perspective view of an air circuit comprising an outlet connector and a tube, a swivelling disc, a cable and a cable housing according to an example of the present technology.

Figure 14B:
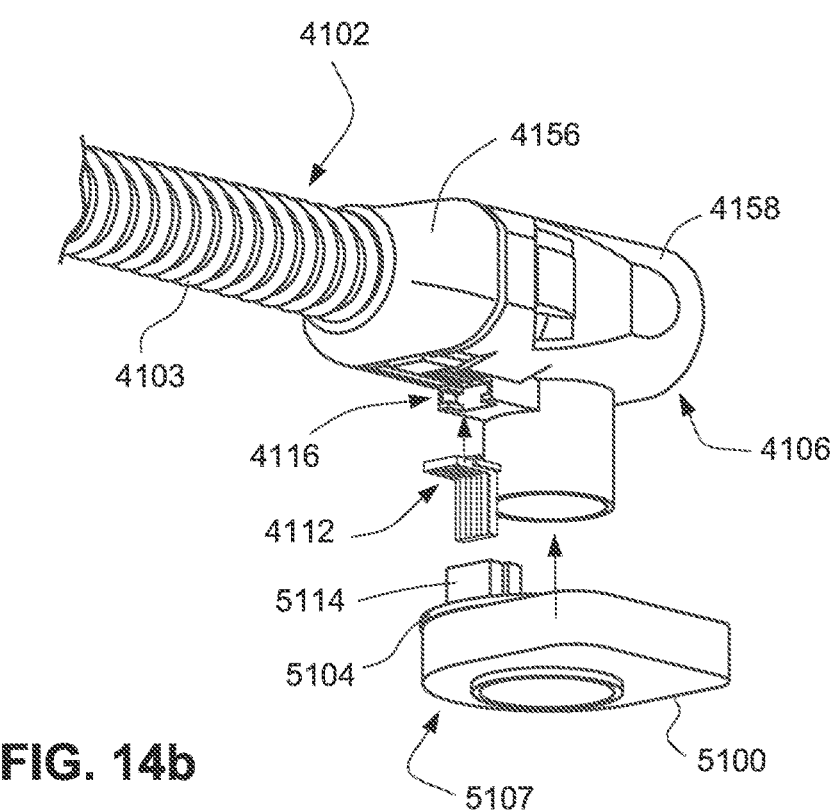

FIG. 14b shows another partially exploded perspective view of an air circuit comprising an outlet connector and a tube, a swivelling disc, and a cable housing according to an example of the present technology.

Figure 14C:
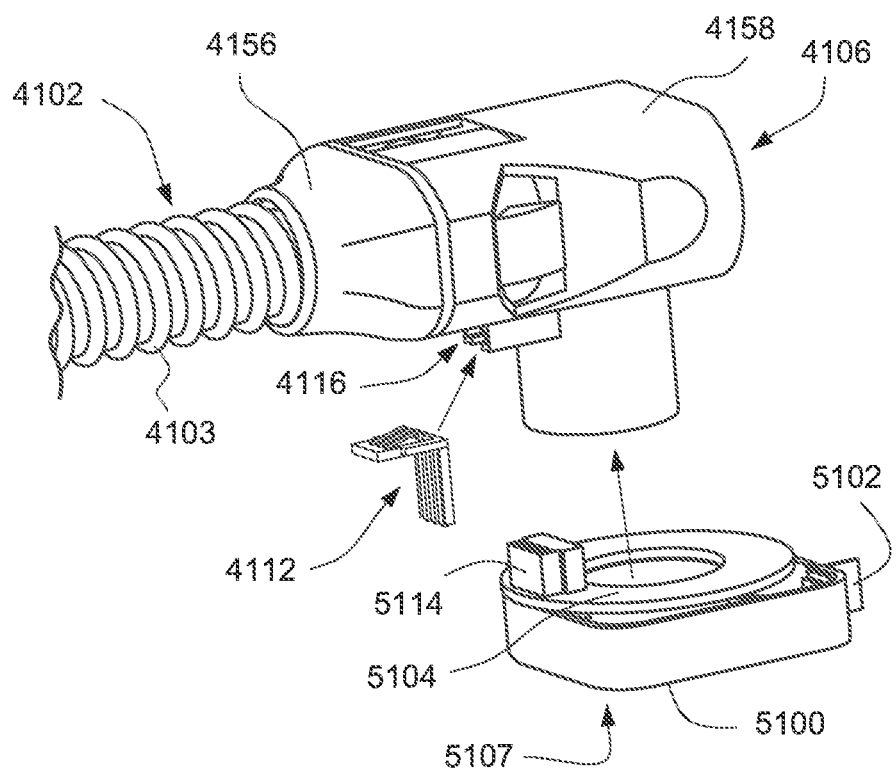

FIG. 14c shows another partially exploded perspective view of an air circuit comprising an outlet connector and a tube, a swivelling disc, a cable and a cable housing according to an example of the present technology.

Figure 14D:
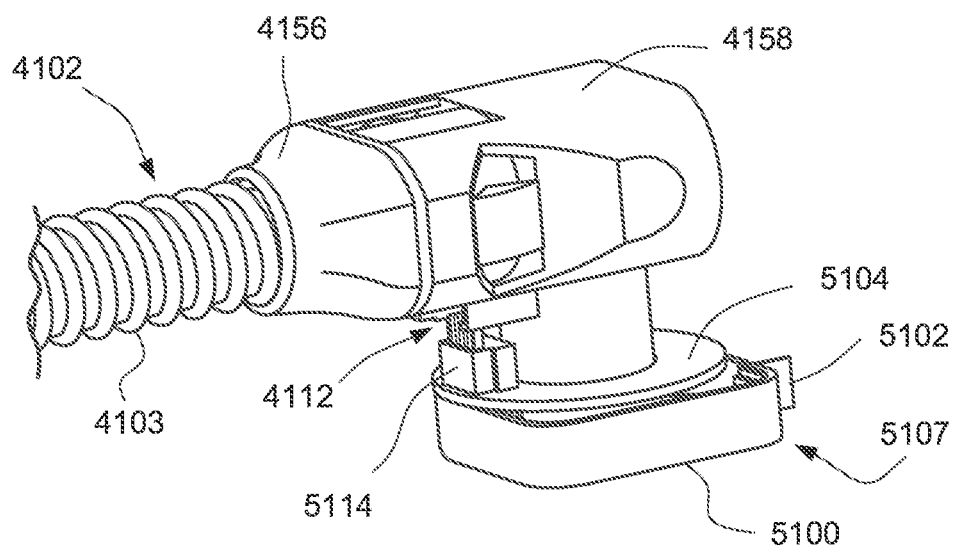

FIG. 14d shows a perspective view of an air circuit comprising an outlet connector and a tube connected to a swivelling disc, a cable and a cable housing according to an example of the present technology.

Figure 14E:
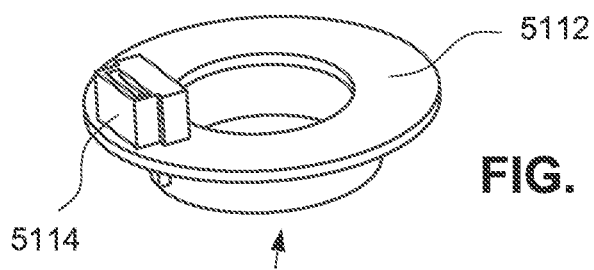

FIG. 14e shows a perspective view of a swivelling disc according to an example of the present technology.

Figure 14F:
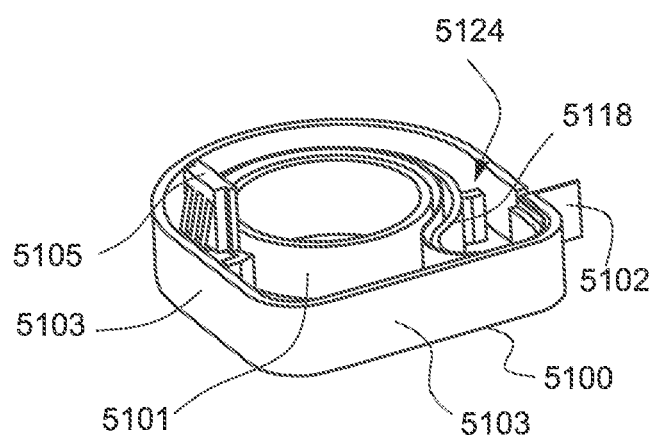

FIG. 14f shows a perspective view of a cable housing and a cable according to an example of the present technology.

Figure 14G:
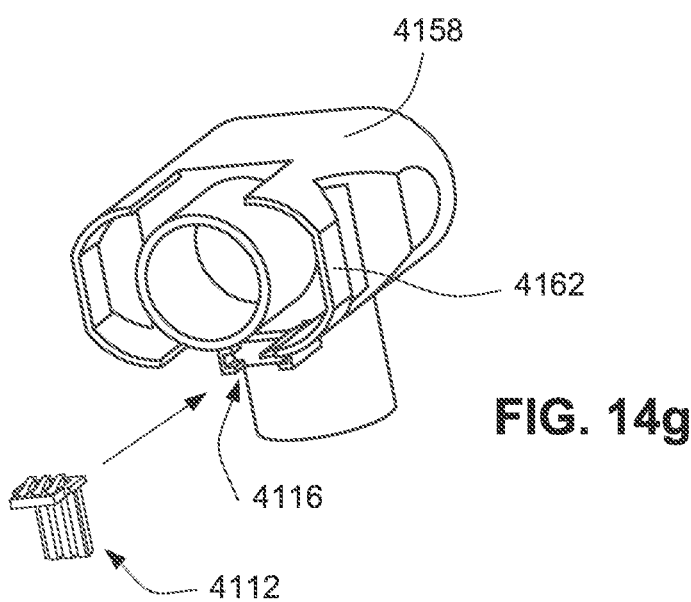

FIG. 14g shows a perspective view of an electrical connector detached from an elbow according to an example of the present technology.

Figure 14H:
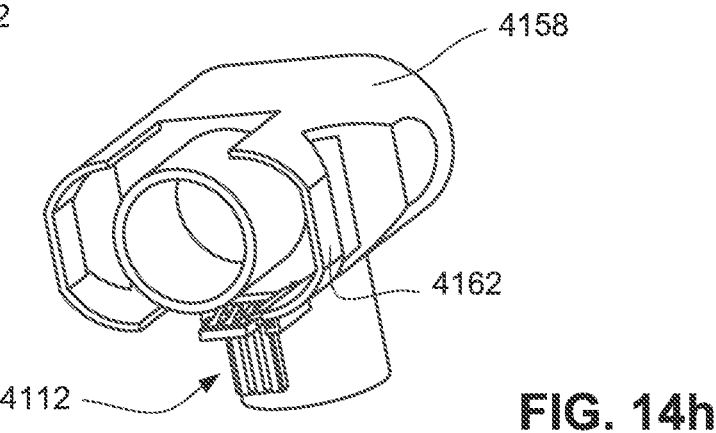

FIG. 14h shows a perspective view of an electrical connector connected to an elbow according to an example of the present technology.

Figure 14I:
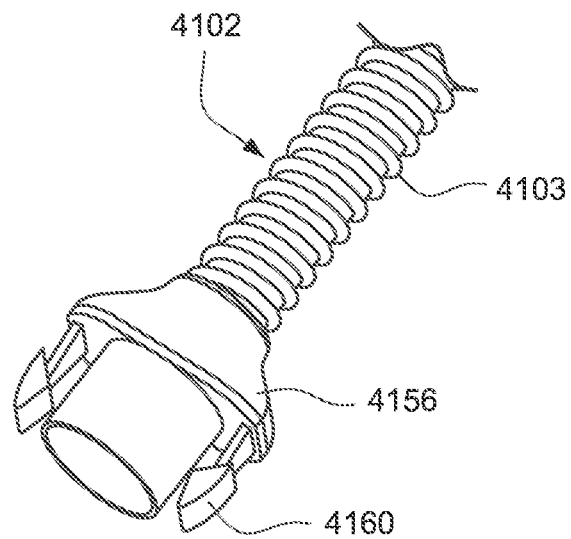

FIG. 14i shows a top perspective view of a tube and tube cuff according to an example of the present technology.

Figure 14J:
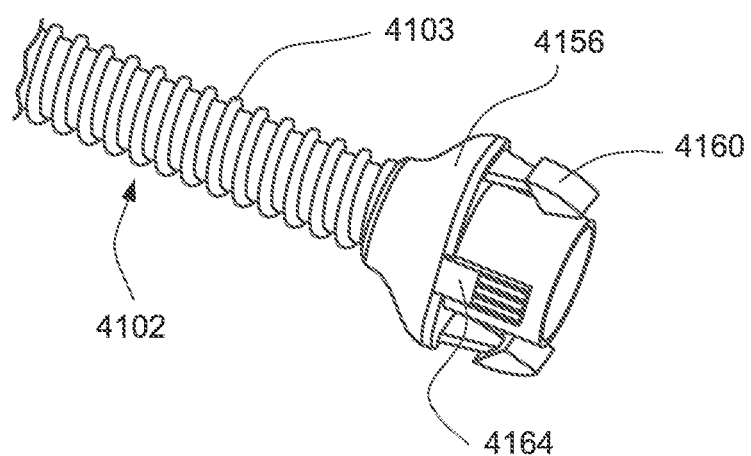

FIG. 14j shows a bottom perspective view of a tube and tube cuff according to an example of the present technology.

Figure 15A:
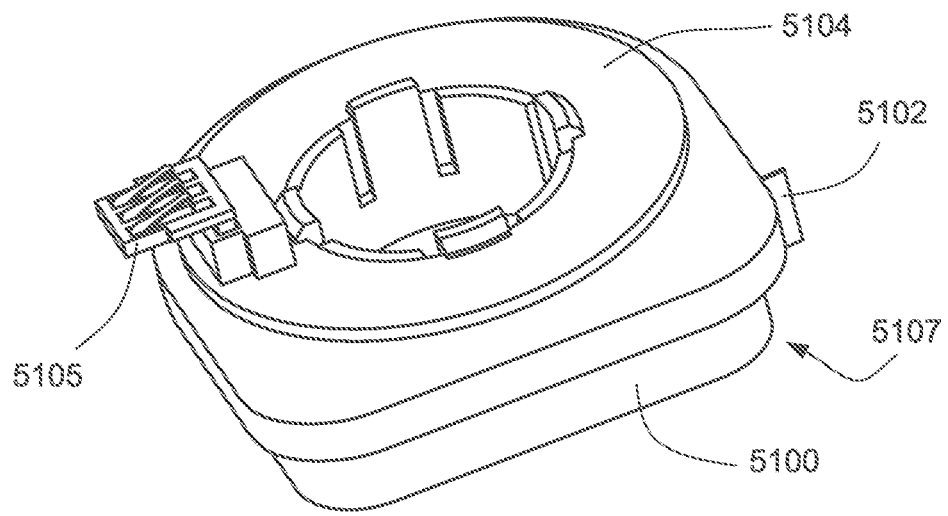

FIG. 15a shows a perspective view of a swivelling disc, a swivel electrical connector, and a cable housing assembled together according to an example of the present technology.

Figure 15B:
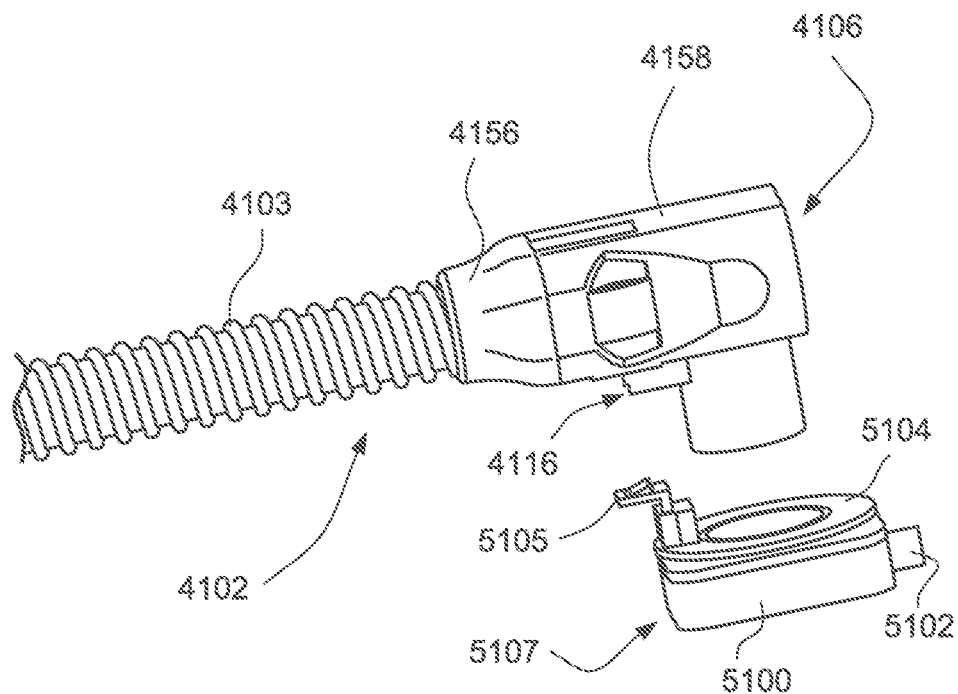

FIG. 15b shows a side view of an air circuit comprising an outlet connector and a tube detached from a swivelling disc, a swivel electrical connector, and a cable housing according to an example of the present technology.

Figure 16A:
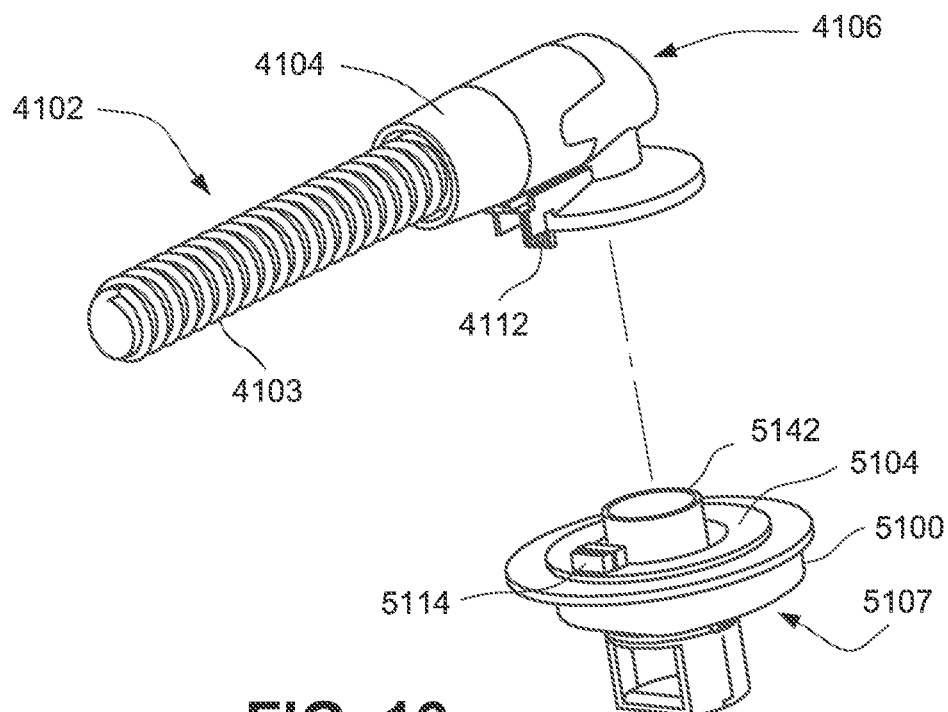

FIG. 16a shows a side view of an air circuit comprising an outlet connector and a tube detached from a swivelling disc, and a cable housing according to an example of the present technology.

Figure 16B:
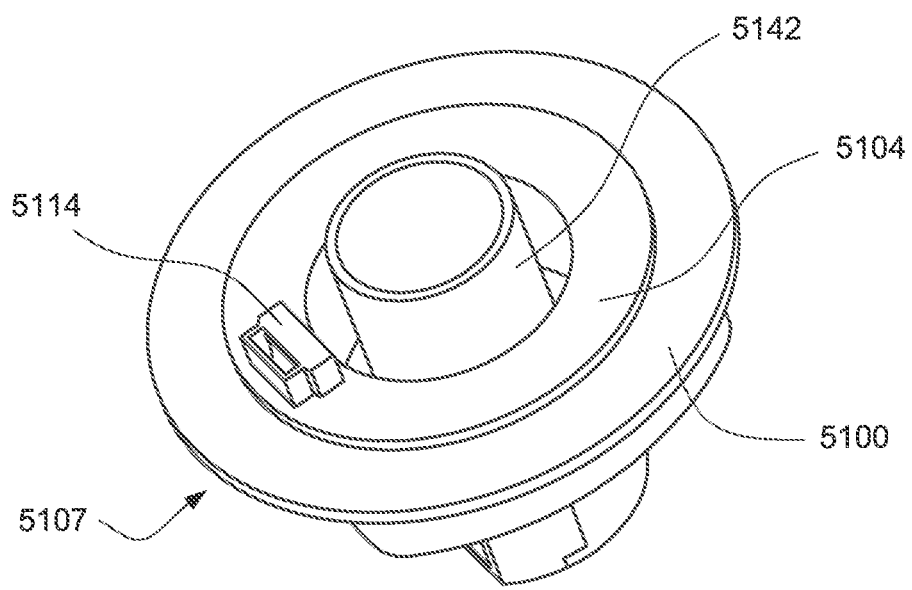

FIG. 16b shows a top perspective view of a cable housing and a swivelling disc according to an example of the present technology.

Figure 17:
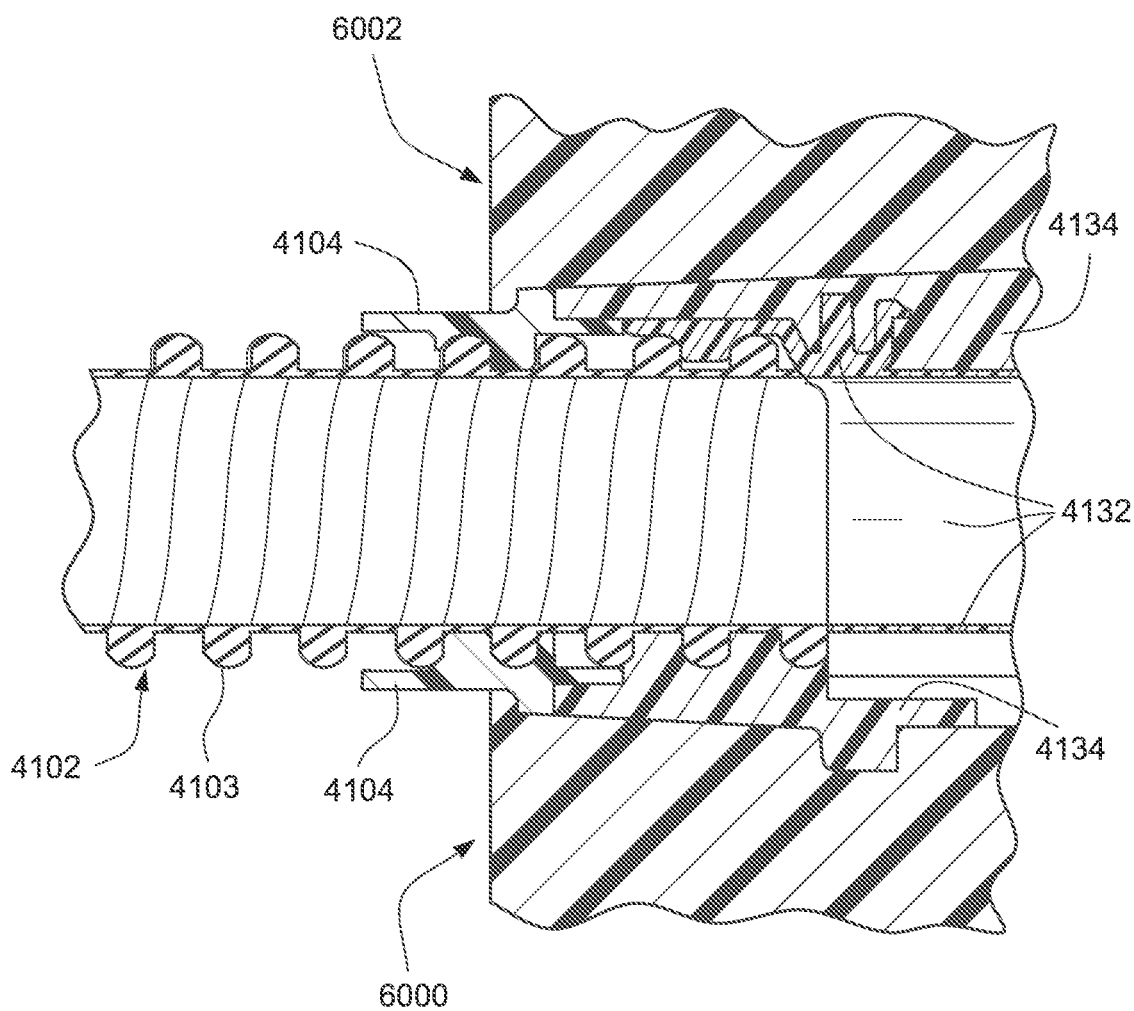

FIG. 17 shows a cross-sectional view of an air circuit comprising an outlet connector and a tube with mold tools according to an example of the present technology.

Figure 18A:
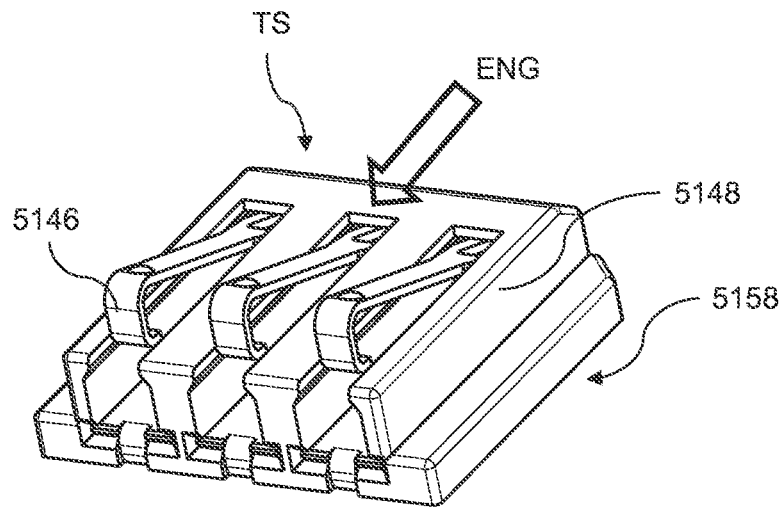

FIG. 18a shows a perspective view of a female electrical connector according to an example of the present technology.

Figure 18B:
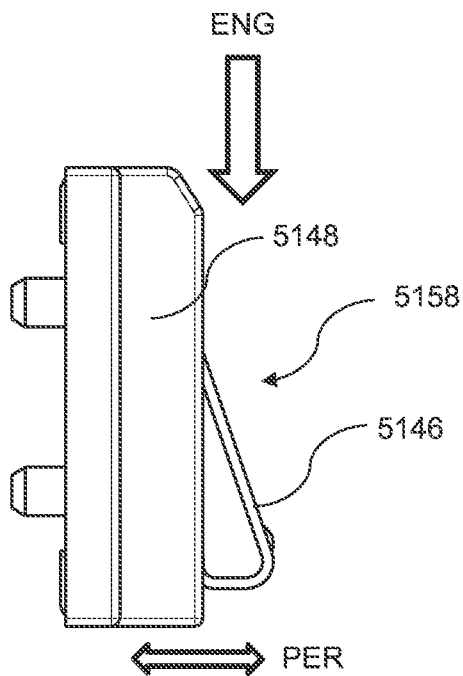

FIG. 18b shows a side view of a female electrical connector according to an example of the present technology.

Figure 18C:
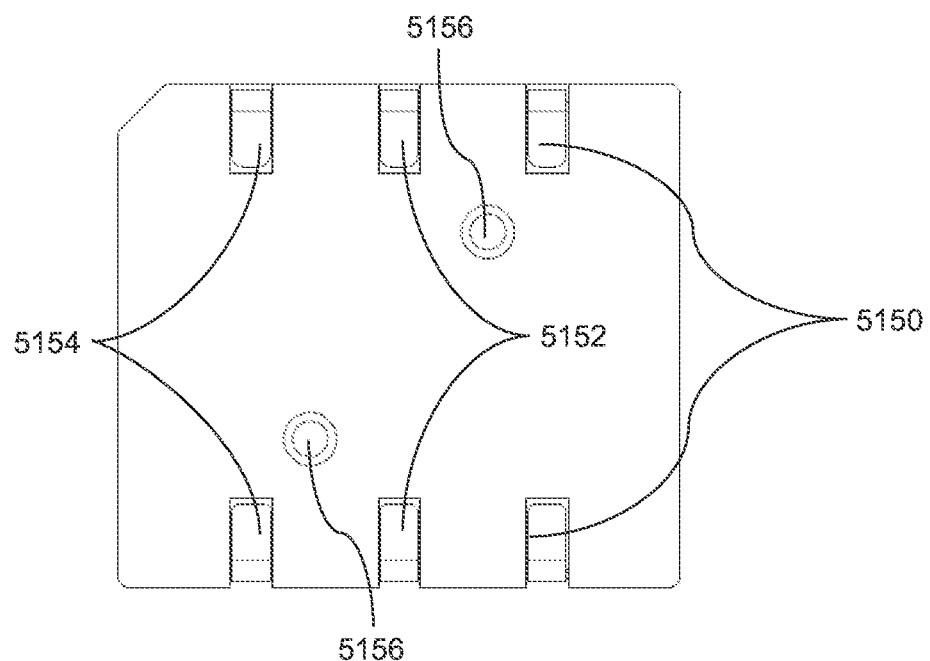

FIG. 18c shows a rear view of a female electrical connector according to an example of the present technology.

Figure 18D:
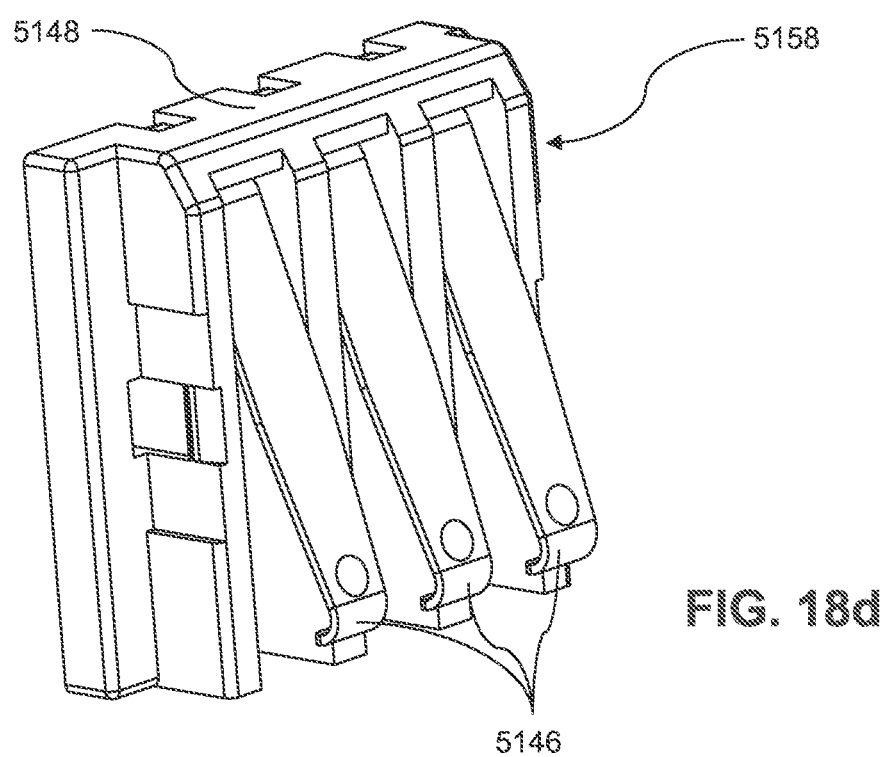

FIG. 18d shows a perspective view of a female electrical connector according to an example of the present technology.

Figures 18E, 18F:
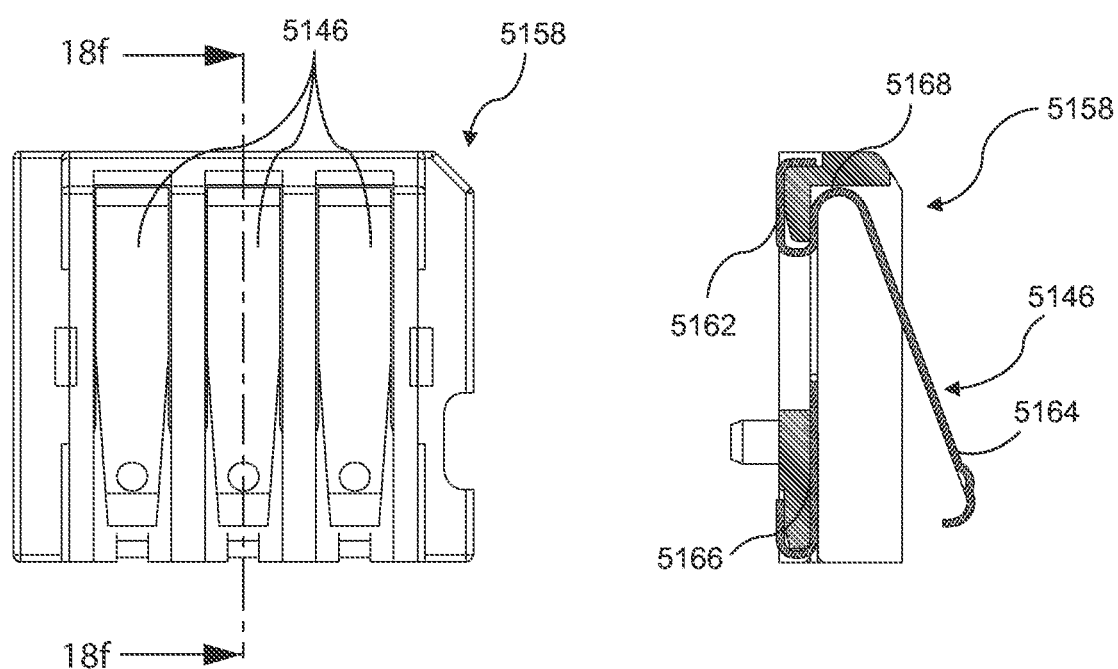

FIG. 18e shows a front-on view of a female electrical connector according to an example of the present technology, indicating the cross section taken for FIG. 18f.

FIG. 18f shows a side cross-sectional view of a female electrical connector according to an example of the present technology.

Figure 18G:
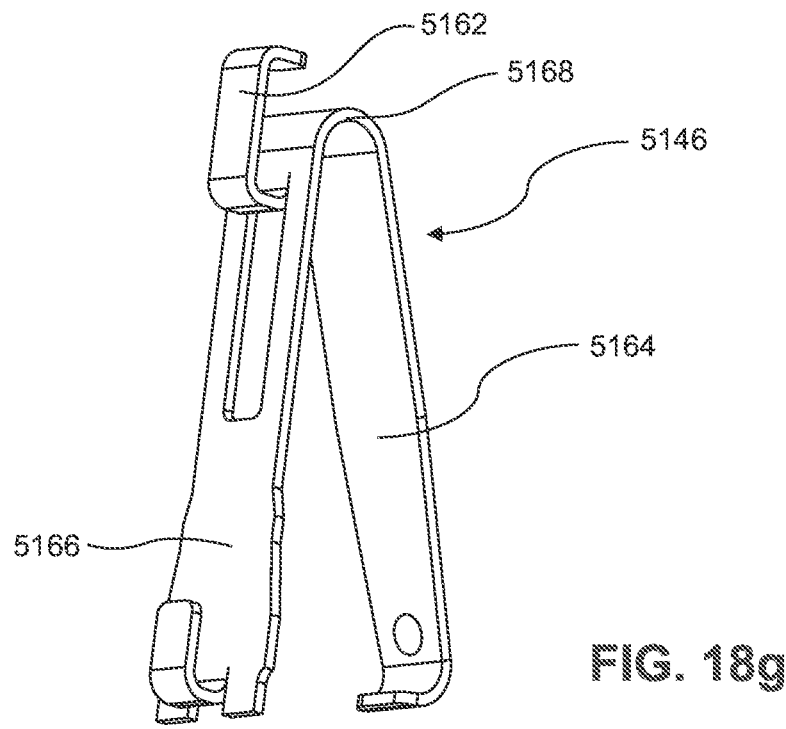

FIG. 18g shows a rear perspective view of an electrical connector receiver contact element according to an example of the present technology.

Figure 18H:
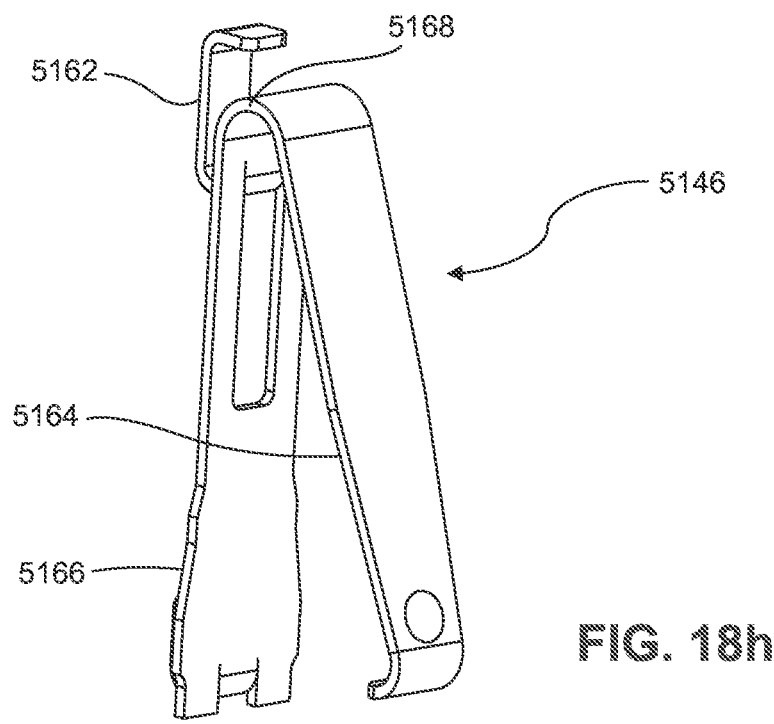

FIG. 18h shows a front perspective view of an electrical connector receiver contact element according to an example of the present technology.

Figure 19A:
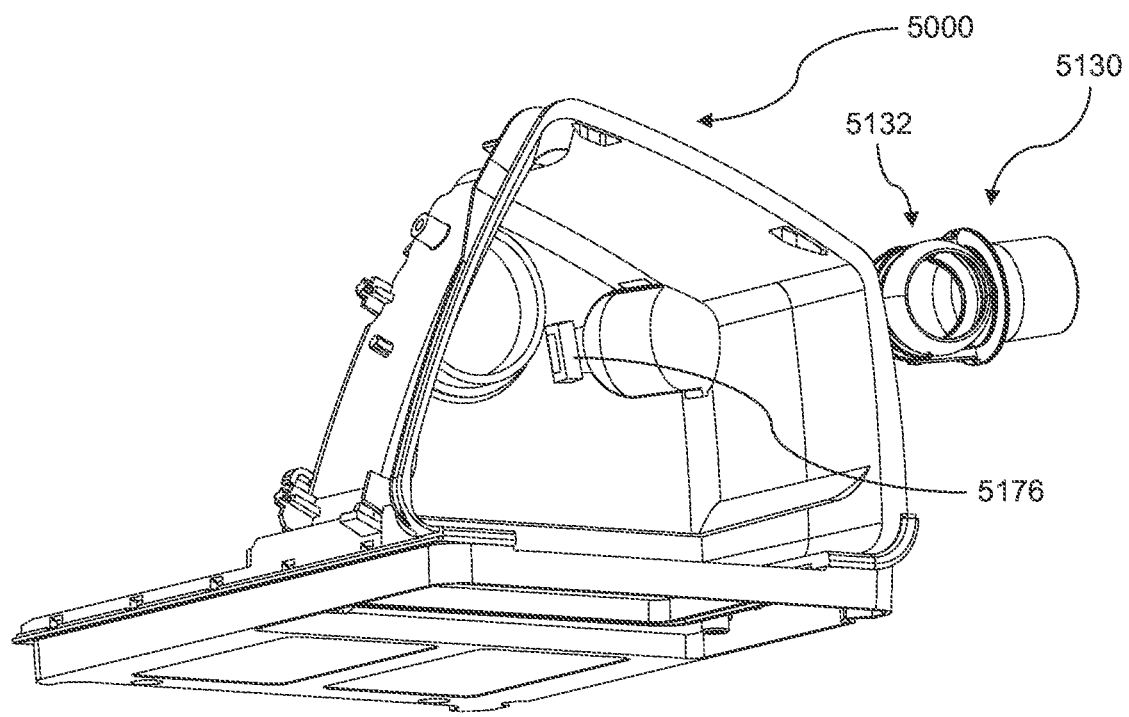

FIG. 19a shows an exploded bottom perspective view of a portion of a RPT device/humidifier and an airflow tube according to an example of the present technology.

Figure 19B:
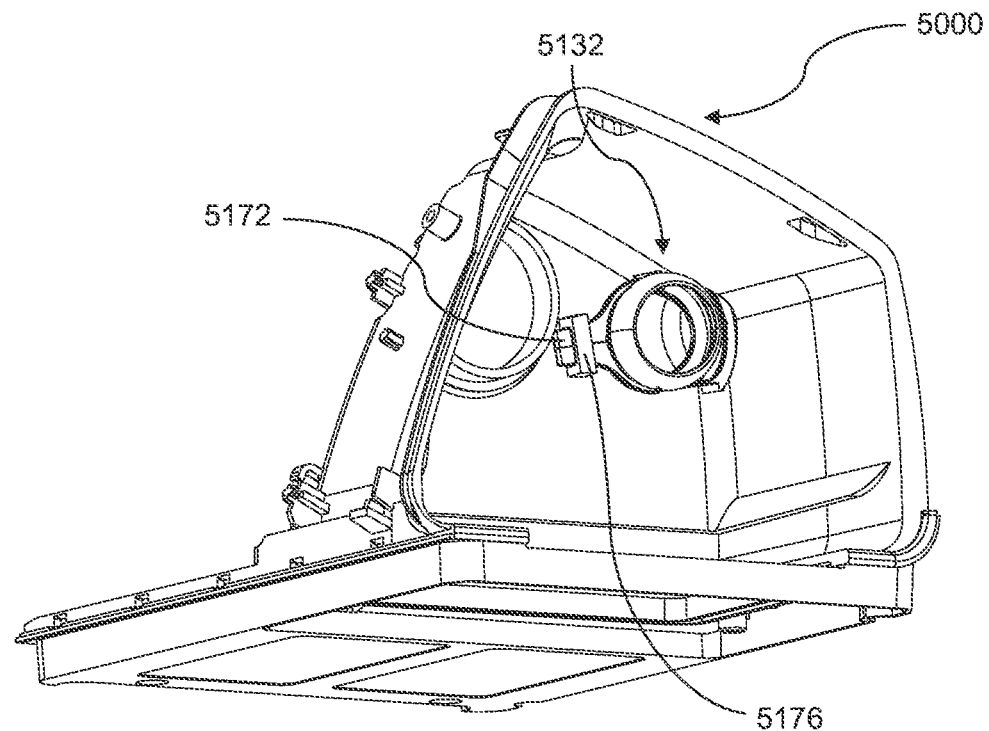

FIG. 19b shows a bottom perspective view of a portion of a RPT device/humidifier and an airflow tube according to an example of the present technology.

Figure 19C:
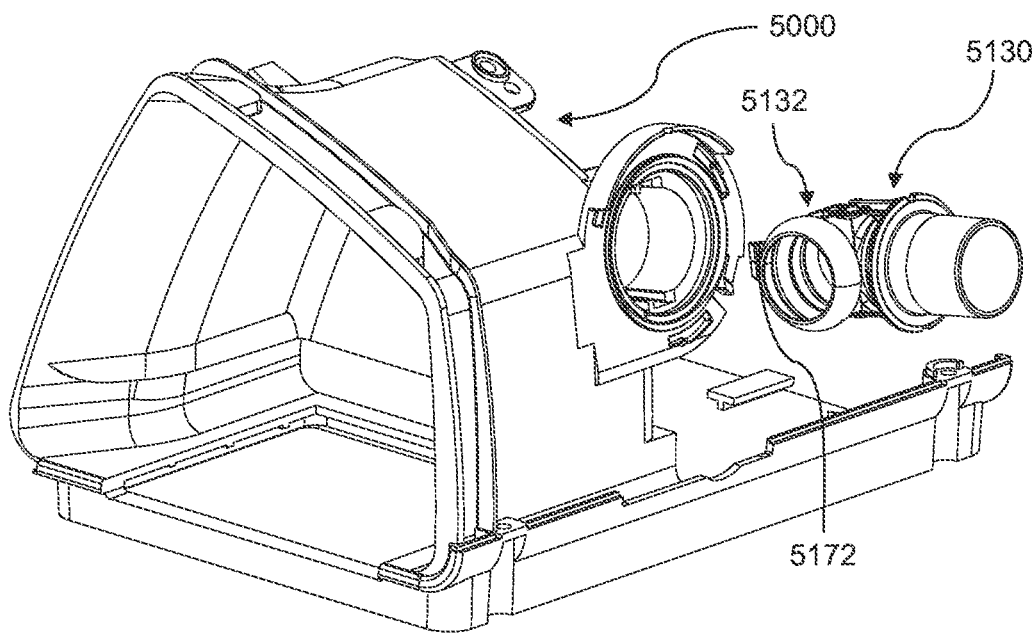

FIG. 19c shows an exploded rear perspective view of a portion of a RPT device/humidifier and an airflow tube according to an example of the present technology.

Figure 19D:
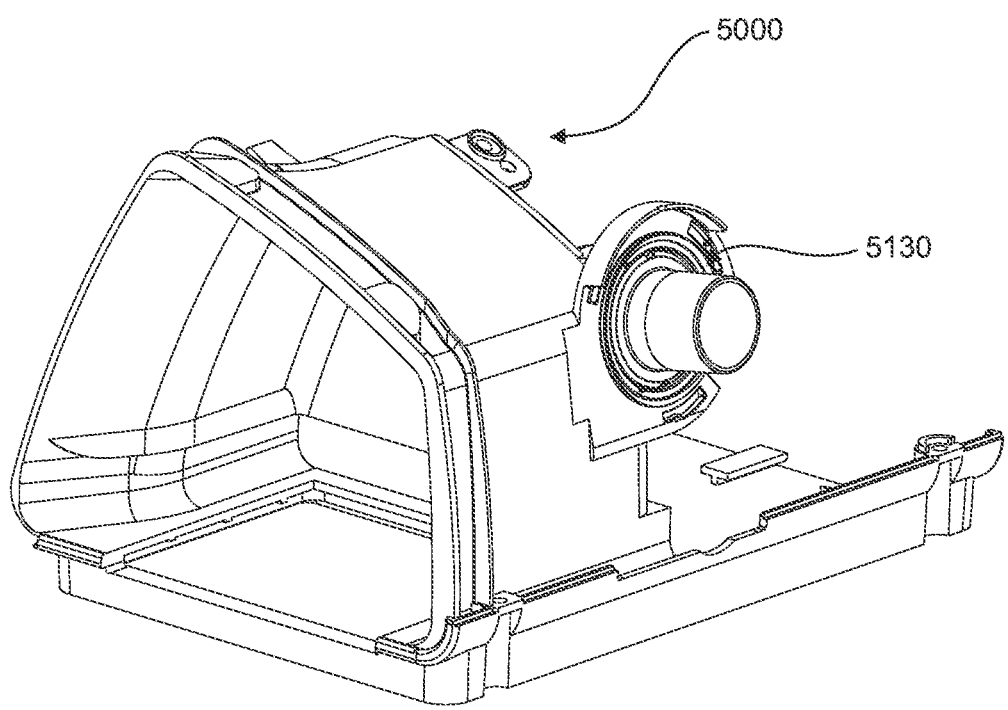

FIG. 19d shows a rear perspective view of a portion of a RPT device/humidifier and an airflow tube according to an example of the present technology.

Figure 19E:
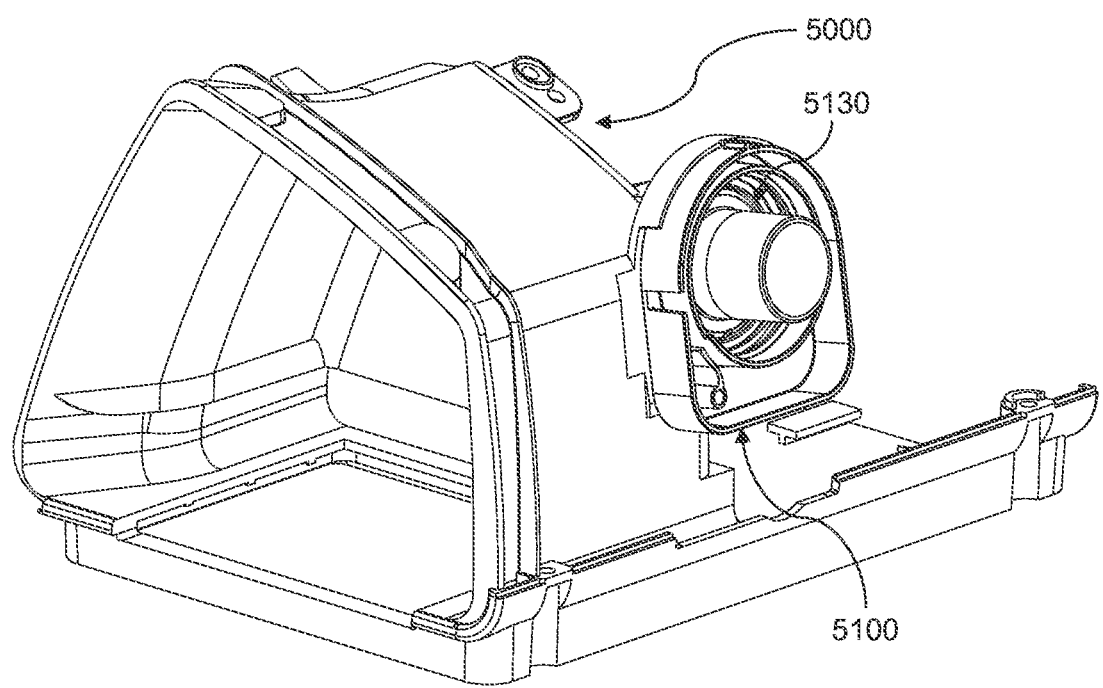

FIG. 19e shows a rear perspective view of a portion of a RPT device/humidifier, an airflow tube and a cable housing according to an example of the present technology.

Figure 20A:
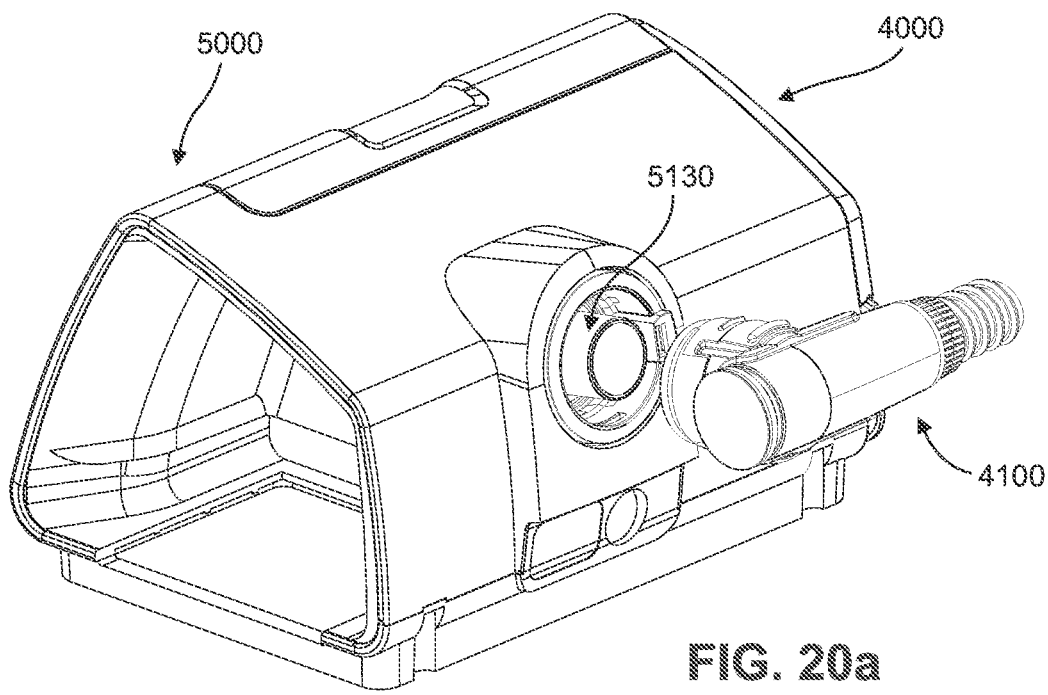

FIG. 20a shows an exploded rear perspective view of a RPT device/humidifier and an airflow tube according to an example of the present technology.

Figure 20B:
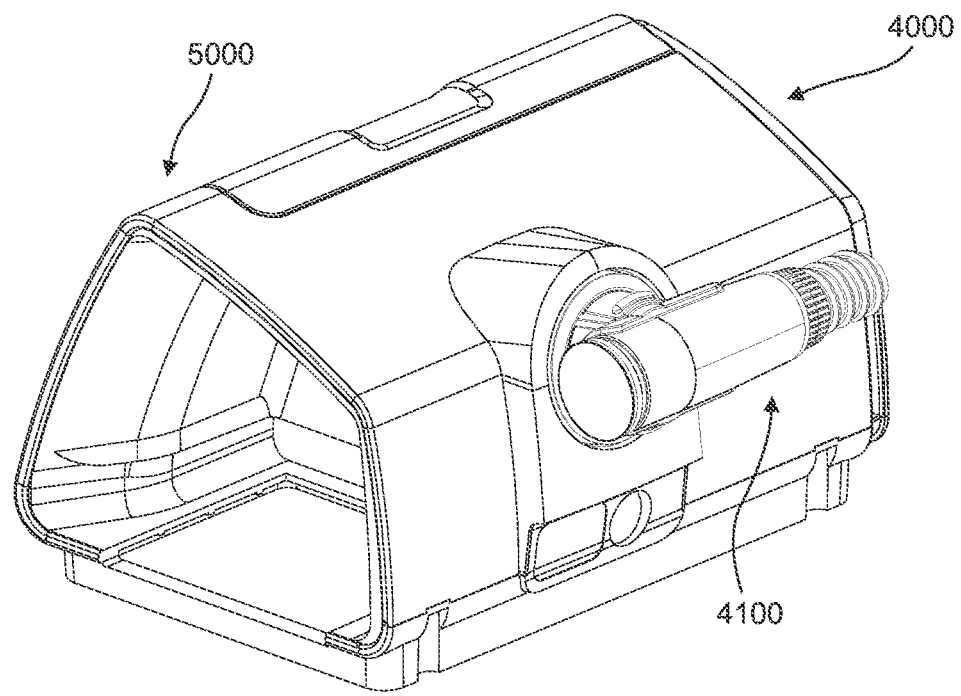

FIG. 20b shows a rear perspective view of a RPT device/humidifier and an airflow tube according to an example of the present technology.

Figure 21A:
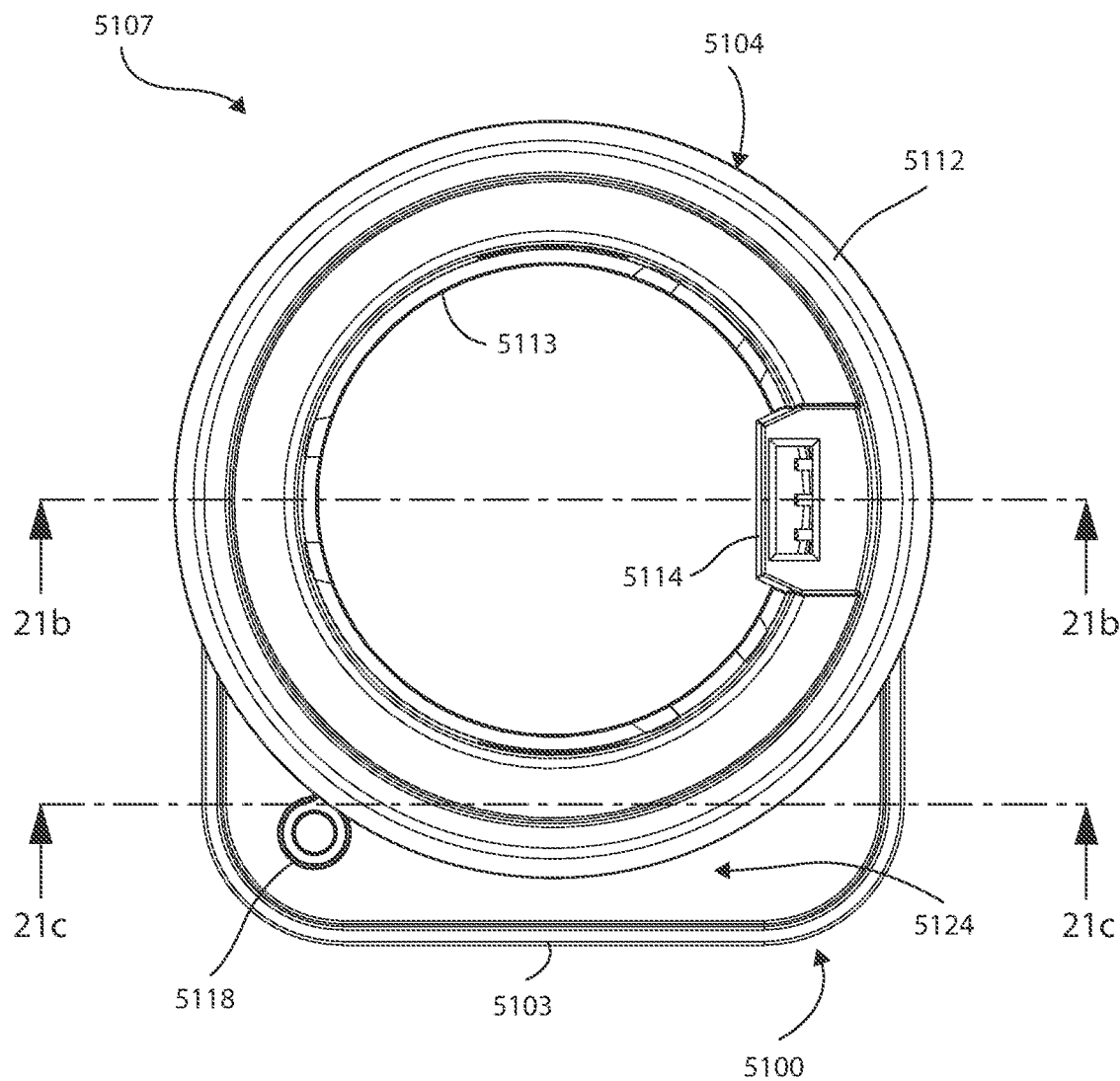

FIG. 21a shows a top view of an outlet assembly according to an example of the present technology.

Figure 21B:
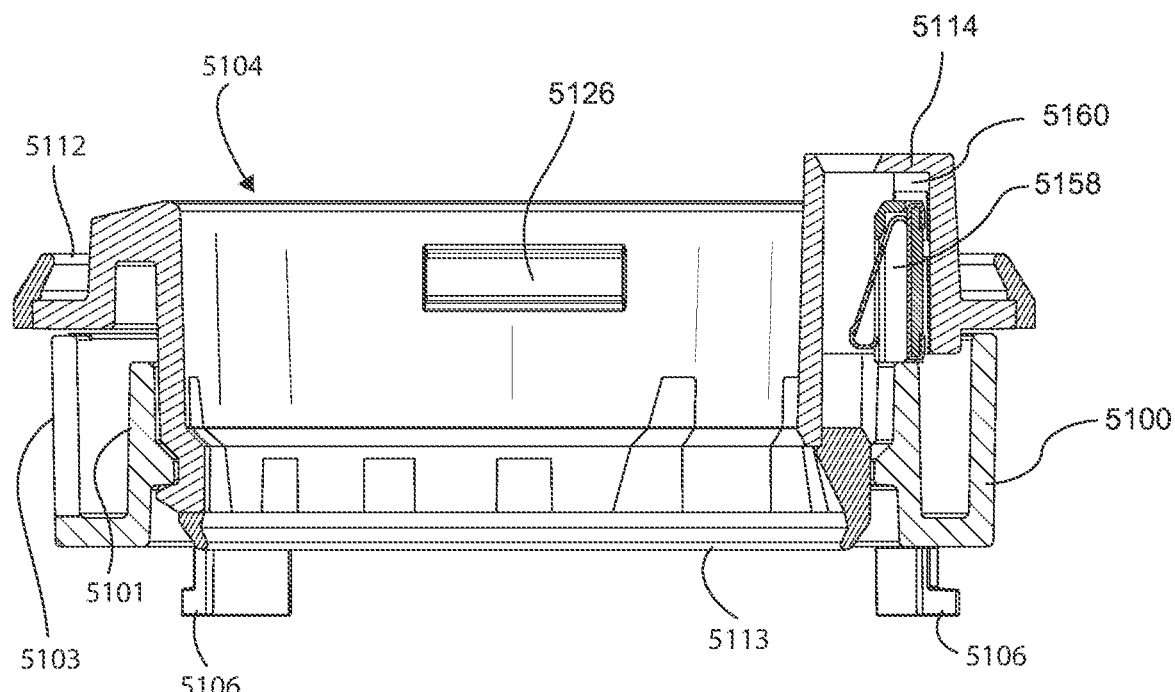

FIG. 21b shows a cross-sectional view of the outlet assembly of FIG. 21a taken through line 21b-21b according to an example of the present technology.

Figure 21C:
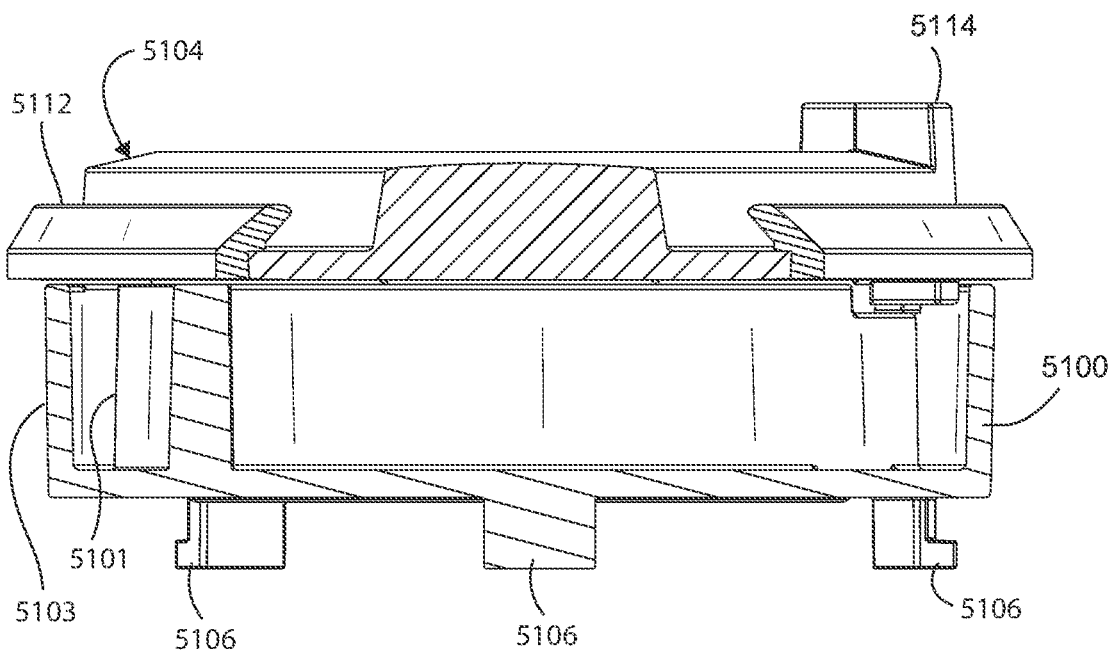

FIG. 21c shows a cross-sectional view of the outlet assembly of FIG. 21a taken through line 21c-21c according to an example of the present technology.

Figure 22A:
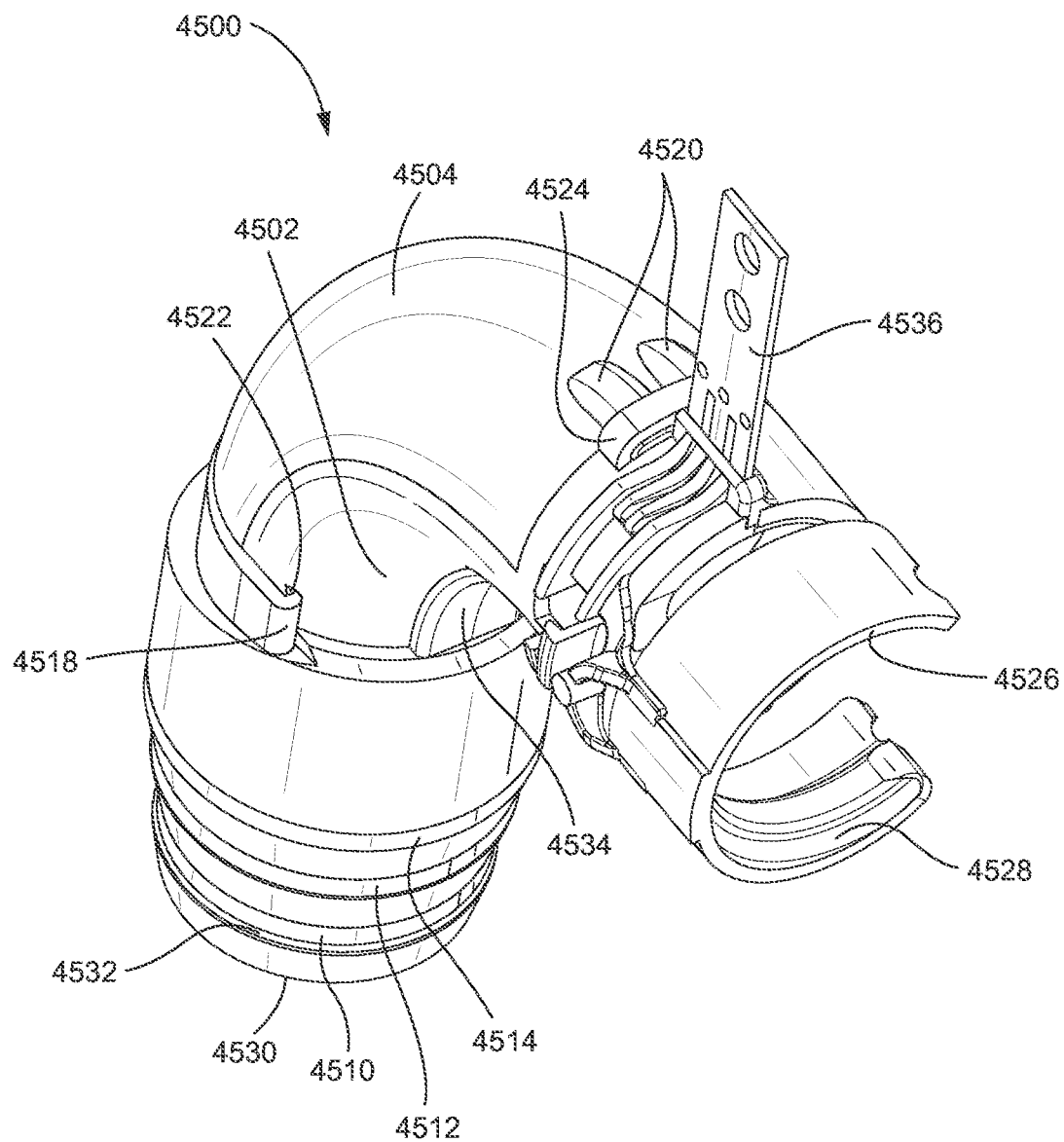

FIG. 22a shows a front perspective view of a substructure assembly of an outlet connector according to an example of the present technology.

Figure 22B:
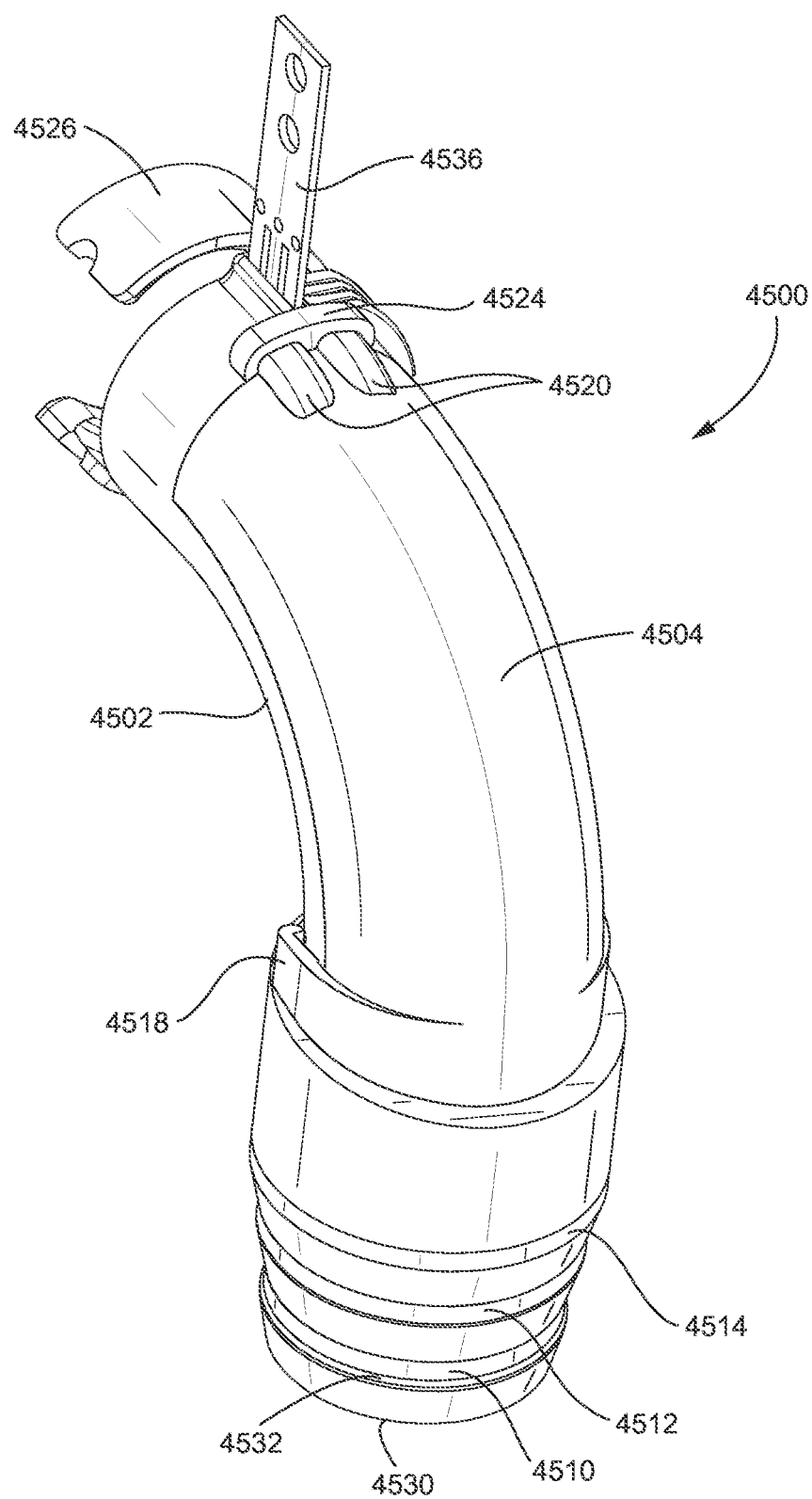

FIG. 22b shows a rear perspective view of a substructure assembly of an outlet connector according to an example of the present technology.

Figure 22C:
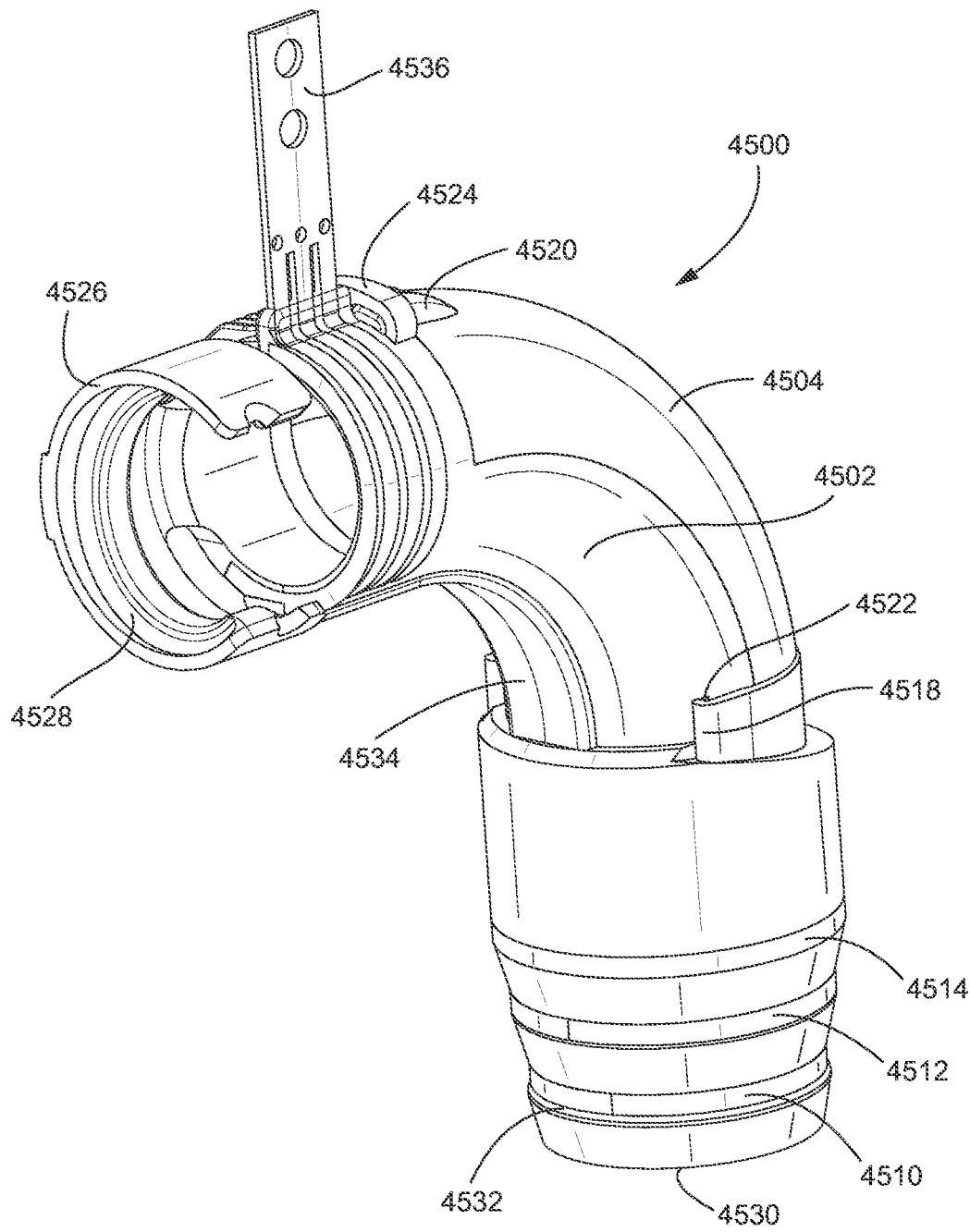

FIG. 22c shows another front perspective view of a substructure assembly of an outlet connector according to another example of the present technology.

FIG. 22d shows a side view of a substructure assembly of an outlet connector according to an example of the present technology.

FIG. 22e shows another side view of a substructure assembly of an outlet connector according to an example of the present technology.

FIG. 22f shows a top view of a substructure assembly of an outlet connector according to an example of the present technology.

Figure 22G:
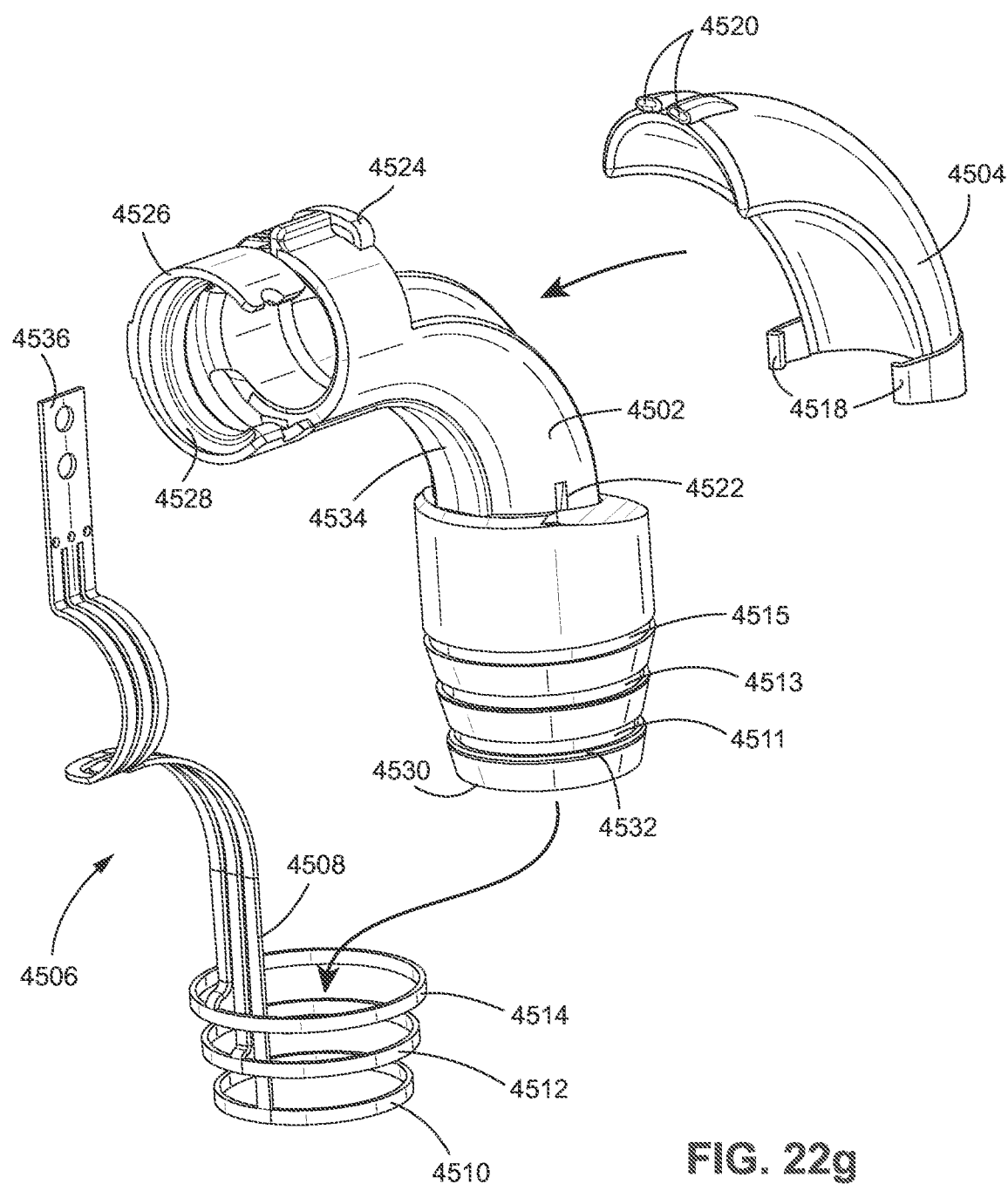

FIG. 22g shows an exploded front perspective view of a substructure assembly of an outlet connector according to an example of the present technology.

Figure 22H:
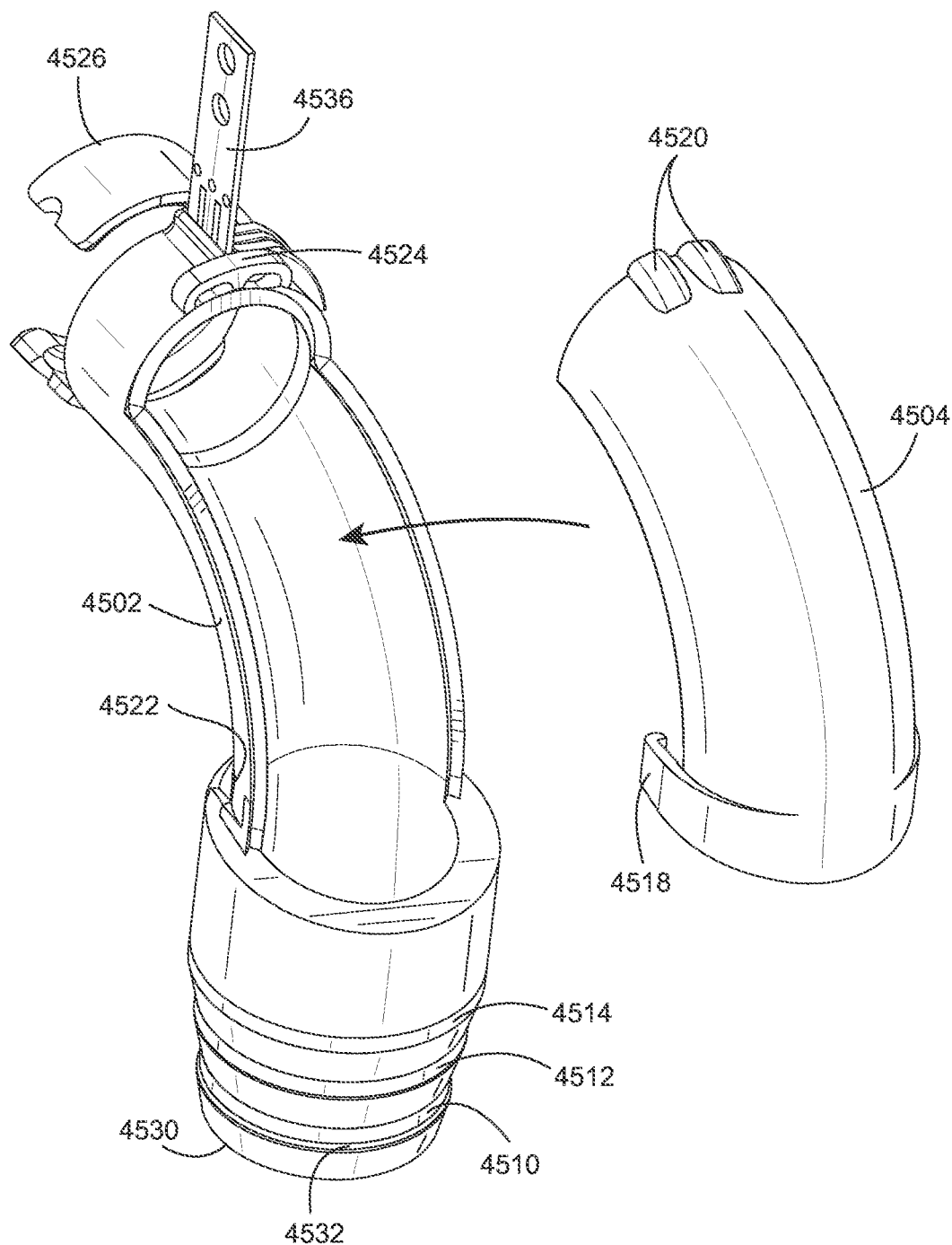

FIG. 22h shows a partially exploded rear perspective view of a substructure assembly of an outlet connector according to an example of the present technology.

Figure 23A:
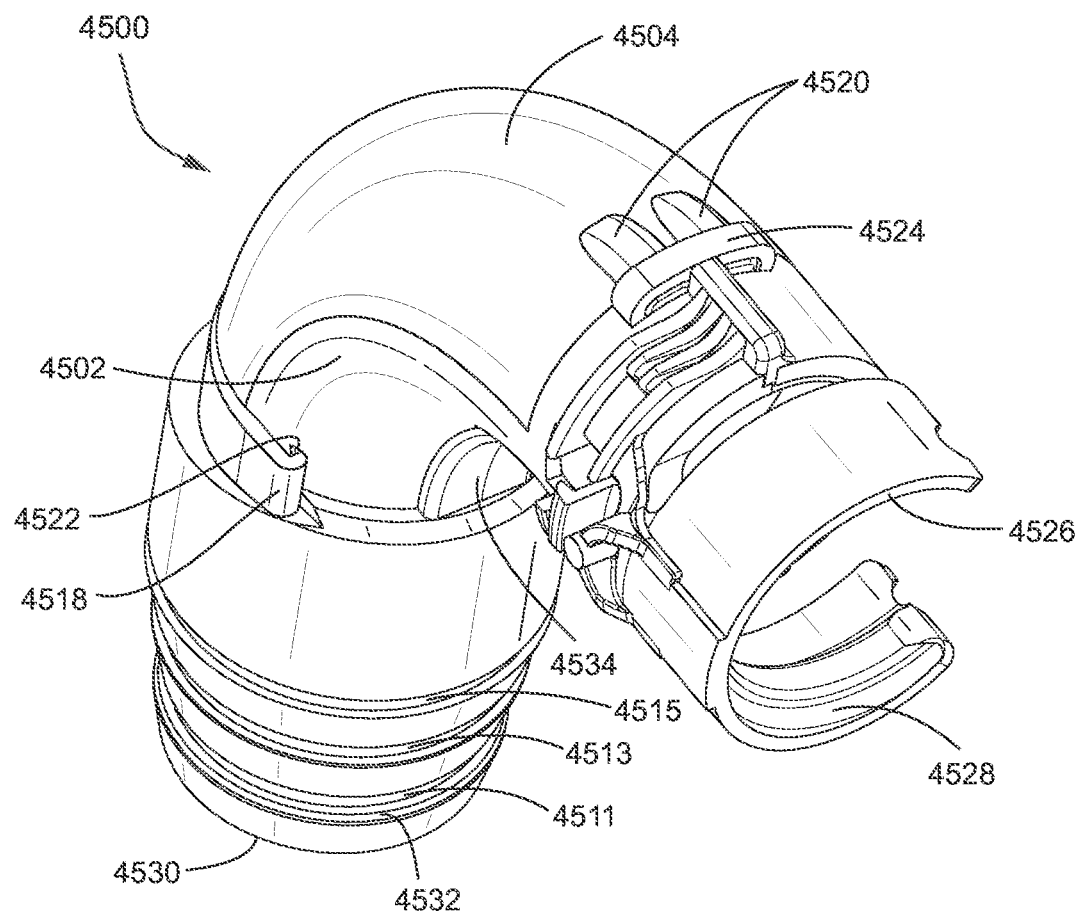

FIG. 23a shows a front perspective view of a substructure assembly of an outlet connector without electrical connectors according to an example of the present technology.

Figure 23B:
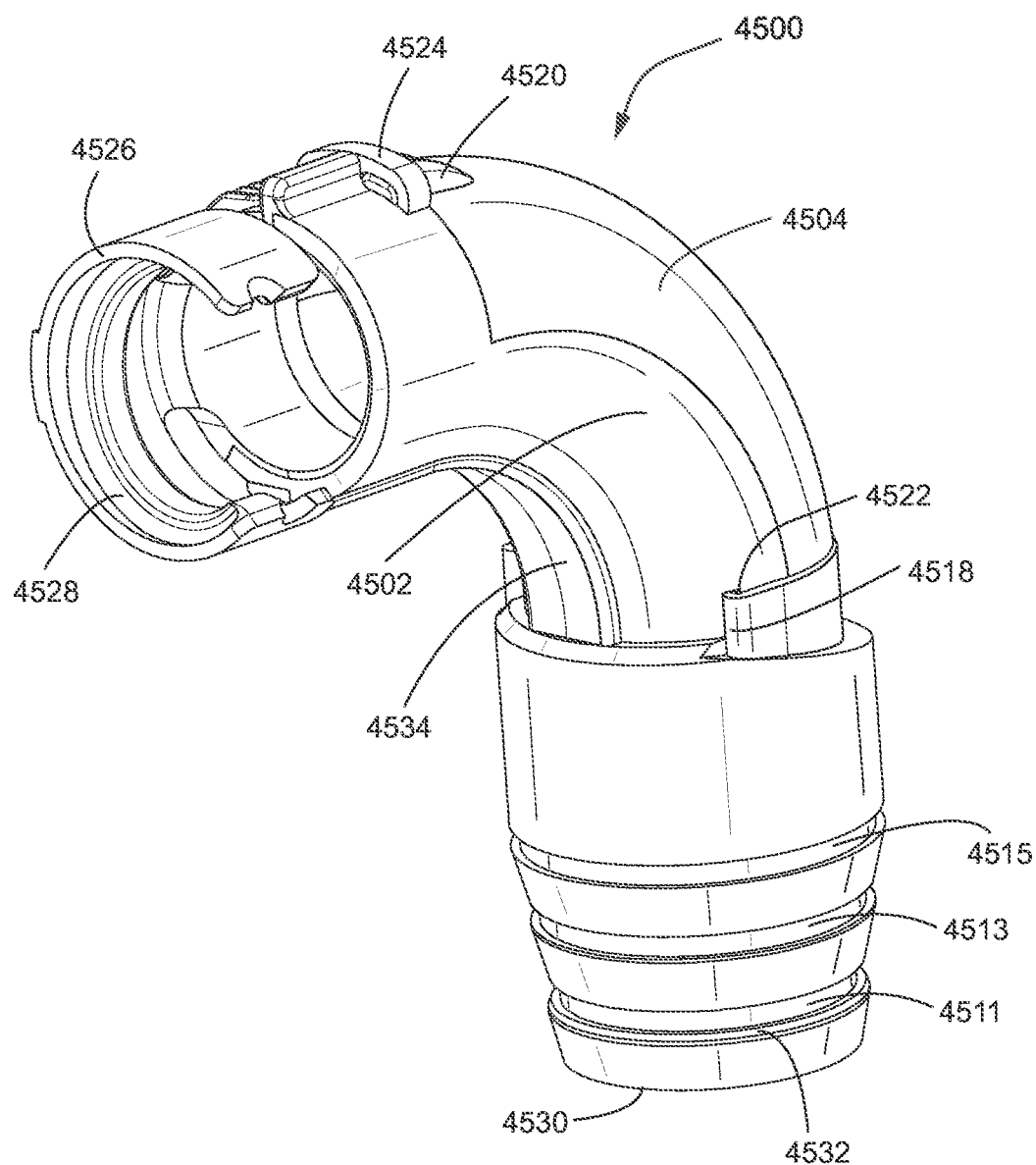

FIG. 23b shows another front perspective view of a substructure assembly of an outlet connector without electrical connectors according to an example of the present technology.

Figure 23C:
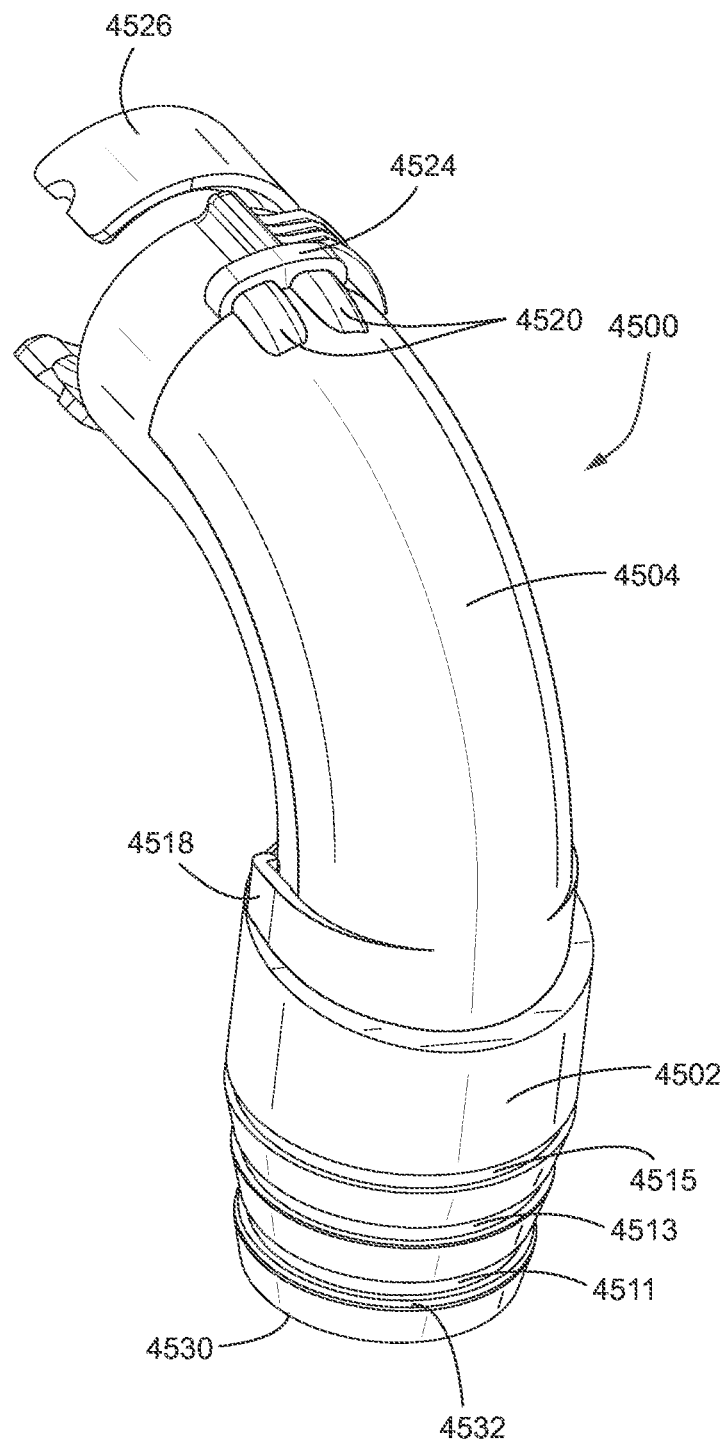

FIG. 23c shows a rear perspective view of a substructure assembly of an outlet connector without electrical connectors according to an example of the present technology.

Figure 23D:
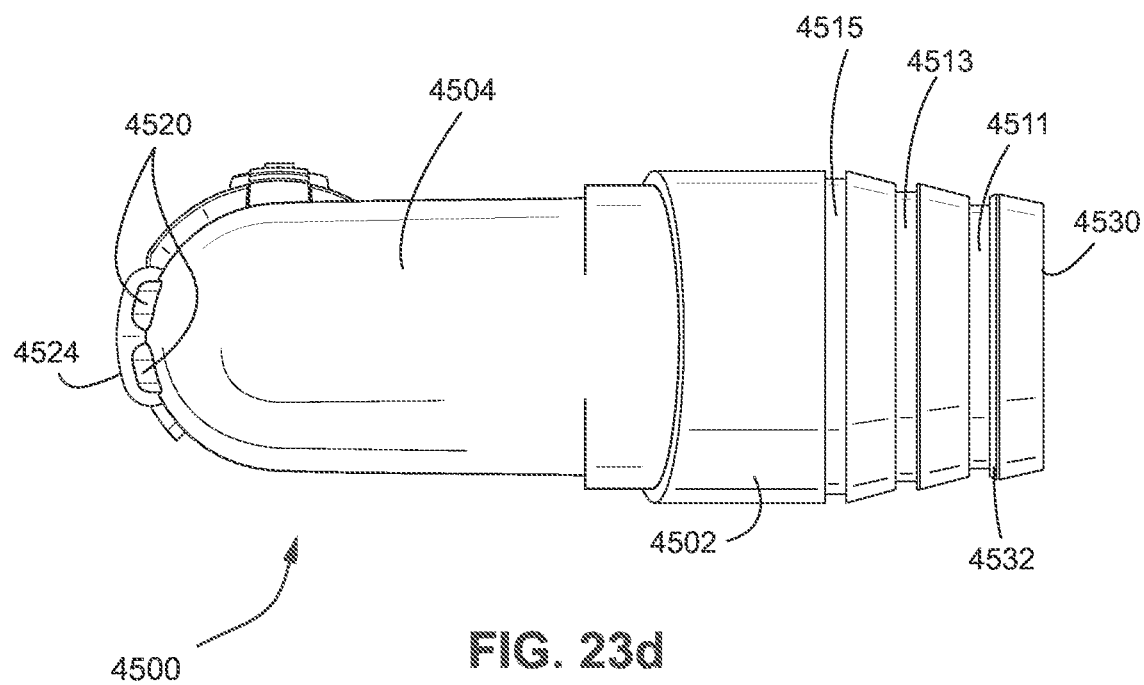

FIG. 23d shows a side view of a substructure assembly of an outlet connector without electrical connectors according to an example of the present technology.

Figure 23E:
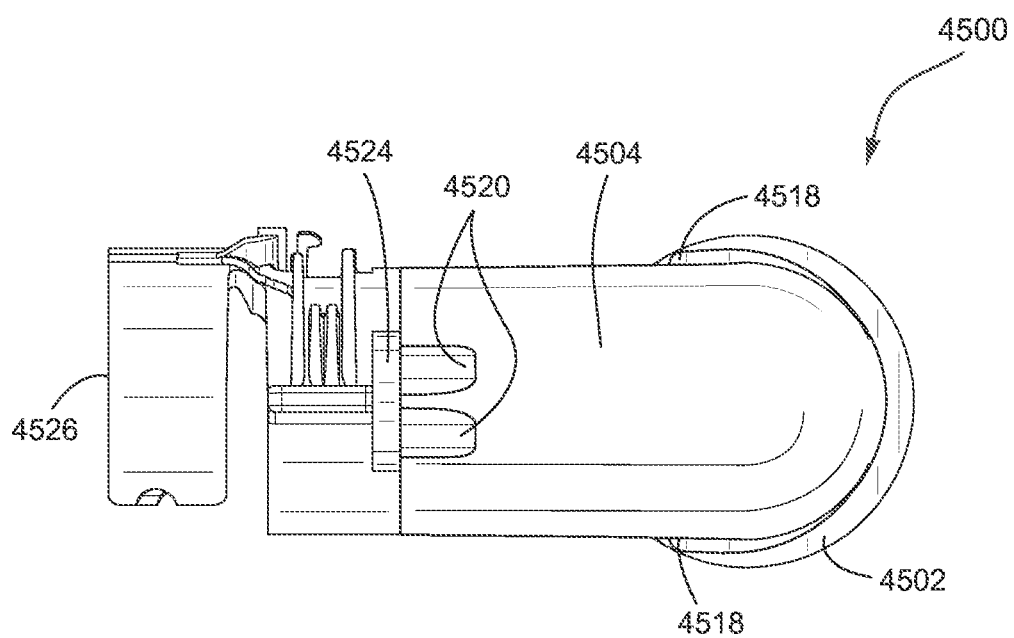

FIG. 23e shows a top view of a substructure assembly of an outlet connector without electrical connectors according to an example of the present technology.

Figure 23F:
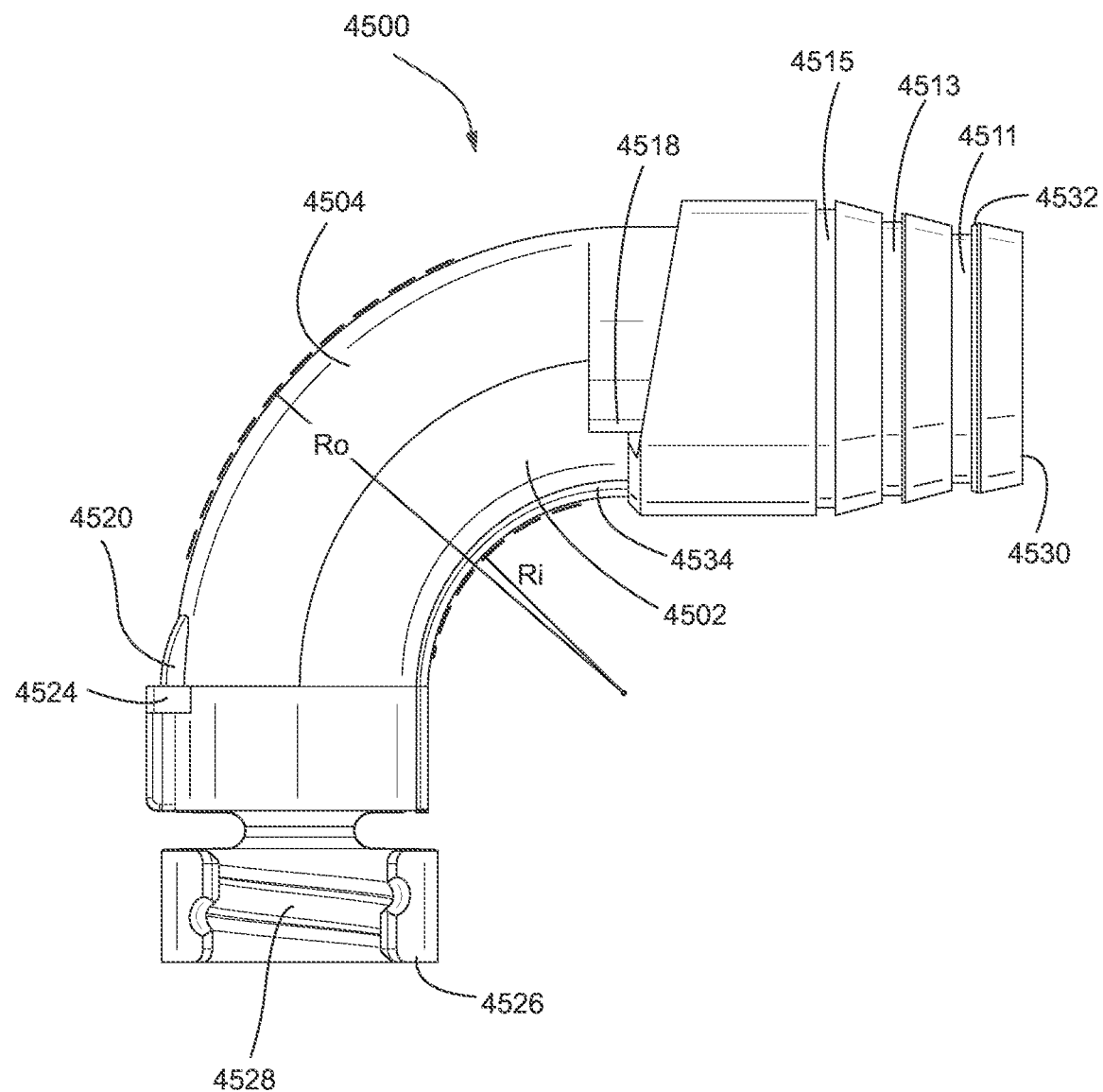

FIG. 23f shows another side view of a substructure assembly of an outlet connector without electrical connectors according to an example of the present technology.

Figure 24:
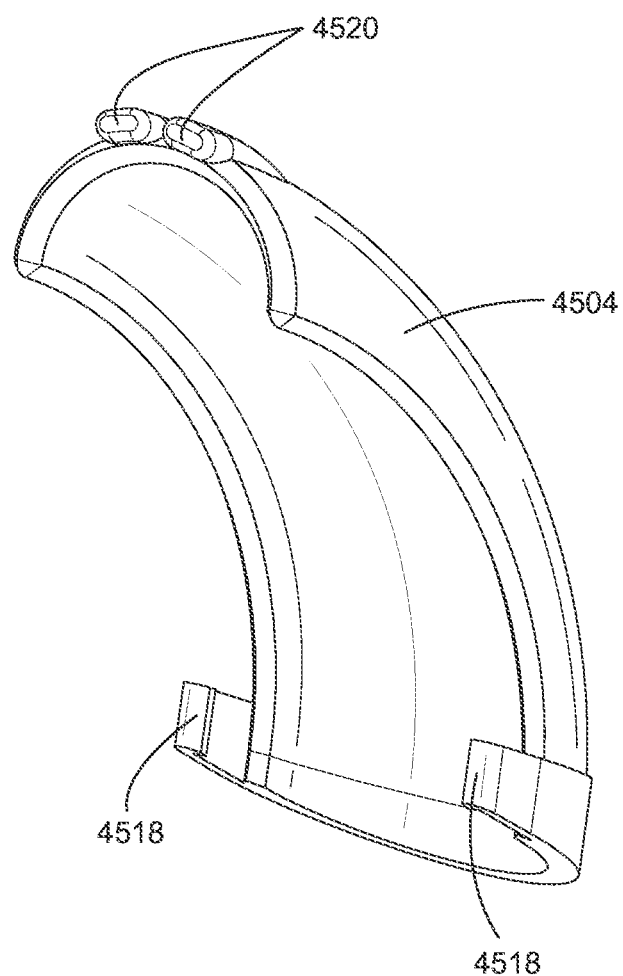

FIG. 24 shows a cap for a substructure assembly of an outlet connector according to an example of the present technology.

Figure 25A:
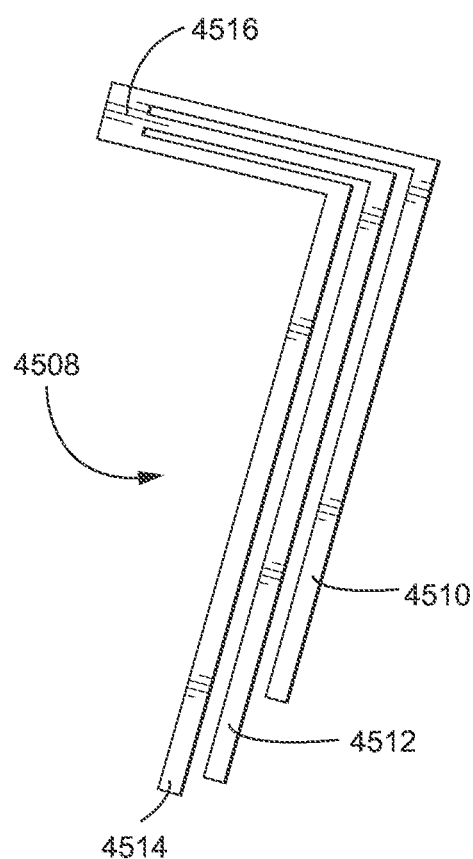

FIG. 25a shows unformed electrical connectors for an outlet connector according to an example of the present technology.

Figure 25B:
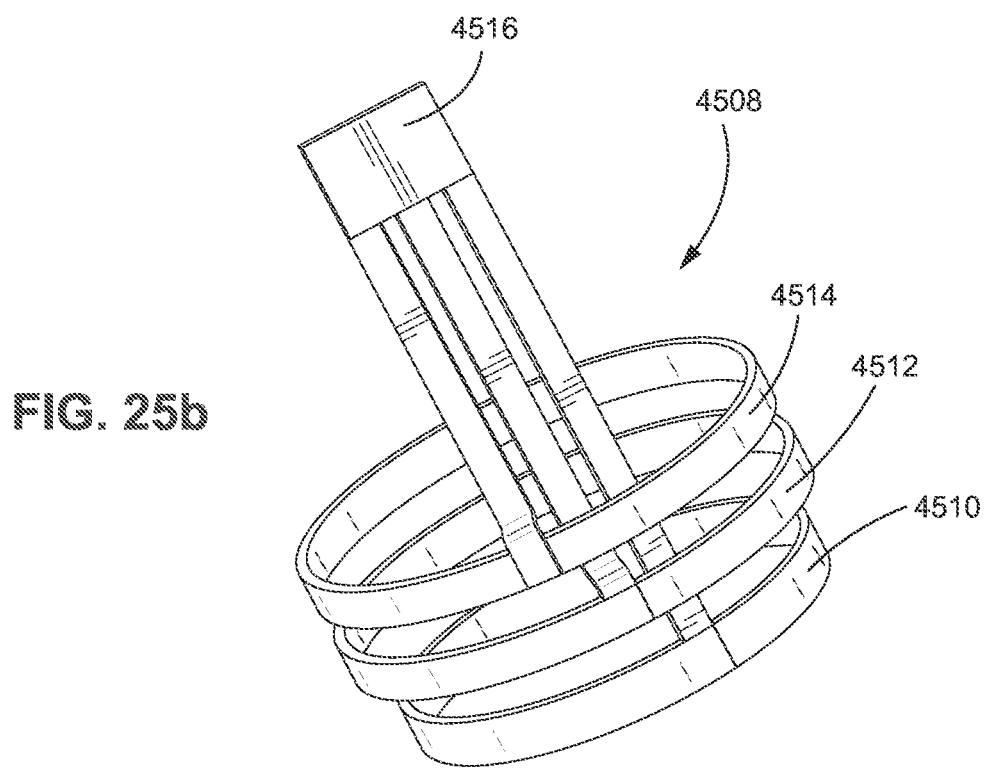

FIG. 25b shows formed electrical connectors for an outlet connector according to an example of the present technology.

FIG. 26a shows a cross-sectional view an outlet end of an outlet connector joined to a respiratory apparatus according to an example of the present technology.

Figure 26B:
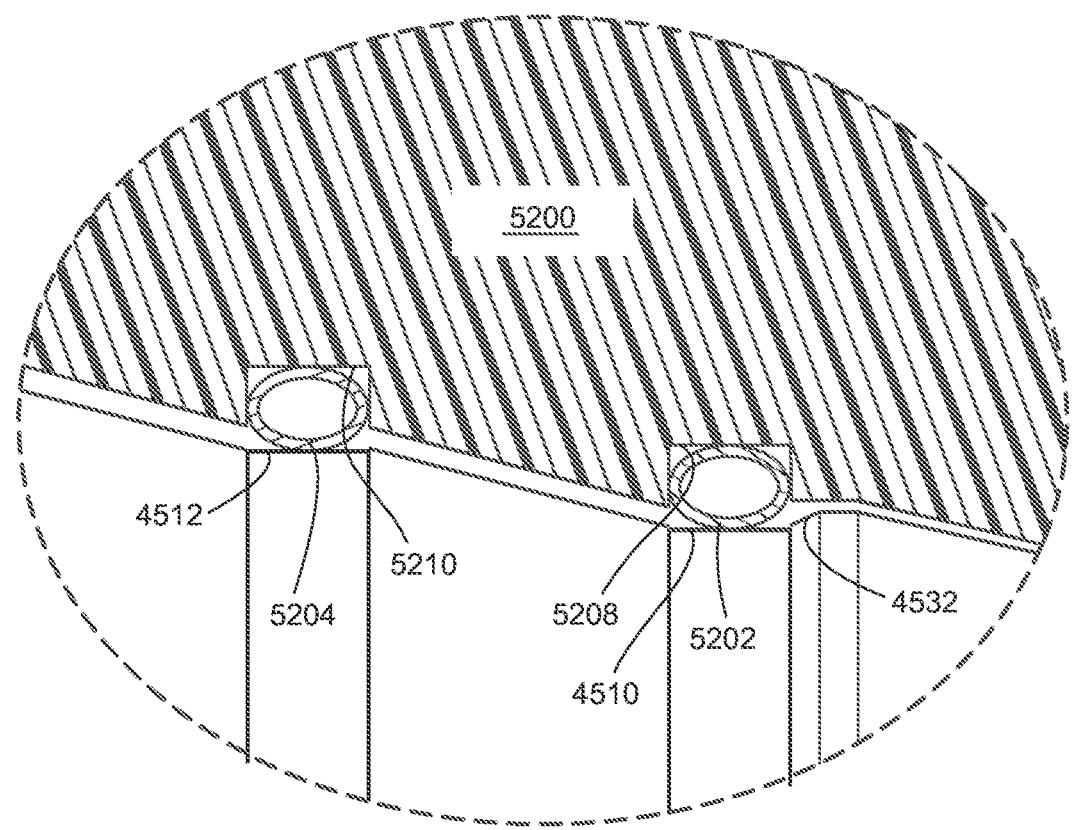

FIG. 26b shows a detailed cross-sectional view an outlet end of an outlet connector joined to a respiratory apparatus according to an example of the present technology.

FIG. 27a shows a cross-sectional view an outlet end of an outlet connector joined to a respiratory apparatus according to an example of the present technology.

FIG. 27b shows a cross-sectional view an outlet end of an outlet connector joined to a respiratory apparatus according to an example of the present technology.

FIG. 27c shows a detailed cross-sectional view an outlet end of an outlet connector joined to a respiratory apparatus according to an example of the present technology.

FIG. 28a shows a cross-sectional view an outlet end of an outlet connector joined to a respiratory apparatus according to an example of the present technology.

FIG. 28b shows a cross-sectional view an outlet end of an outlet connector joined to a respiratory apparatus according to an example of the present technology.

FIG. 28c shows a detailed cross-sectional view an outlet end of an outlet connector joined to a respiratory apparatus according to an example of the present technology.

Figure 29A:
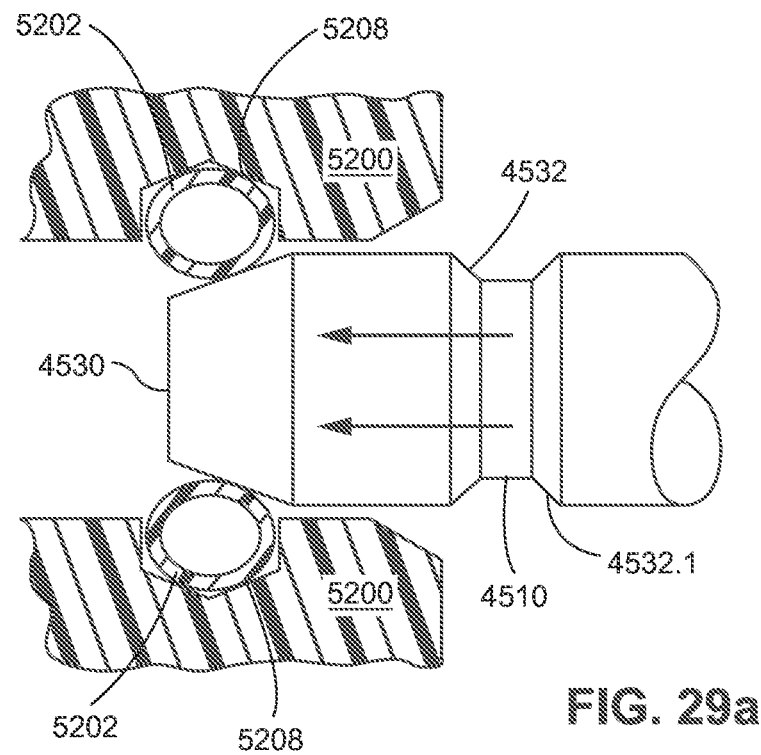

FIG. 29*a* shows a cross-sectional view an outlet end of an outlet connector being joined to a respiratory apparatus according to an example of the present technology.

Figure 29B:
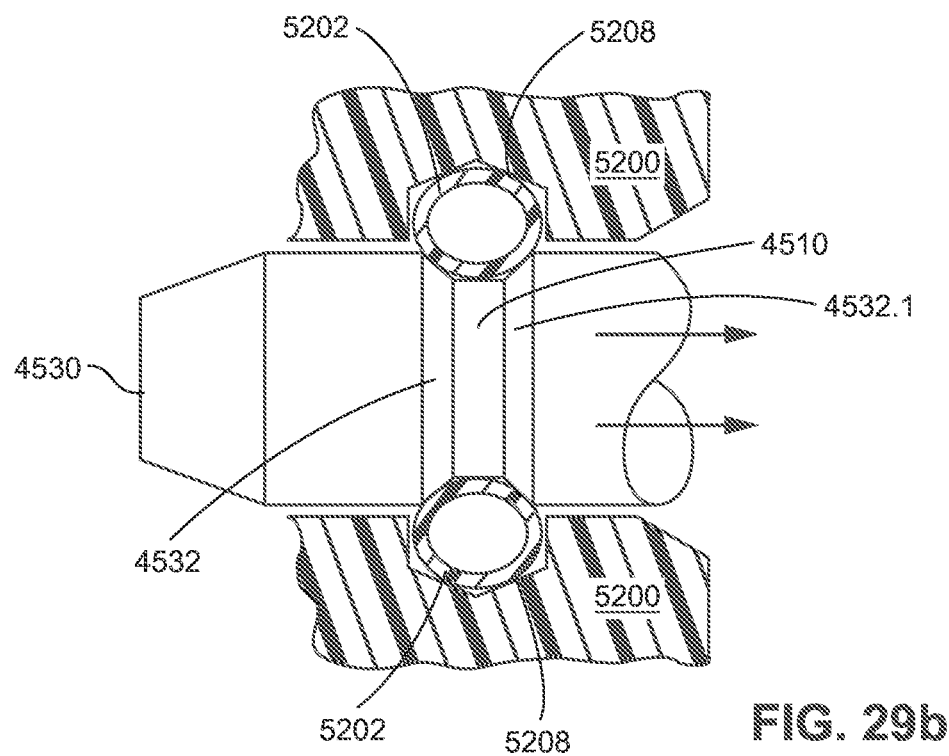

FIG. 29*b* shows a cross-sectional view an outlet end of an outlet connector after being joined to a respiratory apparatus according to an example of the present technology.

Figure 30A:
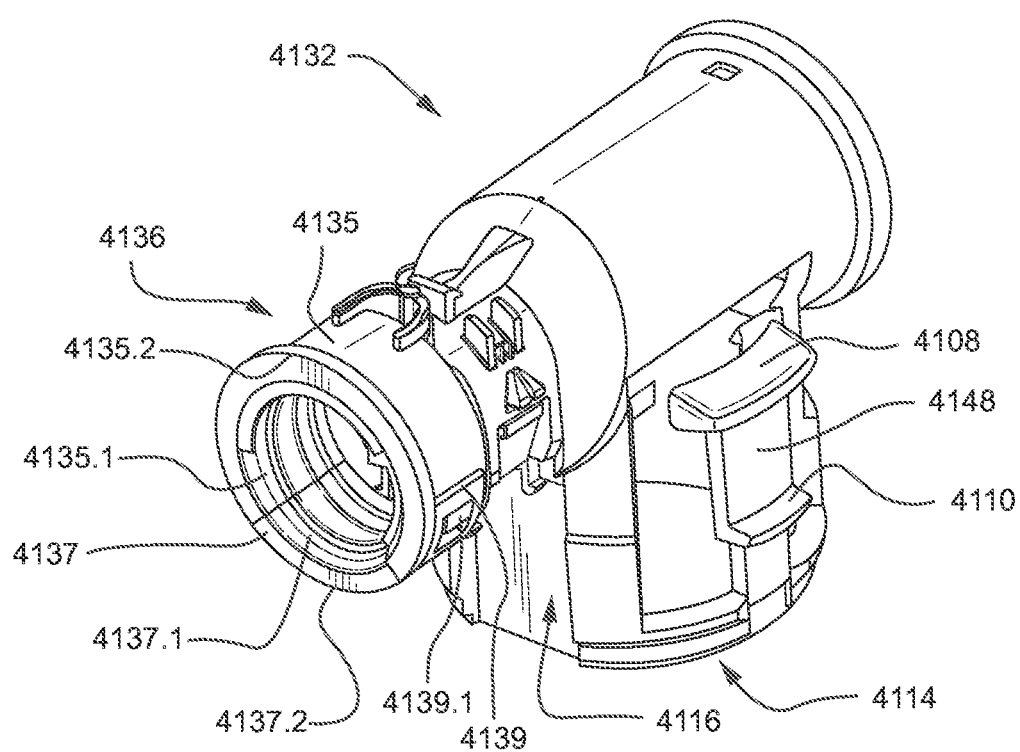

FIG. 30*a* shows a front perspective view of a substructure assembly of an outlet connector according to an example of the present technology.

Figure 30B:
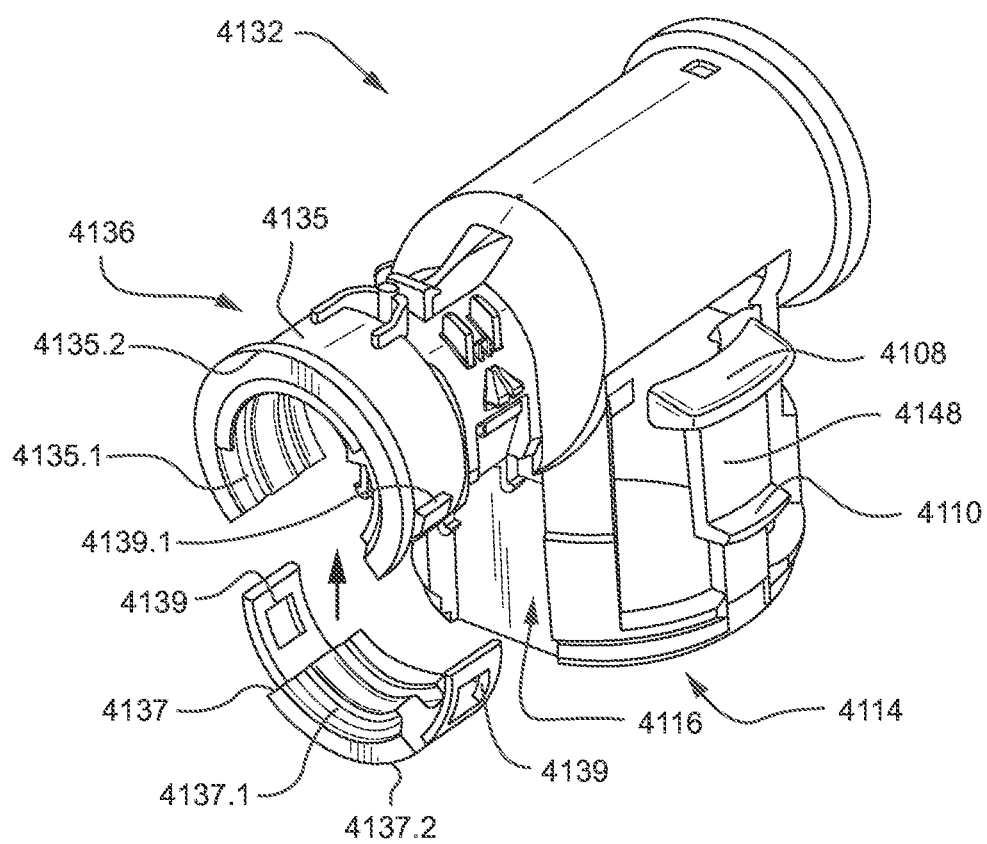

FIG. 30*b* shows an exploded front perspective view of a substructure assembly of an outlet connector according to an example of the present technology.

Figure 30C:
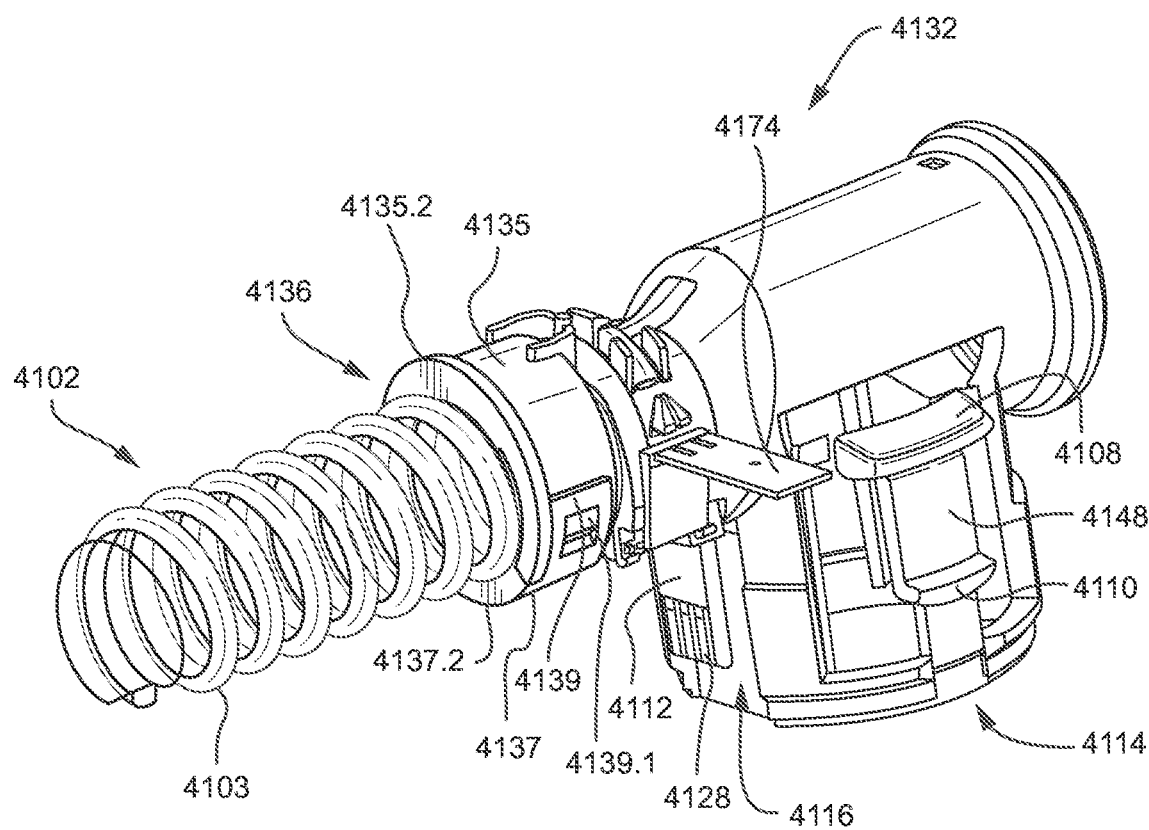

FIG. 30*c* shows a perspective view of a substructure assembly of an outlet connector joined to a tube portion according to an example of the present technology.

Figure 30D:
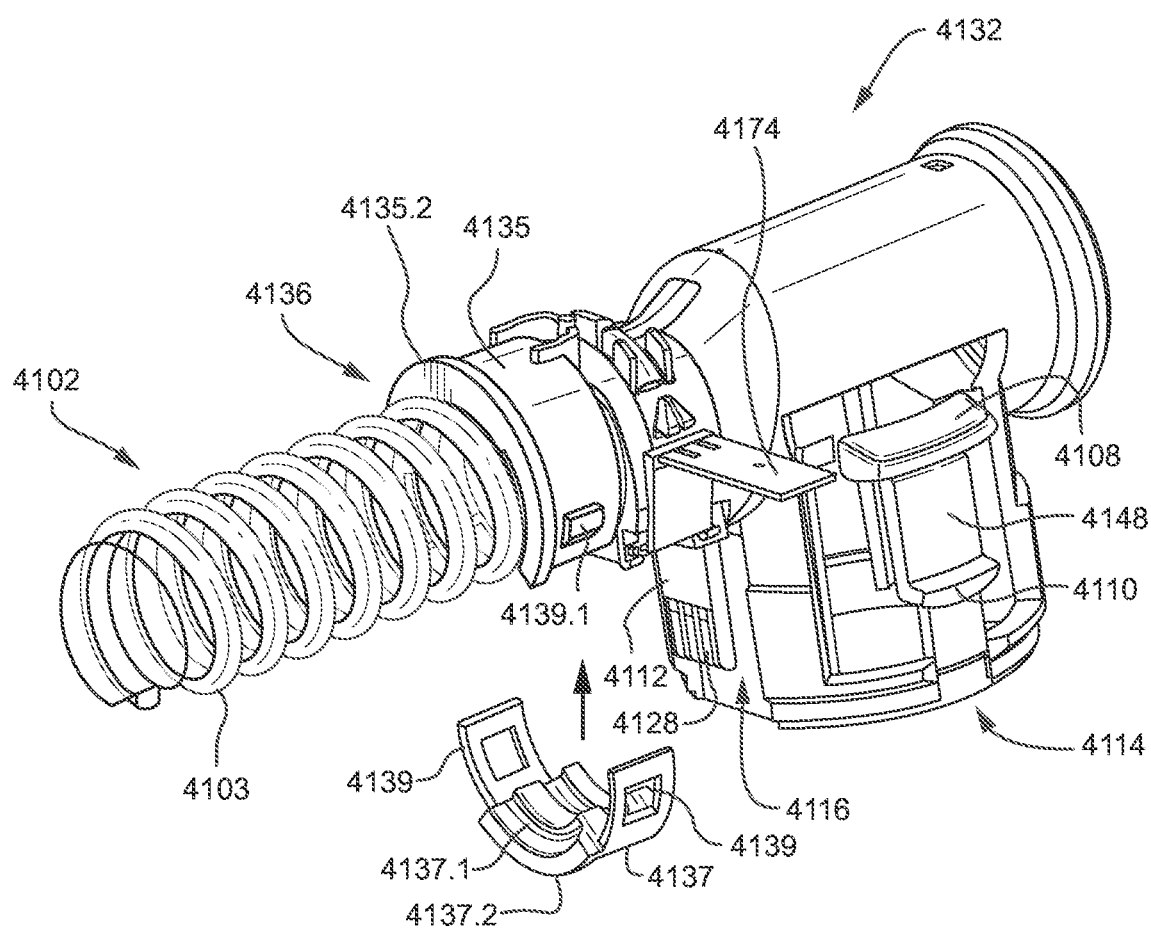

FIG. 30*d* shows a partially exploded perspective view of a substructure assembly of an outlet connector joined to a tube portion according to an example of the present technology.

Figure 30E:
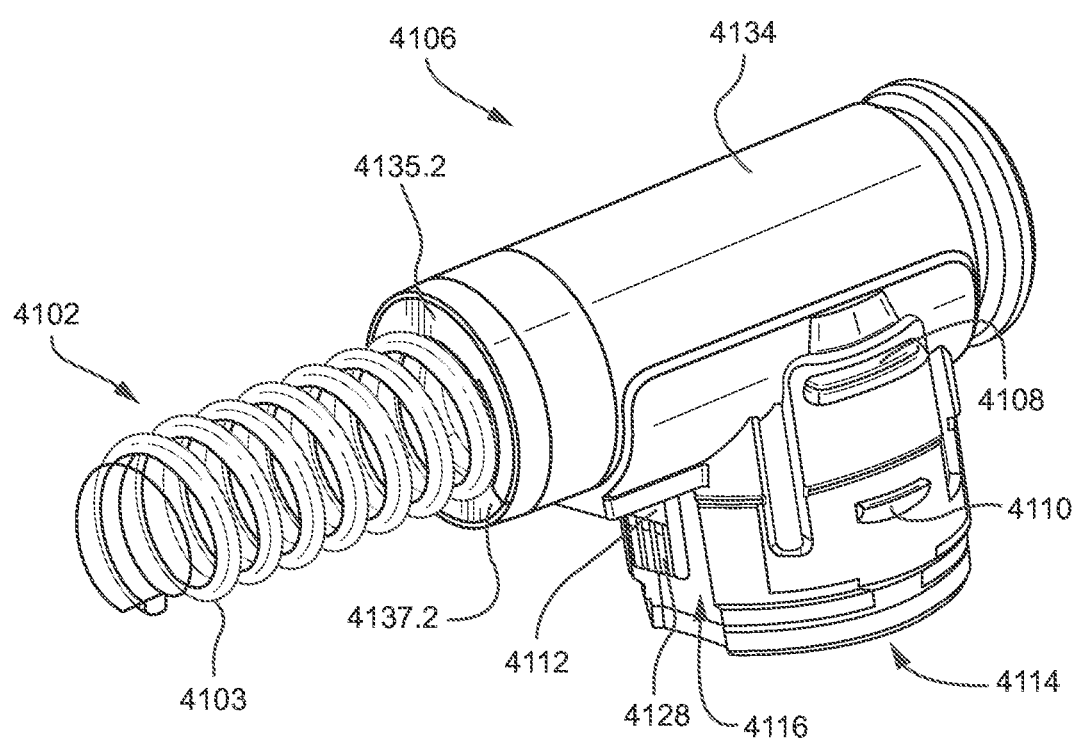

FIG. 30*e* shows a perspective view of an outlet connector joined to a tube portion according to an example of the present technology.

Figure 30F:
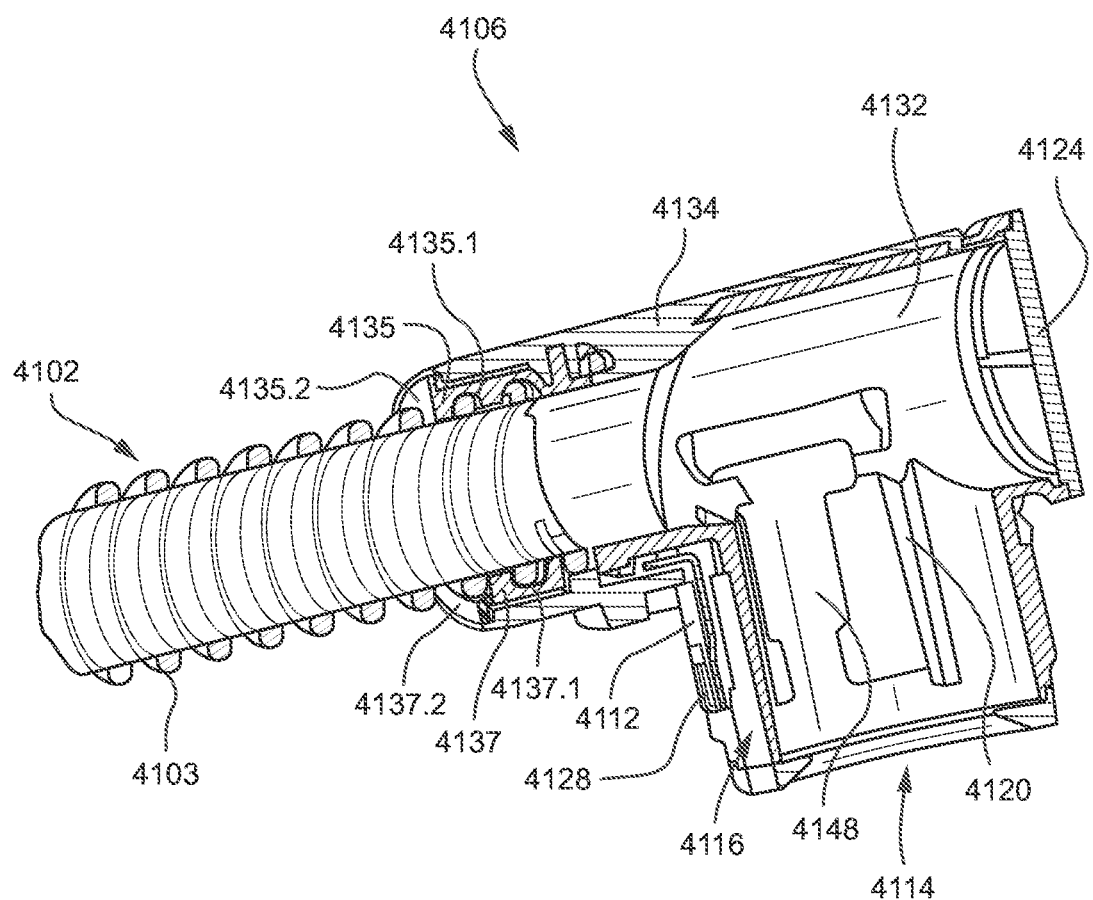

FIG. 30*f* shows a cross-sectional view of a substructure assembly of an outlet connector joined to a tube portion according to an example of the present technology.

Figure 30G:
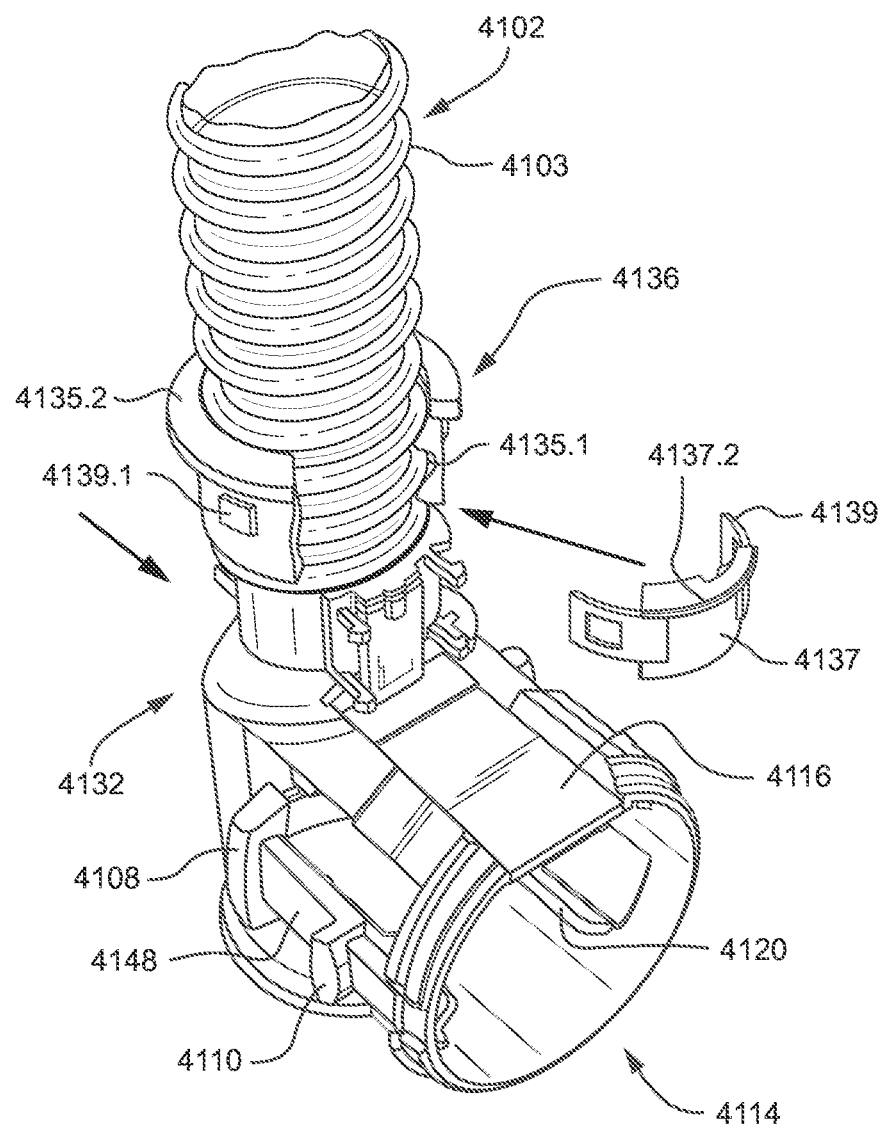

FIG. 30*g* shows a partially exploded bottom perspective view of a substructure assembly of an outlet connector joined to a tube portion according to an example of the present technology.

Figure 30H:
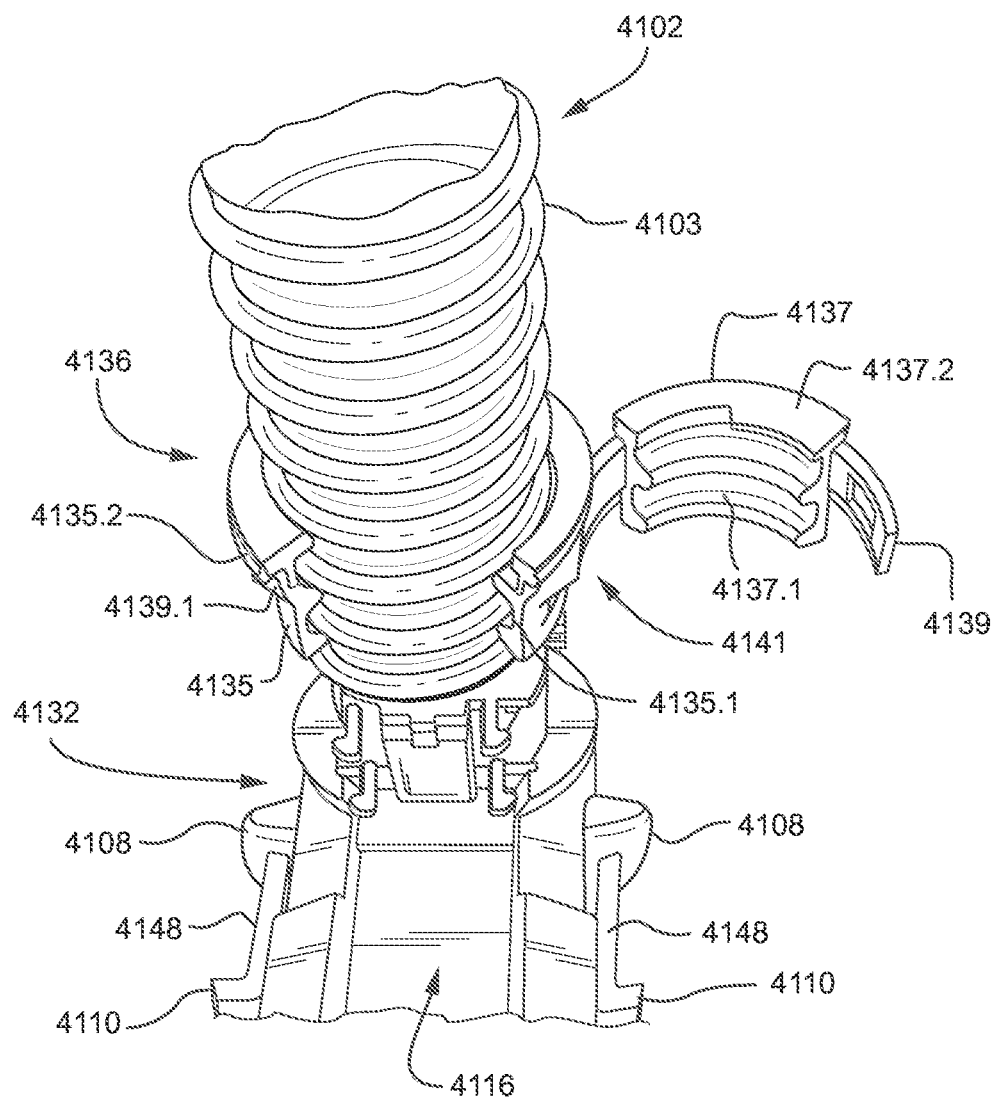

FIG. 30*h* shows a partially exploded bottom perspective view of a substructure assembly of an outlet connector joined to a tube portion according to an example of the present technology.

Figure 30I:
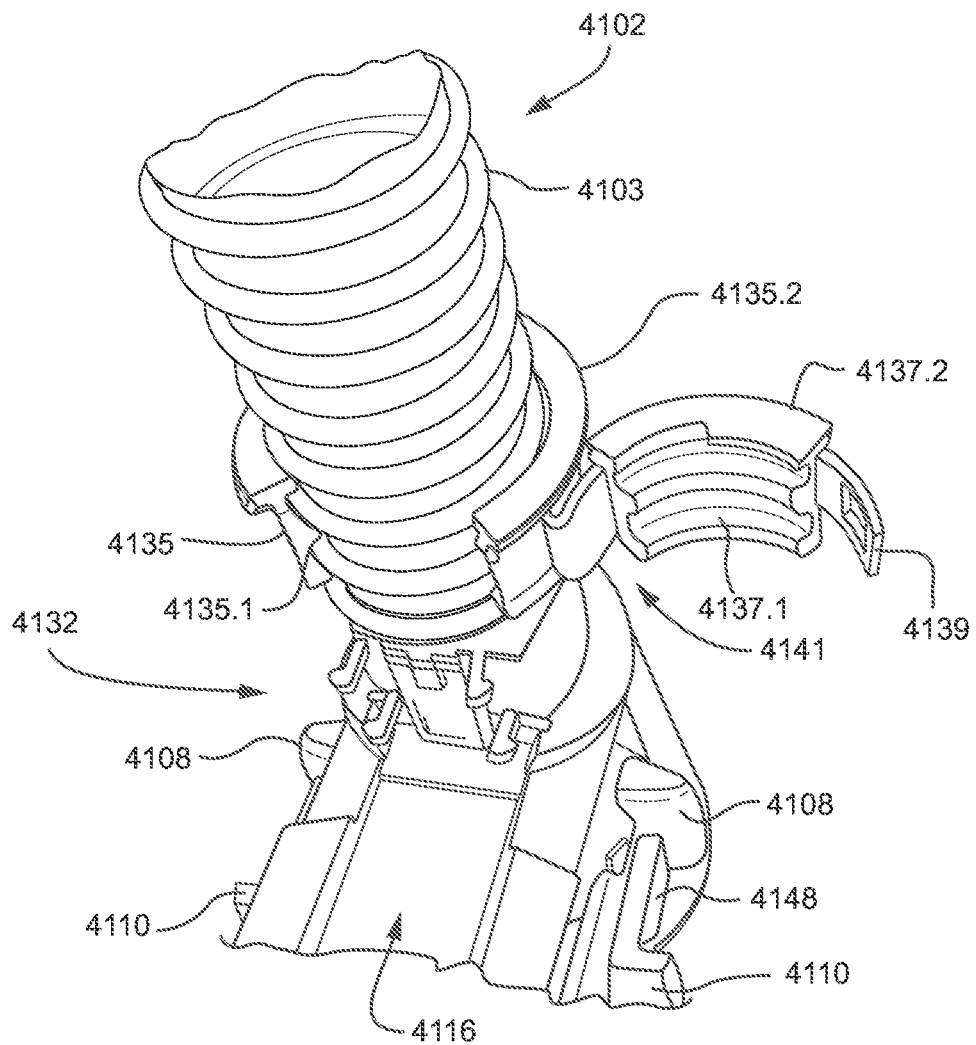

FIG. 30*i* shows another partially exploded bottom perspective view of a substructure assembly of an outlet connector joined to a tube portion according to an example of the present technology.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

6.1 Therapy Systems

In one form, the present technology comprises a respiratory therapy system for treating a respiratory disorder. The respiratory therapy system may comprise a RPT device 4000 for supplying a flow of breathable gas, such as air, to the patient 1000 via an air circuit 4100 leading to a patient interface 3000. In some forms, the respiratory therapy system may further comprise a humidifier 5000 configured to humidify the flow of air relative to the ambient.

6.2 Therapy

In one form, the present technology comprises a method for treating a respiratory disorder comprising the step of applying positive pressure to the entrance of the airways of a patient 1000.

In one form, the present technology comprises a method of treating Obstructive Sleep Apnea in a patient by applying nasal continuous positive airway pressure to the patient.

In certain examples of the present technology, a supply of air at positive pressure is provided to the nasal passages of the patient via one or both nares.

In certain examples of the present technology, mouth breathing is limited, restricted or prevented.

6.3 Patient Interface 3000

A non-invasive patient interface 3000 in accordance with one aspect of the present technology comprises the following functional aspects: a seal-forming structure 3100, a plenum chamber 3200, a positioning and stabilising structure 3300 and a connection port 3600 for connection to air circuit 4100. For example, see FIG. 2*c*. In some forms a functional aspect may be provided by one or more physical components. In some forms, one physical component may provide one or more functional aspects. In use the seal-forming structure is arranged to surround an entrance to the airways of the patient so as to facilitate the supply of air at positive pressure to the airways.

6.3.1 Seal-Forming Structure

In one form of the present technology, a seal-forming structure 3100 provides a sealing-forming surface, and may additionally provide a cushioning function.

A seal-forming structure in accordance with the present technology may be constructed from a soft, flexible, resilient material such as silicone.

In one form, the seal-forming structure comprises a sealing flange and a support flange. The sealing flange may comprise a relatively thin member with a thickness of less than about 1 mm, for example about 0.25 mm to about 0.45 mm, that extends around the perimeter of the plenum chamber. A support flange may be relatively thicker than the sealing flange. The support flange is disposed between the sealing flange and the marginal edge of the plenum chamber, and extends at least part of the way around the perimeter. The support flange is or includes a spring-like element and functions to support the sealing flange from buckling in use. In use the sealing flange can readily respond to system pressure in the plenum chamber acting on its underside to urge it into tight sealing engagement with the face.

In another form, the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose; a stalk, a flexible region on the underside of the cone and connecting the cone to the stalk. In addition, the structure to which the nasal pillow of the present technology is connected includes a flexible region adjacent the base of the stalk. The flexible regions can act in concert to facilitate a universal joint structure that is accommodating of relative movement—both displacement and angular—of the frusto-cone and the structure to which the nasal pillow is connected. For example, the frusto-cone may be axially displaced towards the structure to which the stalk is connected.

In one form the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

6.3.2 Plenum Chamber

The plenum chamber 3200 may have a perimeter that is shaped to be complementary to the surface contour of the face of an average person in the region where a seal will form in use. In use, a marginal edge of the plenum chamber is positioned in close proximity to an adjacent surface of the face. Actual contact with the face is provided by the seal-forming structure. The seal-forming structure may extend in use about the entire perimeter of the plenum chamber.

6.3.3 Positioning and Stabilising Structure

The seal-forming portion of the patient interface 3000 of the present technology may be held in sealing position in use by the positioning and stabilising structure 3300, for example a headgear system or strap.

6.3.4 Vent

In one form, the patient interface 3000 may include a vent 3400 constructed and arranged to allow for the washout of exhaled carbon dioxide.

One form of the vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent may be located in a decoupling structure, e.g. a swivel or ball and socket.

6.3.5 Other Patient Interface Components

The patient interface 3000 may include one or more of the following additional components:
 (i) a forehead support 3700 that assists with supporting the patient interface on the face;
 (ii) an anti-asphyxia valve to allow a patient 1000 to receive fresh air into the patient interface 3000 if required; and
 (iii) one or more ports (e.g. connection port 3600) to allow access to the volume within the plenum chamber. In one form this allows a clinician to supply supplemental oxygen. In one form, this allows for the direct measurement of a property of gases within the plenum chamber, such as the pressure.

6.4 RPT Device 4000

A RPT device 4000 in accordance with one aspect of the present technology (see FIG. 3*a*) comprises mechanical and pneumatic components 4300, electrical components 4200 and is programmed to execute one or more algorithms. An exemplary RPT device has an external housing 4010, formed in two parts, an upper portion 4012 and a lower portion 4014. Furthermore, the external housing 4010 may include one or more panel(s) 4015. The RPT device 4000 may comprise a chassis 4016 that supports one or more internal components of the RPT device 4000. In one form a pneumatic block 4020 is supported by, or formed as part of the chassis 4016. The RPT device 4000 may include a handle 4018. Another example of an RPT device 4000 including an integrated humidifier 5000 is shown in FIGS. 3*b*-3*d*.

The pneumatic path of the RPT device 4000 (e.g. shown in FIG. 3*e*) may comprise an inlet air filter 4312, an inlet muffler 4322, a controllable pressure device 4340 capable of supplying air at positive pressure (e.g., a blower 4342), and an outlet muffler 4324. One or more pressure transducers and flow transducers may be included in the pneumatic path.

A pneumatic block 4020 houses at least the controllable pressure device 4340 (e.g. blower 4342). The pneumatic block may comprise a portion of the pneumatic path that is located within the external housing 4010. In one form, the chassis 4016 may form a part of the pneumatic block 4020 as shown in FIG. 3*a*. In another form, the chassis 4016 may support the pneumatic block 4020 without forming a part thereof as shown in FIG. 3*b*.

The RPT device 4000 may have an electrical power supply 4210, one or more input devices 4220, a central controller 4230, a therapy device controller 4240, a pressure device, one or more protection circuits, memory, transducers 4270, data communication interface and one or more output devices. Electrical components 4200 may be mounted on a single Printed Circuit Board Assembly (PCBA) 4202. In an alternative form, the RPT device 4000 may include more than one PCBA 4202.

The central controller of the RPT device 4000 may be programmed to execute one or more algorithm modules, including a pre-processing module, a therapy engine module, a pressure control module, and further a fault condition module.

6.4.1 RPT Device Mechanical & Pneumatic Components 4300

6.4.1.1 Air Filter(s) 4310

A RPT device in accordance with one form of the present technology may include an air filter 4310, or a plurality of air filters 4310.

In one form, an inlet air filter 4312 is located at the beginning of the pneumatic path upstream of a blower 4342. See FIG. 3*e*.

In one form, an outlet air filter 4314, for example an antibacterial filter, is located between an outlet of the pneumatic block 4020 and a patient interface 3000. See FIG. 3*e*.

6.4.1.2 Muffler(s) 4320

In one form of the present technology, an inlet muffler 4322 is located in the pneumatic path upstream of a blower 4342. See FIG. 3*e*.

In one form of the present technology, an outlet muffler 4324 is located in the pneumatic path between the blower 4342 and a patient interface 3000. See FIG. 3*e*.

6.4.1.3 Pressure Device 4340

In a form of the present technology, a pressure device 4340 (also referred to as a pressure generator) for producing a flow of air at positive pressure is a controllable blower 4342. For example, the blower may include a brushless DC motor 4344 with one or more impellers housed in a volute. The blower may be capable of delivering a supply of air, for example about 120 litres/minute, at a positive pressure in a range from about 4 cmH$_2$O to about 20 cmH$_2$O, or in other forms up to about 30 cmH$_2$O.

The pressure device 4340 is under the control of the therapy device controller 4240.

6.4.1.4 Transducer(s) 4270

One or more transducers 4270 may be constructed and arranged to measure properties of the air at one or more predetermined points in the pneumatic path, or of the ambient air.

In one form of the present technology, one or more transducers 4270 are located downstream of the pressure device 4340, and upstream of the air circuit 4100. In one form of the present technology, one or more transducers 4270 are located upstream of the pressure device 4340.

In one form of the present technology, one or more transducers 4270 are located proximate to the patient interface 3000.

6.4.1.5 Anti-Spill Back Valve 4360

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4344.

6.4.1.6 Air Circuit 4100

An air circuit 4100 in accordance with an aspect of the present technology is constructed and arranged to allow a flow of air or breathable gasses between the pneumatic block 4020 and the patient interface 3000.

6.4.1.7 Oxygen Delivery 4380

In one form of the present technology, supplemental oxygen 4380 is delivered to a point in the pneumatic path.

In one form of the present technology, supplemental oxygen 4380 is delivered upstream of the pneumatic block 4020.

In one form of the present technology, supplemental oxygen 4380 is delivered to the air circuit 4100.

In one form of the present technology, supplemental oxygen 4380 is delivered to the patient interface 3000.

6.4.2 RPT Device Electrical Components 4200

6.4.2.1 Power Supply 4210

Power supply 4210 supplies power to the other components of the basic RPT device 4000: the input device 4220, the central controller 4230, the pressure device 4340, and the output device 4290 (see FIG. 3*f*).

In one form of the present technology, power supply 4210 is internal of the external housing 4010 of the RPT device 4000. In another form of the present technology, power supply 4210 is external of the external housing 4010 of the RPT device 4000.

6.4.2.2 Input Device(s) 4220

Input device 4220 comprises buttons, switches or dials to allow a person to interact with the RPT device 4000. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller.

In one form, the input device 4220 may be constructed and arranged to allow a person to select a value and/or a menu option.

6.4.2.3 Central Controller 4230

In one form of the present technology, the central controller 4230 is one or a plurality of processors suitable to control an RPT device 4000. The central controller 4230 may be configured to receive input signal(s) from the input device 4220, and to provide output signal(s) to the output device 4290 and/or the therapy device controller 4240

Suitable processors may include an x86 INTEL processor, a processor based on ARM Cortex-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

6.4.2.4 Output Device 4290

An output device 4290 in accordance with the present technology may take the form of one or more of a visual, audio, and haptic output. A visual output may be a Liquid Crystal Display (LCD) or Light Emitting Diode (LED) display. An audio output may be a speaker or audio tone emitter.

6.5 Humidifier 5000

6.5.1 Humidifier Overview

In one form of the present technology there is provided a humidifier 5000 to change the absolute humidity of air for delivery to a patient relative to ambient air. Typically, the humidifier 5000 is used to increase the absolute humidity and increase the temperature of the flow of air relative to ambient air before delivery to the patient's airways. The humidifier 5000 typically comprises an inlet to receive a flow of air, and an outlet to deliver the flow of air with added humidity.

In one form, a humidifier 5000 may comprise a humidifier reservoir 5180, a heating element 5240 and one or more transducers. The humidifier 5000 may be configured to receive a flow of air from a RPT device and deliver a flow of humidified air to a patient interface 3000 for example via an air circuit 4100. The air circuit 4100 may be coupled to the humidifier 5000 through an outlet, such as the humidifier reservoir outlet 5182 as shown in FIG. 3*g* and FIG. 3*h*.

As described above, the humidifier 5000 may deliver a pressurised flow of air to the patient 1000 with sufficient humidity to prevent drying of the mucosa and increase patient airway comfort. At the same time, the humidifier 5000 and the air circuit 4100 is configured to prevent occurrence of any condensation, especially in the air circuit 4100. To this end, the air circuit 4100 may be provided with a heating element as will be described in greater detail below. The humidifier 5000 and the air circuit 4100 may be further configured to allow the patient 1000 to arrange the air circuit 4100 to improve their sleeping comfort. Further, the humidifier 5000 and the air circuit 4100 are configured to allow cleaning of the air circuit 4100 and/or the humidifier 5000, and to prevent ingress of water into any electronic components, such as in the humidifier 5000, the air circuit 4100 or the RPT device 4000.

An example of a humidifier 5000 which is integrated with an RPT device 4000 is shown in FIGS. 3*b*-3*d*. Another example of a humidifier 5000 is shown in FIGS. 3*g*-3*h*.

6.6 Air Circuit-Outlet Connection

6.6.1 Connection Overview

As described in some detail above, a respiratory therapy system may include certain components such as a RPT device 4000, a humidifier 5000, and a patient interface 3000. The RPT device 4000 and humidifier 5000 may be combined into a single, integrated unit as shown in FIG. 3*b*-3*d*. Alternatively, the RPT device 4000 and the humidifier 5000 may be separable such that the patient can use the RPT device without the humidifier. In either scenario a connection must be made to the patient interface 3000 so that the patient can receive the flow of gas from the RPT device 4000 and/or the humidifier 5000. An air circuit 4100, as described above, may be provided to pneumatically connect the patient interface 3000 to the RPT device 4000 and/or the humidifier 5000. As shown in FIG. 4*a*, the air circuit 4100 may include a tube portion 4102 and an outlet connector 4106 to connect the air circuit to the RPT device 4000 and/or the humidifier 5000. The tube portion 4102 may also include a helical coil 4103 to provide support for the tube portion. The air circuit 4100 may also incorporate a heating element, which may be provided within the helical coil 4103. The heating element in the air circuit 4100 may heat the air circuit 4100 and the flow of gas travelling therethrough in order to prevent rainout (condensation of water vapor, for example, within the tube portion 4102 or the patient interface 3000). When a heating element is provided in the helical coil 4103 electrical power and/or signalling may be necessary if, for example, the heating element is an electrical resistance heater. In some instances, an electrical connection may be required between the patient interface 3000 and the RPT device 4000 and/or the humidifier 5000 for electrical power and/or communication therebetween.

FIG. 20a and FIG. 20b show an example of the RPT device 4000 and a humidifier 5000 that has been combined into a single, integrated unit, wherein a water reservoir is not shown. FIG. 20a shows an air circuit 4100 separated from the RPT device 4000 in an exploded view, and FIG. 20b shows the air circuit 4100 assembled with the RPT device 4000.

6.6.1.1 Pneumatic and Electrical Connections with a Single Connector

The air circuit 4100 may require both pneumatic and electrical connections to be formed to the humidifier 5000 (or the RPT device 4000), as well as a mechanical connection. These connections may be formed through the outlet connector 4106 to allow the pressurized gas to flow to the patient interface 3000, to provide electrical power and signalling to the heating element in the helical coil 4103 and to locate and secure the air circuit 4100 relative to the humidifier 5000 (or the RPT device 4000). These connections may be formed simultaneously or in series such that one of the mechanical, pneumatic or electrical connections is completed before others. The air circuit 4100 may comprise on another end a patient interface connector 4107 to couple to a patient interface 3000. In some forms, the patient interface connector 4107 may be different to the outlet connector 4106 as shown in FIGS. 4g-4h.

FIGS. 4a-h and 5a-i depict air circuits or portions thereof according to examples of the present technology. FIGS. 12a-f also depict exemplary air circuits that are connected to an outlet assembly 5107. As can be seen in FIG. 4a, for example, a tube portion 4102 having a helical coil 4103 may be connected to an outlet connector 4106. As shown in FIG. 5a the connection of the helical coil 4103 to the outlet connector 4106 may be facilitated by the use of a grommet 4104. The helical coil 4103, as discussed above, may include a heating element and it may also function as a support structure for the tube portion 4102. An electrical connection may be formed by inserting the outlet connector 4106 on the outlet assembly 5107 (to be discussed in greater detail below) so that an electrical connector 4112 comes into electrical contact with electrical components of the outlet assembly. As can be seen in FIGS. 4c-d, the electrical connector 4112 may be oriented parallel a centre axis of the outlet connection region 4114 and extend downward from an underside of the outlet connector 4106 and out from an opening 4118.

6.6.1.1.1 Formation of Pneumatic and Electrical Connections

A recess 4116 may also be formed on the outlet connector 4106, the recess 4116 being configured to couple to an electrical connector receiver 5114 of a swivelling disc 5104 (see FIG. 8d and further discussion below) to aid in releasably securing the outlet connector 4106 to the humidifier 5000, for example at the outlet assembly 5107. The recess 4116 may also provide a visual aid to the patient to locate the outlet connector 4106 in relation to the outlet assembly 5107 by being shaped to correspond to the electrical connector receiver 5114 (see FIG. 12e). The electrical connector receiver 5114 may house a female electrical connector 5158 such as that shown in FIGS. 18a-18h. The outlet connector 4106 may also include an actuator 4108 that controls a retention feature 4110. When the outlet connector is inserted onto the outlet assembly 5107, the retention feature 4110 may engage with a corresponding notch 5126 of the swivelling disc 5104 (see FIG. 21b and further discussion below). The actuator 4108 in conjunction with the notch 5126 may produce an audible sound and/or provide tactile feedback at the actuator 4108 upon engagement. The actuator 4108 and/or the retention feature 4110 may be produced with higher wear characteristics than the swivelling disc 5104 to allow wear to occur on the air circuit 4100, which is typically a consumable component. This may be achieved by use of a material with lower hardness to form the retention feature 4110 compared to the material from which the swivelling disc 5104 is formed. The retention feature 4110 and notch 5126 may engage by a snap-fit and the actuator 4108 may be depressible to bring in the retention feature to release it from the notch 5126. In some cases, the retention feature 4110 and the notch 5126 may be configured so that when they are not completely engaged, they may be forced into place at commencement of therapy by the therapy pressure, for example by being configured so that the therapy pressure acting on the tab 4148 urges the retention feature 4110 towards the notch 5126. As shown in FIG. 6a, the actuator 4108 and the retention feature 4110 may both be located on a tab 4148 such that pushing the actuator inward also causes the retention feature to be moved inward, thereby freeing it from the notch 5126. In one form, the actuator 4108 may be located further from a pivot of the tab 4148 than the retention feature 4110, which would impart a mechanical advantage to the user and increase the travel required to depress the actuator 4108 to improve the resolution of movement of the retention feature 4110 to the user. This arrangement may further improve the feedback provided to the user during engagement/disengagement of the outlet connector 4106. An outlet connection region 4114 may be shaped to correspond with the shape of the swivelling disc 5104, as shown in FIG. 9a, for example.

As shown in FIGS. 6h and 6g, a travel stop 4178 located at the inner ends of the ribs 4120 may be used in some examples of this technology in order to limit the travel, or level of squeezing, of the actuator 4108 during insertion and removal to prevent plastic deformation of the surrounding portions and/or to prevent tear of the housing 4134. The travel stops 4178 extend from the inner ends of the ribs 4120 and are aligned with the inner surface of the outlet connector 4106 in the location of the actuator 4108. When the actuator is squeezed or pushed inwards the inner surface of the outlet connector 4106 is correspondingly squeezed or pushed inwards until it contacts the travel stop 4178. The travel stop prevents further squeezing or pushing of the actuator.

In a further example of the technology, the notch may be replaced with a radial slot that is capable of retaining the outlet connector via the retention feature(s) but allowing rotation thereof. In such an example the swivelling disc may be fixed relative to the outlet housing or it may be eliminated completely such that the radial slot is located on the housing. Furthermore, it should be understood that such examples would retain the need for a movable electrical connector within the outlet assembly such that the electrical connection may be maintained while the outlet connector rotates.

FIGS. 4e and 4f show detailed bottom views of examples of the outlet connector 4106 and specifically the outlet connection region 4114. FIG. 4e shows the outlet connector 4106 connected at the outlet connection region 4114 to an outlet end 5134 of an airflow tube 5130 (shown in FIGS. 10a-d and discussed further below). The airflow tube 5130 may be formed as a multiple patient/multiple user (MPMU) tube that is removable, replaceable and/or cleanable. It should be noted that for the sake of clarity the outlet end 5134 is shown in this view and reference should be made to FIGS. 10a-d for further depiction. The airflow tube 5130 may function as a removable intermediate pneumatic coupling between the outlet connector 4106 of the air circuit 4100 and the air outlet of RPT device 4000 and/or the humidifier 5000.

6.6.1.1.2 Internal Ribs of the Outlet Connector 4106

FIG. 4e shows a plurality of ribs 4120 disposed around the inner periphery of the outlet connection region 4114 of the outlet connector 4106. In the illustrated example four ribs 4120 are shown but a different number of ribs such as two, three, five or more ribs may be utilised. The ribs 4120 may function to support and position the outlet connector 4106 relative to the outlet end 5134 of the airflow tube 5130. The ribs 4120 may function to guide the outlet connector 4106 during insertion to couple to the outlet end 5134 of the airflow tube 5130 in the outlet assembly 5107 to form the pneumatic connection. This guidance may also assist in aligning the outlet connection region 4114 to facilitate the electrical connection between the electrical connector 4112 and the electrical connector receiver 5114 on the swivelling disc 5104 of the outlet assembly 5107. In this arrangement, although a single action is required for insertion or connection of the air circuit outlet connector 4106 to the RPT device outlet assembly 5107, the pneumatic connection is formed first and the electrical connection is formed second. The outlet connector 4106, the outlet assembly 5107 and the airflow tube 5130 may be configured such that airflow tube 5130 engages the seal 4170 of the outlet connector 4106 prior to the electrical connector receiver 5114 forming an electrical connection with the electrical connector 4112. Accordingly, during removal or disconnection, the electrical connection is the first to be disconnected and the pneumatic connection is disconnected second. This may be advantageous to ensure that a pneumatic seal is maintained from the RPT device 4000 and/or the humidifier 5000 to the air circuit 4100 and, more specifically, between the outlet connector 4106 and the airflow tube 5130. Furthermore, this may provide improved safety, for examples if supplemental oxygen is added to the flow of air delivered by the humidifier 5000, as this arrangement may prevent oxygen from being exposed to connection and/or disconnection of the electrical connections. FIG. 4f shows a similar view to FIG. 4e, however, the outlet end 5134 of the airflow tube 5130 is not shown to provide a clearer depiction of an example of the ribs 4120. Both of these views also show the profile of the recess 4116.

In some cases, a non-heated air circuit 4100 may be used that does not incorporate a heating element. Accordingly, the diameter of the central opening in the swivelling disc 5104 may be arranged (e.g., sufficiently sized and/or shaped) to accept such a non-heated air circuit 4100. Accordingly, in one example of the current technology, the external diameter of the airflow tube may be approximately 22 mm to allow connection to a standard 22 mm external diameter non-heated air circuit, and the external diameter of the outlet connector 4106 may be approximately 36 mm. However, it is recognised that other external diameter sizes may be utilised.

Internal ribs 4120 may be used to reduce any radial gaps between the interior of the outlet connection region 4114 and the airflow tube 5130. Still further, the ribs 4120 and the airflow tube 5130 may be configured so that the gaps therebetween are relatively smaller than the gap between the exterior of the outlet connection region 4114 and the swivelling disc 5104. This may allow more of the wear from rotation to occur on the airflow tube 5130 in comparison to the swivelling disc 5104, which may be advantageous as the airflow tube 5130 may be more readily replaced than the swivelling disc 5104.

Another advantage of the ribs 4120 may be to allow a greater portion of any mechanical load that may result from tilting and/or non-axial movement to be transferred from the outlet connector 4106 to the airflow tube 5130. This may be advantageous in that this may help wear occur on the consumable components such as the air circuit 4100 and/or the airflow tube 5130 than the non-consumable components of the humidifier 5000, such as the swivelling disc 5104. Yet another advantage of the ribs 4120 may be to maintain or restrict the deformation of the base seal 4170 (as shown in FIG. 5e) during engagement of the outlet connector 4106 with the outlet assembly 5107 by limiting the maximum axial deformation that the base seal 4170 can undergo towards the interior of the outlet connector 4106.

6.6.1.1.3 Electrical Connection

The electrical connector 4112 may include one or more lead-in features, such as chamfers, or curved radii on its edges on the leading surface in the direction of insertion such as shown in FIG. 5c. This may assist insertion of the electrical connector 4112 into the electrical connector receiver 5114 to provide a surface wipe connection and prevents damage to the conductors on the electrical connector 4112. The thickness of the electrical leads 4128 on the electrical connector 4112 may be approximately between 0.2 mm to 1.2 mm, for example 0.4 mm, 0.6 mm, 0.8 mm or 1 mm. The thickness may vary according to a number of parameters such as, the design life of the electrical connector 4112, material chosen for the electrical leads 4128 and the material chosen for the receiver contact elements 5146. One suitable example of material for the electrical leads 4128 may be high temper phosphor bronze, that is nickel plated and then gold plated. In some circumstances, an increased amount of conductive material and/or high conductivity plating (such as gold and/or platinum) may be used on the electrical leads 4128. This may have the advantage of improving wear characteristics and/or dissipating heat from the connector 4112. The electrical leads 4128 may have exposed conductive surfaces on the lower end of the electrical connector 4112 to ensure full insertion is required to make the electrical connection.

Another feature provided by the connection of the electrical connector 4112 to the electrical connector receiver 5114 on the swivelling disc 5104 may be that when assembled together, the electrical connector receiver 5114 is covered by the outlet connector 4106 as shown in FIG. 12e and FIG. 12f. FIG. 12e shows an exploded view wherein the outlet connector 4106 is shown above the swivelling disc 5104, and FIG. 12f shows the outlet connector 4106 in engagement with the swivelling disc 5104. Discussed above was the shape of the recess 4116, as shown in FIG. 4c, such that it may conform to the inward portion of the electrical connector receiver 5114 depicted in FIG. 9a, for example. FIGS. 4c and 4d also depict the region of the outlet connector 4106 that surrounds the opening 4118 of the outlet connector where the electrical connector 4112 (not shown in FIG. 4*d*) is received. When the outlet connector 4106 is inserted onto the swivelling disc 5104, as shown in FIGS. 12*c* and 12*d*, the region of the outlet connector that surrounds the electrical connector 4112 may cover over the opening in the electrical connector receiver 5114 to prevent debris and contaminants (such as liquids) from entering into the electrical connector receiver. As mentioned above, the connector 4112 and the receiver 5114 are configured so that the electrical connection between them is to be made after the outlet connector 4106 is mechanically engaged with the swivelling disc 5104. This reduces the proportion of any deformation or load from misalignment between the outlet connector 4106 and the swivelling disc 5104 that is supported by the electrical connector 4112 and the receiver 5114. This may be achieved by configuring the outlet connector 4106 and the swivelling disc 5104 so that during insertion of the outlet connector 4106 with the swivelling disc 5104, the airflow tube 5130 and the ribs 4120 engage prior to engagement of the electrical connector 4112 and the receiver 5114. This configuration may also be advantageous in cases where the gas provided via the air circuit 4100 includes supplementary oxygen, as it may prevent occurrence of electrical arcing while the pneumatic circuit is not isolated.

A yet another feature of the current technology may be found in the arrangement of the receiver contact elements 5146 on the female electrical connector 5158 in the electrical connector receiver 5114 as shown in FIG. 18*a*-18*b*. The electrical leads 4128 may engage the receiver contact elements 5146 as the electrical connector 4112 is inserted into the receiver 5114 from the top of the connector TS. This engagement may occur via a sliding action in the direction of the arrow ENG shown in FIG. 18*a*-18*b*. The receiver contact elements 5146 may be configured in a sloped, triangular profile as shown in FIG. 18*b* and/or to be compliant in a perpendicular direction PER to the sliding plane to assist in their engagement with the electrical leads 4128.

The aforementioned triangular profile and/or compliance may allow improved engagement between the electrical leads 4128 on the connector 4112 and the receiver contact elements 5146 as the connector 4112 is progressively inserted into the electrical connector receiver 5114. During engagement with the connector 4112, as the connector 4112 slides along the length of the female electrical connector 5158 the contact elements 5146 may be depressed inwards and maintain contact to the electrical leads 4128. This may allow improved accommodation of mechanical tolerances from such sources as manufacturing variance or in-use deformation.

Still further, the receiver contact elements 5146 may be biased, so that when deformed from its original configuration (as shown in FIG. 18*b*) and depressed inwards, the receiver contact elements 5146 may be biased towards returning to the undeformed position, thereby improving the fidelity of its connection with the electrical leads 4128. Another advantage of such an arrangement of the female electrical connector 5158 may be that it is self-cleaning. As the female electrical connector 5158 and the connector 4112 may engage each other in a slide-on, slide-off action, it may prevent build-up of contaminants which, if left uncleaned, may affect the fidelity of the electrical connection formed between the two parts. Any contaminants that have been removed by the wiping action may be prevented from entering the air path, for example by swivel disc seal 5113. In addition when the female electrical connector 5158 is arranged in a vertical position and the connection is made in a vertical direction any contaminants that are wiped off the electrical contacts will fall down below the connector. A cavity may be formed below the female electrical connector 5158 within the receiver 5114 into which the contaminants may collect. This cavity is not in communication with the airpath.

FIG. 18*c* shows the surface of the female electrical connector 5158 that may be connected to the cable 5102. The connector comprises a plurality of weld points 5150, 5152, 5154, for example there may be two weld points for each of the conductive tracks, which allows for improved mechanical strength against load. The connector may also incorporate one or more pegs, rivets or pins 5156 for alignment during assembly and/or mechanical bonding. Optionally the one or more pegs, rivets or pins 5156 may be heat staked to provide a mechanical restraint. In certain arrangements a washer or plate may be provided between the one or more pegs, rivets or pins 5156 and the cable to spread the mechanical restraint force over a larger surface of the connector.

FIGS. 18*d*-18*f* show another example of the female electrical connector 5158, including another example of receiver contact elements 5146, shown in further detail in FIGS. 18*g*-18*h*. A feature of this example of the receiver contact element 5146 is that a bifurcated retention feature 5162 is formed from the base portion 5166 rather than the contact portion 5164 and/or the curved portion 5168. The receiver contact elements 5146 may be made from a material of high electrical and thermal conductivity with high strength and hardness, such as beryllium copper.

Having the exposed electrical connections on the outlet connector 4106 of the air circuit 4100 provides additional electrical safety as the air circuit does not include a power supply but requires connection to swivelling disc 5104 on the RPT device 4000 and/or humidifier 5000 to receive power. Also, the exposed electrical connections that may be exposed to cleaning processes are also on the replaceable air circuit 4100 component.

6.6.1.2 Elbow Outlet Connector

Figure 1A:
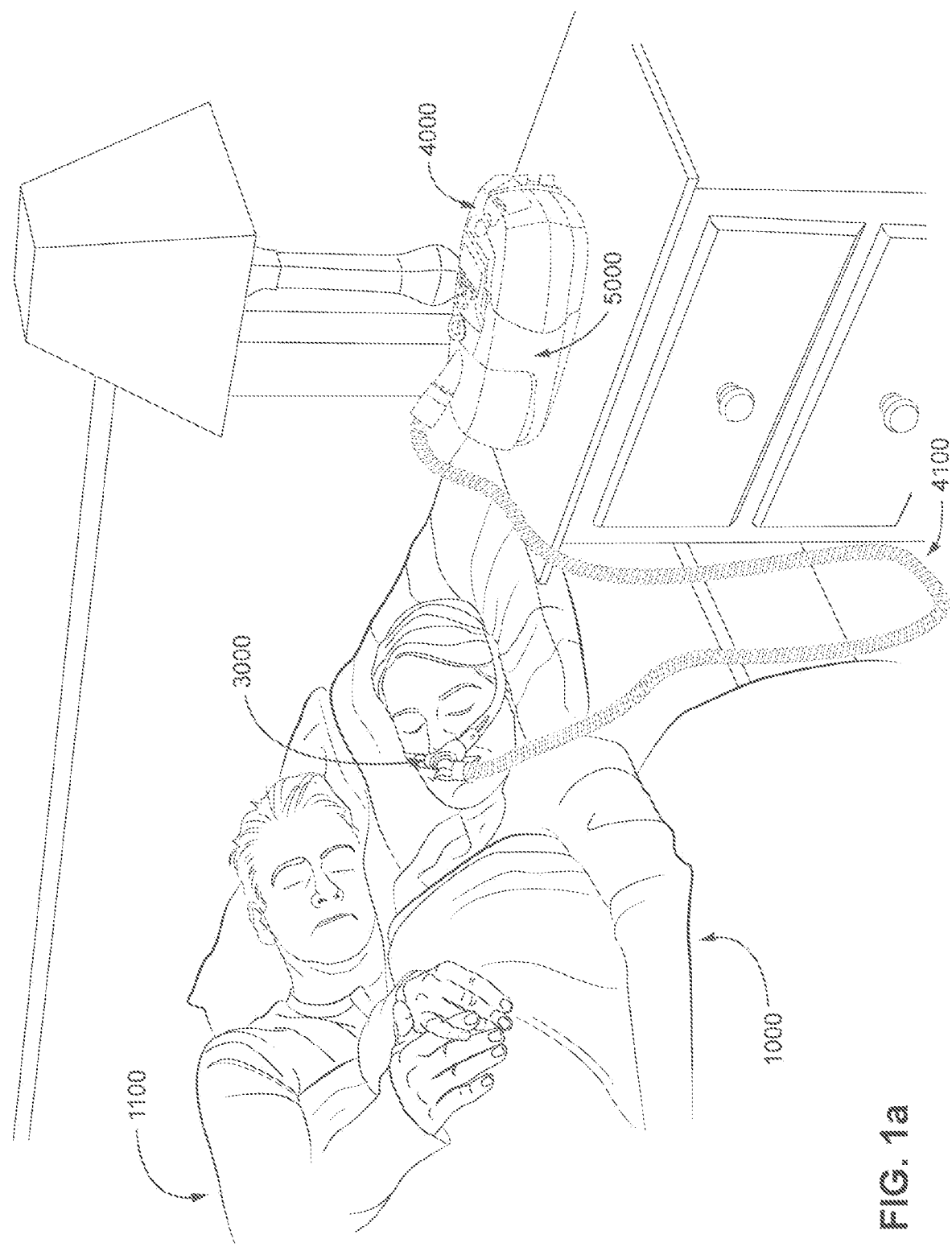
FIG. 1a shows a system in accordance with the present technology. A patient 1000 wearing a patient interface 3000, in the form of a nasal pillows, receives a supply of air at positive pressure from a RPT device 4000. Air from the RPT device is humidified in a humidifier 5000, and passes along an air circuit 4100 to the patient 1000.
Figure 1B:
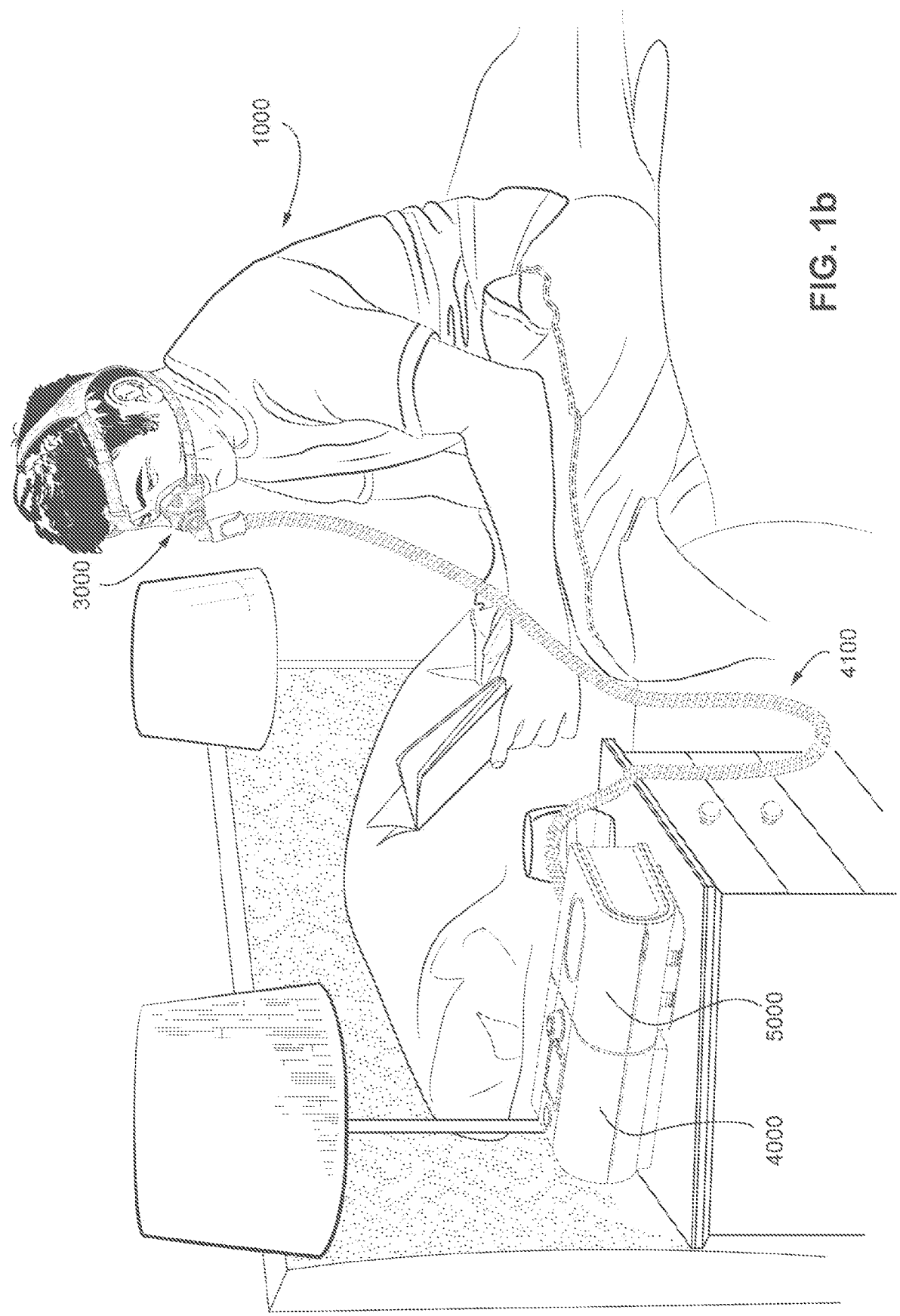
FIG. 1b shows a system including a patient 1000 wearing a patient interface 3000, in the form of a nasal mask, receiving a supply of air at positive pressure from a RPT device 4000. Air from the RPT device is humidified in a humidifier 5000, and passes along an air circuit 4100 to the patient 1000.
Figure 1C:
FIG. 1c shows a system including a patient 1000 wearing a patient interface 3000, in the form of a full-face mask, receiving a supply of air at positive pressure from a RPT device 4000. Air from the RPT device is humidified in a humidifier 5000, and passes along an air circuit 4100 to the patient 1000.

By forming the outlet connector 4106 with an elbow, as can be seen in FIGS. 4*a*-*b*, 5*a*-*f*, and 12*a*-*d*, the chance that the air circuit 4100 is accidentally or unintentionally pulled off of the RPT device 4000 and/or the humidifier 5000 (e.g., by the patient tugging at the air circuit 4100 during sleep by accident) may be reduced, because the direction of the tension force vector of the air circuit will be located at an angle (e.g., perpendicular) to the direction of engagement of the air circuit 4100 with RPT device 4000 and/or the humidifier 5000. Also, as shown in FIGS. 1*a*-*c*, the RPT device 4000 and/or the humidifier 5000 may be located on a nightstand, for example, during treatment such that the patient lying in bed is at substantially the same height as the RPT device and/or the humidifier. In such a situation, the inclusion of an elbow as part of the outlet connector 4106 may allow the air circuit 4100 to be pointed more directly at the patient such that bend angles of the air circuit may be reduced, particularly at or near the elbow, which in turn may reduce stress on the air circuit. In one example of the present technology, the outlet connector 4106 may include an elbow having an angle of about 90°. It should be understood, however, that any number of angles may be possible, such as for example between 0° and 120°, including 20°, 40°, 60°, 800 or 100°. The choice of this angle may be affected by any number of design requirements such as flow impedance, convenience, location of the outlet connector 4106 or noise implications.

6.6.1.3 Rotatable Outlet Connector

As the patient may move during treatment, thus pulling the air circuit 4100, it may be advantageous to further reduce the bend angles of the air circuit and reduce stress on the assembly, in particular the air circuit, as well as the connection thereto from the outlet connector 4106. This may be accomplished by allowing the outlet connector 4106 to rotate relative to the RPT device 4000 and/or the humidifier 5000 while the mechanical, pneumatic and electrical connections are maintained.

As described above, the air circuit 4100 may be connected to the RPT device 4000 and/or the humidifier 5000 by inserting the outlet connector 4106 onto the outlet assembly 5107, as shown in FIGS. 12a-d. Rotatability may be provided by features shown in FIGS. 8a-h, 9a-c, 11a-d, 12a-d, and 21a-c.

FIGS. 8a, 8b, 8d-h, 9a-c, 21a-c show various views of the swivelling disc 5104 according to various examples of the technology. It has been described above that the swivelling disc 5104 may be the component that receives the outlet connector 4106 when connecting the air circuit 4100 to the RPT device 4000 and/or the humidifier 5000. The swivelling disc 5104 may also provide rotatability (e.g., for the outlet connector 4106) relative to the RPT device and/or the humidifier while maintaining the pneumatic and the electrical connections.

FIGS. 8a and 9a-c show views of swivelling disc 5104 according to examples of the present technology. FIG. 8a shows a perspective view of the bottom of the exemplary swivelling disc 5104. In other words, this view depicts features of the swivelling disc 5104 that are located opposite the side to which the outlet connector 4106 may connect. A cable 5102, to be discussed in greater detail below, can be seen extending from an underside of the electrical connector receiver 5114. An end of the cable 5102 that is inside of the electrical connector receiver 5114 may be in electrical communication with the electrical connector 4112 when the outlet connector 4106 is inserted onto the swivelling disc 5104. The free end of the cable 5102 shown may be in electrical communication with at least one electrical component 4200 of the RPT device 4000 and/or the humidifier 5000 (e.g., a controller, printed circuit board (PCB) and/or a power supply), for example at another end of the cable 5102 (not shown). It should also be understood that the cable 5102 may be of any sufficient length to perform its connective function, as will be discussed in greater detail below.

A pair of disc stop surfaces 5108, 5110 on either side of and adjacent to the cable 5102 are shown in FIG. 8a. These disc stop surfaces 5108, 5110 may limit rotation of the swivelling disc 5104 relative to a cable housing 5100, as will be described in greater detail below. The exit flange 5109 around the cable 5102 also supports the cable 5102 as it extends through the outlet assembly 5107 from where it is connected to the female electrical connector 5158 in the electrical connector receiver 5114. A flange 5112 may be disposed radially about the swivelling disc 5104 to perform sealing and/or cable 5102 containment functions, as will be discussed in greater detail below as well. The notch 5126, of which there may be more than one, may also be seen.

FIGS. 9b-e show similar features to those described in relation to FIG. 8a, but also show tangs 5128 that may allow the swivelling disc 5104 to be snap-fit onto the cable housing 5100. The tangs 5128 may also retain the swivelling disc 5104 on the cable housing 5100 while allowing it to rotate relative thereto.

The swivelling disc 5104 may also incorporate a swivel disc seal 5113 as shown in FIG. 9a-9e that may comprise a compliant material such as TPE. The swivel disc seal 5113 may function to maintain a seal between the swivelling disc 5104 and the airflow tube 5130 to prevent any contaminants from entering the air path.

As described above, the outlet connector 4106 may be releasably coupled to the swivelling disc 5104 by engagement of the retention features 4110 in corresponding notches 5126 and by engagement of the recess 4116 onto the electrical connector receiver 5114. When connected to the swivelling disc 5104, the outlet connector 4106 may be able to rotate in unison with the swivelling disc and relative to the cable housing 5100.

FIGS. 21a-c show views of the swivelling disc 5104 joined to the cable housing 5100. FIG. 21a shows a top view of an outlet assembly according to an example of the present technology. In FIGS. 21a-c the swivelling disc 5104 may be in an intermediate rotational position relative to the cable housing 5100.

FIG. 21b shows a cross-section of the outlet assembly 5107 across the symmetrical plane of the female electrical connector 5158 taken through line 21b-21b of FIG. 21a. This example of the current technology shows an internal shoulder 5160 that recesses the female electrical connector 5158 from the opening of the electrical connector receiver 5114, which may improve the electrical safety of the electrical connector receiver 5114 when engaging with and/or disengaging from the connector 4112. Recessed placement of the female electrical connector 5158 from the opening of the electrical connector receiver 5114 may also prevent occurrence of any electrical arcing at or near an exposed area. The current arrangement of the female electrical connector 5158 and the electrical connector receiver 5114 may also prevent any powered components from being touched by a user.

FIG. 21c shows another cross-sectional view of the outlet assembly 5107 taken through line 21c-21c of FIG. 21a. Inner wall 5101 of the swivelling disc 5104 can be seen within the outer wall of the cable housing 5100. The tabs 5106 of the cable housing 5100 can also be seen. The flange 5112 of the swivelling disc 5104 can also be seen above the outer wall 5103 of the cable housing 5100.

6.6.1.3.1 Limited Rotation

Another feature of the present technology can be seen in FIGS. 8a and 8c. The disc stop surfaces 5108, 5110 (shown in FIG. 8a), discussed above, have a pair of complementary housing stop surfaces 5120, 5122 (shown in FIG. 8c) that may be located on an inner wall 5101 of the cable housing 5100. By connecting the swivelling disc 5104 to and within the inner wall 5101 of the cable housing 5100, for example as shown in FIGS. 8d-8f, the rotation of the swivelling disc 5104 relative to the cable housing 5100 may be limited by engagement of corresponding stop surfaces at or near its extreme positions. Rotation of the swivelling disc 5104, in one example of the technology, may be limited to less than about 360°. Rotation may also be limited to an amount that is greater than about 180°. In a further example, rotation may be limited to about 270°. The desired range of rotation of the swivelling disc 5104 may be determined by a number of factors, such as the location of the swivelling disc 5104 with respect to the RPT device 4000 and/or humidifier 5000, the elbow angle of the outlet connector 4106, and material properties of the components.

The depicted examples show two pairs of complementary stop surfaces, as discussed above, that may represent opposite ends or surfaces of one structure. It may be possible to have multiple stop structures formed on respective components. For example, the stop surfaces on the inner wall of the housing may be provided with two separate protrusions thereon and likewise for the swivelling disc. It is also envisioned that multiple configurations of stop surfaces may be provided on a single combination of housing and swivelling disc such that one combination may include a number of available rotational limits.

FIG. 8*d* shows the swivelling disc 5104 rotated into one extreme position in the counter-clockwise direction relative to the cable housing 5100. FIG. 8*f* shows the swivelling disc 5104 rotated into another extreme position towards the other limit of travel in the clockwise direction relative to the cable housing 5100. FIG. 8*e* shows the swivelling disc 5104 in a position relative to the cable housing 5100 that is between the extreme positions shown in FIGS. 8*d* and 8*f*. Although the swivelling disc 5104 does not allow the stop surfaces 5108, 5110, 5120, 5122 to be seen in FIGS. 8*d-f*, it should be understood that when the swivelling disc 5104 is in either extreme position shown in FIGS. 8*d* and 8*f* that one of the disc stop surfaces 5108, 5110 is engaged and/or abutted against a corresponding housing stop surface 5120, 5122.

FIGS. 8*g* and 8*h* also show examples of the swivelling disc 5104 rotated into clockwise and counter-clockwise extreme positions relative to the cable housing 5100. FIGS. 8*g* and 8*h* also show a substructure 4132 (shown in greater detail in FIGS. 6*a-g* and described further below) of the outlet connector 4106 connected to the swivelling disc 5104. The position of the swivelling disc 5104 and the substructure 4132 in FIG. 8*g* corresponds to the position shown in FIG. 8*f* and, likewise, FIG. 8*h* corresponds to FIG. 8*d*. While not visible in FIGS. 8*g* and 8*h*, it should be understood that each tab 4148 includes a retention feature 4110 that is engaged with a corresponding notch 5126 of the swivelling disc 5104 to releasably connect the substructure to the swivelling disc so that they may rotate in unison relative to the cable housing 5100. It should also be understood that FIGS. 8*g* and 8*h* depict possible extreme positions of the rotation of the substructure 4132 in this example by virtue of the connection of the substructure to the swivelling disc 5104.

6.6.1.4 Electrical Cable Connection

As discussed above, the cable 5102 may be provided to electrically connect the electrical connector 4112 to at least one electrical component of the RPT device 4000 and/or the humidifier 5000. The cable 5102 shown in FIGS. 8*a-h* may be a flexible circuit board (FCB) or a ribbon cable. The cable 5102 may also include multiple wires to provide multiple electrical connections for powering and signalling functions. The cable 5102 may be oriented such that the major or longer side is oriented in parallel to the axis of rotation of the swivelling disc. If an FCB is used as the cable 5102, it may be oriented so that the surface of the FCB where the conductive tracks are located is protected from frictional contact with the cable housing 5100 as it rotates with the swivelling disc 5104, in order to help prolong the life of the cable 5102. Still further, the contacting surface (away from the conductive tracks) may comprise a low-friction surface so that when it slides relative to the cable housing 5100 the friction force created is minimised. This may have the effect of reducing the amount of wear occurring on the cable 5102, as well as reducing the load imposed on the solder/mounting joints between the cable 5102 and any electrical connectors connected thereto, such as the female electrical connector 5158. An example of such a low-friction surface may be a polyamide substrate.

6.6.1.4.1 Cable Management

In accordance with an example of the present technology, the cable 5102 may be fixed at one end to the electrical connector receiver 5114 of the swivelling disc 5104. Although not shown, it should be understood that the opposite end of the cable 5102 may be fixedly connected to at least one electrical component 4200 of the RPT device 4000 and/or the humidifier 5000 such as a PCB to provide power to the cable. Thus, the cable 5102 may have a fixed length between the connection to the swivelling disc 5104 and the connection to at least one electrical component 4200 of the RPT device 4000 and/or the humidifier 5000.

The cable 5102, in an example of the present technology shown in FIGS. 8*d-h*, may also include a slack portion that may be contained within either an annular section 5174 between the inner wall 5101 and the outer wall 5103, or a recess or void 5124 defined, at least in part, by the cable housing 5100 depending upon the position of the swivelling disc 5104. The flange 5112 of the swivelling disc 5104 may also contribute to defining the upper cover of the annular section 5174, however, the flange 5112 does not contact the cable 5102 within the annular section 5174. The cable housing 5100 (see FIG. 8*c*) may also include the inner wall 5101 and an outer wall 5103, both of which may further define the void 5124. The cable housing 5100 may also include a retainer 5118, which may help to maintain the cable 5102 in the proper orientation by reducing the chance of entanglement or pinching and to prevent the slack portion from being pushed out of the cable housing 5100. The outer diameter of the retainer 5118 may be designed to provide a minimum diameter for bend of the cable 5102 without damaging the electrical elements of the cable 5102, for example an outer diameter of approximately 4 mm, 4.5 mm, 5 mm or some other outer diameter. It is to be understood that the outer diameter size of the retainer 5118 may be varied depending upon the size and type of cable used. As can be seen in FIG. 8*c*, the exemplary cable housing 5100 depicted may include an opening 5116 that may be formed in the shape of a slot and through which the cable 5102 may pass, while maintaining a substantially fixed length of the cable 5102 within the cable housing 5100.

The cable 5102 is at least partially wrapped around the inner wall 5101 within the annular section 5174 when the swivelling disc is rotated towards the extreme position shown in FIG. 8*f*. The cable 5102 does not wrap around the swivelling disc 5104 but moves with the swivelling disc within the annular section 5174 as the swivelling disc 5104 is rotated.

FIGS. 8*d-i* depict another feature of the depicted examples of the technology. As the swivelling disc 5104 is rotated between extreme positions the cable 5102 may be pushed and pulled between the void 5124 and annular section 5174 of the cable housing 5100 due to its connection to the swivelling disc. For example, when the swivelling disc 5104 is rotated from the position shown in FIG. 8*d* to the position shown in FIG. 8*e* it can be seen that a portion of the cable 5102 is pulled out of the void 5124 and into the annular section 5174. It should be understood that the portion of the cable 5102 shown doubled back in the void 5124 in FIG. 8*d*, for example, may be considered the slack portion. In other words, the slack portion may be the excess cable that represents a length of the cable beyond what is necessary for direct connection to the swivelling disc 5104. Thus, as the swivelling disc 5104 is rotated from the position shown in FIG. 8*d* to the position shown in FIG. 8*e* the slack portion may be progressively removed from the void 5124 so that the slack portion of the cable 5102 may be progressively pulled into the annular section 5174 and begin to wrap around the inner wall 5101 as the cable is pulled. As the swivelling disc 5104 is rotated further, from the position shown in FIG. 5*e* to the position shown in FIG. 5*f*, the portion of the cable 5102 that is pulled into the annular section 5174 increases and the slack portion may be pulled completely or nearly completely from the void 5124. The recess or void 5124 and the annular section 5174 may be form on opposing sides of the inner wall 5101.

Rotation of the swivelling disc 5104 in the opposite direction, from the position in FIG. 8*f* to the position in FIG. 8*e* to the position in FIG. 8*d*, may cause the cable 5102 to be progressively pushed from the annular section 5174 and unwrapped from around the inner wall 5101 such that the slack portion in the void 5124 may increase and begin to double back. In an example of the present technology, the maximum slack portion of the cable 5102 may be of a fixed length. In another example, that fixed length may be less than about the circumference of the swivelling disc 5104 and/or about equal to the distance of an arc swept out by the electrical connector receiver 5114 as the swivelling disc rotates between extreme positions. It should also be understood that in an example of the present technology when the swivelling disc 5104 is in the position shown in FIG. 8*d* the largest amount of the slack portion of the cable 5102 is gathered or contained in the void 5124. Also, it should be understood that the examples of the technology depicted in FIGS. 8*g* and 8*h* illustrate similar features to those depicted in FIGS. 8*d* and 8*f* and as described above.

6.6.1.4.2 Cable Housing

FIGS. 8*b-i* and 11*a-d* depict features of the cable housing 5100 according to examples of the present technology. As described above, the cable housing 5100 may include the inner wall 5101 and the outer wall 5103 that together may define the void 5124 and the annular section 5174. The inner wall 5101 may define an opening through which the airflow tube 5130 may extend when the outlet assembly 5107 is assembled onto the RPT device 4000 and/or the humidifier 5000. Further facilitating this assembly, tabs 5106 may be located on the cable housing 5100 to attach the cable housing to the RPT device 4000 and/or the humidifier 5000, or a further housing thereof. This may improve the manufacturability and serviceability of the cable housing 5100. The tabs 5106 may be configured so that they are, by themselves and/or as a set, able to support the weight of the humidifier 5000 and/or the RPT device 4000. This may prevent damage from occurring to the humidifier 5000, the RPT device 4000 and/or the cable housing 5100 when the assembly is accidentally lifted by the air circuit 4100 and/or the outlet connector 4106. In some instances, the air circuit 4100 and/or the outlet connector 4106 may be configured to mechanically fail if the humidifier 5000 and/or the RPT device 4000 is held in place and a force is imposed onto the air circuit 4100 and/or the outlet connector 4106 in the upwards direction (in relation to FIG. 5*c*).

Returning to the inner wall 5101 and the outer wall 5103, in an example of the present technology, the slack portion of the cable 5102 can be seen (for example, in FIG. 8*e*) to form a radius in the void 5124. This radius may affect the stress imposed on the cable 5102 (and therefore potentially its operating life) and is defined in part by the distance (VO_H in FIG. 8*i*) between the inner wall 5101 and the outer wall 5103 in the void 5124. Therefore, these walls may be separated by a distance in the range of 2 mm to 5 mm across the void 5124 based on a desired minimum radius of the cable 5102. In one example, the distance is in the range of 4 mm to 5 mm. It should be understood that the desired minimum radius of the cable may change as a function of the properties of the cable 5102 and its design parameters such as design life, or usage cases. Similarly, the length (VOL in FIG. 8*i*) of the void 5124 may be lengthened or shortened according to the maximum slack length of the cable 5102, which may be driven by the maximum rotation of the swivelling disc 5104.

The width (AN_W in FIG. 8*i*) of the annular section 5174 between the inner wall 5101 and the outer wall 5103 may be minimised as the cable 5102 travels therein as the swivelling disc 5104 rotates from one extreme position to the other. This may have the benefit of reducing noise produced by the cable and preventing buckling of the cable in the annular section. The width of the annular section may be between approximately 1 mm and 4 mm, such as 2 mm or 3 mm, and it should be understood that the width may depend on various characteristics and/or properties of the assembly, such as the characteristics of the cable chosen or the radius of the inner wall 5101. In some arrangements the inner wall 5101 of the annular section 5174 and/or the outer wall 5103 of the annular section 5174 may include dampening material to help improve sound performance when the swivelling disc is rotated. A dampening material may also ensure the cable moves around the inner wall 5101 rather than the outer wall 5103 or vice versa.

In an example of the present technology, the cable housing 5100 may be formed from polypropylene, or polycarbonate/acrylonitrile butadiene styrene (PC/ABS). The swivelling disc 5104 may be formed from a combination of polycarbonate/acrylonitrile butadiene styrene (PC/ABS) and a thermoplastic elastomer (TPE).

6.6.1.5 Airflow Tube

FIGS. 10*a-d* show various views of the airflow tube 5130. As noted above, the airflow tube may be a multiple patient/multiple user (MPMU) tube formed as a removable component that may be replaced or cleaned. The airflow tube 5130 may include an inlet end 5132 that connects to the humidifier 5000 or the RPT device 4000 as shown in FIG. 19*a*-19*d*. The inlet end 5132 may comprise a pressure activated face seal or bellows seal to provide sealed pneumatic connection from an outlet of the RPT device 4000 and/or the humidifier 5000. A seal may be used such as that described in U.S. Patent Application Publication No. 2011/0271956, which is incorporated herein by reference in its entirety. In another example of the present technology, the airflow tube 5130 may be connected at the inlet end 5132 to at least one conduit that is in turn connected to the RPT device 4000 and/or the humidifier 5000. In any of these scenarios one function of the airflow tube 5130, and specifically the inlet end 5132, may be to receive the flow of gas from the RPT device 4000 and/or the humidifier 5000 and direct it outside of the device to the air circuit 4100 via the outlet connector 4106. The airflow tube 5130 also facilitates rotation of the outlet connector 4106 of the air circuit 4100 by allowing the outlet connector 4106 to rotate around the outlet end 5134.

A portion of the humidifier 5000 is shown in FIGS. 19*a*-19*e* with the airflow tube 5130 and/or the cable housing 5100. The airflow tube 5130 may also incorporate a latch portion 5172 to connect with a receiving portion 5176 of the RPT device 4000 and/or the humidifier 5000 to locate and/or retain the airflow tube in a correct position within the RPT device 4000 and/or the humidifier 5000. The latch portion 5172 may assist in locating the inlet end 5132 of the airflow tube in the correction position. The engagement of the latch portion 5172 with the receiving portion may provide a sensory feedback, such as a click, to indicate correct connection. The latch portion 5172 may be further configured so that the airflow tube 5130 would be dislodged from receiving portion as it disengages therefrom. The latch portion 5172 may be a different colour to the complementary receiving portion or RPT device 4000 and/or the humidifier 5000 component for improved visibility. In certain circumstances, the airflow tube 5130 and/or the receiving portion 5176 may be configured so that a button such as at the end of the latch portion 5172 may be used to release the airflow tube 5130 from the receiving portion 5176. A tool may be used to release the airflow tube 5130 from the receiving portion 5176.

The airflow tube 5130 may be configured so that engagement of the latch portion 5172 with the receiving portion 5176 also completes a pneumatic connection between the air circuit 4100 and the RPT device 4000 and/or the humidifier 5000 when the air circuit 4100 is attached to the RPT device 4000 and/or humidifier 5000. Accordingly, it may be possible to detect the absence or incorrect connection of the airflow tube 5130 or a disengagement thereof by detection of air leak.

In a further optional arrangement, when the outlet connector 4106 of the air circuit 4100 is connected to the RPT device 4000 and/or the humidifier 5000 the connection action may be configured to ensure the correct connection of the airflow tube 5130 with the receiving portion 5176. Incorrect connection of the airflow tube 5130 to the receiving portion 5176 may prevent the outlet connector 4106 from being able to connect correctly to the airflow tube 5130, which may be indicated by the RPT device 4000 through detection of a high leak flow, for example. In a further alternative the outlet connector 4106 of the air circuit 4100 may be used to facilitate insertion and/or removal of the airflow tube 5130 from the RPT device 4000 and/or the humidifier 5000.

As discussed above, when the air circuit 4100 is attached to the RPT device 4000 and/or humidifier 5000, the outlet end 5134 of the airflow tube 5130 may be coupled to the outlet connection region 4114 of the outlet connector 4106. The outlet end 5134 may also be formed with an ISO taper, such as a 22 mm outer diameter ISO taper, to allow connection of standard non-heated air circuit.

As seen in FIG. 10*a* the airflow tube 5130 may comprise a flow bend, having an internal circular or curved cross-section configured to reduce the impedance of the air flow through the airflow tube 5130. The airflow tube 5130 may be constructed as a two-part process as shown in FIG. 10*d*, wherein the first portion 5130*a* is moulded from rigid material such as Bisphenol A (BPA) free polycarbonate/ acrylonitrile butadiene styrene (PC/ABS), and the second portion 5130*b* comprising at least a part of the flow bend is overmoulded from a compliant material such as silicone. Use of a compliant material to form the second portion 5130*b* that comprises a portion of the bend may allow withdrawal of a moulding tool that comprises the internal bend from the internal cavity at the end of the moulding process by deforming the second portion 5130*b*.

The airflow tube 5130 may also include a retaining flange 5136 to assist in locating and/or securing the airflow tube 5130 to the RPT device 4000 and/or the humidifier 5000, or a housing or chassis thereof. The retaining flange 5136 may assist in correctly locating or positioning the outlet end 5134 of the airflow tube 5130 within the outlet of the RPT device 4000 and/or humidifier 5000 as shown in FIG. 19*c*-19*d* by abutting a locating flange in the RPT device 4000 and/or humidifier 5000. It should be understood that the retaining flange 5136 may allow for fixed attachment of the airflow tube 5130. The retaining flange 5136 may, alternatively, allow for removable attachment of the airflow tube 5130 so that it may be cleaned or replaced, for example.

6.6.2 Producing the Air Circuit

Certain features of the air circuit 4100 and their relationship to its production, according to examples of the present technology, will now be described. FIG. 5*f* shows an exploded view of the components of the air circuit 4100 according to an example of the present technology. The substructure 4132 of the outlet connector 4106 may be a molded part that includes the tube connection region 4136 with structure to attach the tube portion 4102. The orifice 4144 opposite the tube connection region 4136 may receive an end cap 4124 to partially provide a pneumatic seal to the outlet connector 4106. A housing 4134 may be provided over the top of the substructure 4132 to further seal the outlet connector 4106 pneumatically and to provide additional structural support. The housing 4134 may be introduced to the substructure 4132 by way of an overmoulding process. The electrical connector 4112 may include a support structure 4126 to support at least one electrical lead 4128. The electrical connector 4112 may be produced by insert moulding, whereby the electrical lead 4128 is moulded into the electrical connector 4112 by moulding the support structure 4126 around the electrical lead 4128. The electrical connector 4112 may be located and/or connected onto the outlet connector 4106 by the protruding tabs 4180 near the tube connection region 4136 of the substructure 4132. The grommet 4104 is also shown with threads 4130 to allow the grommet to be threaded onto the tube portion 4102, as will be discussed in greater detail below.

FIGS. 6*a* and 6*c*-*e* show various views of the substructure 4132 including the electrical connector 4112. The substructure 4132 and the support structure 4126 of the electrical connector 4112 may be molded from polycarbonate/acrylonitrile butadiene styrene (PC/ABS). Also visible in FIG. 6*a* are the tube connection region 4136 and the tab 4148 having the actuator 4108 and the retention feature 4110 disposed thereon. The orifice 4144 can also be seen opposite the tube connection region. The orifice 4144 may be formed on the substructure 4132 during molding of the substructure. A mandrel may be used to form the tube connection region 4136 and the interior of the substructure 4132 during molding and the orifice 4144 may be formed around the mandrel leaving this region open when the mandrel is pulled out after the substructure is molded. The end cap 4124, as shown in FIG. 5*f*, may be welded ultrasonically onto the substructure 4132 to sealingly cover the orifice 4144. The end cap 4124 may comprise an internal profile configured to reduce flow impedance through the outlet connector 4106. For instance, the end cap 4124 may incorporate a flow radius 4176 as shown in FIG. 5*g*-5*i* configured to increase the radius of the internal corners of the outlet connector 4106. The flow radius 4176 may also be constructed from materials suited for improved thermal and/or acoustic performance, and/or comprise an air gap between the flow radius 4176 and the housing 4134 for improved thermal and/or acoustic performance.

FIG. 6*b* shows the support structure 4126 of the electrical connector 4112 together with the at least one electrical lead 4128. A connection end 4138 and a tube end 4140 of the support structure 4126 are also shown. It is noted that in FIG. 6*b*, the electrical lead 4128 shows a snap-off plate 4174 protruding towards the tube end 4140, which is not shown in the assembly figure (FIG. 6*f*). The snap-off plate 4174 is used during assembly only, and does not form a part of the completed outlet connector 4106. In one form, the snap-off plate 4174 is removed after individual wires (e.g., of the helical coil 4103) are connected to their corresponding electrical lead 4128.

FIG. 6f shows a perspective view of the assembled outlet connector 4106 with the housing 4134 removed to show the internal structures. FIG. 6g shows a similar view in cross-section. FIG. 6g shows engagement of the threads 4130 of the grommet 4104 onto the helical coil 4103 of the tube portion 4102. Also, a portion of the tube portion 4102 can be seen extending through the grommet 4104 for attachment to the tube connection region 4136 of the substructure 4132 at connector threads 4142. These connector threads 4142 can also be seen in FIG. 6c. In some forms, the portion of tube portion 4102 which engages with the tube connection region 4136 may be torn to enable a portion of the helical coil 4103 to be unwound. This may allow the unwound portion of the helical coil 4103 to be routed around the tube connection region 4136 to form the electrical connections with the electrical connector 4112.

FIG. 17 shows a hatched cross-sectional view, in accordance with the present technology, of how the housing 4134 may be formed around the assembly of the tube portion 4102, the grommet 4104, and the substructure 4132. FIG. 17 shows the outlet connector 4106 assembled as shown in FIGS. 6f and 6g with upper and lower mold tools 6000, 6002 above and below the assembly. The mold tools 6000, 6002 can be seen to define the exterior of the housing 4134, and the interior of the housing 4134 may be defined by the grommet 4104, and the substructure 4132. A function of the grommet 4104 may also be understood from this view and may be explained as follows. When molding the housing 4134 to complete the outlet connector 4106 the mold tools 6000, 6002 may need to complete a seal around the internal structures which may require some pressure to affect a sufficient seal. The requisite amount of pressure from the mold tools 6000, 6002 to achieve this seal may damage the tube portion 4102 if the mold tools are pressed against it. Typically, a mandrel (not shown) would be inserted in the tube portion 4102 to maintain its shape while molding, which may then effectively 'clamp' any exposed portions of the tube portion 4102 against the mold tools 6000, 6002. Thus, the grommet 4104 may be included to allow the mold tools 6000, 6002 to form a sealed chamber to mold the housing 4134 while the grommet protects the tube portion 4102. Another feature that can also be seen in FIGS. 6f, 6g, and 17 is that the gas delivery tube portion 4102 may be threaded through the grommet 4104 such that the grommet will abut against the tube connection region 4136 of the substructure 4132. This may provide a further sealing function.

6.6.2.1 The Grommet

FIGS. 7a-f show views of the grommet 4104 according to examples of the present technology. As shown in FIGS. 7b-d, the grommet 4104, according to examples of the present technology, may include threads 4130 internally to allow the grommet to be threaded onto the tube portion 4102. Threads 4130 may be configured to accept the helical coil 4103 of the tube portion 4102 and may be shaped and dimensioned to cover one complete turn of the helical coil. As shown in FIGS. 7c-f, the grommet 4104 may also include a grip section or grips 4154 around a radial portion. The grips 4154 may allow for easier gripping of the grommet 4104 as it is threaded onto the tube portion 4102.

6.6.2.1.1 Producing the Grommet

The grommet 4104, according to an example of the present technology, may be pre-molded or molded separately from the other components of the air circuit 4100. In such a situation it may be advantageous to include at least one keyway 4150 on the grommet 4104, as shown in FIG. 7a. The inclusion of a keyway in this exemplary grommet 4104 may allow the grommet to be restrained by the keyway 4150 while an internal mold tool is rotated and extracted from the molded grommet. The grips 4154 may also be used for securement of the grommet 4104 during removal of an internal tool.

The grommet 4104, in accordance with an example of the present technology, may be formed of a material of sufficient strength and hardness to protect the tube portion 4102 during molding of the housing 4134, as shown in FIG. 17. At the same time, the material should not be so hard such that the grommet 4104 itself damages the tube portion 4102.

The grommet 4104 may also include at least one flange 4152 disposed about a radial portion thereof. The flange 4152 may allow the upper and lower mold tools 6000, 6002 to better seal around the grommet 4104 during molding, as shown in FIG. 17. The flange 4152 may also help to distribute the pressure of the mold tools 6000, 6002 around the grommet 4104 to prevent pinching, as lower pressures may be required for the mold tools 6000, 6002 to achieve sealing in comparison to if the flange 4152 was absent.

Another feature of the grommet 4104 may be to lengthen the life of the tube portion 4102 by reducing the peak stress created at the joint of the tube portion 4102 and the tube connection region 4136. Typically, the tube connection region 4136 is of much higher stiffness than in the tube portion 4102 in the bending direction, and a sudden change in stiffness as such may lead to a localised high stress area. The grommet 4104 may achieve the stress reduction by decreasing the change in stiffness along the length of the assembled outlet connector 4106 between the tube connection region 4136 and the tube portion 4102. This may decrease the stress concentration created on the tube portion 4102.

Thus, according to an example of the present technology, a thermoplastic elastomer may be used to form the grommet 4104. It should be understood, however, that other materials having similar properties may be equally suitable.

6.6.2.2 Clip-Receiver Tube Attachment

FIGS. 30a to 30i depict further examples of the present technology for connecting the tube portion 4102 to the substructure 4132. According to these examples of the present technology, a clip-receiver arrangement is provided to locate and/or secure the tube portion 4102 to the substructure 4132 prior to overmolding to form the outlet connector 4106. The clip-receiver arrangement may also protect the tube portion 4102 from damage while the substructure 4132 is overmoulded, for example with the housing 4134.

The tube connection region 4136 of these examples is formed with a receiver 4135. The receiver 4135 may be integrally molded with the substructure 4132 in one piece. Receiver threads 4135.1 are provided internally to the receiver 4135 so that the helical coil 4103 may be threaded onto the receiver threads to locate the tube portion 4102 in the substructure 4132. In one form, the receiver 4135 may not completely surround the periphery (or circumference) of the tube portion 4102, yet allow the tube portion 4102 to be inserted into the receiver such that the receiver threads 4135.1 fit onto the helical coil 4103. In this form, a clip 4137 may be provided to fit around the remainder of the periphery of the tube portion 4102, and may engage with the receiver 4135. Clip threads 4137.1 may be formed internally on the clip 4137 such that when the clip is attached to the receiver 4135 the outer periphery of the tube portion 4102 is surrounded by the clip and the receiver. Also, the clip threads 4137.1 and the receiver threads 4135.1 may be formed so that when assembled these threads have complementary shapes that substantially match the helical coil 4103.

To attach the clip 4137 onto the receiver 4135 to secure the tube portion 4102, a protrusion 4139.1 may be provided on each side of the receiver 4135 and corresponding tabs 4139 may be formed on the clip. The tabs 4139 may snap onto the respective protrusions 4139.1 to hold the clip 4137 onto the receiver 4135 with a snap-fit. FIG. 30*a* shows the clip 4137 attached to the receiver 4135 and FIG. 30*b* shows how the clip may be attached. FIGS. 30*d* and 30*g* show the tube portion 4102 inserted into the receiver 4135 prior to attachment of the clip 4137 and FIG. 30*c* shows the clip attached to secure the tube in the tube connection region 4136.

FIGS. 30*e* and 30*f* show views of the substructure 4132 attached to the tube portion 4102 and then overmolded with the housing 4134 to complete the outlet connector 4106 of the air circuit 4100. Once the tube portion 4102 is attached to the substructure 4132 and secured at the tube connection region 4136 between the receiver 4135 and the clip 4137, as shown in FIG. 30*c*, this assembly may be overmolded in a manner similar to what is shown in FIG. 17. However, since the grommet 4104 described above is not used in the present example, the receiver 4135 may be provided with a receiver flange 4135.2 and the clip 4137 may be provided with a clip flange 4137.2 in place of the flange 4152 on the grommet to form a seal with the mold tools 6000, 6002 during overmolding of the housing 4134. FIG. 30*f* shows a cross-sectional view of the outlet connector 4106 after overmolding the housing 4134 onto the substructure 4132. The helical coil 4103 can be seen to be engaged to the receiver threads 4135.1 and the clip threads 4137.1. In order to connect the helical coil 4103 electrically to the electrical connector 4112, an end of the tube portion 4102 may be torn to allow the helical coil 4103 to be moved into position (e.g., by unwinding). Also, the housing 4134 can be seen molded around the receiver 4135 and the clip 4137 up to the receiver flange 4135.2 and the clip flange 4137.2.

FIGS. 30*h* and 30*i* show another example of the present technology where the clip 4137 is attached to the receiver 4135 by a pivoting structure such as a hinge 4141. According to this example, the hinge 4141 and the clip 4137 may be integrally molded with the substructure 4132 such that these components are one piece. To secure the tube portion 4102 to the substructure 4132, the tube may be inserted into the receiver 4135, as described above, then the clip 4137 may be positioned over the exposed periphery of the tube portion 4102 and secured by snapping the tab 4139 onto the protrusion 4139.1. Accordingly, this example may have only one protrusion 4139.1 and one tab 4139 for attachment of the clip 4137.

6.6.2.3 Separable Gas Delivery Tube and Elbow Connector

FIGS. 14*a-j* depict another example of the present technology where the tube portion 4102 may be separable from an elbow connector 4158. In this example the tube portion 4102 may be connected to a tube cuff 4156 that includes at least one cuff retention feature 4160 and a cuff electrical connector 4164 (see FIGS. 14*l* and 14*j*). The tube cuff 4156 may be attachable to the elbow connector 4158 which may be a component of the outlet connector 4106. The elbow connector 4158 may include at least one cuff receiver 4162 to receive a corresponding cuff retention feature 4160, thereby releasably attaching the tube cuff 4156 to the elbow connector 4158.

The tube cuff 4156 may also include a cuff electrical connector 4164 to form an electrical connection with the electrical connector 4112 of the outlet connector 4106. The electrical connector 4112 may, in turn, connect electrically to the cable 5102 via a swivel electrical connector 5105.

This arrangement may, in similar fashion to other examples described herein, provide for the formation of both pneumatic and electrical connections with the outlet connector 4106. In this example one electrical and pneumatic connection may be formed by the connection of the cuff 4156 to the elbow connector 4158 and another may be formed by the connection of the outlet connector 4106 to the outlet assembly 5107. Also, this example may provide a rotatable arrangement.

6.6.2.3.1 Electrical Connector Fixed to the Outlet Assembly

FIGS. 15*a* and 15*b* show an alternative example to the arrangement depicted in FIGS. 14*a-j*. In this example the swivel electrical connector 5105 is shaped to form an electrical connection with the cuff electrical connector 4164 (shown in FIG. 14*j*) such that the electrical connector 4112 is not required. It should be understood that the swivel electrical connector 5105 may be fixedly attached to the outlet assembly 5107 and electrical and pneumatic connections are both made by the attachment of the outlet connector 4106 to the outlet assembly 5107. In other words, this arrangement may be the inverse of that which is disclosed in other examples such that the exposed electrical connector in this example is located on the outlet assembly 5107 and the outlet connector 4106 has a feature to receive and form an electrical connection.

6.6.2.4 Connection Assembly with Extended Tube

FIGS. 16*a* and 16*b* depict another example of the present technology. Similar to other examples, this example may provide for both electrical and pneumatic connections to be made between an outlet assembly 5107 and an outlet connector 4106. The connection may also be rotatable in similar fashion to the other examples. This example also includes an outlet tube 5142 that may extend from the outlet assembly 5107 to form the pneumatic connection and define the axis of rotation of the connection. The outlet tube 5142 may be part of an airflow tube 5130 as described above.

6.6.3 Air Circuit-Outlet Connection Having Multiple Discrete Positions

According to another example of the present technology, as shown in FIGS. 13*a-n*, provides for a connection assembly wherein the air circuit 4100, specifically the outlet connector 4106, may be connected to an outlet 5140 in one of a plurality of discrete positions. The outlet 5140 of this example of the present technology may be located on a housing 5138 of the RPT device 4000 and/or the humidifier 5000. The outlet 5140 may also include an outlet tube 5142 and at least one outlet electrical connector 5144. The outlet tube 5142 may be part of an airflow tube 5130 as described above. Although not shown in these views, it should be understood that the outlet connector 4106 will be connectable to a gas delivery tube that is connectable to a patient interface at the opposite end and may include a heating element as described above. The gas delivery tube may be formed integrally with the outlet connector 4106 or it may be removable, in which case a further electrical connection would need to be provided for the tube. The examples depicted in these views may also provide for an electrical and pneumatic connection as disclosed above. The outlet connector 4106 depicted in these examples may be shaped as an elbow and may be bent about 90°, although it should be understood that a number angles may be possible, such as straight (180°), 150°, 120° or 60°.

One feature of the exemplary arrangement shown in FIGS. 13*a*-13*n* is the provision of multiple discrete positions for removable attachment of the outlet connector 4106 on the outlet 5140. This may be accomplished by providing multiple outlet electrical connectors 5144 on the outlet 5140 as shown in FIGS. 13*f-h*. The outlet connector 4106 may then include an electrical connector 4112 as shown in FIG. 13*k*. Thus, when the outlet connector 4106 is connected to the outlet 5140, the electrical connector 4112 electrically communicates with a corresponding one of the outlet electrical connectors 5144. FIGS. 13*b* and 13*d* show the outlet connector 4106 connected to the outlet 5140 in a first position and FIG. 13*j* shows the outlet connector in a second position. The examples depicted in these Figures show two possible positions for the outlet connector 4106 relative to the outlet 5140, however it should be understood that any number of positions may be provided by additional outlet electrical connectors 5144.

It should also be understood that an alternative to the examples heretofore described may provide for a plurality of electrical connectors 4112 on the outlet connector 4106 while the outlet 5140 includes a single outlet electrical connector 5144. Such an arrangement would provide for a similar arrangement described above with multiple discrete positions for the outlet connector. In other words, this arrangement is merely the inverse of the arrangement described above such that in the instant arrangement the outlet connector is provided with multiple electrical connectors.

As can be seen in FIGS. 13*b*, 13*d*, and 13*j*, the outlet 5140 and the outlet connector 4106 may be shaped complementary to one another. While complementary rectangular shapes are shown in these views it should be understood that the outlet 5140 and the outlet connector 4106 may take on any other complementarily shaped arrangement.

FIG. 13*n* depicts a view of the connection assembly that is similar to that shown in FIG. 13*j*, for example, with the external components removed to show the internal components. An outlet connector tube 4168 is shown as an elbow with a bend of about 90° and is connected to the outlet 5140. The electrical connector 4112 can also be seen connected to a corresponding outlet electrical connector 5144 and another outlet electrical connector is not occupied. The cable 5102 is also shown passing across and in communication with the outlet electrical connectors 5144. This view shows how the components of the outlet connector 4106, the outlet connector tube 4168 and the electrical connector 4112, may provide both pneumatic and electrical connections. It also may be envisioned that the electrical connector 4112 may be connected to the other outlet electrical connector 5144 and, accordingly, the outlet connector tube 4168 may be pointed in the opposite direction. Alternative examples may include the outlet electrical connectors 5144 positioned in various vertical and horizontal orientations.

The cable 5102 may be a flexible circuit board (FCB), as shown in FIG. 13*n*, to connect to at least one electrical component 4200 of the RPT device 4000 and/or the humidifier 5000. In such an arrangement a multi-layer FCB may facilitate multiple signalling paths for each outlet electrical connector 5144. Alternatively, a number of separate wiring looms may be provided. Each wiring loom would, in such an arrangement, be connected to individual outlet electrical connectors 5144.

The outlet electrical connectors 5144, the electrical connector 4112, and the cable 5102 may also include multiple connections for the provision of powering and/or signalling functions.

6.6.3.1.1 Protection of Electrical Connectors

The outlet connector 4106 may also include at least one dummy connector 4113. The dummy connector 4113 may function to cover and protect the unused outlet electrical connector 5144 when the outlet connector 4106 is attached to the outlet 5140, as shown in FIGS. 13*e* and 13*h*. By covering the unused outlet electrical connector 5144 it may be protected from damage due to debris and contaminants. In arrangements where more than one unused electrical connector is provided a corresponding number of dummy connectors may also be provided. Also, in the situation where there are multiple electrical connectors 4112 on the outlet connector 4106 and one outlet electrical connector 5144, the outlet 5140 may include a number of dummy connectors sufficient to protect the unused electrical connectors.

6.6.4 Rotatable Outlet Connector

FIGS. 22*a* to 29*b* show examples of the present technology where an outlet connector may provide pneumatic, electrical, and mechanical connections simultaneously while allowing a full rotational degree of freedom, or freedom of rotation over 360° when connected. The outlet connector may be used, for example, to join an air circuit comprising electrical circuitry (such as a heated air circuit, or an air circuit capable of communicating electrical signals) to a respiratory apparatus such as a RPT device, a humidifier, or an integrated PAP-humidifier device.

FIGS. 22*a* to 22*h* show an exemplary substructure assembly 4500 of an outlet connector. FIG. 22*g* shows an exploded view of the substructure assembly 4500 to depict individual components of the substructure assembly. A body 4502 may provide structure to the substructure assembly 4500. The body 4502 may facilitate the mechanical connection with the respiratory apparatus at the outlet connection region 4530 and with the tube portion 4102 at a tube connection region 4526. A shoulder 4532 may be formed on the body 4502 near the outlet connection region 4530 to resist detachment from the respiratory apparatus, as will be described in greater detail below. The tube connection region 4526 may have threads 4528 to join with the helical coil of a tube portion 4102.

The body 4502 alone may not form a completely pneumatically sealed path for the flow of gas generated by the respiratory apparatus from the outlet connection region 4530 to the tube connection region 4526, as can be seen in FIG. 22*g*. Thus, a cap 4504, shown separately in FIG. 24, may be joined to the body 4502 to provide an airflow path from the outlet connection region 4530 to the tube connection region 4526. The cap 4504 may be provided with a retaining feature, such as tabs 4520 to engage with notches 4524 on the body 4502. The cap 4504 may also be provided with prongs 4518 to engage with detents 4522 on the body 4502. The engagement between the tabs 4520 and the notches 4524 and between the prongs 4518 and the detents 4522 may locate and/or securely connect the cap 4504 to the body 4502. FIG. 22*h* shows an example of the attachment of the cap 4504 to the body 4502. While this engagement may provide a mechanical connection between the body 4502 and the cap 4504, it should be understood that a complete pneumatic seal for the airflow path between the outlet connection region 4530 and the tube connection region 4526 may not be formed between the cap and the body. The complete pneumatic seal may be formed by an overmoulding process similar to that described above in section 5.6.2. Thus, the substructure assembly 4500 may be joined to a tube portion at the tube connection region 4526 and then this assembly may be overmoulded to form a seal around the substructure assembly and the tube portion by molding a housing around the substructure assembly 4500.

As the air circuit 4100 may be heated according to this example of the technology, connector contacts 4510, 4512, 4514 are provided to the substructure assembly 4500 at the outlet connection region 4530. The connector contacts 4510, 4512, 4514 may form electrical connections with the respiratory apparatus to provide electrical power and/or signal to the air circuit. The connector contacts 4510, 4512, 4514 may surround the outer periphery of the outlet connection region 4530. The connector contacts 4510, 4512, 4514 may be joined to wires 4508 of an electrical contact assembly 4506. A snap-off plate 4536 may be provided to the electrical contact assembly 4506 and the snap-off plate may be removed when joining electrical wires of the tube portion to the electrical contact assembly 4506 during production. The electrical contact assembly 4506 may be joined to the body 4502 by moulding the body over the electrical contact assembly such that only the connector contacts 4510, 4512, 4514 and the snap-off plate 4536 are exposed. The connector contacts 4510, 4512 and 4514 are protected from being covered by the injected polymer during the moulding process. For example, the connector contacts 4510, 4512 and 4514 are held tightly within a mould tool so they are not displaced during the moulding process and are not covered by the injected polymer. Moulding the body 4502 over the electrical contact assembly 4506 may protect the wires 4508 and/or preserve the electrical power and/or signal carried by the wires 4508. For instance, by moulding the body 4502 over electrical contact assembly 4506, the wires 4508 may be protected from moisture in the airflow path during operation of the respiratory apparatus, and any risk of short-circuiting within the wires 4508 may be also reduced. It should be understood that the components of the electrical contact assembly 4506 may be comprised of a material that conducts electricity, e.g., a metal or a metallic alloy. Although the electrical contact assembly 4506 is shown with three connector contacts 4510, 4512 and 4514, it will be understood that any number of connector contacts may be utilised.

FIGS. 25a and 25b show a portion of wires 4508 and the connector contacts 4510, 4512, 4514 with snap-off plate 4536. FIG. 25a shows the wires 4508, the connector contacts 4510, 4512, 4514, and the snap-off plate 4536 in a flat shape and these parts may be stamped and formed from a flat sheet of material. FIG. 25b shows the wires 4508 wrapped in a circular shape to form the connector contacts 4510, 4512, 4514 that will be exposed at the outlet connection region 4530 when the body 4502 is moulded over the electrical contact assembly 4506. It will be appreciated that the portion of wires 4508 shown in FIGS. 25a and 25b may be joined with one or more portions of wires to produce the electrical contact assembly 4506 as shown in FIG. 22g, or in some forms, the electrical contact assembly 4506 may be produced from one sheet (e.g., by stamping and/or bending from a sheet of electrically conductive material).

As noted above, it may be desirable to shield the electrical contact assembly 4506 from exposure to moisture in the airflow path and this may be accomplished by moulding the body 4502 onto the electrical contact assembly, for example by insert moulding. Moulding the body 4502 onto the electrical contact assembly 4506 in this manner may result in the formation of a wire overmould 4534. The wire overmould 4534 may be formed as a portion of the body 4502 to enclose the wires 4508 and protect the wires from moisture in the airflow path up to the point in the body where the wires emerge to be joined with the tube portion at the tube connection region.

FIG. 22d shows a side view of an exemplary substructure assembly 4500 to depict a sweep bend of the substructure assembly. The sweep bend may be understood in a two-dimensional (planar) sense as bend shape of the substructure assembly 4500 where an inner radius Ri and an outer radius Ro of the substructure assembly may have a common arc center. In a three-dimensional sense, a sweep bend may be understood as a bend wherein the entire outline of a cross section has a common arc center, thereby provides a constant cross-sectional shape through the length of the bend in the substructure assembly 4500 along the airflow path. In some forms, Ro may be between about 1 and about 3 times that of a diameter of the cross-section. In further examples, Ro may be between 1.5 and 2 times that of a diameter of the cross-section.

A sweep bend (in a two- or three-dimensional sense) may be advantageous in that a smaller pressure drop may result from a sweep bend as compared to a sharper and/or more abrupt bend, for example a right-angle bend, or a right-angle bend which comprise internal radii of substantially similar diameters. Additionally, an exemplary sweep bend may have a relatively large radius of curvature in that the center radius of the sweep bend (average of the inner radius and the outer radius) may be 0.5-3 times the internal diameter of the airflow path defined by the interior of the substructure assembly 4500.

FIGS. 23a to 23f show examples of the substructure assembly 4500 without the electrical contact assembly 4506. While the substructure assembly 4500 has been described above as having the electrical contact assembly 4506 moulded with the body 4502, it should be understood that these views depict some structural features of the substructure assembly 4500 that may not be visible because of the presence of the electrical contact assembly. For example, contact recesses 4511, 4513, 4515 may be formed in the body 4502 at the outlet connection region 4530. The contact recesses 4511, 4513, 4515 may be formed around the connector contacts 4510, 4512, 4514 when moulding the body 4502 onto the electrical contact assembly 4506. FIGS. 23d and 23f, for example, show the absence of the connector contacts 4510, 4512, 4514 at the outlet connection region 4530. Also, the outlet connection region 4530 can be seen to taper down to decrease in external diameter towards a housing end of the outlet connection region 4530. As will be described in further detail below, this arrangement may comprise one detent 4522, and thus provide one point of force feedback to the user upon engagement. It is also envisaged that multiple detents may be used, however in some cases this may not be desirable, as the user may potentially perceive engagement of one detent (whilst others may not be engaged) as the engagement of the connection.

6.6.4.1 Manufacture of the Outlet Connector

In one form, the substructure assembly 4500 may be manufactured according to the following steps. The electrical contact assembly 4506 may be formed by stamping a flat sheet of material, and forming the bends and curvatures as required to a final shape as shown in FIG. 22g. The body 4502 may be moulded including the electrical contact assembly 4506, for example by insert moulding over the electrical contact assembly 4506.

Then, the cap 4504 may then be located on the body 4502, for example joined by the detents 4522 and tabs 4520, and the electrical contact assembly 4506 may be joined to wires to form electrical connections with the tube portion 4102. The plate 4536 may then be removed, and the substructure assembly 4500 may be overmoulded with the housing (not shown) similarly to above. During this process, one or more internal jigs (not shown) may be inserted into the substructure assembly 4500 to prevent the cap 4504 from collapsing to the interior of the air path of the body 4502.

6.6.4.2 Connecting the Outlet Connector

FIG. 26a shows a cross-sectional view of a connection arrangement between the outlet connection region 4530 and a housing 5200 of a respiratory apparatus according to an example of the present technology. The connector contacts 4510, 4512, 4514 at the outlet connection region 4530 are shown in contact with outlet contacts 5202, 5204, 5206. The outlet contacts 5202, 5204, 5206 may be positioned in grooves 5208, 5210, 5212 in the periphery of an opening 5201 of the housing 5200.

FIG. 26b shows a detailed view of this connection arrangement. In FIG. 26b it can also be seen how the shoulder 4532 may be shaped to engage with the outlet contact 5202 to facilitate retention of the outlet connection region 4530 within the housing 5200. Although the outlet contact 5202 may primarily perform the retention function in the depicted example, it should be understood that in further examples more than one of the outlet contacts may perform the retention function. Accordingly, additional corresponding shoulders may be formed on the outlet connection region 4530.

According to an example of the present technology, each of the outlet contacts 5202, 5204, 5206 may comprise a canted spring in a corresponding groove 5208, 5210, 5212. Exemplary canted springs are BalContact™ springs from Bal Seal Engineering Co. Inc. In the example where the outlet contacts 5202, 5204, 5206 are canted springs, the canted springs may be comprised of an elastic material that conducts electricity, e.g., a metal or a metallic alloy. It may be advantageous for the material and/or a configuration of the outlet contacts 5202, 5204, 5206 to be elastic so that the outlet contacts will elastically deform during engagement and/or disengagement with the outlet connection region 4530. This may ensure that the outlet contacts 5202, 5204, 5206 maintain electrical contact with the connector contacts 4510, 4512, 4514 when the outlet connection region 4530 is engaged with the housing 5200. It may also be advantageous to use canted springs as the outlet contacts 5202, 5204, 5206 because their elasticity may provide mechanical and/or audible feedback to indicate to the user that a connection has been made, while also providing secure retention of the outlet connection region 4530. Moreover, canted springs may also allow for some play within the connection necessary for rotation, while maintaining secure engagement. Also, each of the grooves 5208, 5210, 5212 may be formed from a material that conducts electricity, e.g., a metal or a metallic alloy. Although not shown in these views, it should be understood that the grooves 5208, 5210, 5212 are in electrical communication with a source of electrical power, for example with a source of electrical power in the respiratory apparatus. Thus, the respiratory apparatus may deliver electrical power to heat the tube, which is provided from the grooves 5208, 5210, 5212 through the outlet contacts 5202, 5204, 5206 to the connector contacts 4510, 4512, 4514. The electrical connections formed may also provide communication functions such as electrical signalling.

According to these depicted examples, electrical, pneumatic, and mechanical connections may be formed and maintained when the outlet connection region 4530 is inserted into the housing 5200. The outlet connector may be rotated once this connection is formed while maintaining these electrical, pneumatic, and mechanical connections. The electrical connection may be maintained because the connector contacts 4510, 4512, 4514 extend peripherally around the outlet connection region 4530 such that at least a portion of each connector contact is always in contact with a respective one of the outlet contacts 5202, 5204, 5206 during within the housing 5200. Engagement of the shoulder 4532 with the outlet contact 5202 may serve to maintain the mechanical connection during rotation. It should be understood that additional shoulders may be provided to engage with the other outlet contacts should additional retention be desired. The pneumatic connection may be maintained during rotation because the outlet connection region 4530 may be sized and shaped to form close fit with the opening 5201 of the housing 5200. Additionally, peripheral seal(s) may be provided to ensure a secure pneumatic connection between the outlet connector and the respiratory apparatus.

FIGS. 27a to 27c show cross-sectional views of further examples of connection arrangements according to the present technology. FIG. 27a shows an example where the outlet connection region 4530 includes the connector contact 4510 with the shoulder 4532 on one side and an additional shoulder 4532.1 on the other side such that the connector contact 4510 is recessed. The outlet contact 5202 may extend from the groove 5208 into the recessed connector contact 4510 between the shoulder 4532 and the additional shoulder 4532.1. FIG. 27c depicts a detailed view of this arrangement. FIG. 27b shows a further alternative where the connector contact 4510 may be further recessed between the shoulder 4532 and the additional shoulder 4532.1. Also, in this example the outlet contact 5202 is carried on the outlet connection region 4530 between the shoulder 4532 and the additional shoulder 4532.1, rather than in the groove 5208 of the housing 5200. The peripheral surfaces of the connector contact 4510 and of the groove 5208 in these examples may be flat where they engage with the outlet contact 5202.

FIGS. 28a to 28c show cross-sectional views of further examples of connection arrangements according to examples of the present technology. The example shown in FIGS. 28a and 28c varies from the example shown in FIGS. 27a and 27c in that the surface of the groove 5208 is V-shaped. The example shown in FIG. 28b varies from the example shown in FIG. 27b in that the connector contact 4510 is V-shaped.

FIGS. 29a and 29b show examples of the present technology where the outlet connection region 4530 may be attached and retained in the housing 5200. FIG. 29a shows the outlet connection region 4530 being inserted into the housing 5200. The outlet connection region 4530 may be tapered to progressively compress the outlet contact 5202 into the groove 5208 as the outlet connection region is inserted into the housing. Once inserted, as shown in FIG. 29b, the outlet contact 5202 may abut against the shoulder 4532 and/or the additional shoulder 4532.1 to limit axial movement of the outlet connection region 4530 relative to the housing 5200.

While FIGS. 27a-c, 28a-c, and 29a-b each show one set of a connector contact 4510, an outlet contact 5202, and a groove 5208, it should be understood that a plurality of sets of these components may be provided.

While the examples discussed above have referred to connecting the depicted outlet connector to a respiratory apparatus, it should be understood that these connection arrangements may be suitable for forming electrical, mechanical and pneumatic connections between other components, such as two air circuits, a RPT device to a humidifier, a RPT device to a patient interface and/or a humidifier to a patient interface. For example, the ability to maintain electrical, mechanical, and pneumatic connections while allowing a full rotational degree of freedom may be beneficial because it may help to reduce tube stress resulting from patient movement while wearing a patient interface at the opposite end of the tube. Another advantage of the present technology may be that rotational alignment may not be required to engage and/or disengage the connection arrangement, such as between the outlet connector and the respiratory apparatus.

6.7 Glossary

For the purposes of the present technology disclosure, in certain forms of the present technology, one or more of the following definitions may apply. In other forms of the present technology, alternative definitions may apply.

6.7.1 General

Air: In certain forms of the present technology, air supplied to a patient may be atmospheric air, and in other forms of the present technology atmospheric air may be supplemented with oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

6.7.2 Aspects of RPT Devices

Air circuit: A conduit or tube constructed and arranged in use to deliver a supply of air or breathable gas between two components such as a RPT device and a patient interface, a RPT device and humidifier, or a humidifier and a patient interface. The air circuit may be referred to as air delivery tube. In some cases there may be separate limbs of the circuit for inhalation and exhalation. In other cases a single limb is used.

Controller: A device, or portion of a device that adjusts an output based on an input. For example one form of controller has a variable that is under control—the control variable—that constitutes the input to the device. The output of the device is a function of the current value of the control variable, and a set point for the variable. A servo-ventilator may include a controller that has ventilation as an input, a target ventilation as the set point, and level of pressure support as an output. Other forms of input may be one or more of oxygen saturation (SaO2), partial pressure of carbon dioxide (PCO2), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure.

Transducers: A device for converting one form of energy or signal into another. A transducer may be a sensor or detector for converting mechanical energy (such as movement) into an electrical signal. Examples of transducers include pressure transducers, flow transducers, carbon dioxide ($CO_2$) transducers, oxygen ($O_2$) transducers, effort transducers, movement transducers, noise transducers, a plethysmograph, and cameras.

6.7.3 Humidifiers

Dew Point: The atmospheric temperature (varying according to pressure and humidity) below which water droplets begin to condense and dew can form.

Humidity, absolute: The amount of water vapor present in a unit volume of air, usually expressed in mass per volume (e.g. $g/m^3$).

Humidity, relative: The amount of water vapor present in air expressed as a percentage of the amount needed for saturation at the same temperature.

6.7.4 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using ASTM D2240.

Polycarbonate: a typically transparent thermoplastic polymer of Bisphenol-A Carbonate.

6.7.5 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

6.7.6 Terms Used in Relation to Patient Interface

Curvature (of a surface): A region of a surface having a saddle shape, which curves up in one direction and curves down in a different direction, will be said to have a negative curvature. A region of a surface having a dome shape, which curves the same way in two principle directions, will be said to have a positive curvature. A flat surface will be taken to have zero curvature.

Floppy: A quality of a material, structure or composite that is the combination of features of:

Readily conforming to finger pressure.

Unable to retain its shape when caused to support its own weight.

Not rigid.

Able to be stretched or bent elastically with little effort.

The quality of being floppy may have an associated direction, hence a particular material, structure or composite may be floppy in a first direction, but stiff or rigid in a second direction, for example a second direction that is orthogonal to the first direction.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during positive airway pressure therapy.

6.8 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| 7 REFERENCE NUMERAL LIST | |
|---|---|
| patient | 1000 |
| bed partner | 1100 |
| patient interface | 3000 |
| structure | 3100 |
| plenum chamber | 3200 |
| structure | 3300 |
| vent | 3400 |
| connection port | 3600 |
| forehead support | 3700 |
| rpt device | 4000 |
| external housing | 4010 |
| upper portion | 4012 |
| portion | 4014 |
| panel | 4015 |
| chassis | 4016 |
| handle | 4018 |
| pneumatic block | 4020 |
| air circuit | 4100 |
| tube portion | 4102 |
| helical coil | 4103 |
| grommet | 4104 |
| outlet connector | 4106 |
| patient interface connector | 4107 |
| actuator | 4108 |
| retention feature | 4110 |
| electrical connector | 4112 |
| dummy connector | 4113 |
| outlet connection region | 4114 |
| recess | 4116 |
| opening | 4118 |
| rib | 4120 |
| end cap | 4124 |
| support structure | 4126 |
| electrical lead | 4128 |
| thread | 4130 |
| substructure | 4132 |
| housing | 4134 |
| receiver | 4135 |
| receiver thread | 4135.1 |
| receiver flange | 4135.2 |
| tube connection region | 4136 |
| clip | 4137 |
| clip thread | 4137.1 |
| clip flange | 4137.2 |
| connection end | 4138 |
| tab | 4139 |
| protrusion | 4139.1 |
| tube end | 4140 |
| hinge | 4141 |
| connector thread | 4142 |
| orifice | 4144 |
| tab | 4148 |
| keyway | 4150 |
| flange | 4152 |
| grip | 4154 |
| cuff | 4156 |
| elbow connector | 4158 |
| cuff retention feature | 4160 |
| least one cuff receiver | 4162 |
| cuff electrical connector | 4164 |
| outlet connector tube | 4168 |
| base seal | 4170 |
| plate | 4174 |
| flow radius | 4176 |
| travel stop | 4178 |

| 7 REFERENCE NUMERAL LIST | |
|---|---|
| tab | 4180 |
| electrical component | 4200 |
| PCBA | 4202 |
| power supply | 4210 |
| input device | 4220 |
| central controller | 4230 |
| therapy device controller | 4240 |
| transducer | 4270 |
| output device | 4290 |
| pneumatic component | 4300 |
| air filter | 4310 |
| inlet air filter | 4312 |
| outlet air filter | 4314 |
| muffler | 4320 |
| inlet muffler | 4322 |
| outlet muffler | 4324 |
| pressure device | 4340 |
| blower | 4342 |
| motor | 4344 |
| back valve | 4360 |
| supplemental oxygen | 4380 |
| substructure assembly | 4500 |
| body | 4502 |
| cap | 4504 |
| electrical contact assembly | 4506 |
| wire | 4508 |
| connector contact | 4510 |
| contact recess | 4511 |
| connector contact | 4512 |
| contact recess | 4513 |
| connector contact | 4514 |
| contact recess | 4515 |
| prong | 4518 |
| tab | 4520 |
| detent | 4522 |
| notches | 4524 |
| tube connection region | 4526 |
| thread | 4528 |
| outlet connection region | 4530 |
| shoulder | 4532 |
| additional shoulder | 4532.1 |
| wire overmould | 4534 |
| plate | 4536 |
| humidifier | 5000 |
| cable housing | 5100 |
| inner wall | 5101 |
| cable | 5102 |
| outer wall | 5103 |
| swivelling disc | 5104 |
| swivel electrical connector | 5105 |
| tab | 5106 |
| outlet assembly | 5107 |
| stop surface | 5108 |
| exit flange | 5109 |
| stop surface | 5110 |
| flange | 5112 |
| swivel disc seal | 5113 |
| electrical connector receiver | 5114 |
| opening | 5116 |
| retainer | 5118 |
| stop surface | 5120 |
| stop surface | 5122 |
| void | 5124 |
| notch | 5126 |
| tang | 5128 |
| airflow tube | 5130 |
| first portion | 5130a |
| second portion | 5130b |
| inlet end | 5132 |
| outlet end | 5134 |
| flange | 5136 |
| housing | 5138 |
| outlet | 5140 |
| outlet tube | 5142 |
| outlet electrical connector | 5144 |
| contact element | 5146 |
| point | 5150 |
| point | 5152 |
| point | 5154 |
| pin | 5156 |
| female electrical connector | 5158 |
| internal shoulder | 5160 |
| retention feature | 5162 |
| contact portion | 5164 |
| base portion | 5166 |
| curved portion | 5168 |
| latch portion | 5172 |
| annular section | 5174 |
| portion | 5176 |
| humidifier reservoir | 5180 |
| humidifier reservoir outlet | 5182 |
| housing | 5200 |
| opening | 5201 |
| outlet contact | 5202 |
| outlet contact | 5204 |
| outlet contact | 5206 |
| groove | 5208 |
| groove | 5210 |
| groove | 5212 |
| heating element | 5240 |
| mold tool | 6000 |
| mold tool | 6002 |

The invention claimed is:

1. A respiratory pressure therapy (RPT) device for providing a flow of pressurized air to a patient interface to treat a respiratory disorder in a patient, the RPT device comprising:
   a pressure generator configured to pressurize air in a range from about 4 cmH$_2$O above atmosphere to about 30 cmH$_2$O above atmosphere;
   a chassis;
   a receiving portion formed on the chassis;
   an airflow tube comprising:
      a latch configured to releasably attach to the receiving portion;
      a first portion constructed from a compliant material and forming an inlet end configured to receive air pressurized by the pressure generator; and
      a second portion constructed from a rigid material and forming an outlet end configured to be connected to an air circuit to direct pressurized air to the patient interface,
   wherein the latch is configured to be attached to and detached from the receiving portion while the airflow tube moves along a linear path.

2. The RPT device of claim 1, wherein the latch is configured to provide sensory feedback to indicate correct connection with the receiving portion.

3. The RPT device of claim 1, wherein the latch and the receiving portion are different colors.

4. The RPT device of claim 1, wherein the latch further comprises a tab to release the latch from the receiving portion.

5. The RPT device of claim 1, wherein the RPT device comprises an outlet,
   wherein the chassis further comprises a locating flange, and
   wherein the airflow tube further comprises a retaining flange configured to abut the locating flange to position the airflow tube within the outlet.

6. The RPT device of claim 1, wherein the latch is configured to extend through the receiving portion when attached thereto.

7. The RPT device of claim 1, wherein the latch is cantilevered from the airflow tube.

8. The RPT device of claim 1, wherein the latch is positioned on the airflow tube proximal to the inlet end.

9. The RPT device of claim 1, wherein the first portion includes a seal, the seal is configured to contact and seal against a humidifier reservoir.

10. The RPT device of claim 1, wherein the chassis includes a hole, and
wherein the airflow tube extends through the hole and is surrounded by the chassis when releasably attached to the chassis.

11. The RPT device of claim 1, wherein:
when the latch is attached to the receiving portion, the airflow tube is not rotatable relative to the chassis,
the chassis includes a hole,
the airflow tube extends through the hole and is surrounded by the chassis when releasably attached to the chassis,
the latch is configured to provide sensory feedback to indicate correct connection with the receiving portion,
the latch and the receiving portion are different colors,
the latch is configured to extend through the receiving portion when attached thereto,
the latch is cantilevered from the airflow tube,
the latch is positioned on the airflow tube proximal to the inlet end,
the second portion includes the latch, and
the first portion includes a seal that is configured to contact and seal against a humidifier reservoir.

12. The RPT device of claim 11, wherein:
the latch further comprises a tab to release the latch from the receiving portion,
the RPT device comprises an outlet,
the chassis further comprises a locating flange, and
the airflow tube further comprises a retaining flange configured to abut the locating flange to position the airflow tube within the outlet.

13. The RPT device of claim 1, wherein when the latch is attached to the receiving portion, the airflow tube is not rotatable relative to the chassis.

14. The RPT device of claim 1, wherein the second portion includes the latch.

15. The RPT device of claim 1, wherein the outlet end is a male connector configured to be removably connected to the air circuit in a male-female arrangement.

16. An airflow tube for a respiratory pressure therapy (RPT) device that includes a chassis with a receiving portion and a blower to provide a flow of pressurized air to a patient interface to treat a respiratory disorder in a patient, the airflow tube comprising:
a latch configured to releasably attach to the receiving portion;
a first portion constructed from a compliant material and forming an inlet end configured to receive air pressurized by the blower; and
a second portion constructed from a rigid material and forming an outlet end configured to be connected to an air circuit to direct pressurized air to the patient interface,
wherein the latch is configured to be attached to and detached from the receiving portion while the airflow tube moves along a linear path.

17. The airflow tube of claim 16, wherein the latch is configured to provide sensory feedback to indicate correct connection with the receiving portion.

18. The airflow tube of claim 16, wherein the latch further comprises a tab to release the latch from the receiving portion.

19. The airflow tube of claim 16, wherein the latch is configured to extend through the receiving portion when attached thereto.

20. The airflow tube of claim 16, wherein the latch is cantilevered from the airflow tube.

21. The airflow tube of claim 16, wherein the latch is positioned on the airflow tube proximal to the inlet end.

22. The airflow tube of claim 16, wherein the first portion includes a seal that is configured to contact and seal against a humidifier reservoir.

23. The airflow tube of claim 16, wherein the outlet end is a male connector configured to be removably connected to the air circuit in a male-female arrangement.

24. A respiratory pressure therapy (RPT) device for providing a flow of pressurized air to a patient interface to treat a respiratory disorder in a patient, the RPT device comprising:
a blower configured to pressurize air to a therapeutic pressure above atmosphere;
a chassis;
a receiving portion formed on the chassis; and
the airflow tube of claim 16,
wherein the latch is a different color from the receiving portion.

25. The RPT device of claim 24, further comprising an outlet,
when the latch is attached to the receiving portion, the airflow tube is not rotatable relative to the chassis,
wherein the chassis further comprises a locating flange,
wherein the airflow tube further comprises a retaining flange configured to abut the locating flange to position the airflow tube within the outlet,
wherein the chassis includes a hole, and
wherein the airflow tube extends through the hole and is surrounded by the chassis when releasably attached to the chassis.

26. The RPT device of claim 24, wherein:
when the latch is attached to the receiving portion, the airflow tube is not rotatable relative to the chassis,
the chassis includes a hole,
the airflow tube extends through the hole and is surrounded by the chassis when releasably attached to the chassis,
the latch is configured to provide sensory feedback to indicate correct connection with the receiving portion,
the latch is configured to extend through the receiving portion when attached thereto,
the latch is cantilevered from the airflow tube,
the latch is positioned on the airflow tube proximal to the inlet end,
the second portion includes the latch, and
the first portion includes a seal that is configured to contact and seal against a humidifier reservoir.

27. The RPT device of claim 26, wherein:
the latch further comprises a tab to release the latch from the receiving portion,
the RPT device comprises an outlet,
the chassis further comprises a locating flange, and
the airflow tube further comprises a retaining flange configured to abut the locating flange to position the airflow tube within the outlet.

28. The airflow tube of claim 16, wherein:
the latch is configured to provide sensory feedback to indicate correct connection with the receiving portion, the latch is configured to extend through the receiving portion when attached thereto, the latch is cantilevered from the airflow tube, the latch is positioned on the airflow tube proximal to the inlet end, the second portion includes the latch, and the first portion includes a seal that is configured to contact and seal against a humidifier reservoir.

29. The RPT device of claim 24, wherein when the latch is attached to the receiving portion, the airflow tube is not rotatable relative to the chassis.

30. The airflow tube of claim 16, wherein the second portion includes the latch.

* * * * *